United States Patent
Kamei et al.

(10) Patent No.: US 10,000,476 B2
(45) Date of Patent: Jun. 19, 2018

(54) PYRIDONE DERIVATIVE, PHARMACEUTICAL CONTAINING THE SAME AND METHODS OF USE THEREOF

(71) Applicant: KAKEN PHARMACEUTICAL CO., LTD., Bunkyo-ku, Tokyo (JP)

(72) Inventors: Noriyuki Kamei, Kyoto (JP); Yoshitake Sumikawa, Kyoto (JP); Daigo Kamimura, Kyoto (JP); Shingo Todo, Fujieda (JP); Takuya Yamada, Kyoto (JP); Shota Tokuoka, Kyoto (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days. days.

(21) Appl. No.: 15/232,000

(22) Filed: Aug. 9, 2016

(65) Prior Publication Data

US 2016/0340349 A1 Nov. 24, 2016

Related U.S. Application Data

(62) Division of application No. 14/363,198, filed as application No. PCT/JP2012/081735 on Dec. 7, 2012, now Pat. No. 9,447,072.

(30) Foreign Application Priority Data

Dec. 9, 2011 (JP) ................. 2011-270492

(51) Int. Cl.
| | |
|---|---|
| *A61K 31/44* | (2006.01) |
| *C07D 413/14* | (2006.01) |
| *C07D 401/14* | (2006.01) |
| *C07D 405/14* | (2006.01) |
| *C07D 401/06* | (2006.01) |
| *C07D 409/14* | (2006.01) |

(52) U.S. Cl.
CPC ......... *C07D 413/14* (2013.01); *C07D 401/06* (2013.01); *C07D 401/14* (2013.01); *C07D 405/14* (2013.01); *C07D 409/14* (2013.01)

(58) Field of Classification Search
CPC .................................................. A61K 31/44
USPC ....................................................... 514/351
See application file for complete search history.

(56) References Cited

U.S. PATENT DOCUMENTS

| | | | |
|---|---|---|---|
| 9,447,072 B2* | 9/2016 | Kamei ................. | C07D 401/14 |
| 2004/0242928 A1 | 12/2004 | Shimano et al. | |
| 2006/0205797 A1 | 9/2006 | Yu et al. | |
| 2006/0276506 A1 | 12/2006 | Yu et al. | |
| 2007/0197564 A1 | 8/2007 | Lavey et al. | |
| 2007/0219218 A1 | 9/2007 | Yu et al. | |
| 2007/0265299 A1 | 11/2007 | Lavey et al. | |

FOREIGN PATENT DOCUMENTS

| | | |
|---|---|---|
| WO | 03/022801 A1 | 3/2003 |
| WO | 2004/024721 A1 | 3/2004 |
| WO | 2004/033632 A2 | 4/2004 |
| WO | 2004/108086 A2 | 12/2004 |
| WO | 2005/085232 A1 | 9/2005 |
| WO | 2006/019768 A1 | 2/2006 |
| WO | 2007/084415 A2 | 7/2007 |
| WO | 2007/084451 A1 | 7/2007 |
| WO | 2007/084455 A1 | 7/2007 |
| WO | 2010/036638 A2 | 4/2010 |
| WO | 2010/036640 A2 | 4/2010 |
| WO | 2010/054278 A2 | 5/2010 |

OTHER PUBLICATIONS

Yu et al., "Discovery and SAR of hydantoin TACE inhibitors", Bioorganic & Medicinal Chemistry Letters, Elsevier Ltd., 2010, vol. 20, 1877-1880.
Yu et al., "Biaryl substituted hydantoin compounds as TACE inhibitors", Bioorganic & Medicinal Chemistry Letters, Elsevier Ltd., 2010, vol. 20, 5286-5289.
Nelson et al., "The therapeutic potential of small molecule TACE inhibitors", Expert Opinion on Investigational Drugs, Ashley Publications Ltd., 1999, vol. 8, No. 4, pp. 383-392, ISSN 1354-3784.
Murumkar et al., "Novel TACE inhibitors in drug discovery: a review of patented compounds", Expert Opin. Ther. Patents, Informa UK Ltd., 2010, vol. 20, No. 1, pp. 31-57.
Girijavallabhan et al., "Novel TNF—a converting enzyme (TACE) inhibitors as potential treatment for inflammatory diseases", Bioorganic & Medicinal Chemistry Letters, Elsevier Ltd., 2010, vol. 20, 7283-7287.
DasGupta et al., "Current perspective of TACE inhibitors: A review", Bioorganic & Medicinal Chemistry, Elsevier Ltd., 2009, vol. 17, pp. 444-459.

* cited by examiner

*Primary Examiner* — Raymond J Henley, III
(74) *Attorney, Agent, or Firm* — Sughrue Mion, PLLC

(57) ABSTRACT

General formula (I): The present invention pertains to: a pyridone derivate or a salt thereof represented by general formula (I); or a medicine containing the pyridone derivative or salt thereof as an active ingredient. [In the formula, ring A, $R^1$, $R^2$, $R^3$ and $R^4$ are specific groups.]

(I)

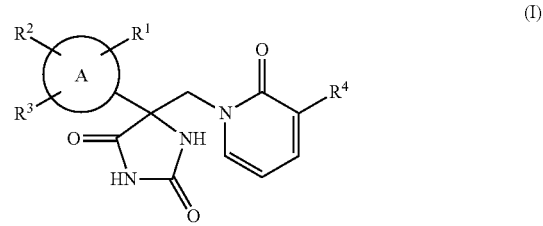

5 Claims, No Drawings

PYRIDONE DERIVATIVE, PHARMACEUTICAL CONTAINING THE SAME AND METHODS OF USE THEREOF

CROSS REFERENCE TO RELATED APPLICATIONS

This is a divisional of U.S. patent application Ser. No. 14/363,198, filed Jun. 5, 2014 (now U.S. Pat. No. 9,447,072), which is a National Stage entry of International Application No. PCT/JP2012/081735, filed Dec. 7, 2012, which claims priority to Japanese Patent Application No. 2011-270492 filed Dec. 9, 2011. The entire disclosures of the prior applications are considered part of the disclosure of the accompanying divisional application, and are hereby incorporated by reference.

TECHNICAL FIELD

The present invention relates to a novel pyridone derivative, or a salt thereof, and to a pharmaceutical containing such pyridone derivative, or a salt thereof, as an active ingredient, which have a tumor necrosis factor-alpha (TNF-α) converting enzyme (TACE) inhibitory effect.

BACKGROUND ART

TNF-α is one of the cytokines secreted from macrophages, monocytes and the like activated by exogenous and endogenous factors. TNF-α is extensively involved in promoting the secretion of various cytokines and in protecting against infection. However, the persistent and excessive production and secretion of TNF-α cause overproduction of inflammatory cytokines, apoptosis of cells, and interference of intracellular signal transduction and the like, resulting in the primary and secondary tissue damage, and eventually becomes a factor responsible for etiology and exacerbation of various disorders (see Non-Patent Literature 1). Therefore, to treat a pathological condition thought to be caused by the excessive production and secretion of TNF-α, it is important to suppress the production and secretion of TNF-α, or to suppress the action of TNF-α. Examples of such diseases in which TNF-α participate include rheumatoid arthritis, systemic lupus erythematosus (SLE), Crohn's disease, Behcet's disease, multiple sclerosis, arteriosclerosis, myasthenia gravis, diabetes, sepsis, acute infectious diseases, asthma, atopic dermatitis, contact dermatitis, psoriasis, acne, fever, anemia and the like.

Tumor necrosis factor alpha converting enzyme (TACE) (also called ADAM 17), which is classified in the ADAM (a disintegrin and metalloproteinase) family, is a membrane-bound protease having zinc at a catalytic site thereof and TACE produces soluble TNF-α by cleaving membrane-bound TNF-α (pro-TNF-α). Therefore, compounds that inhibit the enzyme action of TACE are likely to suppress the production of soluble TNF-α, thereby serving as a therapeutic agent for the above-described various disease conditions caused by TNF-α. Based on this, research into compounds having a TACE inhibitory effect is being actively carried out (see Non-Patent Literature 2 and 3).

On the other hand, matrix metalloproteinase (also called matrixin) (MMP) is a protease having zinc at a catalytic site thereof and has an effect of degrading the extracellular matrix. Approximately 20 subtypes of MMP are known.

A compound that inhibits certain types of MMP has been reported as inhibiting the production of TNF-α as well (see Non-Patent Literature 4). Further, since TACE and MMP are both enzymes having zinc at a catalytic site and also have a similar three-dimensional structure, compounds that inhibit both MMP and TACE have also been reported (see Non-Patent Literature 5). However, it has been reported that rats continuously administered with an agent which inhibits many kinds of MMPs at the same time had a hypertrophic degeneration on the cartilage growth plates (see Non-Patent Literature 6), and that MT1-MMP (MMP-14) knockout mice were observed to present a symptom of arthritis (see Non-Patent Literature 7). There are concerns about the various side-effects that occur due to MMP inhibition based on these reports. In addition, since most of MMPs are involved in the maintenance and homeostasis of the extracellular matrix, which form the basic structure of a living body, inhibiting the catalytic activities of many MMPs nonselectively is likely to cause serious adverse effects on the living body. Therefore, it is preferred that a compound directed to TNF-α production inhibition based on TACE inhibition does not essentially exhibit an inhibitory effect against MMPs.

Patent Literature 1, Non-Patent Literature 8 and Non-Patent Literature 9 contain reports about compounds that selectively inhibit TACE. Further, Patent Literature 2 to Patent Literature 10 contain reports about TACE inhibitor compounds that have a hydantoin structure.

CITATION LIST

Patent Literature

[Patent Literature 1] WO 03/022801 Pamphlet
[Patent Literature 2] WO 10/054278 Pamphlet
[Patent Literature 3] WO 10/036640 Pamphlet
[Patent Literature 4] WO 07/084455 Pamphlet
[Patent Literature 5] WO 07/084415 Pamphlet
[Patent Literature 6] WO 06/019768 Pamphlet
[Patent Literature 7] WO 05/085232 Pamphlet
[Patent Literature 8] WO 04/024721 Pamphlet
[Patent Literature 9] WO 04/033632 Pamphlet
[Patent Literature 10] WO 04/108086 Pamphlet

Non Patent Literature

[Non-Patent Literature 1] Aggarwall B. B., Puri R. K., eds. 1995. Human Cytokines: Their Role in Disease and Therapy. Cambridge, Mass., USA: Blackwell Sci.
[Non-Patent Literature 2] Nelson, F. C. et al., Exp. Opin. Invest. Drugs 1999, 8, 383-392
[Non-Patent Literature 3] Murumkar, P. R. et al., Exp. Opin. Ther. Patents 2010, 20, 31-57
[Non-Patent Literature 4] Mohler, K. M. et al., Nature 1994, 370, 218-220
[Non-Patent Literature 5] DasGupta, S. et al., Bioorg. Med. Chem., 2009, 17, 444-459
[Non-Patent Literature 6] Nakajima, M., The Bone 2001, 15, 161-166
[Non-Patent Literature 7] Holmbeck, K. et al., Cell 1999, 99, 81-92
[Non-Patent Literature 8] Yu, W. et al., Bioorg. Med. Chem. Lett., 2010, 20, 1877-1880
[Non-Patent Literature 9] Yu, W. et al., Bioorg. Med. Chem. Lett., 2010, 20, 5286-5289

SUMMARY OF INVENTION

Technical Problem

In view of such circumstances, there is a continuing need for a TNF-α production inhibitor that is based on TACE inhibition. And, the discovery of a novel compound exhibiting a TACE inhibitory effect is desired. As described above, from the point of safety, it is considered that a novel compound directed to TNF-α production inhibition based on TACE inhibition needs to exhibit hardly any inhibitory effects against MMP, namely, that the compound needs to have selectivity against MMP. On the other hand, from the point of the usefulness of such compound, it may be more desirable that the compound has another useful property.

The present invention has been accomplished with the aim on the treatment and prevention of such TNF-α-related diseases. Namely, the present invention is directed to providing a novel compound, or a salt thereof, that exhibits a selective TACE inhibitory effect (i.e. a weak inhibitory effect against MMP), and to providing a pharmaceutical having such compound as an active ingredient.

As a result of diligent research into the above problems, the present inventors made the surprising discovery that a compound which contains a novel skeleton as a TACE inhibitor has an excellent TACE inhibitory effect, and high selectivity for an inhibitory effect against MMP. The present inventors progressed with their research to complete the present invention on the basis of this finding.

Specifically, the present invention relates to at least the following respective aspects.

(1) A pyridone derivative, or a salt thereof, represented by formula (I),

[Formula 1]

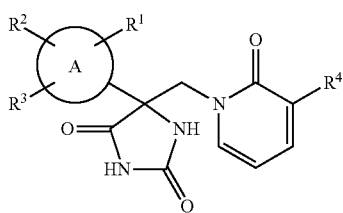

(I)

[wherein ring A represents an aryl, a heteroaryl, or a group represented by the following formula (a),

[Formula 2]

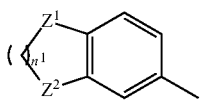

(a)

(wherein $Z^1$ and $Z^2$ each independently represent —CH$_2$— or —O—, and $n^1$ denotes an integer of 1 to 3), $R^1$ represents a hydrogen atom, a halogen atom, a hydroxyl group, a cyano group, a nitro group, a C1-C6 haloalkyl group, a carboxyl group, an optionally substituted C1-C6 alkyl group, an optionally substituted C1-C6 alkoxy group, an optionally substituted C1-C6 alkoxycarbonyl group, an optionally substituted cycloalkyl group, an optionally substituted cyclohexylalkylalkyl group, an optionally substituted heterocycloalkyl group, an optionally substituted heterocycloalkylalkyl group, an optionally substituted aryl group, an optionally substituted aralkyl group, an optionally substituted heteroaryl group, an optionally substituted heteroarylalkyl group, an optionally substituted C2-C6 alkenyl group, an optionally substituted alkenylalkyl group, an optionally substituted cycloalkenyl group, an optionally substituted cycloalkenylalkyl group, an optionally substituted heterocycloalkenyl group, an optionally substituted heterocycloalkenylalkyl group, an optionally substituted C2-C6 alkynyl group, or an optionally substituted alkynylalkyl group, or -$J^1$-$X^1$—$R^5$ {wherein $J^1$ represents a single bond, alkylene, alkenylene, or alkynylene, $X^1$ represents a single bond, an oxygen atom, a sulfur atom, SO, SO$_2$, —CO—, —NR$^6$—, —NR$^6$SO$_2$—, —SO$_2$NR$^6$—, —NR$^6$CO—, —CONR$^6$—, —NR$^6$COO—, —OCONR$^6$—, —NR$^6$CONR$^7$—, or —NR$^6$SO$_2$NR$^7$— (wherein $R^6$ and $R^7$ each independently represent a hydrogen atom or a C1-C6 alkyl group), $R^5$ represents a hydrogen atom, a trifluoromethyl group, an optionally substituted C1-C6 alkyl group, an optionally substituted C1-C6 alkoxy group, an optionally substituted cycloalkyl group, an optionally substituted cycloalkylalkyl group, an optionally substituted heterocycloalkyl group, an optionally substituted heterocycloalkylalkyl group, a group represented by the following formula (b):

[Formula 3]

(b)

(wherein $n^2$ denotes an integer of 1 to 3 and $n^3$ denotes an integer of 0 to 3), an optionally substituted aryl group, an optionally substituted aralkyl group, an optionally substituted heteroaryl group, an optionally substituted heteroarylalkyl group, an optionally substituted C2-C6 alkenyl group, an optionally substituted alkenylalkyl group, an optionally substituted C2-C6 alkynyl group, or an optionally substituted alkynylalkyl group}, $R^2$ represents a hydrogen atom, a halogen atom, a cyano group, a nitro group, a C1-C6 haloalkyl group, a carboxyl group, an optionally substituted C1-C6 alkyl group, a C1-C6 alkoxy group, a C1-C6 alkoxycarbonyl group, an optionally substituted cycloalkyl group, an optionally substituted cyclohexylalkylalkyl group, an optionally substituted heterocycloalkyl group, an optionally substituted heterocycloalkylalkyl group, an optionally substituted aryl group, an optionally substituted aralkyl group, an optionally substituted heteroaryl group, an optionally substituted heteroarylalkyl group, an optionally substituted C2-C6 alkenyl group, an optionally substituted alkenylalkyl group, an optionally substituted heterocycloalkenyl group, an optionally substituted heterocycloalkenylalkyl group, an optionally substituted C2-C6 alkynyl group, or an optionally substituted alkynylalkyl group, $R^3$ represents a hydrogen atom, a halogen atom, or a C1-C6 alkyl group, and $R^4$ represents a hydrogen atom, a halogen atom, a cyano group, a C1-C6 haloalkyl group, a C1-C6 alkoxy group, a hydoxymethyl group, a C1-C6 alkyl group, or a C2-C6 alkenyl group].

(2) The pyridone derivative, or a salt thereof, according to (1), wherein ring A in the formula (I) represents an aryl or a heteroaryl.

(3) The pyridone derivative, or a salt thereof, according to (1) or (2), wherein $R^1$ in the formula (I) represents a halogen atom, a cyano group, a C1-C6 alkyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group).

(4) The pyridone derivative, or a salt thereof, according to any of (1) to (3), wherein $R^2$ in the formula (I) represents a hydrogen atom, a halogen atom, a C1-C6 alkoxy group, or a C1-C6 alkyl group.

(5) The pyridone derivative, or a salt thereof, according to any of (1) to (4), wherein $R^3$ in the formula (I) represents a hydrogen atom, a fluorine atom, or a methyl group.

(6) The pyridone derivative, or a salt thereof, according to (5), wherein, in the formula (I), $R^1$ represents a halogen atom, a cyano group, a C1-C6 alkyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group), $R^2$ represents a hydrogen atom, a halogen atom, a C1-C6 alkoxy group, or a C1-C6 alkyl group, and $R^3$ represents a hydrogen atom, a fluorine atom, or a methyl group.

(7) The pyridone derivative, or a salt thereof, according to (6), wherein, in the formula (I), $R^1$ represents a halogen atom, a cyano group, a methyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group), $R^2$ represents a hydrogen atom, a halogen atom, a methoxy group, or a methyl group, and $R^3$ represents a hydrogen atom, a fluorine atom, or a methyl group.

(8) The pyridone derivative, or a salt thereof, according to any of (1) to (7), wherein $R^4$ in the formula (I) represents a halogen atom, a cyano group, a C1-C6 haloalkyl group, a C1-C6 alkoxy group, a hydoxymethyl group, a C1-C6 alkyl group, or a C2-C6 alkenyl group.

(9) The pyridone derivative, or a salt thereof, according to (8), wherein $R^4$ in the formula (I) represents a methyl group.

(10) The pyridone derivative, or a salt thereof, according to any of (1), (2), (7), and (9), wherein the compound represented by the formula (I) is one selected from the following.

[Formula 4-1]

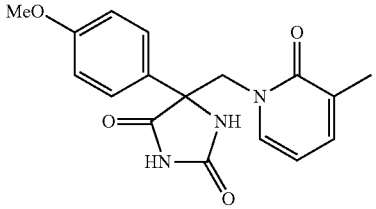
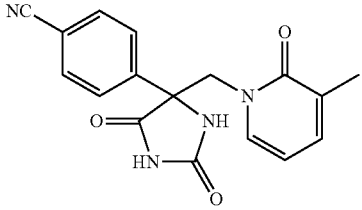
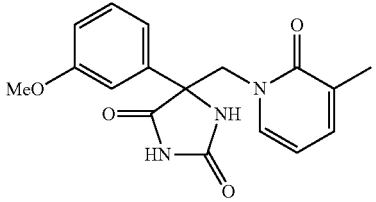
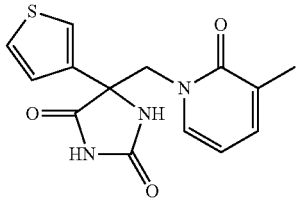
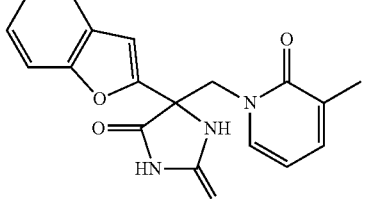
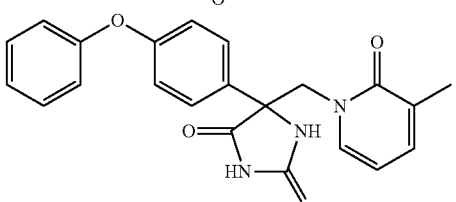
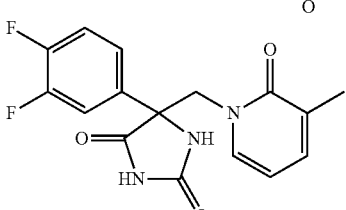
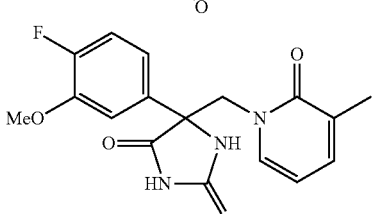

-continued
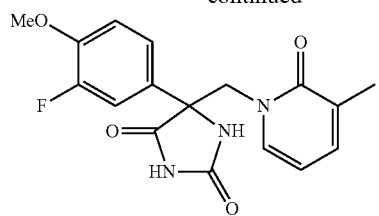
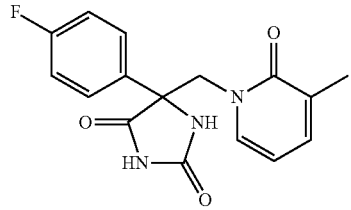
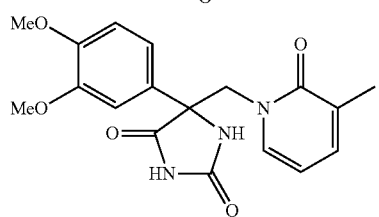
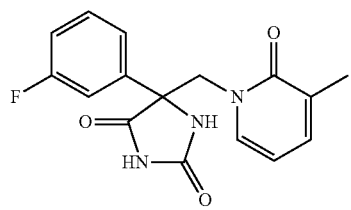
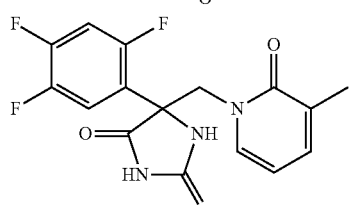
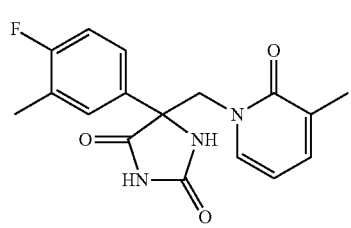
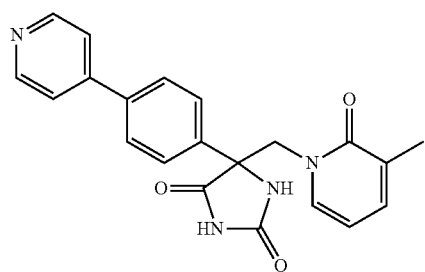
-continued
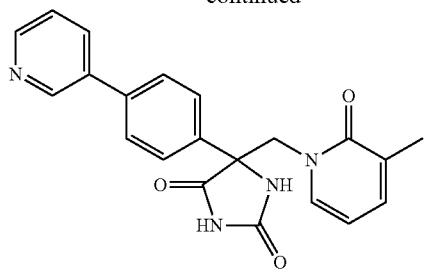
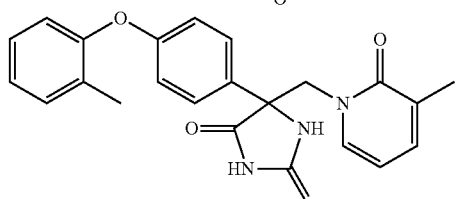
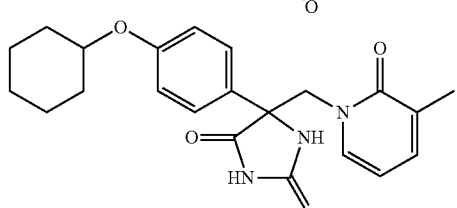
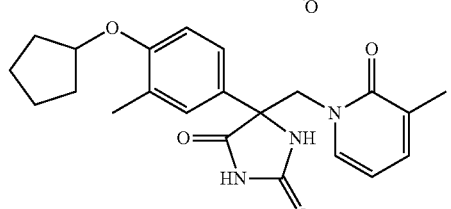
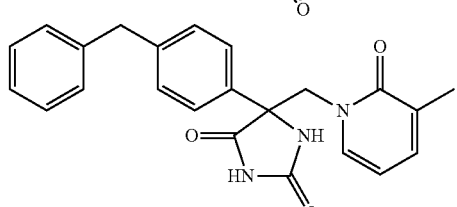
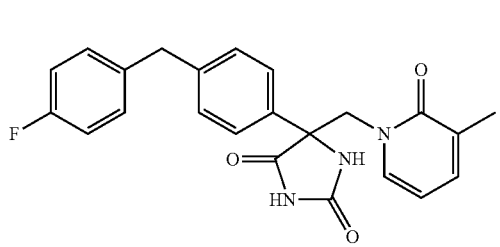
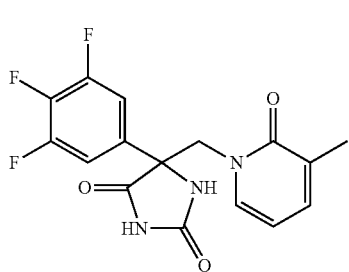

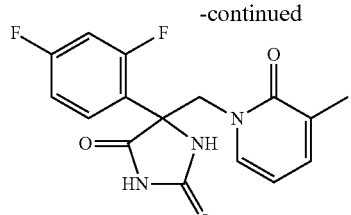
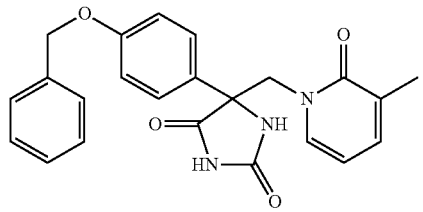
[Formula 4-2]
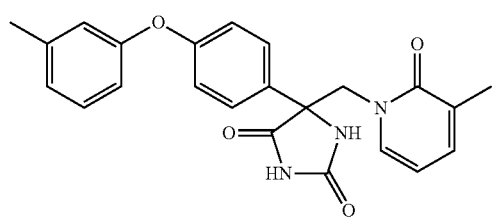
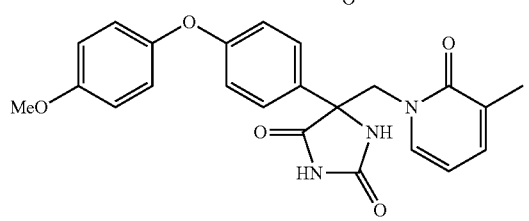
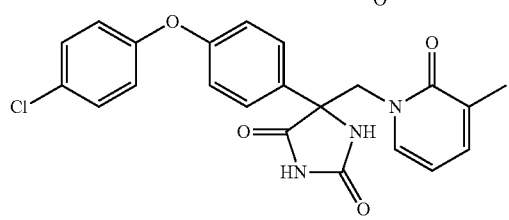
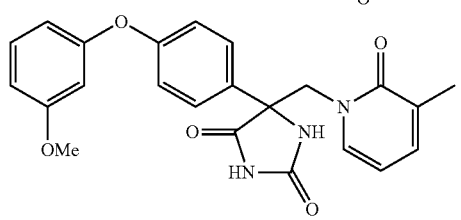
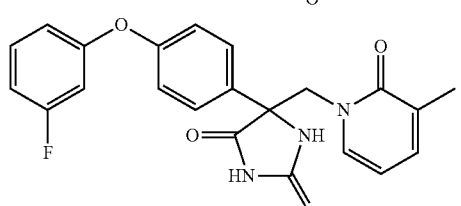
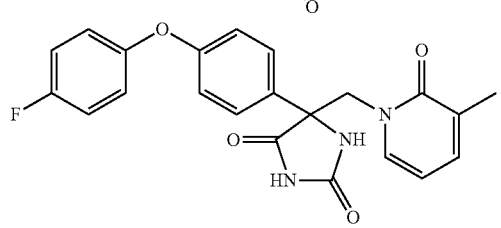
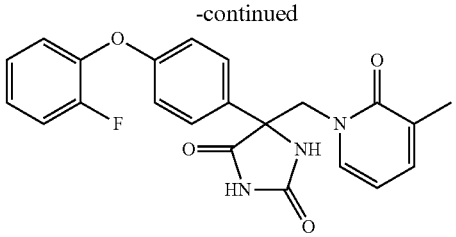
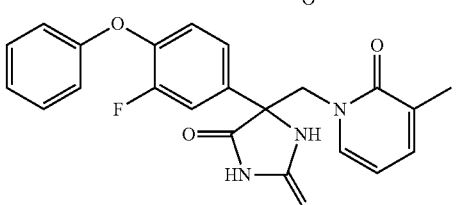
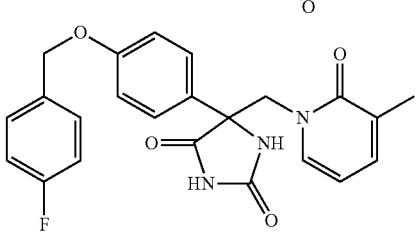
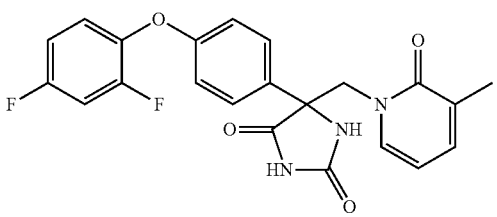
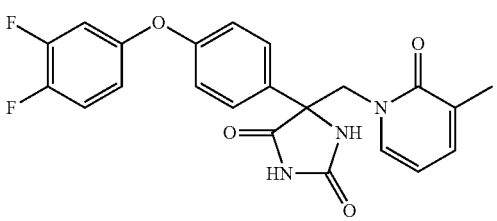
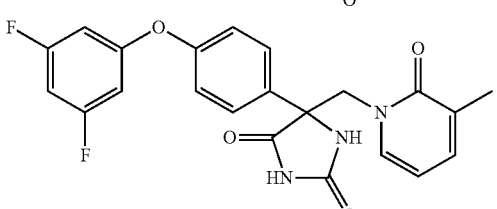
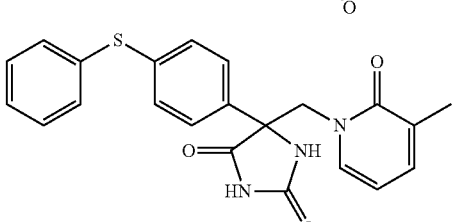
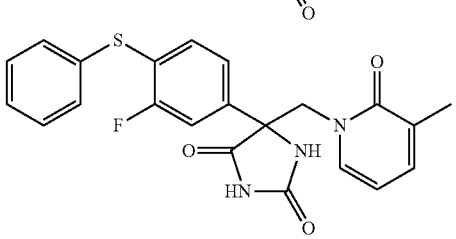

-continued
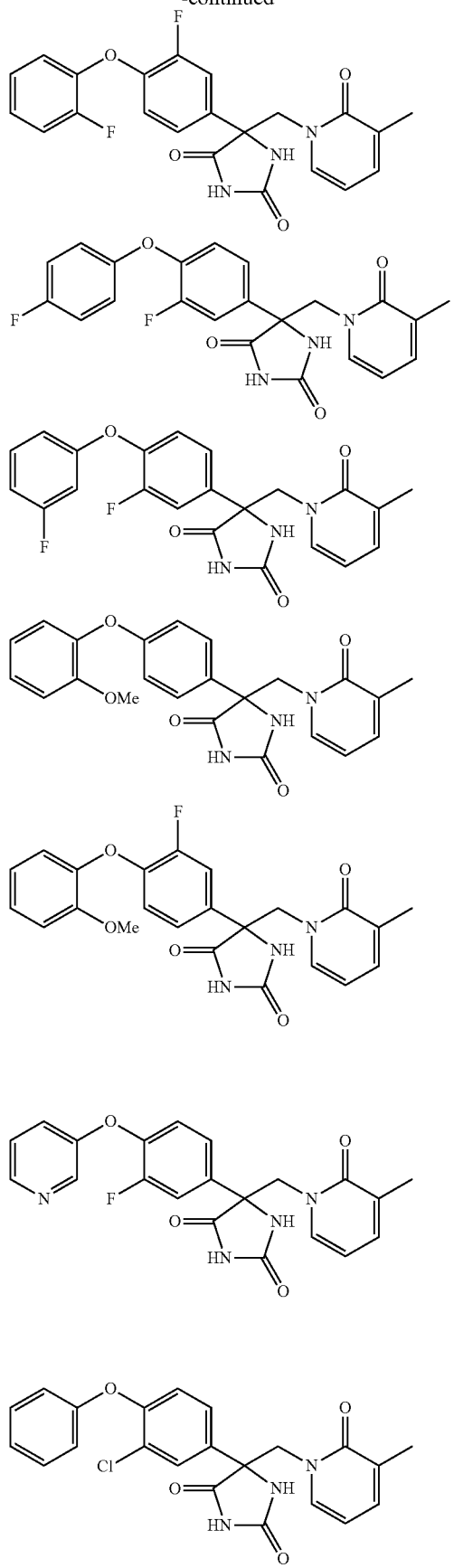
-continued
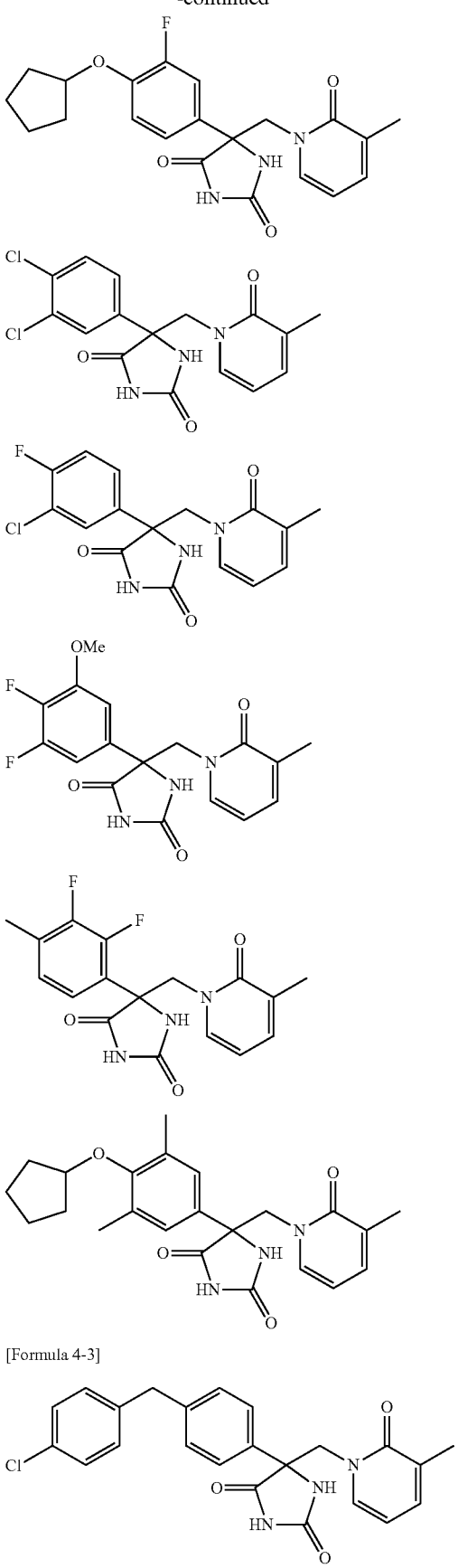
[Formula 4-3]

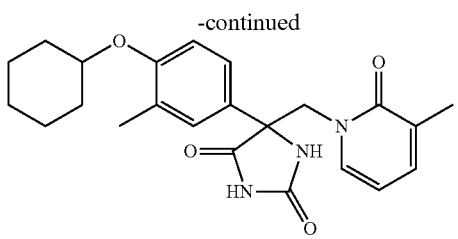

(11) A pharmaceutical comprising the pyridone derivative, or a salt thereof, according to any of (1) to (10) as an active ingredient.
(12) The pharmaceutical according to (11), wherein the pharmaceutical is a soluble TNF-α production inhibitor.
(13) The pharmaceutical according to (11), wherein the pharmaceutical is a preventive or therapeutic agent for a TNF-α-related disease.
(14) The pharmaceutical according to (13), wherein the TNF-α-related disease is one or more selected from the group consisting of rheumatoid arthritis, psoriatic arthritis, systemic lupus erythematosus (SLE), lupus nephritis, systemic scleroderma, localized scleroderma, Sjogren's syndrome, polymyositis, dermatomyositis, ulcerative colitis, Crohn's disease, Behcet's disease, multiple sclerosis, arteriosclerosis, myasthenia gravis, ankylosing spondylitis, diabetes, arteriosclerosis, sepsis, acute infectious diseases, asthma, chronic obstructive pulmonary disease (COPD), atopic dermatitis, psoriasis, acne, osteoporosis, burns, the onset of rejection associated with organs or tissue transplantation, fever, anemia, cancer, periodontal disease, glaucoma, diabetic complications, and uveitis.
(15) The pharmaceutical according to (13) or (14), wherein the TNF-α-related disease is a skin disease.
(16) The pharmaceutical according to (15), wherein the skin disease is one or more selected from the group consisting of a localized scleroderma, atopic dermatitis, contact dermatitis, psoriasis, and acne.

Advantageous Effects of the Invention

The pyridone derivative, or a salt thereof, according to the present invention has an excellent selective TACE inhibitory effect, and is effective as a preventive or therapeutic agent for a TNF-α-related disease.
None of the literature described above discusses a compound having a pyridone skeleton like the compound according to the present application.

DESCRIPTION OF EMBODIMENTS

Next, the present invention is described in more detail.
First, to describe the respective substituents in the above-described formula (I), the meaning of the terms used in the definition of these substituents is as follows.
A "halogen atom" is a fluorine atom, a chlorine atom, a bromine atom or an iodine atom.
The term "C1-C6 alkyl group" means a straight or branched alkyl group having 1 to 6 carbon atoms. Specific examples include a methyl group, an ethyl group, an n-propyl group, an isopropyl group, an n-butyl group, an isobutyl group, a tert-butyl group, a sec-butyl group, an n-pentyl, a tert-pentyl group, a 3-methylbutyl group (isopentyl group), a neopentyl group, an n-hexyl group and the like.
The term "C1-C6 haloalkyl group" means a group in which one or more of the above-described halogen atoms are substituted at any substitutable position(s) on the above-described C1-C6 alkyl group. Specific examples include a trifluoromethyl group, a pentafluoroethyl group, a trichloromethyl group, a 3-chloropropyl group, a 4-bromobutyl group, a 1,1,1,3,3,3-hexafluoropropan-2-yl group and the like.
The term "C1-C6 alkoxy group" means an alkoxy group in which the alkyl moiety is the same meaning as that of the above-described "C1-C6 alkyl group". Examples include a straight or branched alkoxy group, such as a methoxy group, an ethoxy group, an n-propoxy group, an isopropoxy group, an n-butoxy group, an isobutoxy group, a tert-butoxy group, a sec-butoxy group, an n-pentyloxy group, a tert-amyloxy group, a 3-methylbutoxy group, a neopentyloxy group, and an n-hexyloxy group.
The term "C1-C6 alkoxycarbonyl group" means an alkoxycarbonyl group in which the alkyl moiety is the above-described "C1-C6 alkyl group". Examples include a straight or branched C1-C6 alkoxycarbonyl group, such as a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, a sec-butoxycarbonyl group, an n-pentyloxycarbonyl group, a tert-amyloxycarbonyl group, a 3-methylbutoxycarbonyl group, a neopentyloxycarbonyl group, and an n-hexyloxy carbonyl group.
The term "cycloalkyl group" refers to a monocyclic saturated carbon ring having 3 to 7 carbon atoms, examples thereof including a cyclopropyl group, a cyclobutyl group, a cyclopentyl group, a cyclohexyl group, a cycloheptyl group, and the like.
The term "carbon ring" refers to a 3- to 10-membered monocyclic or bicyclic ring composed of carbon atoms. Specific examples include, but are not limited thereto, a cyclopentene ring, a cyclohexene ring, a benzene ring and the like.
It should be noted that "carbon ring" herein means the above-described "carbon ring".
The term "cycloalkylalkyl group" refers to the above-described "C1-C6 alkyl group" which is substituted with an above-described "cycloalkyl group". Such substitution may be carried out at any of the substitutable position(s). Examples include a cyclopropylmethyl group, a cyclobutylmethyl group, a cyclopentylmethyl group, a cyclopentylethyl group (e.g., a 2-cyclopentylethyl group), a cyclohexylmethyl group, a cyclohexylpropyl group (e.g., a 3-cyclohexylpropyl group) and the like, each of which may have an optional substituent in cycloalkyl moiety.
The term "heterocycloalkyl group" represents a saturated monocyclic heterocyclic ring. Examples include a pyrrolidinyl group (e.g., a 1-pyrrolidinyl group, a 2-pyrrolidinyl group, and a 3-pyrrolidinyl group), a piperidinyl group (e.g., a 1-piperidinyl group and a 4-piperidinyl group), a homopiperidinyl group (e.g., a 1-homopiperidinyl group and a 4-homopiperidinyl group), a tetrahydrofuranyl group (e.g., a 2-tetrahydrofuranyl group, a 3-tetrahydrofuranyl group), a tetrahydropyranyl group (e.g., a 4-tetrahydropyranyl group), a piperazinyl group (e.g., a 1-piperazinyl group), a homopiperazinyl group (1-piperazinyl group) and the like.
The term "heterocyclic ring" represents a 3- to 10-membered monocyclic ring or bicyclic ring composed of carbon atoms and 1 to 3 hetero atoms independently selected from N, O, and S. In this heterocyclic ring, the nitrogen atom and the sulfur atom may be optionally oxidized, and the nitrogen atom may also be optionally quaternized. In addition, this heterocyclic ring may be optionally substituted, and optionally fused with a carbon ring or another heterocyclic ring.

Furthermore, this heterocyclic ring can be bonded at any of the substitutable position. Specific examples include, but are not limited thereto, a dioxole ring, an oxathiole ring, a dihydroxathiine ring, a dihydrodioxine ring, a dihydrofuran ring, a dihydrothiophene ring, a dihydropyrrole ring, a furan ring, a thiophene ring, a pyrrole ring, an oxazole ring, a thiazole ring, a pyridine ring and the like.

It should be noted that "heterocyclic ring" herein means the above-described "heterocyclic ring".

The term "heterocycloalkylalkyl group" refers to the above-described "C1-C6 alkyl group" which is substituted with the above-described "heterocycloalkyl group". Such substitution may be carried out at any of the substitutable position(s). Examples include a pyrrolidinylmethyl group (e.g., a 1-pyrrolidinylmethyl group, a 2-pyrrolidinylmethyl group, and a 3-pyrrolidinylmethyl group), a piperidinylmethyl group (e.g., a 1-piperidinylmethyl group and a 4-piperidinylmethyl group), a piperidinylethyl group (e.g., a 1-piperidinylethyl group and a 4-piperidinyl-2-ethyl group), a homopiperidinylmethyl group (e.g., a 1-homopiperidinylmethyl group and a 4-homopiperidinylmethyl group), a tetrahydrofuranylmethyl group (e.g., a 2-tetrahydrofuranylmethyl group and a 3-tetrahydrofuranylmethyl group), a tetrahydropyranylmethyl group (e.g., a 4-tetrahydropyranyl group), a piperazinylmethyl group (e.g., a 1-piperazinylmethyl group), a homopiperazinylmethyl group (e.g., a 1-homopiperazinylmethyl group) and the like.

The term "aryl group" represents an aromatic carbon ring. Examples include a phenyl group, a naphthyl group and the like.

The term "aralkyl group" refers to the above-described "C1-C6 alkyl group" which is substituted with the above-described "aryl group". Such substitution may be carried out at any of the substitutable position(s). Examples include a benzyl group, a phenethyl group, a 1-phenylethyl group, a 1-phenylpropyl group, a 3-phenylpropyl group, an α-naphthylmethyl group, a 3-naphthylmethyl group, a 1-(α-naphthyl)ethyl group, a 2-(α-naphthyl)ethyl group and the like, each of which may have an optional substituent in aryl moiety.

The term "heteroaryl group" represents a 5- to 10-membered monocyclic or bicyclic aromatic heterocyclic ring. Examples include a pyrrolyl group (e.g., a 2-pyrrolyl group), a furyl group (e.g., a 3-furyl group), a thienyl group (e.g., a 2-thienyl group), an imidazolyl group (e.g., a 4-imidazolyl group), a pyrazolyl group (e.g., a 3-pyrazolyl group), an oxazolyl group (e.g., a 2-oxazolyl group), an isoxazolyl group (e.g., a 3-isoxazolyl group), a thiazolyl group (e.g., a 2-thiazolyl group), an isothiazolyl group (e.g., a 3-isothiazolyl group), a pyridyl group (e.g., a 2-pyridyl group, a 3-pyridyl group, and a 4-pyridyl group), a pyridazinyl group (e.g., a 3-pyridazinyl group), a pyrimidyl group (e.g., a 4-pyrimidyl group), a pyrazinyl group (e.g., a 2-pyrazinyl group), an indolyl group (e.g., a 2-indolyl group, a 3-indolyl group, and a 4-indolyl group), a benzofuryl group (e.g., a 2-benzofuryl group and a 5-benzofuryl group), a benzothienyl group (e.g., a 2-benzothienyl group and a 5-benzothienyl group), a benzimidazolyl group (e.g., a 2-benzimidazolyl group), an indazolyl group (e.g., a 4-indazolyl group), a benzooxazolyl group (e.g., a 4-benzoxazolyl group), a benzothiazolyl group (e.g., a 4-benzothiazolyl group), a benzoisoxazolyl group (e.g., a 4-benzoisoxazolyl group), a benzoisothiazolyl group (e.g., a 4-benzoisothiazolyl group), a quinolyl group (e.g., a 2-quinolyl group, a 4-quinolyl group, a 5-quinolyl group, and an 8-quinolyl group), an isoquinolyl group (e.g., a 1-isoquinolyl group, 4-isoquinolyl group, a 5-isoquinolyl group, and an 8-isoquinolyl group), a cinnolinyl group (e.g., a 4-cinnolinyl group, a 5-cinnolinyl group, and an 8-cinnolinyl group), a quinazolinyl group (e.g., a 4-quinazolinyl group, a 5-quinazolinyl group, and an 8-quinazolinyl group), a tetrazolyl group (e.g., a 2H-tetrazol-5-yl group) and the like. Such heteroaryl group may have an optional substituent.

The term "heteroarylalkyl group" refers to the above-described "C1-C6 alkyl group" which is substituted with the above-described "heteroaryl group". Such substitution may be carried out at any of the substitutable position(s). Examples include a pyridylmethyl group (e.g., a 2-pyridylmethyl group), an oxazolylethyl group (e.g., a 2-oxazolyl-2-ethyl group), a thiazolylmethyl group (e.g., a 4-thiazolylmethyl group), an indolylmethyl group (e.g., a 2-indolylmethyl group, a 3-indolylmethyl group, and a 4-indolylmethyl group), a benzofurylmethyl group (e.g., a 3-benzofurylmethyl group and a 4-benzofurylmethyl group), a benzothienylpyridinemethyl group (e.g., a 3-benzothienylpyridinemethyl group and a 4-benzothienylpyridinemethyl group), a benzothiazolylmethyl group (e.g., a 2-benzothiazolylmethyl group), a quinolylmethyl group (e.g., a 2-quinolylmethyl group, a 4-quinolylmethyl group, a 5-quinolylmethyl group, and a 8-quinolylmethyl group), an isoquinolylmethyl group (e.g., a 1-isoquinolylmethyl group, a 4-isoquinolylmethyl group, a 5-isoquinolylmethyl group, and an 8-isoquinolylmethyl group), a cinnolinylmethyl group (e.g., a 4-cinnolinylmethyl group, a 5-cinnolinylmethyl group, and an 8-cinnolinylmethyl group), a quinazolinylmethyl group (e.g., a 4-quinazolinylmethyl, a 5-quinazolinylmethyl group, and an 8-quinazolinylmethyl group) and the like. Such heteroaryl group may have an optional substituent.

The term "C2-C6 alkenyl group" means a straight or branched alkenyl group having 2 to 6 carbon atoms and having one or more double bonds. Specific examples include a vinyl group, a 1-propenyl group, an isopropenyl group, a 1-butenyl group, an isobutenyl group, a 1,3-butadienyl group, a 2-methyl-1-propenyl group, a 1-methyl-1-propenyl group, a 1-pentenyl group, a 1-hexenyl group and the like.

The term "alkenylalkyl group" refers to the above-described "C1-C6 alkyl group" which is substituted with the above-described "C2-C6 alkenyl group". Such substitution may be carried out at any of the substitutable position(s). Examples include an allyl group, a 2-pentenyl group, a 4-pentenyl group, a prenyl group, a 2-hexenyl group, a 5-hexenyl, a 2-methylallyl group, a but-3-en-1-yl group, a 2-methylbut-3-en-1-yl group and the like.

The term "heterocycloalkenyl group" represents a monocyclic heterocyclic ring having one double bond at any position of the ring. Examples include a dihydrofuryl group (e.g., a 2,5-dihydrofuran-3-yl group), a dihydropyranyl group (e.g., a 5,6-dihydro-2H-pyran-4-yl group), a dihydropyrrolyl group (e.g., 3-pyrrolin-3-yl group), a tetrahydropyridyl group (e.g., a 1,2,3,6-tetrahydropyridin-4-yl group), a dihydrothienyl group (e.g., a 2,5-dihydrothiophen-3-yl group), a dihydrothiopyranyl group (e.g., a 5,6-dihydro-2H-thiopyran-4-yl group), a dehydrohomopiperidinyl group (e.g., a 4,5-dehydrohomopiperidin-4-yl group) and the like.

The term "heterocycloalkenylalkyl group" refers to the above-described "C1-C6 alkyl group" which is substituted with the above-described "heterocycloalkenyl group". Such substitution may be carried out at any of the substitutable position(s). Examples include a dihydrofurylmethyl group (e.g., 2,5-dihydrofuran-3-ylmethyl group), a dihydropyranylmethyl group (e.g., a 5,6-dihydro-2H-pyran-ylmethyl group), a dihydropyrrolylmethyl group (a 3-pyrrolin-3-ylmethyl group), a tetrahydropyridylmethyl group (e.g., a 1,2, 3,6-tetrahydropyridin-4-ylmethyl group), a tetrahydropyridylethyl group (e.g., a 1,2,3,6-tetrahydropyridin-4-yl-2-ethyl group), a dihydrothienylmethyl group (e.g., a 2,5-dihydrothiophen-3-ylmethyl group), a dihydrothiopyranylmethyl group (e.g., a 5,6-dihydro-2H-thiopyran-4-ylmethyl group), a dehydrohomopiperidinylmethyl group (e.g., a 4,5-dehydrohomopiperidin-4-ylmethyl group) and the like.

The term "C2-C6 alkynyl group" means a straight or branched alkynyl group having 2 to 6 carbon atoms and having one or more triple bonds. Specific examples include an ethynyl group, a 1-propynyl group, a 1-butynyl group, a 3-methyl-1-butynyl group, a 1,3-butadiynyl group, a 1-pentynyl group, a 3-methyl-1-pentynyl group, a 1-hexynyl group and the like.

The term "alkynyl alkyl group" refers to the above-described "C1-C6 alkyl group" which is substituted with the above-described "C2-C6 alkynyl group". Such substitution may be carried out at any of the substitutable position(s). Examples include a 2-propynyl group, a 2-butynyl group, a 2-pentynyl group, a 4-methyl-2-pentynyl group and the like.

The term "alkylene" means a straight or branched alkylene group having 1 to 6 carbon atoms. Specific examples include —$CH_2$—, —$CH_2CH_2$—, —$CH_2CH_2CH_2$—, —$CH_2CH(CH_3)CH_2$— and the like.

The term "alkenylene" means a straight or branched alkenylene group having 2 to 6 carbon atoms and having one or more double bonds. Specific examples include —CH=CH—, —CH=CH—$CH_2$—, —CH=CH—$CH_2CH_2$—, —CH=C($CH_3$)—$CH_2$— and the like.

The term "alkynylene" means a straight or branched alkynylene group having 2 to 6 carbon atoms and having one or more triple bonds. Specific examples include the following.

[Formula 5]

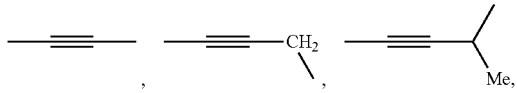

Examples of substituents on the "optionally substituted C1-C6 alkyl group", "optionally substituted C2-C6 alkenyl group", "optionally substituted alkenylalkyl group", "optionally substituted C2-C6 alkynyl group", "optionally substituted alkynylalkyl group", "optionally substituted cycloalkyl group", "optionally substituted cycloalkylalkyl group", "optionally substituted heterocycloalkyl group", "optionally substituted heterocycloalkylalkyl group", "optionally substituted heterocycloalkenyl group", and "optionally substituted heterocycloalkenylalkyl group" include a hydroxyl group, a halogen atom, a cyano group, a nitro group, a trifluoromethyl group, an optionally substituted C1-C6 alkoxy group, a cycloalkyl group, a carboxyl group, a C1-C6 alkoxycarbonyl group, an —$NR^8R^9$ {wherein $R^8$ and $R^9$ each independently represent a hydrogen atom, a C1-C6 alkyl group, a formyl group, an optionally substituted acyl group, —$CONR^{10}R^{11}$ [wherein $R^{10}$ and $R^{11}$ each independently represent a hydrogen atom, a C1-C6 alkyl group, an aryl group optionally substituted with $R^{12}$ (wherein $R^{12}$ represents a C1-C6 alkyl group, a C1-C6 alkoxy group, or a halogen atom), a heteroaryl group optionally substituted with $R^{12}$ ($R^{12}$ being defined as described above), or form a nitrogen-containing heterocyclic ring together with the nitrogen atom to which $R^{10}$ and $R^{11}$ are attached], a cycloalkyl group, or form a nitrogen-containing heterocyclic ring together with the nitrogen atom to which $R^8$ and $R^9$ are attached}, or —$OCOR^{13}$ [wherein $R^{13}$ represents a C1-C6 alkyl group, an aryl group optionally substituted with $R^{12}$ ($R^{12}$ being defined as described above), a heteroaryl group optionally substituted with $R^{12}$ ($R^{12}$ being defined as described above), or —$NR^{14}R^{15}$ (wherein $R^{14}$ and $R^{15}$ each independently represent a hydrogen atom, a C1-C6 alkyl group, an aryl group optionally substituted with $R^{12}$ ($R^{12}$ being defined as described above), a heteroaryl group optionally substituted with $R^{12}$ ($R^{12}$ being defined as described above), or form a nitrogen-containing heterocyclic ring together with the nitrogen atom to which $R^{14}$ and $R^{15}$ are attached)] and the like. At least one substituent of these substituents may be attached to any of the substitutable position(s).

The term "acyl group" means an alkylcarbonyl group, in which the alkyl moiety is the same meaning as that of the above-described "C1-C6 alkyl group". Examples include straight or branched alkylcarbonyl groups such as an acetyl group, a propionyl group, a butyryl group, an isobutyryl group, a valeryl group, an isovaleryl group, a pivaloyl group and the like.

The term "nitrogen-containing heterocyclic ring" represents a saturated or unsaturated heterocyclic ring that includes at least one nitrogen atom. Examples include, but are not limited thereto, an azetidine ring, a pyrrolidine ring, a piperidine ring, a thiazolidine ring, a morpholine ring, a thiomorpholine ring, a dihydropyrrole ring and the like. Examples of the substituents include a C1-C6 alkyl group, a C1-C6 alkoxy group, a hydroxyl group, a nitro group, a cyano group, a trifluoromethyl group, a hydroxymethyl group and the like.

Examples of substituents on the aromatic rings in the "optionally substituted aryl group", the "optionally substituted aralkyl group", the "optionally substituted heteroaryl group", and the "optionally substituted heteroarylalkyl group" include a hydrogen atom, a halogen atom, a cyano group, a nitro group, a trifluoromethyl group, an optionally substituted C1-C6 alkyl group, an optionally substituted C1-C6 alkoxy group, a cycloalkyl group, a carboxyl group, a C1-C6 alkoxycarboxyl group, —$NR^{14}R^{15}$ (wherein $R^{14}$ and $R^{15}$ are defined as described above), —$OCOR^{13}$ (wherein $R^{13}$ is defined as described above) and the like. At least one substituent of these substituents may be attached to any of the substitutable position(s).

Examples of substituents on the "optionally substituted C1-C6 alkoxy group", the "optionally substituted acyl group", and the "optionally substituted C1-C6 alkoxycarbonyl group" include a hydrogen atom, a halogen atom, a cyano group, a nitro group, a C1-C6 alkoxy group and the like. At least one substituent of these substituents may be attached to any of the substitutable position(s).

Regarding the $R^1$, $R^2$, and $R^3$ in formula (I), if two or more of the same substituent are substituted at ring A, any of $R^1$, $R^2$, and $R^3$ may be considered as being that same substituent.

In the present invention, a pyridone derivative, or a salt thereof, in which at least one of $R^1$, $R^2$, and $R^3$ is not a hydrogen atom is preferred. Further, in such a pyridone derivative, or a salt thereof, it is preferred that ring A is an aryl or a heteroaryl, and it is more preferred that ring A is a phenyl group.

The position of $R^1$, $R^2$, and $R^3$ in formula (I) is not especially limited. For example, if ring A is a phenyl group, it is preferred that at least one of $R^1$, $R^2$, and $R^3$ is a group other than a hydrogen atom. Further, if ring A is a phenyl group, compounds in which at least one of $R^1$, $R^2$, and $R^3$ is a group other than a hydrogen atom, and in which said non-hydrogen atom group(s) are present at only the meta-position, or only the para-position, or the meta-position and the para-position, respectively, on ring A with respect to the binding position with the hydantoin ring (imidazolidine-2, 4-dione ring) are more preferred.

A preferred C1-C6 haloalkyl group with $R^1$ and $R^2$ in formula (I) is a C1-C3 haloalkyl group, and a trifluoromethyl group is more preferred.

In the aspect of the invention according to the above (2), from the perspective of pharmacological effects and the like, a pyridone derivative, or a salt thereof, in which ring A in formula (I) is an aryl or a heteroaryl is preferred. Among such compounds, it is more preferred that ring A is an aryl. A preferred example of the aryl for ring A is a phenyl group.

In the aspects of the invention according to the above (3) to (5), from the perspective of pharmacological effect and the like, a pyridone derivative, or a salt thereof, in which one or two or more of $R^1$, $R^2$, and $R^3$ in formula (I) are respectively selected from the following is preferred:

for $R^1$, a halogen atom, a cyano group, a C1-C6 alkyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a halogen atom, a C1-C6 alkoxy group, or a C1-C6 alkyl group; and for $R^3$, a hydrogen atom, a fluorine atom, or a methyl group.

In the aspects of the invention described in the above (3) to (5), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

Describing the aspect of the invention according to the above (6) in more detail, from the perspective of pharmacological effect and the like, more preferred is a pyridone derivative, or a salt thereof, in which $R^1$, $R^2$, and $R^3$ in formula (I) are respectively selected from the following:

for $R^1$, a halogen atom, a cyano group, a C1-C6 alkyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a halogen atom, a C1-C6 alkoxy group, or a C1-C6 alkyl group; and for $R^3$, a hydrogen atom, a fluorine atom, or a methyl group.

In the aspect of the invention described in the above (6), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

Describing the aspect of the invention according to the above (7) in more detail, from the perspective of pharmacological effect and the like, more preferred is a pyridone derivative, or a salt thereof, in which $R^1$, $R^2$, and $R^3$ in formula (I) are respectively selected from the following:

for $R^1$, a halogen atom, a cyano group, a methyl group, a C1-C6 alkoxy group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a halogen atom, a methoxy group, or a methyl group; and for $R^3$, a hydrogen atom, a fluorine atom, or a methyl group.

In the aspect of the invention according to the above (7), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

Among the aspects of the invention described in the above (3) to (5), the pyridone derivative, or a salt thereof, according to (3) is described in more detail below.

(3') Among the pyridone derivatives or salts thereof according to the aspect of the invention described in the above (3), from the perspective of pharmacological effect and the like, more preferred is a pyridone derivative, or a salt thereof, in which one or two or more of $R^1$, $R^2$, and $R^3$ in formula (I) are respectively selected from the following:

for $R^1$, a halogen atom, a cyano group, a methyl group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a fluorine atom, or a methyl group; and for $R^3$, a hydrogen atom, a fluorine atom, or a methyl group.

In the aspect of the invention according to the above (3'), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

Further, for the pyridone derivative, or a salt thereof, according to the aspect of the invention described in the above (3'), from the perspective of pharmacological effect and the like, it is even more preferred that $R^1$, $R^2$, and $R^3$ in formula (I) are respectively selected from the following:

for $R^1$, a halogen atom, a cyano group, a methyl group, or -$J^1$-$X^1$—$R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a fluorine atom, or a methyl group; and for $R^3$, a hydrogen atom, a fluorine atom, or a methyl group.

In this case, it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

(3″) Among the pyridone derivatives or salts thereof according to the aspect of the invention described in the above (3′), from the perspective of pharmacological effect and the like, even more preferred is a pyridone derivative, or a salt thereof, in which one or two or more of $R^1$, $R^2$, and $R^3$ in formula (I) are respectively selected from the following:

for $R^1$, a fluorine atom, a methyl group, or $-J^1-X^1-R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a fluorine atom, or a methyl group; and for $R^3$, a hydrogen atom, a fluorine atom, or a methyl group.

In the aspect of the invention described in the above (3″), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

Further, for the pyridone derivative, or a salt thereof, according to the aspect of the invention described in the above (3″), from the perspective of pharmacological effect and the like, it is still even more preferred that $R^1$, $R^2$, and $R^3$ in formula (I) are respectively selected from the following:

for $R^1$, a fluorine atom, a methyl group, or $-J^1-X^1-R^5$ (wherein $J^1$ represents a single bond or alkylene, $X^1$ represents a single bond, an oxygen atom, or a sulfur atom, and $R^5$ represents an optionally substituted cycloalkyl group, an optionally substituted cycloalkylalkyl group, an optionally substituted heterocycloalkyl group, an optionally substituted heterocycloalkylalkyl group, an optionally substituted aryl group, an optionally substituted aralkyl group, an optionally substituted heteroaryl group, or an optionally substituted heteroarylalkyl group);

for $R^2$, a hydrogen atom, a fluorine atom, or a methyl group; and for $R^3$, a hydrogen atom, a fluorine atom, or a methyl group.

In this case, it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

In the aspect of the invention according to the above (8), from the perspective of pharmacological effect and the like, a pyridone derivative, or a salt thereof, in which $R^4$ in formula (I) represents a halogen atom, a cyano group, a C1-C6 haloalkyl group, a C1-C6 alkoxy group, a hydoxymethyl group, a C1-C6 alkyl group, or a C2-C6 alkenyl group is preferred. More preferred is a pyridone derivative, or a salt thereof, in which $R^4$ represents a C1-C6 alkyl group, and even more preferred is a pyridone derivative, or a salt thereof, in which $R^4$ represents a methyl group (the aspect of the invention according to the above (9)).

For $R^4$, a trifluoromethyl group is preferred as a C1-C6 haloalkyl group, and a methoxy group is preferred as a C1-C6 alkoxy group.

For the pyridone derivative, or a salt thereof, according to the aspect of the invention described in the above (8), it is more preferred that ring A is a phenyl group, and that a non-hydrogen atom group(s) among $R^1$, $R^2$, and $R^3$ are present at only a meta-position, or only a para-position, or a meta-position and a para-position, respectively, on ring A with respect to the binding position with the hydantoin ring.

For the pyridone derivative, or a salt thereof, according to any of the above (1) to (9), if $R^1$ is $-J^1-X^1-R^5$, it is preferred that $J^1$ represents a single bond or a methylene group.

For the pyridone derivative, or a salt thereof, according to any of the above (1) to (9), if $R^1$ is $-J^1-X^1-R^5$, it is preferred that $X^1$ represents a single bond or an oxygen atom.

For the pyridone derivative, or a salt thereof, according to any of the above (1) to (9), if $R^1$ is $-J^1-X^1-R^5$, it is preferred that $R^5$ represents an optionally substituted cycloalkyl group, an optionally substituted cycloalkylalkyl group, an optionally substituted aryl group, an optionally substituted aralkyl group, or an optionally substituted heteroaryl group.

Further, in the present invention, from the perspective of pharmacological effect and the like, a pyridone derivative, or a salt thereof, in which the compound represented by formula (I) is selected from the following is preferred.

[Formula 6-1]

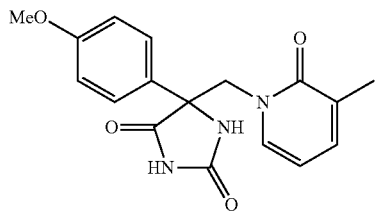

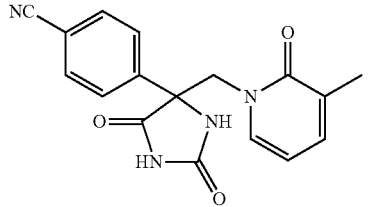

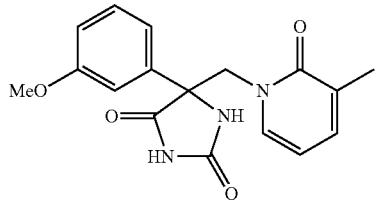

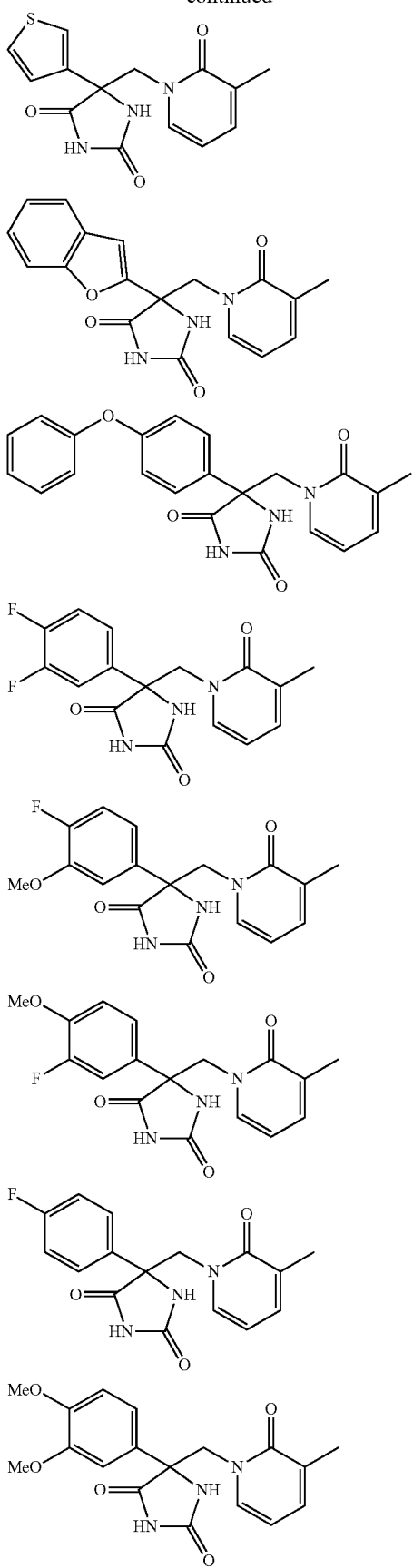
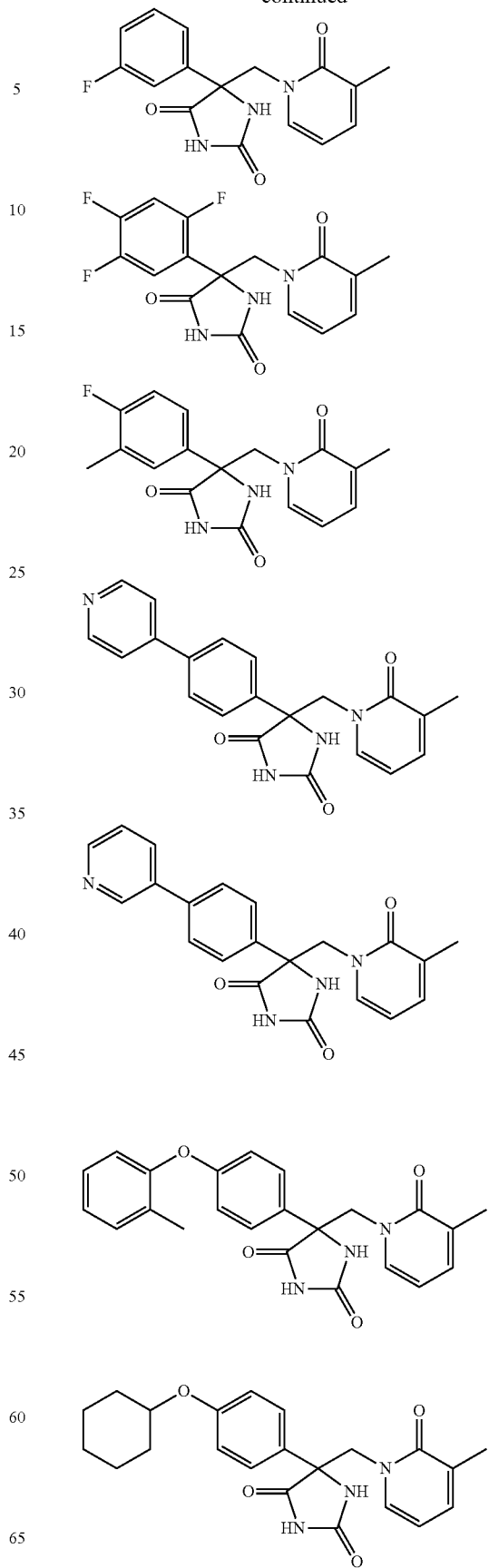

25
-continued
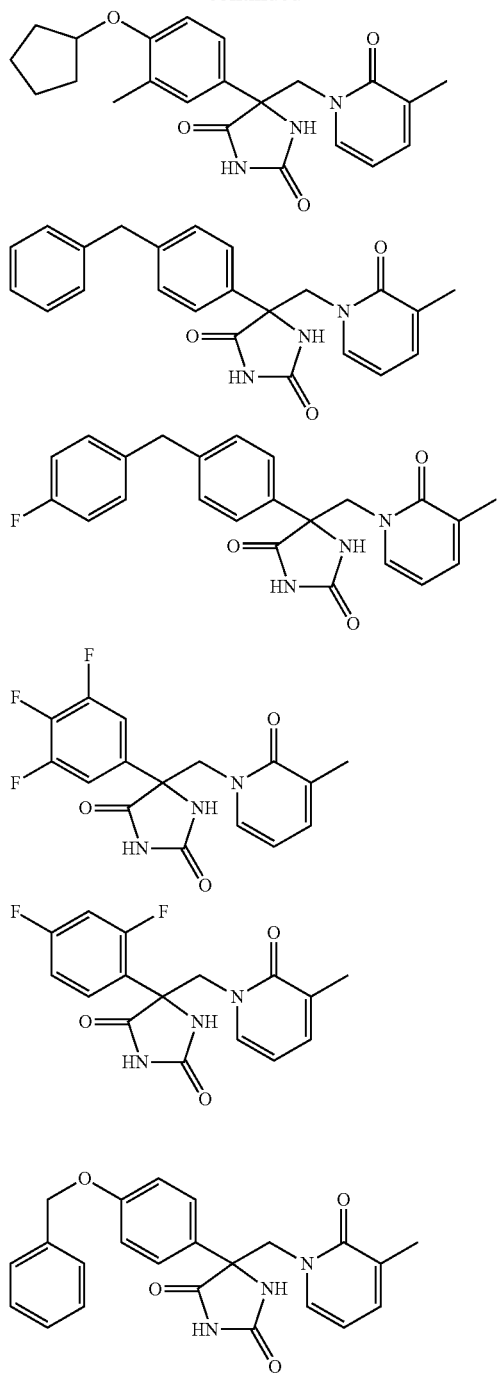
[Formula 6-2]
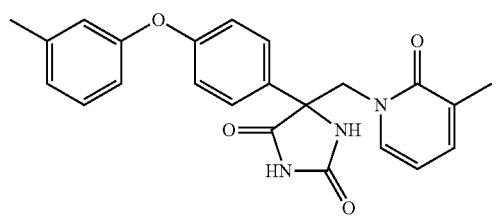
26
-continued
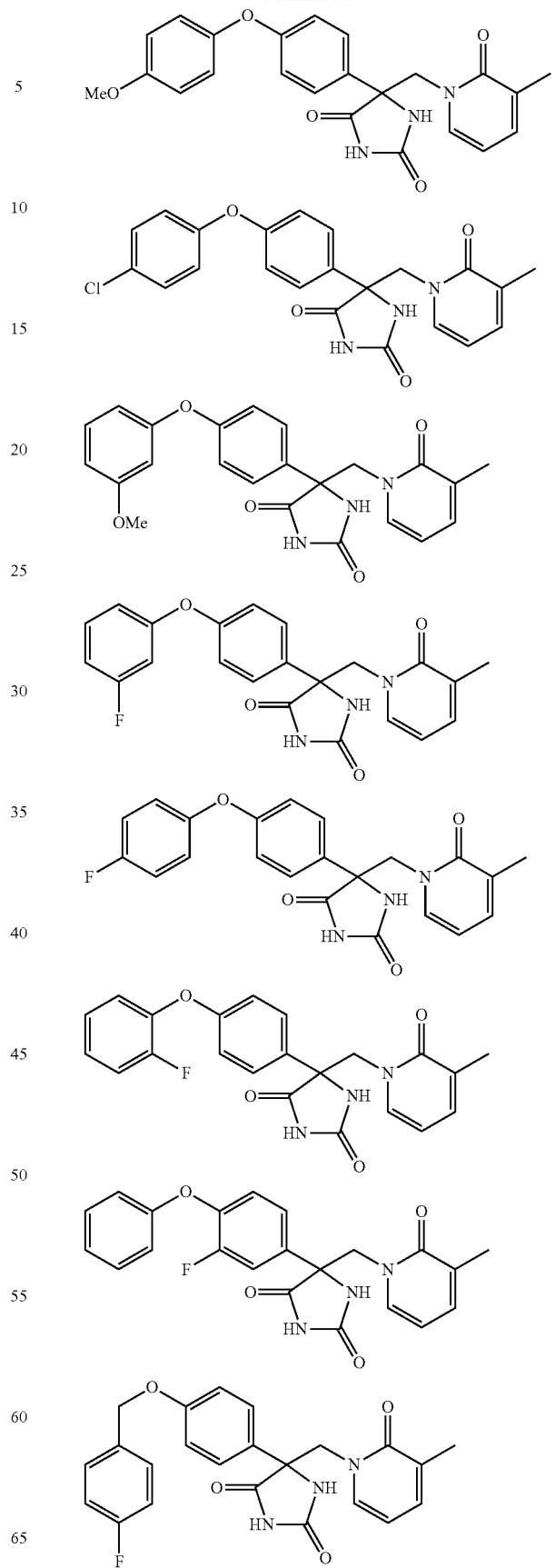

-continued
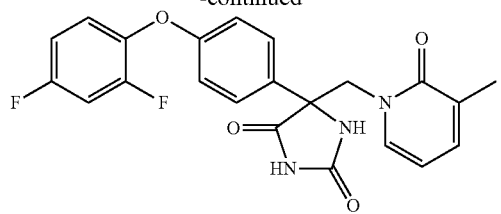
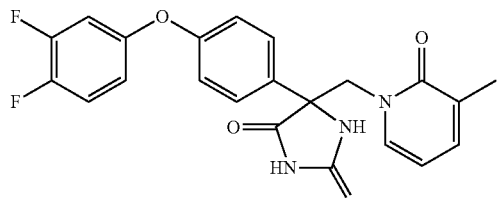
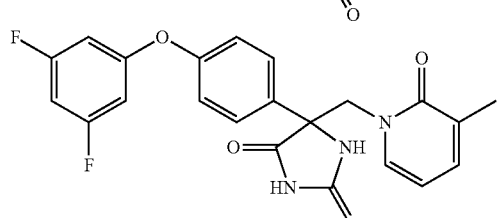
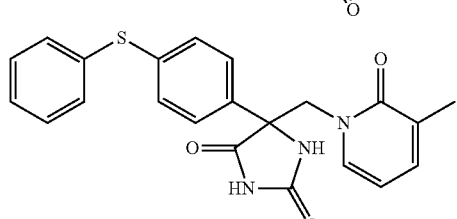
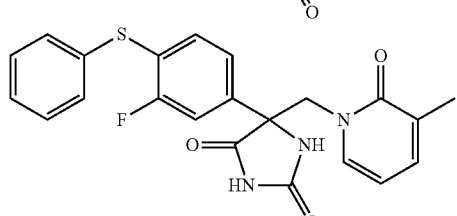
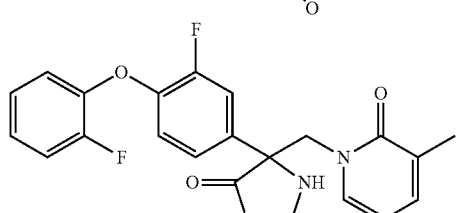
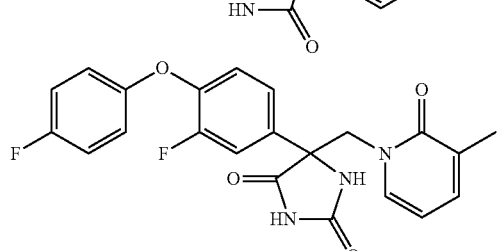
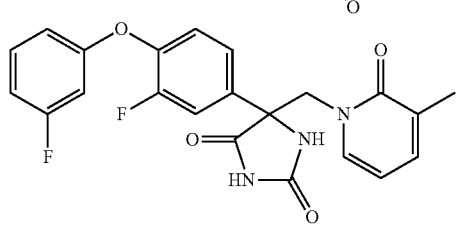
-continued
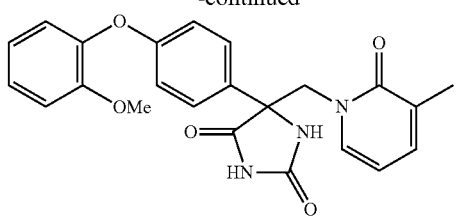
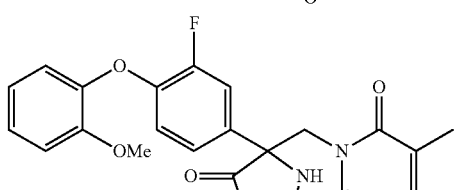
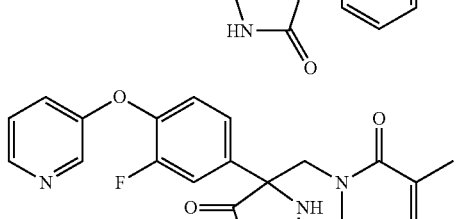
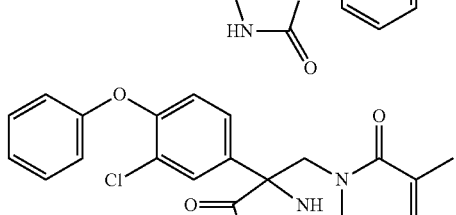
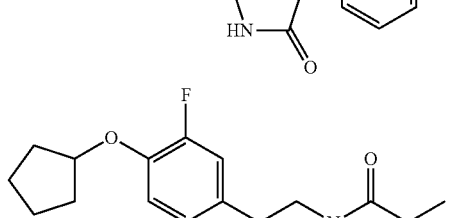
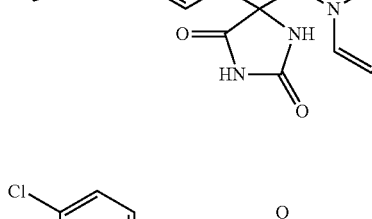
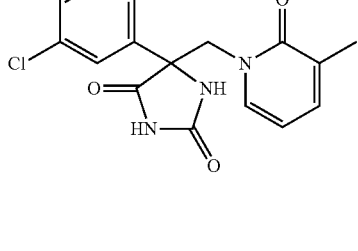
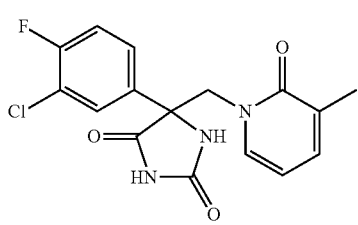

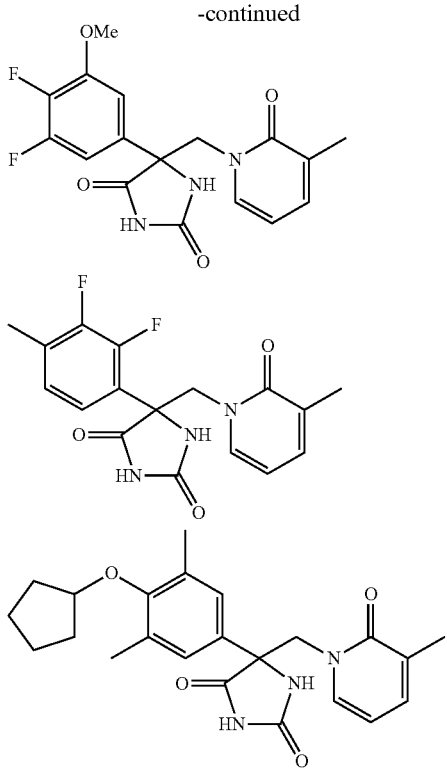

[Formula 6-3]

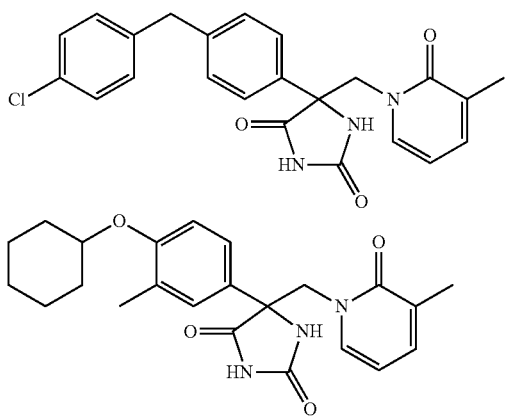

The compound of the present invention represented by formula (I), which contains at least one asymmetric carbon, may be in any form of its racemic form (i.e., the mixture of each optically-active substance), its diastereomeric form or its individual optically-active form. Further, if a geometric isomer is present, the compound of the present invention represented by formula (I) may be in any form of the (E) form, the (Z) form or their mixture form.

In addition, the salt of the pyridone derivative according to the present invention represented by formula (I) is not specifically limited as long as it is a pharmacologically acceptable salt. Such salt include, for example, a salt with an inorganic base, a salt with an organic base and the like. Examples of a salt with an inorganic base include an alkali metal salt and an alkaline earth metal salt, such as a lithium salt, a sodium salt, a potassium salt, a magnesium salt, a calcium salt, and a barium salt. Examples of a salt with an organic base include a triethylamine salt, a pyridine salt, an ethanolamine salt, a cyclohexylamine salt, a dicyclohex- ylamine salt, a dibenzylethanolamine salt, a benzylamine salt, a 2-methylbenzylamine salt, an α-methylbenzylamine salt, a brucine salt, a quinine salt, a quinidine salt, a cinchonine salt, a cinchonidine salt, an arginine salt and the like.

Next, the method for producing the compound represented by formula (I), which is the pyridone derivative according to the present invention is described. This compound can be produced by various methods. For example, the compound can be efficiently produced based on the production method shown below.

Specific examples of the "protecting group" used in the following production method include, as that of a hydroxyl group or a carboxyl group, a tert-butyl group, a benzyl group, an o-methylbenzyl group, a p-nitrobenzyl group, a p-methoxybenzyl group, an o-chlorobenzyl group, a 2,4-dichlorobenzyl group, a p-bromobenzyl group, an allyl group, a tert-butoxycarbonyl group, a benzyloxycarbonyl group, an o-methylbenzyloxycarbonyl group, a p-nitrobenzyloxycarbonyl group, a p-methoxybenzyloxycarbonyl group, an o-chlorobenzyloxycarbonyl group, a 2,4-dichlorobenzyloxycarbonyl group, a p-bromobenzyloxycarbonyl group, an allyloxycarbonyl group, a methoxymethyl group, a tetrahydropyranyl group and the like. As that of a carbonyl protecting group, examples include a protecting group derived from ethanediol, propanediol, mercaptoethanol, mercaptopropanol, ethanedithiol, propanedithiol and the like.

The compounds represented by formula (I) can be produced based on the method shown in the following scheme 1 (step 1 and step 2).

Scheme 1:

[Formula 7]

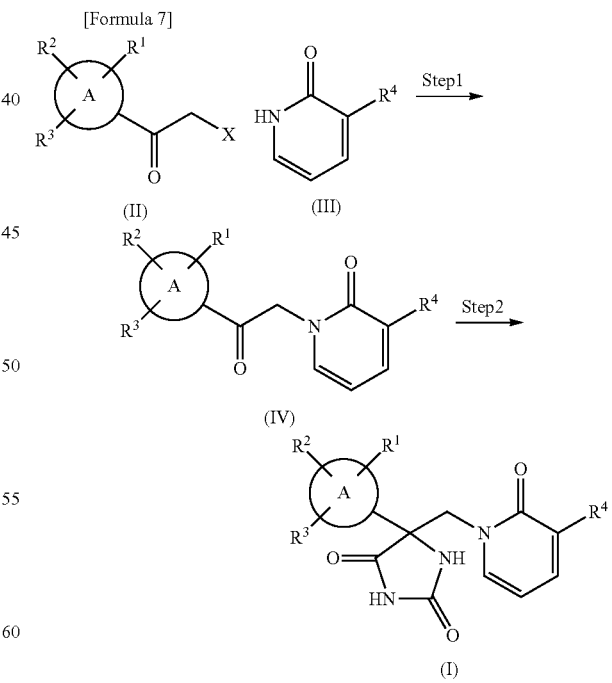

(wherein A, $R^1$, $R^2$, $R^3$, and $R^4$ are the same as defined above; and X represents a chlorine atom, a bromine atom, an iodine atom, a trifluoromethanesulfonyloxy group, a p-toluenesulfonyloxy group, or a methanesulfonyloxy group)

<Step 1>

In step 1, a compound represented by formula (II) and a compound represented by formula (III) are reacted in the presence of a base to produce a compound represented by formula (IV). Instead of the compound represented by formula (III), a compound represented by formula (V),

[Formula 8]

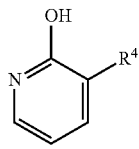

(V)

which is a tautomer of the compound represented by formula (III), may be used. Examples of preferred bases include potassium carbonate, sodium carbonate, cesium carbonate, sodium hydride and the like. In addition, to promote this reaction, an additive may be added Examples of such additives include potassium iodide, sodium iodide, tetrabutylammonium iodide, potassium bromide, sodium bromide, tetrabutylammonium bromide and the like. The reaction solvent is not specifically limited as long as it does not significantly inhibit the reaction. Examples of preferred reaction solvents include N,N-dimethylformamide, dimethyl sulfoxide, acetone, acetonitrile, methanol, ethanol, tetrahydrofuran, 1,4-dioxane, 2-methoxyethanol, a mixed solvent thereof and the like. Further, water can be added to the reaction solvent. Although the added amount of water is not especially limited, it is preferably 10% or less, for example. Although the reaction temperature is not especially limited, for example, from room temperature to 60° C. is preferred. The reaction time is preferably from 1 hour to 2 days.

<Step 2>

In step 2, compound (I) is produced by reacting compound (IV) with a cyanide in the presence of a salt. Examples of preferred salts include ammonium carbonate, ammonium bicarbonate and the like. Examples of preferred cyanides include potassium cyanide, sodium cyanide and the like. The reaction solvent is not specifically limited as long as it does not significantly inhibit the reaction. Examples of preferred reaction solvents include water, ammonia water, methanol, ethanol, tetrahydrofuran, 1,4-dioxane, N,N-dimethylformamide, a mixed solvent thereof and the like. The reaction temperature is not specifically limited. For example, 50° C. to 120° C. is preferred. The reaction time is preferably from 1 hour to 10 days. The compound represented by formula (I) that is obtained in this step can also be obtained in the form of its salt depending on the work-up procedure of this reaction.

Compound (IV) can also be produced based on the method shown in the following scheme 2 (step 3 to step 7).

Scheme 2:

[Formula 9]

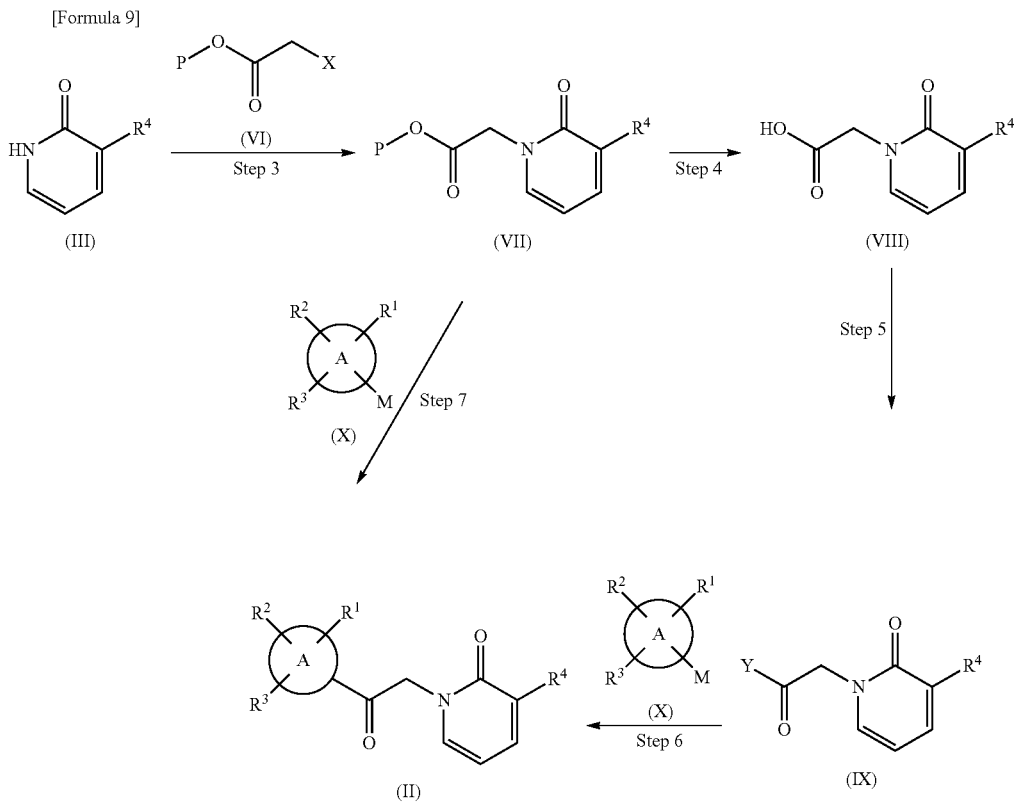

(wherein A, $R^1$, $R^2$, $R^3$, and $R^4$ are the same as defined above; X represents a chlorine atom, a bromine atom, an iodine atom, a trifluoromethanesulfonyloxy group, a p-toluenesulfonyloxy group, or a methanesulfonyloxy group; Y represents an amine derivative group such as

[Formula 10]

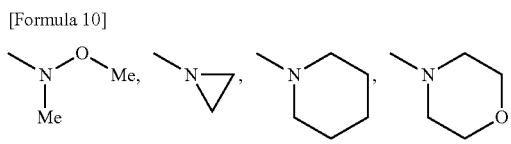

P represents a protecting group; and M represents MgBr, MgCl, Li, ZnBr, or ZnCl)

<Step 3>

In step 3, a compound represented by formula (III) and a compound represented by formula (VI) are reacted in the presence of a base to produce a compound represented by formula (VII). Instead of the compound represented by formula (III), a compound represented by formula (V),

[Formula 11]

(V)

which is a tautomer of the compound represented by formula (III), may be used. Examples of preferred bases include potassium carbonate, sodium carbonate, cesium carbonate, sodium hydride and the like. In addition, to promote this reaction, an additive may be added Examples of such additives include potassium iodide, sodium iodide, tetrabutylammonium iodide, potassium bromide, sodium bromide, tetrabutylammonium bromide and the like. The reaction solvent is not specifically limited as long as it does not significantly inhibit the reaction. Examples of preferred reaction solvents include N,N-dimethylformamide, dimethyl sulfoxide, acetone, acetonitrile, methanol, ethanol, tetrahydrofuran, 1,4-dioxane, 2-methoxyethanol, a mixed solvent thereof and the like. Although the reaction temperature is not specifically limited, for example, from room temperature to 60° C. is preferred. The reaction time is preferably from 1 hour to 2 days.

<Step 4>

In step 4, compound represented by formula (VII) is hydrolysed in an aqueous inorganic base to produce compound (VIII). Examples of preferred aqueous inorganic bases include aqueous sodium hydroxide, aqueous potassium hydroxide, aqueous lithium hydroxide and the like. The reaction solvent is not specifically limited as long as it does not significantly inhibit the reaction. Examples of preferred reaction solvents include water, methanol, ethanol, tetrahydrofuran, 1,4-dioxane, a mixed solvent thereof and the like. Although the reaction temperature is not specifically limited, for example, from room temperature to 60° C. is preferred. The reaction time is preferably from 1 to 96 hours. The form of the compound represented by formula (VIII) that is obtained in this step is a carboxylic acid, a sodium carboxylate, a potassium carboxylate, a lithium carboxylate, a mixture of a carboxylic acid with an inorganic salt (sodium chloride, lithium chloride or potassium chloride) or the like.

<Step 5>

In step 5, the compound (VIII) obtained in step 4 is converted to an activated carboxylic acid derivative, and then reacted with an amine or a salt thereof to produce a compound represented by formula (IX). Examples of the activated carboxylic acid derivative include an acid halide obtained by treating a carboxylic acid (VIII) with thionyl chloride, phosphorus oxychloride, phosphorus pentachloride, oxalyl chloride, thionyl bromide or the like; an active ester obtained by condensation reaction of a carboxylic acid (VIII) with a condensing agent such as 1-ethyl-3'-(3'-dimethylaminopropyl)carbodiimide hydrochloride or dicyclohexylcarbodiimide; and a mixed anhydride obtained by reacting a carboxylic acid (VIII) with ethyl chlorocarbonate, pivaloyl chloride, isobutyl chlorocarboxylate or the like. Further, in this reaction, a base may be added as necessary. Examples of such base include an organic amine, such as triethylamine, tert-butylamine, pyridine, and N-methylmorpholine. Triethylamine, pyridine, or N-methylmorpholine is preferred. The reaction solvent is not specifically limited as long as it does not significantly inhibit the reaction. Examples of preferred reaction solvents include N,N-dimethylformamide, tetrahydrofuran, dichloromethane, chloroform and the like. Although the reaction temperature is not specifically limited, for example, from 0° C. to 60° C. is preferred. The reaction time is preferably from 1 to 96 hours.

<Step 6>

In step 6, compound (II) is produced by reacting the compound (IX) obtained in step 5 with a compound represented by formula (X). Examples of compound (X) include a lithium reagent prepared by halogen-metal exchange with a base such as n-butyllithium, sec-butyllithium, and tert-butyl lithium; a Grignard reagent prepared by treatment with magnesium, isopropyl magnesium bromide, or isopropyl magnesium chloride; and a zinc reagent prepared by treatment with activated zinc, zinc bromide, zinc chloride; and the like. The reaction solvent is not specifically limited as long as it does not significantly inhibit the reaction. Examples of preferred reaction solvents include tetrahydrofuran, diethyl ether, 1,4-dioxane, dimethoxyethane and the like. Although the reaction temperature is not specifically limited, for example, from −100° C. to room temperature is preferred. The reaction time is preferably from 1 to 24 hours.

<Step 7>

In step 7, compound (II) is produced by reacting a compound represented by formula (VII) and a compound represented by formula (X) in the same manner as in step 6.

Compound (II) can also be produced based on the method shown in the following scheme 3 (step 8 to step 10).

Scheme 3:

[Formula 12]

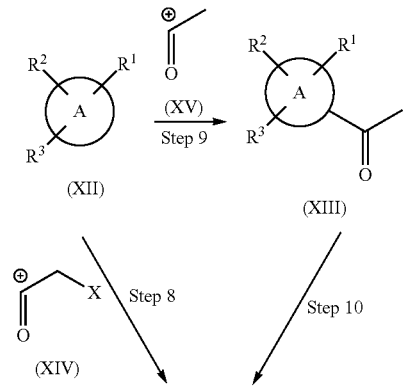

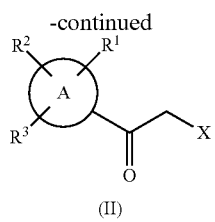

(II)

(wherein A, R$^1$, R$^2$, R$^3$, and R$^4$ are the same as defined above; and X represents a chlorine atom, a bromine atom, an iodine atom, a trifluoromethanesulfonyloxy group, a p-toluenesulfonyloxy group, or a methanesulfonyloxy group)

<Step 8>

In step 8, compound (II) is produced by reacting a compound represented by formula (XII) with an intermediate represented by formula (XIV). Examples of the intermediate (XIV) include an active intermediate obtained from an acid halide and a Lewis acid; an active intermediate obtained from an acid anhydride and a Lewis acid; and an active intermediate obtained from a carboxylic acid and a dehydrating agent. Examples of the acid halide include chloroacetyl chloride, chloroacetyl bromide, bromoacetyl bromide, bromoacetyl chloride, iodoacetyl chloride and the like. Examples of the acid anhydride include chloroacetic anhydride, bromoacetic anhydride, iodoacetic anhydride and the like. Examples of the carboxylic acid include chloroacetic acid, bromoacetic acid, iodoacetic acid and the like. Examples of the Lewis acid include aluminum chloride, zinc chloride and the like. Examples of the dehydrating agent include phosphorus pentoxide and the like. The reaction solvent is not specifically limited as long as it does not significantly inhibit the reaction. Examples of preferred reaction solvents include dichloromethane, dichloroethane and the like. Further, the reaction solvent may not be used. Although the reaction temperature is not specifically limited, for example, from 0° C. to 100° C. is preferred. The reaction time is preferably from 1 to 24 hours.

<Step 9>

In step 9, compound (XIII) is produced by reacting a compound represented by formula (XII) with an intermediate represented by formula (XV). Examples of the intermediate (XV) include an active intermediate obtained from an acetyl halide and a Lewis acid; an active intermediate obtained from an acetic anhydride and a Lewis acid; and an active intermediate obtained from acetic acid and a dehydrating agent. Examples of the acetyl halide include acetyl chloride, acetyl bromide, acetyl iodide and the like. Examples of the Lewis acid include aluminum chloride, zinc chloride and the like. Examples of the dehydrating agent include phosphorus pentoxide and the like. The reaction solvent is not specifically limited as long as it does not significantly inhibit the reaction. Examples of preferred reaction solvents include dichloromethane, dichloroethane and the like. Further, the reaction solvent may not be used. Although the reaction temperature is not specifically limited, for example, from 0° C. to 100° C. is preferred. The reaction time is preferably from 1 to 24 hours.

<Step 10>

In step 10, compound (II) is produced by reacting a compound represented by formula (XIII) with a halogenating agent. Examples of the halogenating agent include N-chlorosuccinicimide, N-bromosuccinicimide, N-iodosuccinicimide, benzyltrimethylammonium tribromide and the like. This reaction can be accelerated by using a suitable acid. The reaction solvent is not specifically limited as long as it does not significantly inhibit the reaction. Examples of preferred reaction solvents include tetrahydrofuran, dichloromethane, dichloroethane and the like. Although the reaction temperature is not specifically limited, for example, from 0° C. to 100° C. is preferred. The reaction time is preferably from 1 to 72 hours.

The inventive compound produced based on the above-described methods is isolated and purified as a free compound, a salt thereof, a hydrate thereof, a various solvate thereof such as ethanol solvate, polymorphilic crystalline products or the like. A pharmaceutically acceptable salt of the inventive compound can be prepared by a conventional salt-forming reaction. The isolation and purification can be carried out employing chemical operations such as fractional extraction, crystallization, and chromatography for fraction. Further, an optical isomer can also be obtained as a stereochemically pure isomer by selecting appropriate starting material compounds or by conventional optical resolution of the racemic compound.

The pyridone derivative, or a salt thereof, according to the present invention exhibits an excellent selective TACE inhibitory effect, and can be used as the active ingredient of a pharmaceutical. Therefore, in view of the fact that the present invention also relates to a pharmaceutical that includes the pyridone derivative, or a salt thereof, based on the TACE inhibitory effect of the above-described pyridone derivative, or a salt thereof, the pharmaceutical according to the present invention is especially useful as a soluble TNF-α production inhibitor, and is also especially useful as a preventive or therapeutic agent for various kinds of TNF-α-related disease. Examples of such diseases include rheumatoid arthritis, psoriatic arthritis, systemic lupus erythematosus (SLE), lupus nephritis, systemic scleroderma, localized scleroderma, Sjogren's syndrome, polymyositis, dermatomyositis, ulcerative colitis, Crohn's disease, Behcet's disease, multiple sclerosis, arteriosclerosis, myasthenia gravis, ankylosing spondylitis, diabetes, arteriosclerosis, sepsis, acute infectious diseases, asthma, chronic obstructive pulmonary disease (COPD), atopic dermatitis, contact dermatitis, psoriasis, acne, osteoporosis, burns, the onset of rejection associated with organs or tissue transplantation, fever, anemia, cancer, periodontal disease, glaucoma, diabetic complications, uveitis and the like. In addition, since the pyridone derivative, or a salt thereof, according to the present invention exhibits excellent pharmacological effects and transdermal absorption even when administered topically as illustrated in the below-described test examples 3 and 4, among TNF-α-related diseases, the pharmaceutical according to the present invention is especially useful as a preventive or therapeutic agent for diseases in which the symptoms appear on the skin (i.e. skin diseases). Examples of such skin diseases include localized scleroderma, atopic dermatitis, contact dermatitis, psoriasis, acne and the like.

The pharmaceutical containing the pyridone derivative, or a salt thereof, according to the present invention may be administered systemically or locally, via an oral, transdermal, nasal, respiratory, pulmonary, ophthalmic, intravenous injection, subcutaneous injection, rectal administration method or the like. Further, the dosage form of this pharmaceutical can be appropriately selected in accordance with the administration route. Examples of such dosage form include a tablet, lozenge, sublingual tablet, sugar-coated tablet, capsule, pill, powder, granule, solution, emulsion, cream, ointment, lotion, gel, jelly, suspension, syrup, eye drop, nasal drop, inhalant, suppository, injection and the like. Further, these formulations can be prepared by blending such as an excipient, preservative, wetting agent, emulsifier, stabilizer, solubilizing agent or the like, as necessary.

The dose of the pharmaceutical containing the pyridone derivative, or a salt thereof, according to the present invention may be appropriately determined based on conditions such as the administration target, the administration route, symptoms and the like. For example, for oral administration to an adult patient, the inventive compound, which is the active ingredient, may normally be administered in the range of about 0.1 to 100 mg/kg per dose, and preferably in the range of 1 to 40 mg/kg, and it is preferred to administer from 1 to 3 times per day. Further, for example, in the case of applying on the skin of an adult patient as a topical agent, the inventive compound, which is the active ingredient, may normally be administered in the range of about 1 to 100,000 µg/cm$^2$ per day, and preferably in the range of 10 to 10,000 µg/cm$^2$, and it is preferred to administer once a day or a split into several times in one day.

EXAMPLES

Features of the present invention are described in more detail with reference to the following working examples and test examples. In the following examples, the materials, its usage amounts and ratios, handling, procedure or the like may be suitably modified as long as such modifications do not go beyond the intent of the invention. Therefore, the scope of the present invention should not be construed as being limited by the specific examples illustrated below.

The $^1$H-NMR spectra shown below were measured with a JNM-ECA 400 spectrometer (400 MHz, manufactured by JEOL, Ltd.) using deuterated chloroform (CDCl$_3$) or deuterated dimethyl sulfoxide (DMSO-d$_6$) as a solvent and tetramethylsilane (TMS) as an internal standard. In the chemical shift measurement results, the δ value is represented in ppm, and the coupling constant J value is represented in Hz. The abbreviation s stands for singlet, d for doublet, t for triplet, q for quartet, m for multiplet, and br for broad. For the mass spectrum (electrospray ionization: ESI-MS) measurement, Exactive manufactured by Thermo Fisher Scientific was employed.

Working Example 1

Production of 5-[(3-methyl-2-oxopyridin-1(2H)-yl)methyl]-5-phenyl-imidazolidine-2,4-dione (I-1)

[Formula 13]

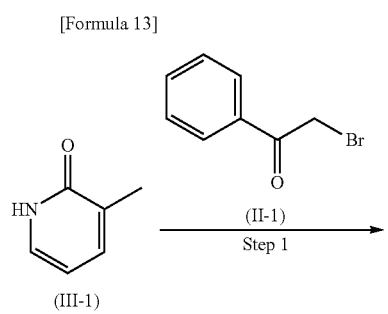

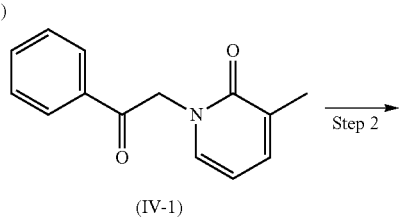

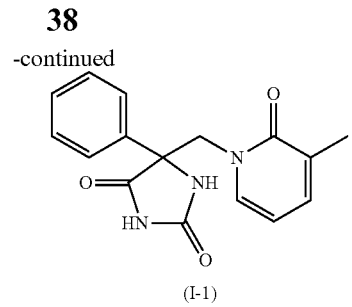

Step 1

Sodium hydride (60%, 1.8 g, 45.8 mmol) was added to a solution of 3-methyl-2-pyridone (III-1) (5.0 g, 45.8 mmol) in N,N-dimethylformamide (91 mL), and the resultant mixture was stirred for 10 minutes at room temperature. Phenacyl bromide (II-1) (9.1 g, 45.8 mmol) was added to the reaction solution, and the resultant mixture was stirred for 1.5 hours at room temperature. After gradually adding water to the reaction solution, the mixture was extracted with ethyl acetate. The organic layer was washed with water, and then dried over anhydrous sodium sulfate. The solvent was removed under reduced pressure to obtain compound (IV-1) (500 mg, 2.2 mmol) as a yellow solid.

Step 2

A suspension of this compound (IV-1) (7.0 g, 30.8 mmol), potassium cyanide (2.7 g, 41.5 mmol), and ammonium carbonate (11.8 g, 123 mmol) in ethanol (30 mL) and water (30 mL) was sealed, and stirred for 89 hours at 90° C. After leaving to cool, the reaction solution was diluted with water, and the resultant mixture was extracted with ethyl acetate. The organic layer was successively washed with water and saturated brine, and then dried over sodium sulfate. The solvent was removed under reduced pressure, and then chloroform was added. The mixture was filtered, and the resultant product was washed with chloroform and dried to obtain compound (I-1) (amount 1.14 g, yield 26%) as a yellow solid. The physical properties are shown below.

$^1$H-NMR (CDCl$_3$) δ: 2.12 (3H, s), 4.28 (1H, d, J=13.7 Hz), 4.85 (1H, d, J=13.7 Hz), 6.08 (1H, t, J=6.8 Hz), 7.14 (1H, dd, J=1.4, 6.8 Hz), 7.21 (1H, dd, J=1.4, 6.8 Hz), 7.37-7.44 (3H, m), 7.63-7.66 (2H, m), 8.35 (1H, s).

MS (ESI-FTMS) m/z: 298 [M+H]$^+$.

Working Example 2

Production of 5-(4-methoxyphenyl)-5-[(3-methyl-2-oxopyridin-1(2H)-yl)methyl]imidazolidine-2,4-dione (I-2)

[Formula 14]

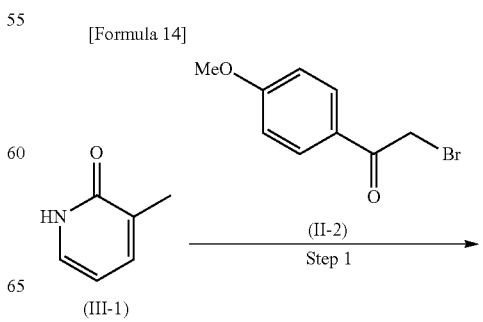

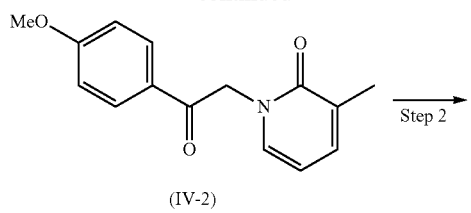

Working Example 3

Production of 4-{4-[(3-methyl-2-oxopyridin-1(2H)-yl)methyl]-2,5-dioxoimidazolidine-4-yl}benzonitrile (I-3)

[Formula 15]

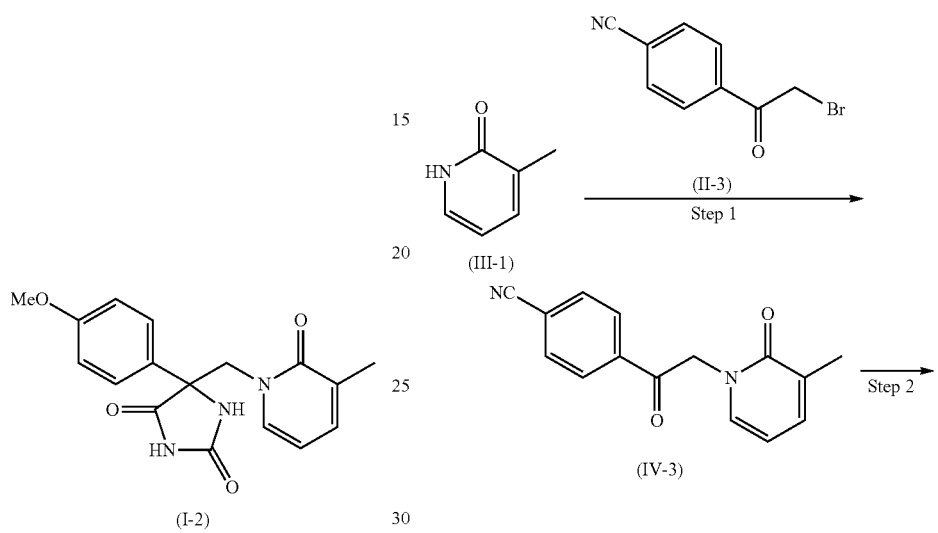

Step 1

Cesium carbonate (745 mg, 2.3 mmol) and 4'-methoxyphenacyl bromide (II-2) (500 mg, 2.2 mmol) were added to a solution of compound (III-1) (227 mg, 2.1 mmol) in N,N-dimethylformamide (10 mL), and the resultant mixture was stirred for 3.5 hours at room temperature. Water was added under ice cooling to stop the reaction, and then the mixture was extracted with ethyl acetate. The organic layer was washed with brine, and then dried over magnesium sulfate. The solvent was removed under reduced pressure to obtain compound (IV-2) (amount 440 mg, yield 82%) as a light yellow solid.

Step 2

Water (1.5 mL) was added to a suspension of this compound (IV-2) (436 mg, 1.7 mmol), potassium cyanide (132 mg, 2.0 mmol), and ammonium carbonate (651 mg, 6.8 mmol) in ethanol (1.5 mL). The resultant mixture was sealed, and stirred for 45 hours at 100° C. After leaving to cool, the reaction solution was diluted with water, and the resultant mixture was extracted with ethyl acetate. The organic layer was washed with saturated brine, and then dried over sodium sulfate. The solvent was removed under reduced pressure to obtain compound (I-2) (amount 370 mg, yield 67%) as a pale yellow solid. The physical properties are shown below.

$^1$H-NMR (DMSO-$d_6$) δ: 2.00 (3H, s), 3.76 (3H, s), 4.44 (1H, d, J=13.7 Hz), 4.55 (1H, d, J=13.7 Hz), 6.11 (1H, t, J=6.9 Hz), 6.98 (2H, td, J=2.5, 9.2 Hz), 7.20-7.31 (2H, m), 7.53 (2H, td, J=2.5, 9.2 Hz), 8.42 (1H, s), 10.80 (1H, s).

MS (ESI-FTMS) m/z 328 [M+H]$^+$.

Step 1

Cesium carbonate (762 mg, 2.4 mmol) and 4'-cyanophenacyl bromide (II-3) (500 mg, 2.2 mmol) were added to a solution of compound (III-1) (232 mg, 2.1 mmol) in N,N-dimethylformamide (10 mL), and the resultant mixture was stirred for 3 hours at room temperature. Water was added under ice cooling to stop the reaction, and then the mixture was extracted with ethyl acetate. The organic layer was washed with saturated brine, and then dried over magnesium sulfate. The solvent was removed under reduced pressure, and the resultant product was purified by column chromatography (silica gel) to obtain compound (IV-3) (amount 440 mg, yield 82%) as a light yellow solid.

Step 2

Compound (I-3) (amount 35 mg, yield 10%) was obtained as a pale yellow solid from compound (IV-3) based on the same production method as for compound (I-2). The physical properties are shown below.

$^1$H-NMR (DMSO-$d_6$) δ: 1.98 (3H, s), 4.47 (1H, d, J=13.7 Hz), 4.67 (1H, d, J=13.7 Hz), 6.13 (1H, t, J=6.7 Hz), 7.25-7.31 (2H, m), 7.80-7.86 (2H, m), 7.90-7.97 (2H, m), 8.74 (1H, s), 11.01 (1H, s).

MS (ESI-FTMS) m/z 323 [M+H]$^+$.

Working Example 4

Production of 5-(3-methoxyphenyl)-5-[(3-methyl-2-oxopyridin-1(2H)-yl)methyl]imidazolidine-2,4-dione (I-4)

[Formula 16]

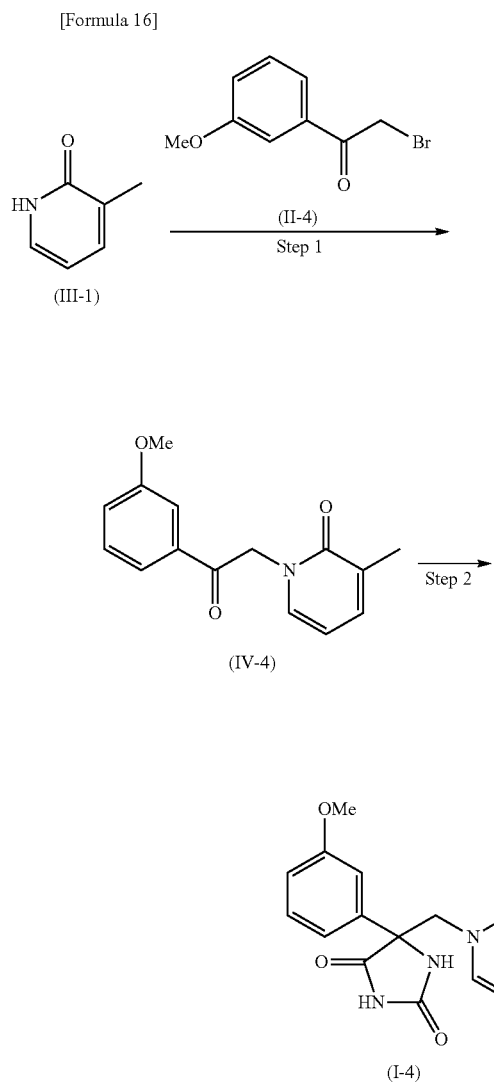

Compound (IV-4) (amount 496 mg, yield 93%) was obtained as a yellow oily substance from compound (III-1) and compound (II-4) based on the same production method as for compound (IV-3).

Compound (I-4) (amount 425 mg, yield 67%) was obtained as a pale yellow solid from compound (IV-4) based on the same production method as for compound (I-2). The physical properties are shown below.

$^1$H-NMR (DMSO-$d_6$) δ: 2.00 (3H, s), 3.78 (3H, s), 4.47 (1H, d, J=13.7 Hz), 4.59 (1H, d, J=13.7 Hz), 6.11 (1H, t, J=6.9 Hz), 6.95 (1H, ddd, J=0.9, 2.3, 8.2 Hz), 7.18-7.26 (3H, m), 7.29 (1H, m), 7.35 (1H, t, J=8.0 Hz), 8.58 (1H, s), 10.85 (1H, s).

MS (ESI-FTMS) m/z 328 [M+H]$^+$.

Working Example 5

Production of 5-[(3-methyl-2-oxopyridin-1(2H)-yl)methyl]-5-(thiophen-3-yl)imidazolidine-2,4-dione (I-5)

[Formula 17]

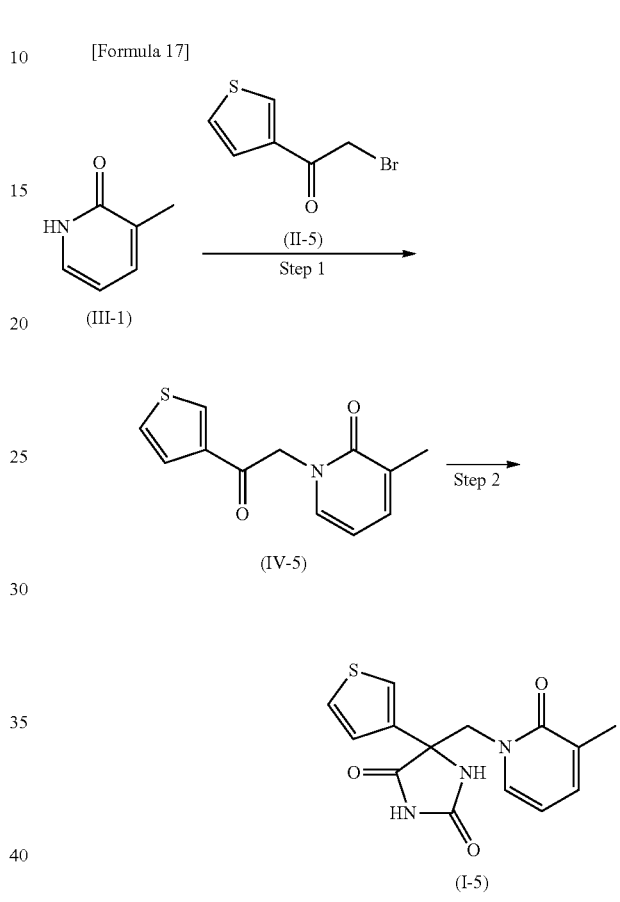

Step 1

Sodium hydroxide (60%, 102 mg, 2.6 mmol) was added to a solution of compound (III-1) (253 mg, 2.3 mmol) in N,N-dimethylformamide (10 mL). Then, 3-(bromoacetyl)thiophene (II-5) (500 mg, 2.4 mmol) was added, and the resultant mixture was stirred for 16 hours at room temperature. Water was added under ice cooling to stop the reaction, and then the mixture was extracted with ethyl acetate. The organic layer was washed with saturated brine, and then dried over magnesium sulfate. The solvent was removed under reduced pressure to obtain compound (IV-5) (amount 371 mg, yield 69%).

Step 2

Compound (I-5) (amount 270 mg, yield 56%) was obtained as a pale yellow solid from compound (IV-5) based on the same production method as for compound (I-2). The physical properties are shown below.

$^1$H-NMR (DMSO-$d_6$) δ: 2.00 (3H, s), 4.48 (1H, d, J=13.7 Hz), 4.53 (1H, d, J=13.7 Hz), 6.10 (1H, t, J=6.9 Hz), 7.21 (1H, dd, J=1.4, 6.9 Hz), 7.25-7.32 (2H, m), 7.59-7.64 (2H, m), 8.58 (1H, s), 10.87 (1H, s).

MS (ESI-FTMS) m/z 304 [M+H]$^+$.

Working Example 6

Production of 5-(benzofuran-2-yl)-5-[(3-methyl-2-oxopyridin-1(2H)-yl)methyl]imidazolidine-2,4-dione (I-6)

[Formula 18]

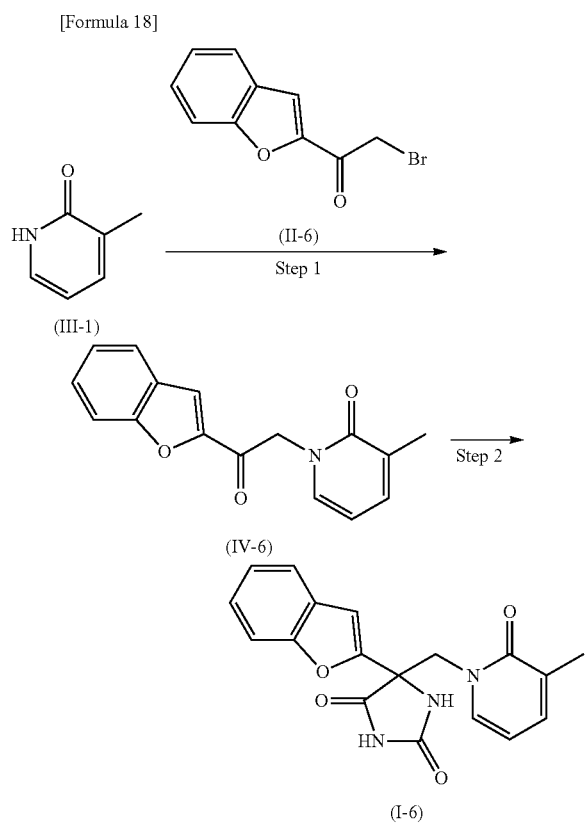

Step 1

Sodium hydroxide (60%, 88 mg, 2.2 mmol) was added to a solution of compound (III-1) (217 mg, 2.0 mmol) in N,N-dimethylformamide (10 mL). Then, 2-(2-bromoacetyl)benzofuran (II-6) (500 mg, 2.1 mmol) was added, and the resultant mixture was stirred for 16 hours at room temperature. Water was added under ice cooling to stop the reaction, and then the mixture was extracted with ethyl acetate. The organic layer was washed with saturated brine, and then dried over magnesium sulfate. The solvent was removed under reduced pressure, and then the resultant product was purified by column chromatography (silica gel) to obtain compound (IV-6) (amount 115 mg, yield 22%).

Step 2

Compound (I-6) (amount 58 mg, yield 40%) was obtained as a pale yellow solid from compound (IV-6) based on the same production method as for compound (I-2). The physical properties are shown below.

$^1$H-NMR (DMSO-$d_6$) δ: 1.99 (3H, s), 4.71 (1H, d, J=13.7 Hz), 4.79 (1H, d, J=13.7 Hz), 6.14 (1H, t, J=6.9 Hz), 7.14 (1H, d, J=0.9 Hz), 7.26-7.33 (3H, m), 7.36 (1H, dt, J=1.4, 7.3 Hz), 7.62 (1H, d, J=8.2 Hz), 7.68 (1H, d, J=7.8 Hz), 8.65 (1H, s), 11.10 (1H, s).

MS (ESI-FTMS) m/z 338 [M+H]$^+$.

Working Example 7

Production of 5-[(3-methyl-2-oxopyridin-1(2H)-yl)methyl]-5-(pyridin-2-yl)imidazolidine-2,4-dione (I-7)

[Formula 19]

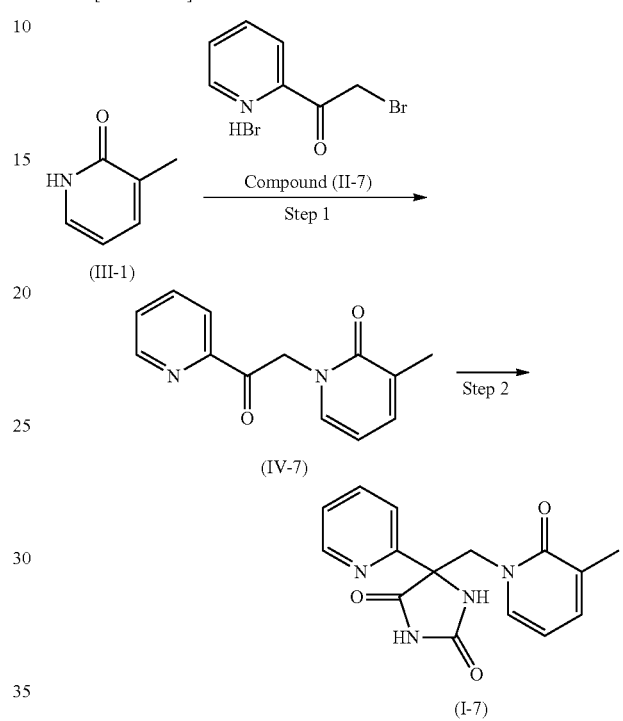

Step 1

Sodium hydroxide (60%, 339 mg, 8.5 mmol) was added to a solution of compound (III-1) (370 mg, 3.4 mmol) in N,N-dimethylformamide (10 mL). Then, 2-(bromoacetyl)pyridine hydrogen bromide (II-7) (1.0 g, 3.6 mmol) was added, and the resultant mixture was stirred for 4.5 hours at room temperature. Water was added under ice cooling to stop the reaction, and then the mixture was extracted with ethyl acetate. The organic layer was washed with saturated brine, and then dried over magnesium sulfate. The solvent was removed under reduced pressure, and then the resultant product was purified by column chromatography (silica gel) to obtain compound (IV-7) (amount 70 mg, yield 9.1%).

Step 2

Water (0.3 mL) was added to a suspension of this compound (IV-7) (70 mg, 0.31 mmol), potassium cyanide (24 mg, 0.37 mmol), and ammonium carbonate (118 mg, 1.22 mmol) in ethanol (0.3 mL). The resultant mixture was sealed, and stirred for 65 hours at 100° C. After leaving to cool, the solvent was removed under reduced pressure, methanol was added, and the precipitated solid was removed by filtration. The filtrate solvent was removed under reduced pressure to obtain compound (I-7) (amount 35 mg, yield 38%) as a colorless solid. The physical properties are shown below.

$^1$H-NMR (DMSO-$d_6$) δ: 1.99 (3H, s), 4.73 (1H, d, J=13.7 Hz), 4.83 (1H, d, J=13.7 Hz), 6.11 (1H, t, J=6.9 Hz), 7.25-7.34 (2H, m), 7.43 (1H, ddd, J=0.9, 5.0, 7.8 Hz), 7.53 (1H, d, J=7.8 Hz), 7.90 (1H, dt, J=1.8, 7.8 Hz), 8.40 (1H, s), 8.65 (1H, m), 10.88 (1H, s)

MS (ESI-FTMS) m/z 299 [M+H]$^+$.

Working Example 8

Production of 5-[(3-methyl-2-oxopyridin-1(2H)-yl)methyl]-5-(pyridin-3-yl)imidazolidine-2,4-dione (I-8)

[Formula 20]

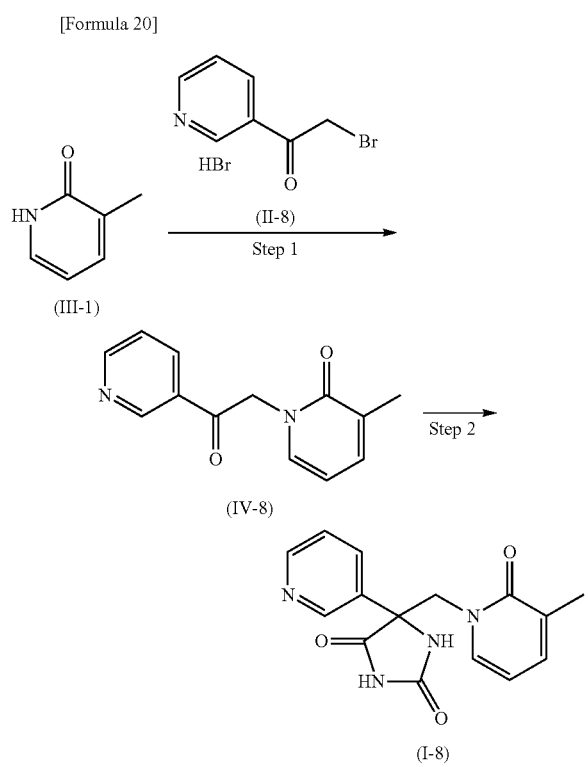

Working Example 9

Production of 5-[(3-methyl-2-oxopyridin-1(2H)-yl)methyl]-5-(4-phenoxyphenyl)imidazolidine-2,4-dione (I-9)

[Formula 21]

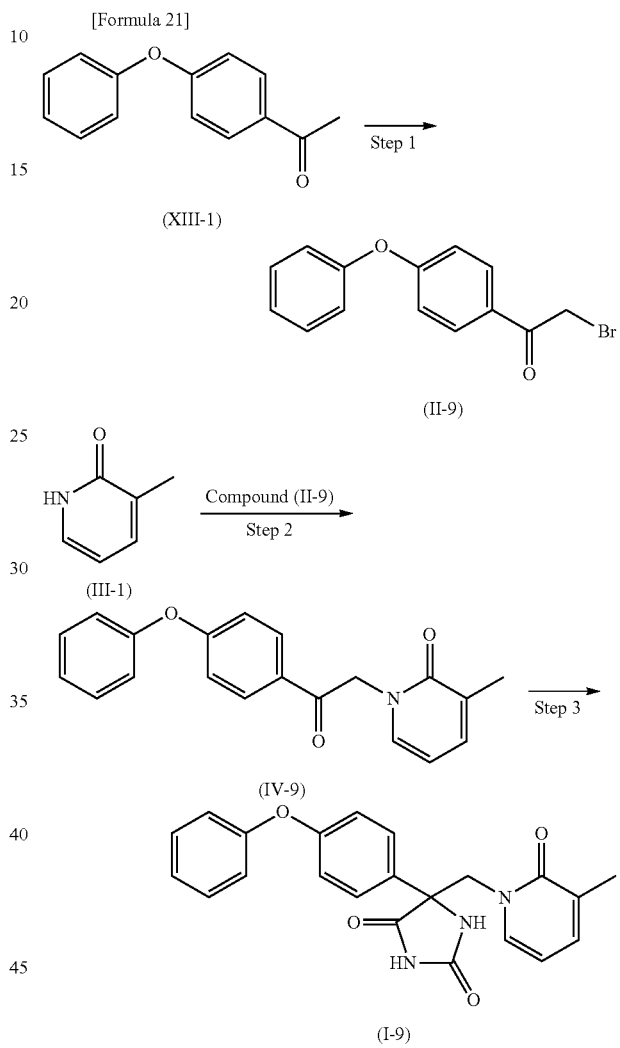

Step 1

Compound (IV-8) (amount 469 mg, yield 61%) was obtained from compound (III-1) and a 3-(bromoacetyl)pyridine hydrogen bromide (II-8) based on the same production method as for compound (IV-7).

Step 2

Water (1 mL) was added to a suspension of this compound (IV-8) (469 mg, 2.1 mmol), potassium cyanide (160 mg, 2.5 mmol), and ammonium carbonate (789 mg, 8.2 mmol) in ethanol (1 mL). The resultant mixture was sealed, and stirred for 65 hours at 100° C. After leaving to cool, the solvent was removed under reduced pressure, methanol was added, and the precipitated solid was removed by filtration. The filtrate solvent was removed under reduced pressure, the resultant product was dissolved in a small amount of chloroform. Hexane was added, the precipitated solid was filtered, and the filtered solid was washed with chloroform to obtain compound (I-8) (amount 295 mg, yield 48%) as a colorless solid. The physical properties are shown below.

$^1$H-NMR (DMSO-$d_6$) δ: 1.98 (3H, s), 4.52 (1H, d, J=13.7 Hz), 4.66 (1H, d, J=13.7 Hz), 6.13 (1H, t, J=6.9 Hz), 7.29 (2H, dd, J=0.9, 6.4 Hz), 7.46 (1H, m), 8.00 (1H, m), 8.58 (1H, dd, J=1.6, 4.8 Hz), 8.81 (1H, s), 8.82 (1H, d, J=1.8 Hz), 11.07 (1H, s).

MS (ESI-FTMS) m/z 299 [M+H]$^+$.

Step 1

Phenyltrimethylammonium tribromide (1.8 g, 4.7 mmol) was added to a solution of 4'-phenoxyacetophenone (XIII-1) (1.0 g, 4.7 mmol) in tetrahydrofuran (5 mL), and the resultant mixture was stirred for 14 hours at room temperature, then heated under reflux for 8 hours. After leaving to cool, the reaction solution was diluted with water, and the resultant mixture was extracted with ethyl acetate. The organic layer was washed with saturated brine, and then dried over magnesium sulfate. The solvent was removed under reduced pressure, and then the resultant product was purified by column chromatography (silica gel) to obtain compound (II-9) (amount 1.0 g, yield 69%).

Step 2

Compound (IV-9) (amount 218 mg, yield 42%) was obtained from compound (III-1) and compound (II-9) based on the same production method as for compound (IV-3).

Step 3

Water (0.7 mL) was added to a suspension of this compound (IV-9) (218 mg, 0.68 mmol), potassium cyanide (53 mg, 0.82 mmol), and ammonium carbonate (262 mg, 2.73 mmol) in ethanol (0.7 mL). The resultant mixture was sealed, and stirred for 66 hours at 100° C. After leaving to cool, the reaction solution was diluted with water. The precipitated solid was collected by filtration, washed with water, and then purified by column chromatography (silica gel) to obtain compound (I-9) (amount 160 mg, yield 58%) as a colorless solid. The physical properties are shown below.

$^1$H-NMR (DMSO-$d_6$) δ: 2.00 (3H, s), 4.46 (1H, d, J=13.7 Hz), 4.61 (1H, d, J=13.7 Hz), 6.12 (1H, t, J=6.6 Hz), 6.99-7.09 (4H, m), 7.17 (1H, m), 7.23-7.32 (2H, m), 7.37-7.44 (2H, m), 7.63 (2H, td, J=2.5, 9.2 Hz), 8.60 (1H, s), 10.87 (1H, s).

MS (ESI-FTMS) m/z 390 [M+H]$^+$.

Working Example 10

Production of 5-(3,4-difluorophenyl)-5-[(3-methyl-2-oxopyridin-1(2H)-yl)methyl] imidazolidine-2,4-dione (I-10)

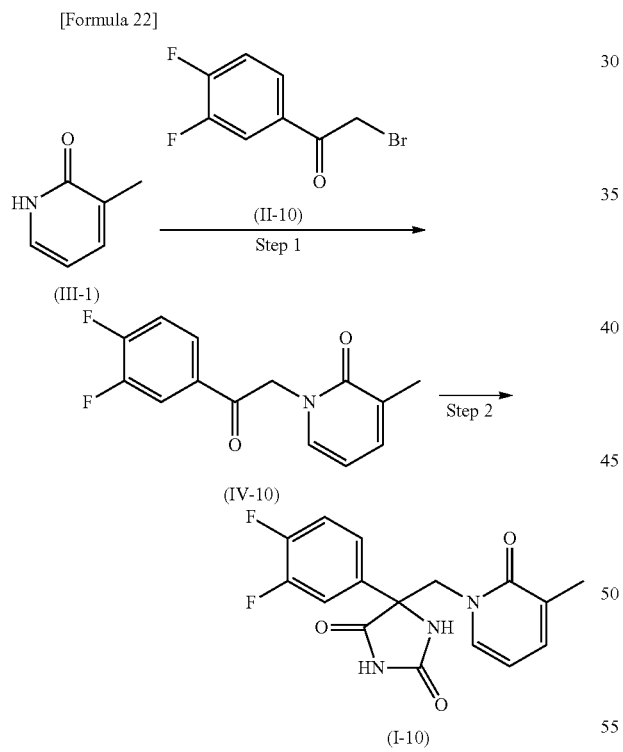

Step 1

Cesium carbonate (436 mg, 1.3 mmol) and 3',4'-difluorophenacyl bromide (II-10) (300 mg, 1.3 mmol) were added to a solution of compound (III-1) (133 mg, 1.2 mmol) in N,N-dimethylformamide (10 mL), and the resultant mixture was stirred for 3 hours at room temperature. The reaction solution was diluted with water. The precipitated solid was collected by filtration and washed with water to obtain compound (IV-10) (amount 206 mg, yield 64%) as a yellow solid.

Step 2

Water (0.8 mL) was added to a suspension of this compound (IV-10) (206 mg, 0.78 mmol), potassium cyanide (61 mg, 0.94 mmol), and ammonium carbonate (301 mg, 3.13 mmol) in ethanol (0.8 mL). The resultant mixture was sealed, and stirred for 67 hours at 100° C. After leaving to cool, the reaction solution was diluted with water, and the mixture was extracted with ethyl acetate. The resultant product was dried over anhydrous sodium sulfate, and the solvent was removed under reduced pressure. Chloroform was added to the residue, and the precipitated solid was collected by filtration to obtain compound (I-10) (amount 119 mg, yield 46%) as a colorless solid. The physical properties are shown below.

$^1$H-NMR (DMSO-$d_6$) δ: 1.98 (3H, s), 4.46 (1H, d, J=13.7 Hz), 4.61 (1H, d, J=13.7 Hz), 6.13 (1H, t, J=6.9 Hz), 7.22-7.33 (2H, m), 7.45-7.58 (2H, m), 7.69 (1H, ddd, J=2.3, 7.8, 12.4 Hz), 8.66 (1H, s), 10.99 (1H, s).

MS (ESI-FTMS) m/z 334 [M+H]$^+$.

Working Example 11

Production of 5-(4-bromophenyl)-5-[(3-methyl-2-oxopyridin-1(2H)-yl)methyl]imidazolidine-2,4-dione (I-11)

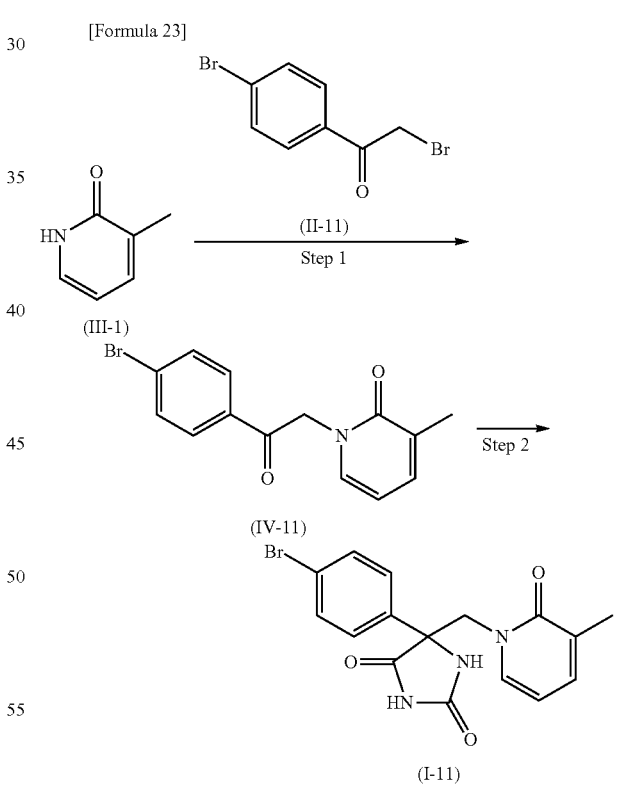

Step 1

Potassium carbonate (791 mg, 5.7 mmol) and 4'-bromophenacyl bromide (II-11) (636 mg, 2.3 mmol) were added to a solution of compound (III-1) (250 mg, 2.3 mmol) in dimethyl sulfoxide (4.6 mL), and the resultant mixture was stirred at room temperature. After confirming the completion of the reaction by TLC, the reaction solution was diluted with water, and the mixture was extracted with ethyl acetate. The organic layer was washed with saturated brine, and then dried over sodium sulfate. The solvent was removed under reduced pressure, and then the resultant product was purified by column chromatography (silica gel) to obtain compound (IV-11) (amount 553 mg, yield 79%).
Step 2

Water (0.98 mL) was added to a suspension of this compound (IV-11) (300 mg, 0.98 mmol), potassium cyanide (77 mg, 1.18 mmol), and ammonium carbonate (377 mg, 3.92 mmol) in ethanol (0.98 mL). The resultant mixture was sealed, and stirred for 48 hours at 100° C. After leaving to cool, water was added to the reaction solution. The precipitated solid was collected by filtration and washed with chloroform to obtain compound (I-11) (amount 230 mg, yield 62%). The physical properties are shown below.

$^1$H-NMR (DMSO-$d_6$) δ: 1.99 (3H, s), 4.45 (1H, d, J=13.7 Hz), 4.62 (1H, d, J=13.7 Hz), 6.12 (1H, t, J=6.7 Hz), 7.27 (2H, dd, J=6.9, 13.7 Hz), 7.58 (2H, d, J=8.7 Hz), 7.65 (2H, d, J=8.7 Hz), 8.65 (1H, s), 10.92 (1H, s).

MS (ESI-FTMS) m/z 376, 378 [M+H]$^+$.

Working Example 12

Production of 5-(4-fluoro-3-methoxyphenyl)-5-[(3-methyl-2-oxopyridin-1(2H)-yl)methyl]imidazolidine-2,4-dione (I-12)

[Formula 24]

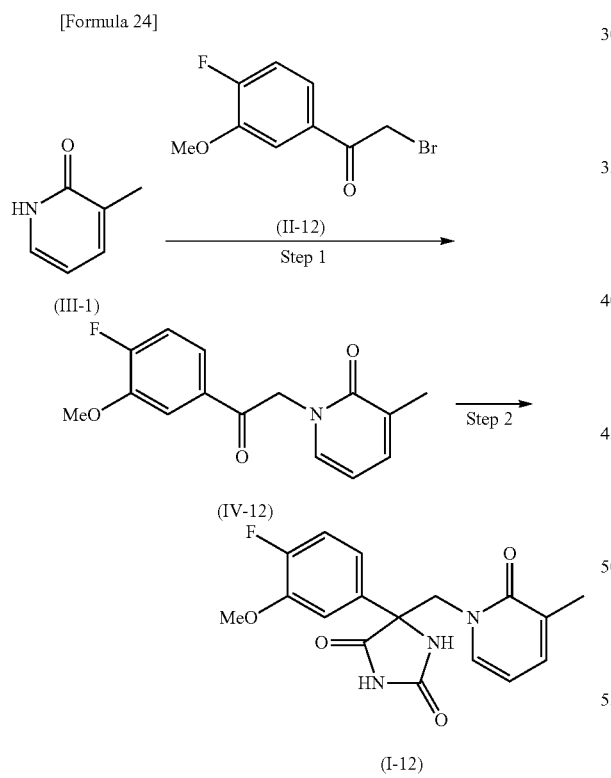

Step 1

Compound (IV-12) (amount 153 mg, yield 48%) was obtained from compound (III-1) and 2-bromo-4'-fluoro-3'-methoxyacetophenone compound (II-12) based on the same production method as for compound (IV-10).
Step 2

Water (1.0 mL) was added to a suspension of this compound (IV-12) (153 mg, 0.56 mmol), potassium cyanide (43 mg, 0.67 mmol), and ammonium carbonate (213 mg, 2.22 mmol) in ethanol (1.0 mL). The resultant mixture was sealed, and stirred for 66 hours at 100° C. After leaving to cool, water was added to the reaction solution. The precipitated solid was collected by filtration and washed with water to obtain compound (I-12) (amount 129 mg, yield 67%) as a colorless solid. The physical properties are shown below.

$^1$H-NMR (DMSO-$d_6$) δ: 1.99 (3H, s), 3.85 (3H, s), 4.45 (1H, d, J=13.7 Hz), 4.57 (1H, d, J=13.7 Hz), 6.12 (1H, t, J=6.9 Hz), 7.20-7.26 (2H, m), 7.29 (1H, m), 7.39 (1H, m), 7.48 (1H, dd, J=2.3, 12.8 Hz), 8.59 (1H, s), 10.90 (1H, s).

MS (ESI-FTMS) m/z 346 [M+H]$^+$.

Working Example 13

Production of 5-[4-(methoxymethoxy)phenyl]-5-[(3-methyl-2-oxopyridin-1(2H)-yl)methyl]imidazolidine-2,4-dione (I-13)

[Formula 25]

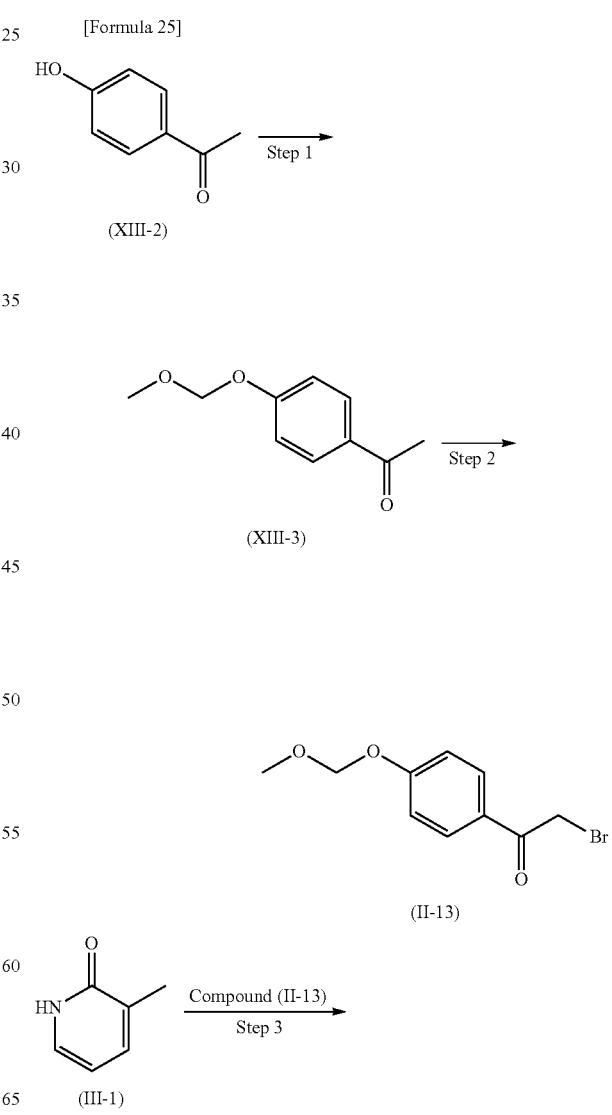

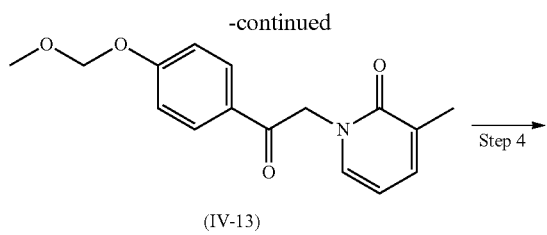

(IV-13)

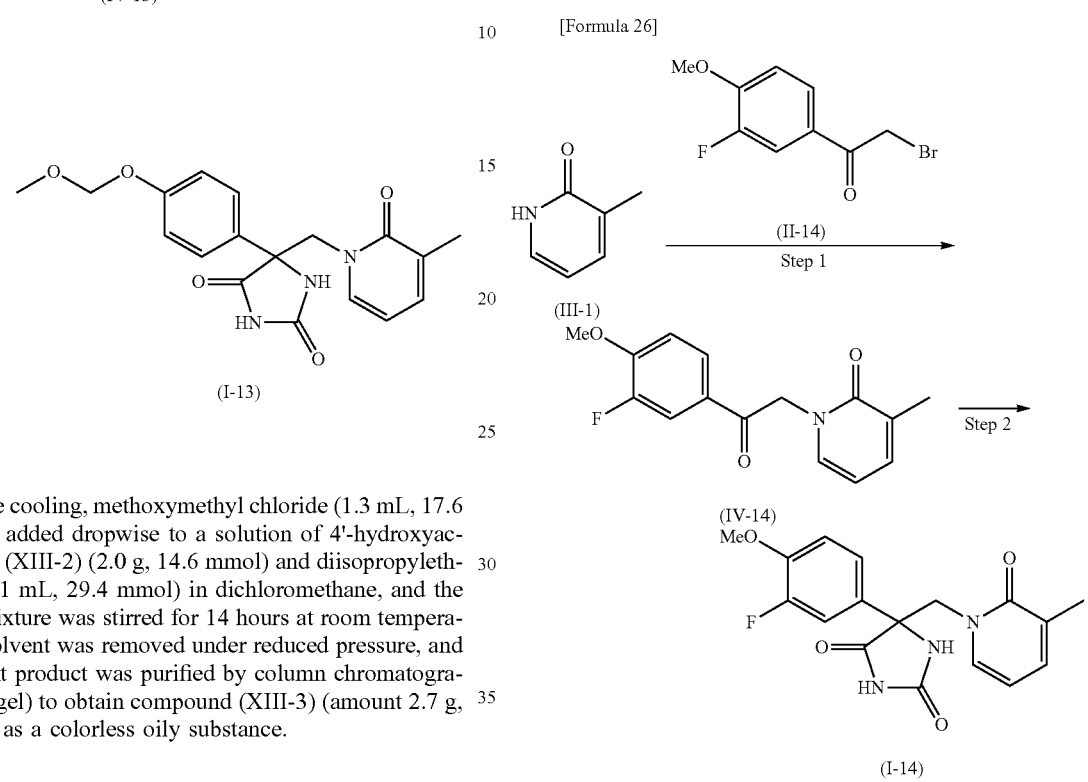

Step 1

Under ice cooling, methoxymethyl chloride (1.3 mL, 17.6 mmol) was added dropwise to a solution of 4'-hydroxyacetophenone (XIII-2) (2.0 g, 14.6 mmol) and diisopropylethylamine (5.1 mL, 29.4 mmol) in dichloromethane, and the resultant mixture was stirred for 14 hours at room temperature. The solvent was removed under reduced pressure, and the resultant product was purified by column chromatography (silica gel) to obtain compound (XIII-3) (amount 2.7 g, yield 99%) as a colorless oily substance.

Step 2

Under ice cooling, phenyltrimethylammonium tribromide (5.6 g, 15.0 mmol) was added to a solution of this compound (XIII-3) (2.7 g, 15.0 mmol) in tetrahydrofuran (30 mL), and the resultant mixture was stirred for 1 hour at room temperature. The reaction solution was diluted with water, and the resultant mixture was extracted with ethyl acetate. The organic layer was washed with saturated brine, and then dried over magnesium sulfate. The solvent was removed under reduced pressure, and then the resultant product was purified by column chromatography (silica gel) to obtain compound (II-13) (amount 312 mg, yield 8.0%).

Step 3

Compound (IV-13) (amount 147 mg, yield 45%) was obtained from compound (III-1) and compound (II-13) based on the same production method as for compound (II-3).

Step 4

Compound (I-13) (amount 38 mg, yield 26%) was obtained as a yellow solid from compound (IV-13) based on the same production method as for compound (I-12).

$^1$H-NMR (DMSO-$d_6$) δ: 2.00 (3H, s), 3.37 (3H, s), 4.45 (1H, d, J=13.7 Hz), 4.58 (1H, d, J=13.7 Hz), 5.21 (2H, s), 6.11 (1H, t, J=6.9 Hz), 7.07 (2H, td, J=2.5, 8.7 Hz), 7.22-7.31 (2H, m), 7.54 (2H, td, J=2.5, 8.7 Hz), 8.52 (1H, s), 10.81 (1H, s).

MS (ESI-FTMS) m/z 358 [M+H]$^+$.

Working Example 14

Production of 5-(3-fluoro-4-methoxyphenyl)-5-[(3-methyl-2-oxopyridin-1(2H)-yl)methyl]imidazolidine-2,4-dione (I-14)

[Formula 26]

Step 1

Compound (IV-14) (amount 239 mg, yield 75%) was obtained from compound (III-1) and 2-bromo-3'-fluoro-4'-methoxyacetophenone compound (I-14) based on the same production method as for compound (IV-5).

Step 2

An aqueous ammonia solution (28%, 950 μL) was added to a suspension of this compound (IV-14) (237 mg, 0.86 mmol), potassium cyanide (67 mg, 1.03 mmol), and ammonium carbonate (331 mg, 3.44 mmol) in ethanol (950 μL). The resultant mixture was sealed, and stirred for 64 hours at 100° C. After leaving to cool, the reaction solution was diluted with water, and the resultant mixture was extracted with ethyl acetate. The organic layer was washed with saturated brine, and then dried over sodium sulfate. The solvent was removed under reduced pressure, and then the resultant product was purified by column chromatography (silica gel) to obtain compound (II-14) (amount 98 mg, yield 33%) as a yellow solid. The physical properties are shown below.

$^1$H-NMR (DMSO-$d_6$) δ: 2.00 (3H, s), 3.86 (3H, s), 4.49 (1H, d, J=13.7 Hz), 4.57 (1H, d, J=13.7 Hz), 6.12 (1H, t, J=6.9 Hz), 7.18-7.31 (4H, m), 7.41 (1H, dd, J=1.8, 8.2 Hz), 8.63 (1H, s), 10.91 (1H, s).

MS (ESI-FTMS) m/z 346 [M+H]$^+$.

Working Example 15

Production of 5-(4-fluorophenyl)-5-[(3-methyl-2-oxopyridin-1(2H)-yl)methyl]imidazolidine-2,4-dione (I-15)

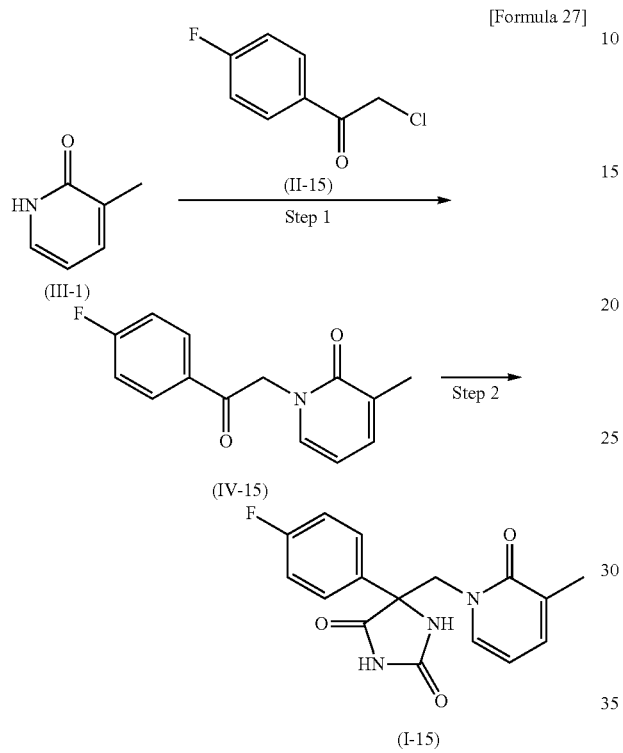

[Formula 27]

Step 1

Potassium carbonate (3.1 g, 22.6 mmol) and 4'-fluorophenacyl chloride (II-15) (3.0 g, 17.4 mmol) were added to a solution of compound (III-1) (2.1 g, 19.1 mmol) in acetone (30 mL), and the resultant mixture was heated under reflux for 19 hours. After leaving to cool, the reaction solution was diluted with water, and the resultant mixture was extracted with ethyl acetate. The organic layer was washed with saturated brine, and then dried over magnesium sulfate. The solvent was removed under reduced pressure, and then the resultant product was purified by column chromatography (silica gel) to obtain compound (IV-15) (amount 2.6 g, yield 61%).

Step 2

An aqueous ammonia solution (28%, 0.8 mL) was added to a suspension of this compound (IV-15) (200 mg, 0.82 mmol), potassium cyanide (64 mg, 0.98 mmol), and ammonium carbonate (313 mg, 3.26 mmol) in ethanol (0.8 mL). The resultant mixture was sealed, and stirred for 64 hours at 100° C. After leaving to cool, the reaction solution was diluted with water. The precipitated solid was collected by filtration and washed with water to obtain compound (I-15) (amount 178 mg, yield 69%) as a colorless solid. The physical properties are shown below.

$^1$H-NMR (DMSO-$d_6$) δ: 1.99 (3H, s), 4.45 (1H, d, J=13.7 Hz), 4.61 (1H, d, J=13.7 Hz), 6.11 (1H, t, J=6.9 Hz), 7.23-7.31 (4H, m), 7.64-7.71 (2H, m), 8.62 (1H, s), 10.89 (1H, s).

MS (ESI-FTMS) m/z 316 [M+H]$^+$.

Working Example 16

Production of 5-(3,4-dimethoxyphenyl)-5-[(3-methyl-2-oxopyridin-1(2H)-yl)methyl]imidazolidine-2,4-dione (I-16)

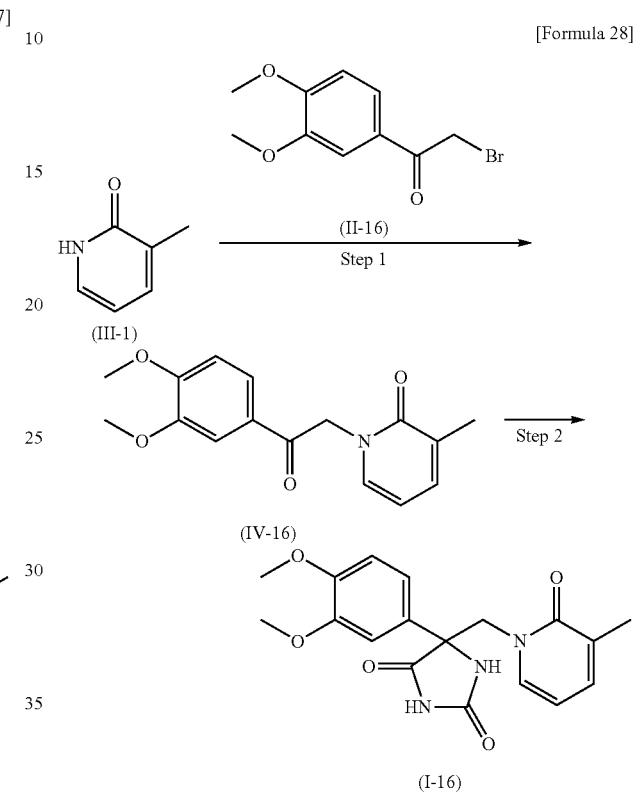

[Formula 28]

Step 1

Compound (IV-16) (amount 231 mg, yield 73%) was obtained as a colorless solid from compound (III-1) and 2-bromo-1-(3,4-dimethoxyphenyl)ethanone (II-16) based on the same production method as for compound (III-1).

Step 2

An aqueous ammonia solution (28%, 0.8 mL) was added to a suspension of this compound (IV-16) (230 mg, 0.80 mmol), potassium cyanide (83 mg, 0.98 mmol), and ammonium carbonate (308 mg, 3.20 mmol) in ethanol (0.8 mL). The resultant mixture was sealed, and stirred for 65 hours at 100° C. After leaving to cool, the solvent was removed under reduced pressure, methanol was added, and the precipitated solid was removed by filtration. The filtrate solvent was removed under reduced pressure, and the resultant product was dissolved in a small amount of chloroform. Hexane was added, the precipitated solid was filtered, and the filtered solid was then washed with chloroform to obtain compound (I-16) (amount 46 mg, yield 16%) as a colorless solid.

$^1$H-NMR (DMSO-$d_6$) δ: 2.00 (3H, s), 3.75 (3H, s), 3.78 (3H, s), 4.48 (1H, d, J=13.7 Hz), 4.54 (1H, d, J=13.7 Hz), 6.11 (1H, t, J=6.6 Hz), 6.99 (1H, d, J=8.7 Hz), 7.15 (1H, dd, J=2.1, 8.7 Hz), 7.19-7.32 (3H, m), 8.55 (1H, s), 10.80 (1H, s).

MS (ESI-FTMS) m/z 358 [M+H]$^+$.

Working Example 17

Production of 5-[4-(tert-butyl)phenyl]-5-[(3-methyl-2-oxopyridin-1(2H)-yl)methyl]imidazolidine-2,4-dione (I-17)

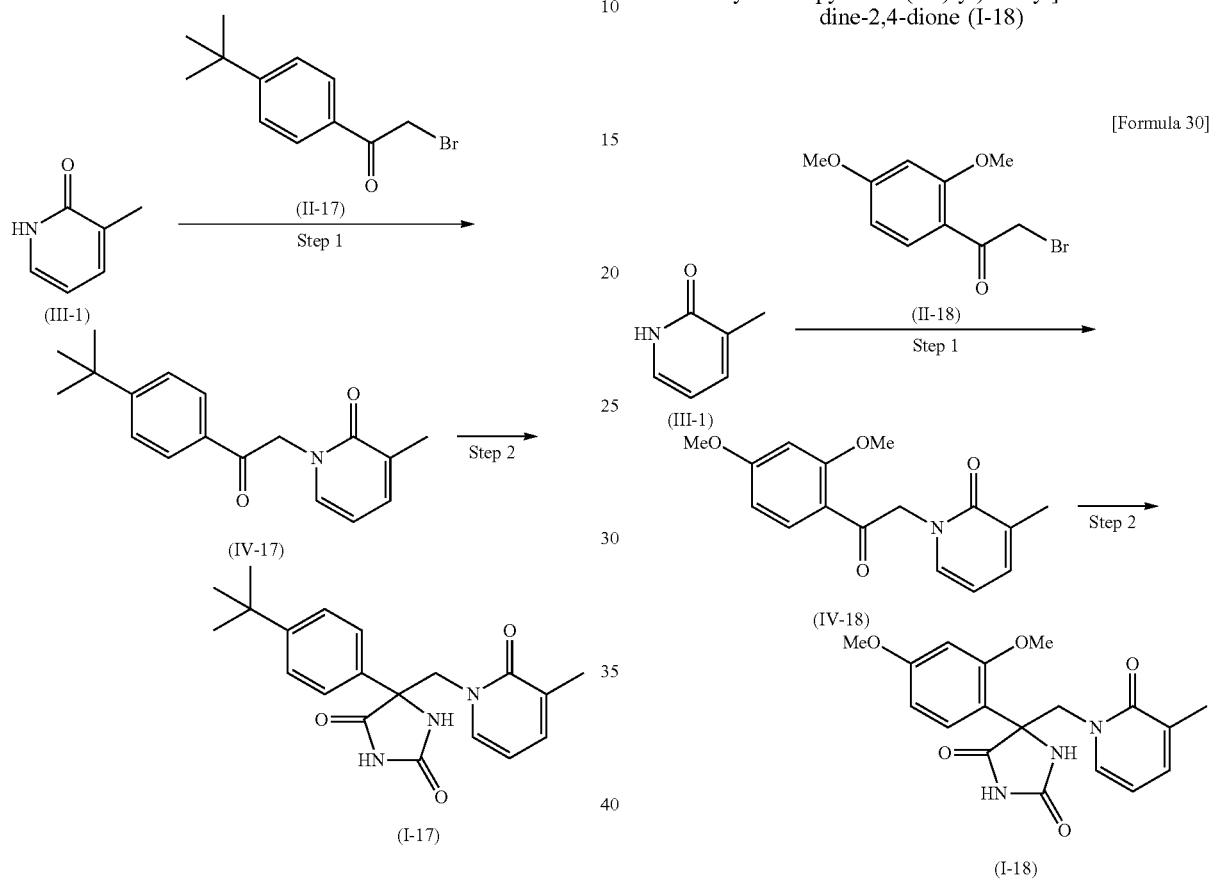

[Formula 29]

(III-1)
(II-17)
Step 1
(IV-17)
Step 2
(I-17)

Step 1

Potassium carbonate (950 mg, 6.9 mmol) and 4'-tert-butylphenacyl chloride (II-17) (300 mg, 2.7 mmol) were added to a solution of compound (III-1) (330 mg, 3.0 mmol) in dimethyl sulfoxide (5.5 mL), and the resultant mixture was stirred at room temperature. After confirming the completion of the reaction by TLC, the reaction solution was diluted with water, and the resultant mixture was extracted with ethyl acetate. The organic layer was washed with saturated brine, and dried over sodium sulfate. The solvent was removed under reduced pressure, and the resultant product was purified by column chromatography (silica gel) to obtain compound (IV-17) (amount 723 mg, yield 93%).

Step 2

An aqueous ammonia solution (28%, 1.1 mL) was added to a suspension of this compound (IV-17) (300 mg, 1.1 mmol), potassium cyanide (83 mg, 1.3 mmol), and ammonium carbonate (407 mg, 4.2 mmol) in ethanol (1.1 mL). The resultant mixture was sealed, and stirred for 64 hours at 100° C. After leaving to cool, the reaction solution was diluted with water. The precipitated solid was collected by filtration and washed with chloroform to obtain compound (I-17) (amount 301 mg, yield 80%). The physical properties are shown below.

$^1$H-NMR (DMSO-$d_6$) δ: 1.28 (9H, s), 2.00 (3H, s), 4.45 (1H, d, J=13.7 Hz), 4.61 (1H, d, J=13.7 Hz), 6.12 (1H, t, J=6.9 Hz), 7.24-7.31 (2H, m), 7.45 (2H, d, J=8.2 Hz), 7.54 (2H, d, J=8.7 Hz), 8.52 (1H, s), 10.79 (1H, s).

MS (ESI-FTMS) m/z 354 [M+H]$^+$.

Working Example 18

Production of 5-(2,4-dimethoxyphenyl)-5-[(3-methyl-2-oxopyridin-1(2H)-yl)methyl]imidazolidine-2,4-dione (I-18)

[Formula 30]

(III-1)
(II-18)
Step 1
(IV-18)
Step 2
(I-18)

Step 1

Compound (IV-18) (amount 594 mg, yield 90%) was obtained from compound (III-1) and 2',4'-dimethoxyphenacyl bromide (II-18) based on the same production method as for compound (IV-11).

Step 2

An aqueous ammonia solution (28%, 1.0 mL) was added to a suspension of this compound (IV-18) (300 mg, 1.0 mmol), potassium cyanide (82 mg, 1.3 mmol), and ammonium carbonate (401 mg, 4.2 mmol) in ethanol (1.0 mL). The resultant mixture was sealed, and stirred for 64.25 hours at 100° C. After leaving to cool, the solvent was removed under reduced pressure. Methanol was added to the residue, and the precipitated solid was removed by filtration. The filtrate solvent was removed under reduced pressure, and the resultant product was then purified by column chromatography (silica gel) to obtain compound (I-18) (amount 285 mg, yield 76%).

$^1$H-NMR (DMSO-$d_6$) δ: 1.99 (3H, s), 3.76 (3H, s), 3.78 (3H, s), 4.36 (1H, d, J=13.3 Hz), 4.86 (1H, d, J=13.3 Hz), 6.11 (1H, t, J=6.9 Hz), 6.55 (1H, dd, J=2.3, 8.7 Hz), 6.64 (1H, d, J=2.3 Hz), 7.21 (1H, d, J=6.9 Hz), 7.28 (1H, d, J=6.4 Hz), 7.40 (1H, d, J=8.7 Hz), 7.66 (1H, s), 10.68 (1H, s)

MS (ESI-FTMS) m/z 358 [M+H]$^+$.

Working Example 19

Production of 5-[(3-methyl-2-oxopyridin-1(2H)-yl)methyl]-5-[3-trifluoromethyl)phenyl]imidazolidine-2,4-dione (I-19)

[Formula 31]

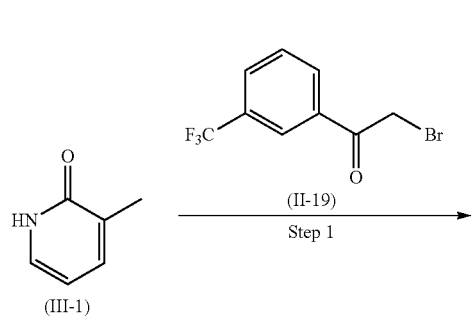

Step 1

Compound (IV-19) (amount 355 mg, yield 64%) was obtained from compound (III-1) and 3'-(trifluoromethyl)phenacyl bromide (II-19) based on the same production method as for compound (IV-3).

Step 2

Compound (I-19) (amount 207 mg, yield 56%) was obtained from this compound (IV-19) based on the same production method as for compound (I-18). The physical properties are shown below.

$^1$H-NMR (DMSO-$d_6$) δ: 1.97 (3H, s), 4.50 (1H, d, J=13.7 Hz), 4.67 (1H, d, J=13.7 Hz), 6.13 (1H, t, J=6.9 Hz), 7.29 (2H, d, J=6.9 Hz), 7.69 (1H, t, J=8.0 Hz), 7.77 (1H, d, J=7.3 Hz), 7.92-8.02 (2H, m), 8.76 (1H, s), 11.00 (1H, s).

MS (ESI-FTMS) m/z 366 [M+H]$^+$.

Working Example 20

Production of 5-(2,5-dimethoxyphenyl)-5-[(3-methyl-2-oxopyridin-1(2H)-yl)methyl]imidazolidine-2,4-dione (I-20)

[Formula 32]

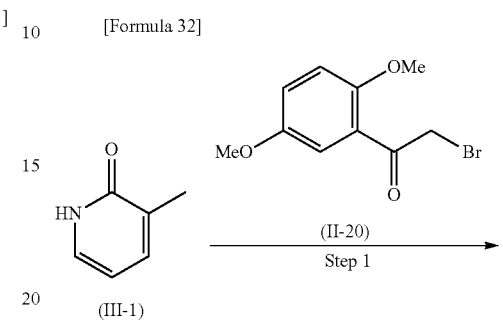

Step 1

Compound (IV-20) (amount 595 mg, yield 72%) was obtained from compound (III-1) and 2',5'-dimethoxyphenacyl bromide (II-20) based on the same production method as for compound (IV-3).

Step 2

Compound (I-20) (amount 170 mg, yield 46%) was obtained from this compound (IV-20) based on the same production method as for compound (I-18). The physical properties are shown below.

$^1$H-NMR (DMSO-$d_6$) δ: 1.99 (3H, s), 3.73 (3H, s), 3.73 (3H, s), 4.43 (1H, d, J=13.3 Hz), 4.84 (1H, d, J=13.3 Hz), 6.11 (1H, t, J=6.7 Hz), 6.97 (1H, dd, J=3.0, 9.0 Hz), 7.05 (1H, d, J=9.2 Hz), 7.09 (1H, d, J=3.2 Hz), 7.23 (1H, d, J=6.9 Hz), 7.29 (1H, d, J=6.9 Hz), 7.73 (1H, s), 10.74 (1H, s).

MS (ESI-FTMS) m/z 358 [M+H]$^+$.

Working Example 21

Production of 5-(4-fluoro-2-methoxyphenyl)-5-[(3-methyl-2-oxopyridin-1(2H)-yl)methyl]imidazolidine-2,4-dione (I-21)

[Formula 33]

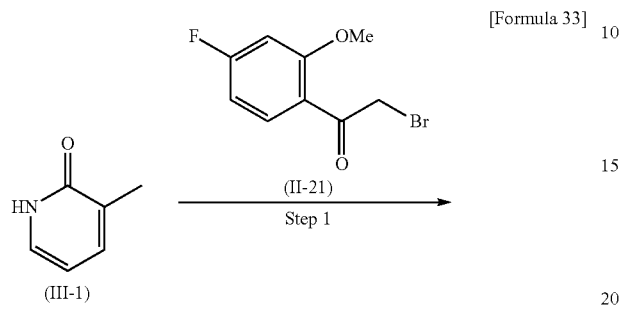

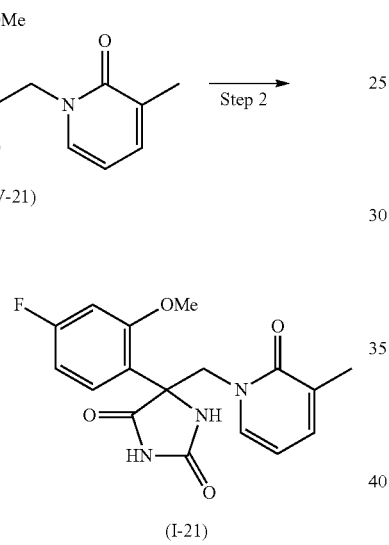

Step 1

Compound (IV-21) (amount 192 mg, yield 60%) was obtained as a colorless solid from compound (III-1) and 4'-fluoro-2'-methoxyphenacyl bromide (II-21) based on the same production method as for compound (IV-3).

Step 2

An aqueous ammonia solution (28%, 0.7 mL) was added to a suspension of this compound (IV-21) (192 mg, 0.70 mmol), potassium cyanide (55 mg, 0.84 mmol), and ammonium carbonate (288 mg, 2.80 mmol) in ethanol (0.7 mL). The resultant mixture was sealed, and stirred for 63 hours at 100° C. After leaving to cool, the reaction solution was diluted with water. The precipitated solid was collected by filtration and washed with water and chloroform to obtain compound (I-21) (amount 176 mg, yield 73%) as a colorless solid. The physical properties are shown below.

$^1$H-NMR (DMSO-$d_6$) δ: 1.99 (3H, s), 3.79 (3H, s), 4.41 (1H, d, J=13.3 Hz), 4.85 (1H, d, J=13.3 Hz), 6.11 (1H, t, J=6.6 Hz), 6.83 (1H, dt, J=2.7, 8.5 Hz), 7.04 (1H, dd, J=2.7, 11.0 Hz), 7.22 (1H, dd, J=1.4, 6.9 Hz), 7.28 (1H, m), 7.54 (1H, dd, J=6.4, 8.7 Hz), 7.78 (1H, s), 10.76 (1H, s).

MS (ESI-FTMS) m/z 346 [M+H]$^+$.

Working Example 22

Production of 5-(benzofuran-5-yl)-5-[(3-methyl-2-oxopyridin-1(2H)-yl)methyl]imidazolidine-2,4-dione (I-22)

[Formula 34]

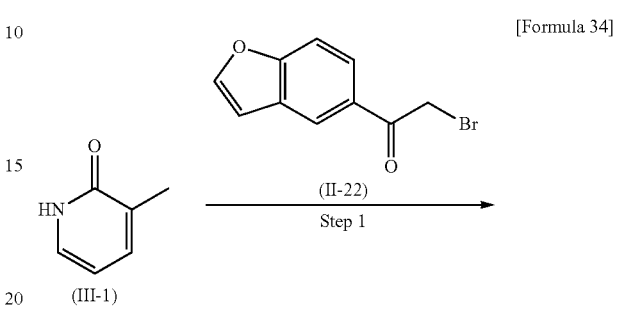

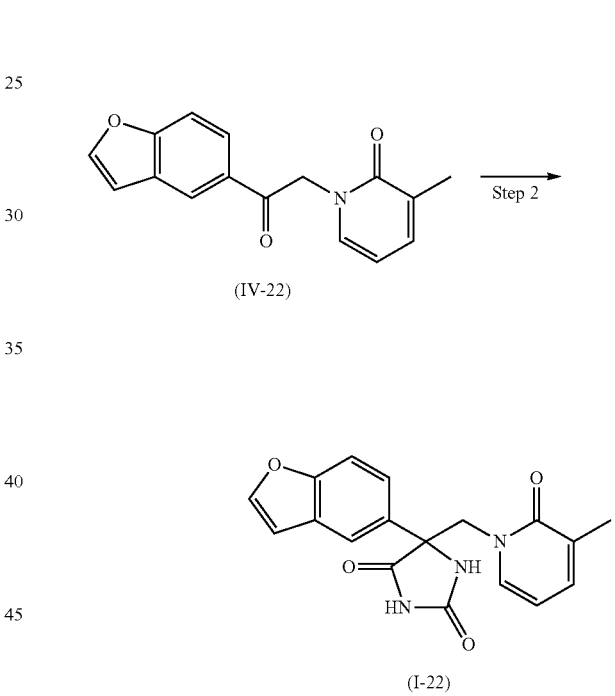

Step 1

Compound (IV-22) (amount 224 mg, yield 70%) was obtained as a colorless solid from compound (III-1) and 5'-(2-bromoacetyl)benzofuran (II-22) based on the same production method as for compound (IV-3).

Step 2

Compound (I-22) (amount 219 mg, yield 77%) was obtained as a colorless solid from this compound (IV-22) based on the same production method as for compound (I-15). The physical properties are shown below.

$^1$H-NMR (DMSO-$d_6$) δ: 2.00 (3H, s), 4.51 (1H, d, J=13.3 Hz), 4.68 (1H, d, J=13.3 Hz), 6.11 (1H, t, J=6.9 Hz), 7.03 (1H, dd, J=0.9, 2.3 Hz), 7.23-7.32 (2H, m), 7.60 (1H, dd, J=2.3, 8.7 Hz), 7.67 (1H, d, J=8.7 Hz), 7.94 (1H, d, J=1.8 Hz), 8.05 (1H, d, J=2.3 Hz), 8.62 (1H, s), 10.85 (1H, s).

MS (ESI-FTMS) m/z 338 [M+H]$^+$.

Working Example 23

Production of 5-(benzo[b]thiophen-5-yl)-5-[(3-methyl-2-oxopyridin-1(2H)-yl)methyl]imidazolidine-2,4-dione (I-23)

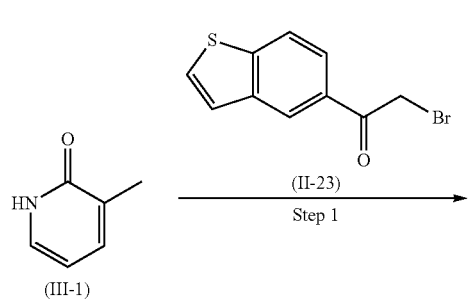

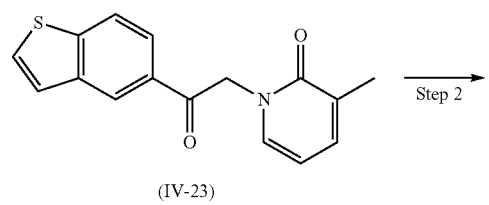

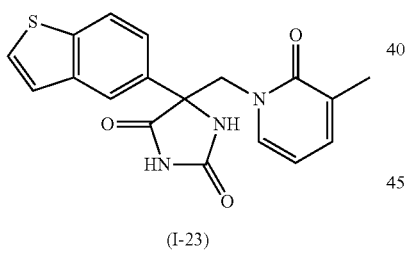

Step 1

Compound (IV-23) (amount 241 mg, yield 76%) was obtained as a colorless solid from compound (III-1) and 1-(1-benzothiophen-5-yl)-2-bromo-1-ethanone (II-23) based on the same production method as for compound (IV-2).

Step 2

Compound (I-23) (amount 262 mg, yield 64%) was obtained as a pale yellow solid from this compound (IV-23) based on the same production method as for compound (I-15). The physical properties are shown below.

$^1$H-NMR (DMSO-$d_6$) δ: 2.00 (3H, s), 4.54 (1H, d, J=13.7 Hz), 4.72 (1H, d, J=13.7 Hz), 6.12 (1H, t, J=6.7 Hz), 7.29 (2H, dd, J=0.9, 6.9 Hz), 7.52 (1H, d, J=7.5 Hz), 7.64 (1H, dd, J=1.8, 8.7 Hz), 7.83 (1H, d, J=5.5 Hz), 8.08 (1H, d, J=8.2 Hz), 8.30 (1H, d, J=1.8 Hz), 8.69 (1H, s), 10.86 (1H, s).

MS (ESI-FTMS) m/z 354 [M+H]$^+$.

Working Example 24

Production of 5-[2-methoxy-5-(trifluoromethoxy)phenyl]-5-[(3-methyl-2-oxopyridin-1(2H)-yl)methyl]imidazolidine-2,4-dione (I-24)

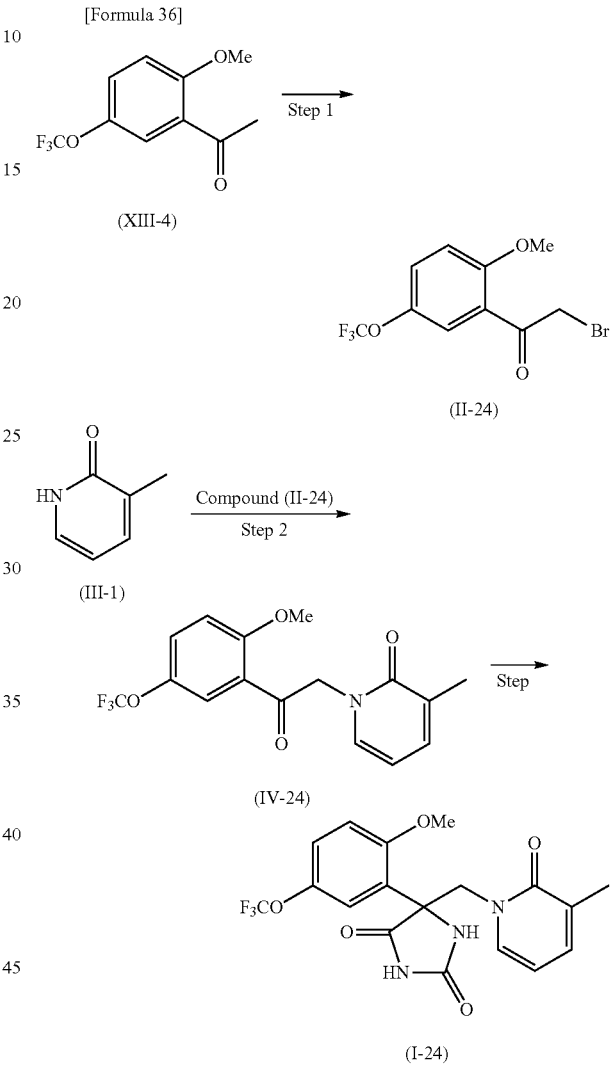

Step 1

Compound (II-24) (amount 820 mg, yield 93%) was obtained as a colorless solid from 2'-methoxy-5'-(trifluoromethoxy)acetophenone (XIII-4) based on the same production method as for compound (II-13).

Step 2

Compound (IV-24) (amount 102 mg, yield 33%) was obtained from compound (III-1) and compound (II-24) based on the same production method as for compound (IV-3).

Step 3

An aqueous ammonia solution (28%, 0.3 mL) was added to a suspension of this compound (IV-24) (102 mg, 0.30 mmol), potassium cyanide (23 mg, 0.36 mmol), and ammonium carbonate (115 mg, 1.20 mmol) in ethanol (0.3 mL). The resultant mixture was sealed, and stirred for 64 hours at 100° C. After leaving to cool, the reaction solution was diluted with water. The precipitated solid was collected by filtration, washed with water, and then purified by column chromatography (silica gel) to obtain compound (I-24) (amount 45 mg, yield 37%) as a colorless solid. The physical properties are shown below.

¹H-NMR (DMSO-d$_6$) δ: 1.98 (3H, s), 3.81 (3H, s), 4.46 (1H, d, J=13.3 Hz), 4.82 (1H, d, J=13.3 Hz), 6.12 (1H, t, J=6.9 Hz), 7.19-7.32 (3H, m), 7.45 (1H, m), 7.51 (1H, d, J=2.7 Hz), 7.90 (1H, s), 10.85 (1H, s).

MS (ESI-FTMS) m/z 412 [M+H]$^+$.

Working Example 25

Production of 5-[(3-methyl-2-oxopyridin-1(2H)-yl)methyl]-5-[4-(methylsulfonyl)phenyl]imidazolidine-2,4-dione (I-25)

[Formula 37]

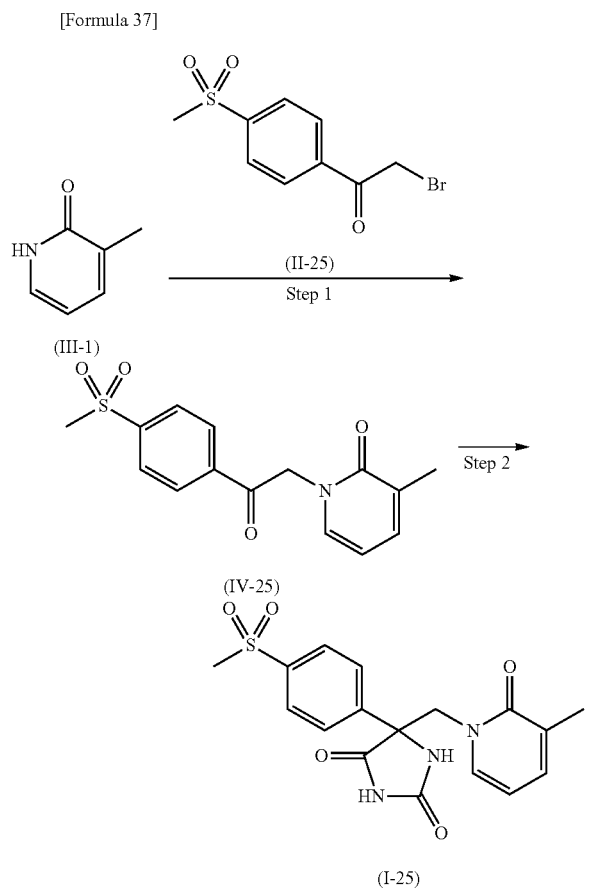

Step 1

Compound (IV-25) (amount 175 mg, yield 21%) was obtained from compound (III-1) and 4'-(methylsulfonyl)phenacyl bromide (II-25) based on the same production method as for compound (IV-3).

Step 2

Compound (I-25) (amount 86 mg, yield 63%) was obtained from this compound (IV-25) based on the same production method as for compound (I-17). The physical properties are shown below.

¹H-NMR (DMSO-d$_6$) δ: 1.99 (3H, s), 3.24 (3H, s), 4.48 (1H, d, J=13.7 Hz), 4.72 (1H, d, J=13.7 Hz), 6.14 (1H, t, J=6.9 Hz), 7.26-7.34 (2H, m), 7.91 (2H, d, J=8.7 Hz), 8.00 (2H, d, J=8.2 Hz), 8.72 (1H, s), 10.99 (1H, s).

MS (ESI-FTMS) m/z 376 [M+H]$^+$.

Working Example 26

Production of 5-(chroman-6-yl)-5-[(3-methyl-2-oxopyridin-1(2H)-yl)methyl]imidazolidine-2,4-dione (I-26)

[Formula 38]

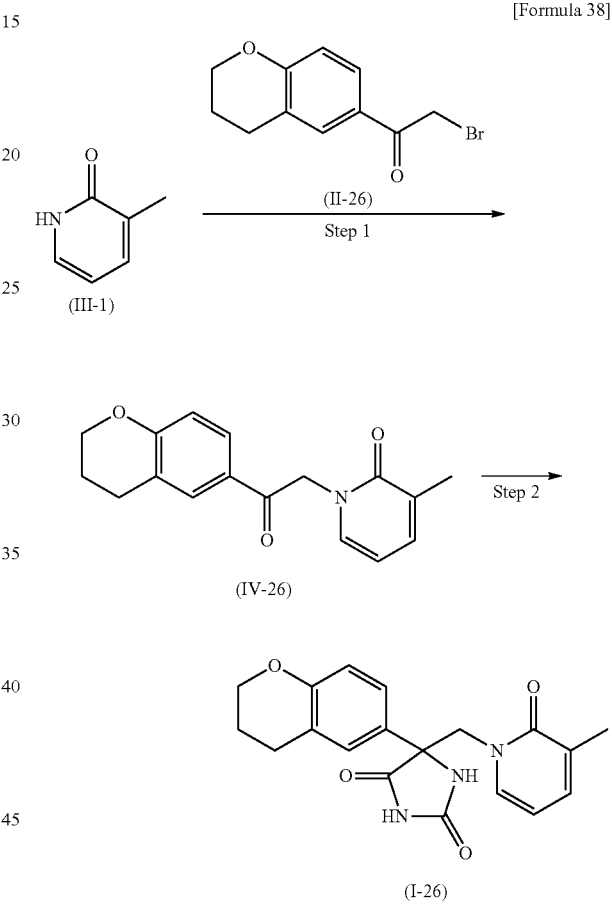

Step 1

Compound (IV-26) (amount 256 mg, yield 99%) was obtained from compound (III-1) and 2-chloro-1-chroman-6-yl-ethanone (II-26) based on the same production method as for compound (IV-15).

Step 2

Compound (I-26) (amount 81 mg, yield 25%) was obtained as a colorless solid from this compound (IV-26) based on the same production method as for compound (I-21). The physical properties are shown below.

¹H-NMR (DMSO-d$_6$) δ: 1.88-1.95 (2H, m), 2.00 (3H, s), 2.70-2.82 (2H, m), 4.06-4.20 (2H, m), 4.42 (1H, d, J=13.7 Hz), 4.54 (1H, d, J=13.3 Hz), 6.11 (1H, t, J=6.9 Hz), 6.77 (1H, d, J=8.7 Hz), 7.22-7.34 (4H, m), 8.43 (1H, s), 10.75 (1H, s).

MS (ESI-FTMS) m/z 354 [M+H]$^+$.

Working Example 27

Production of 5-(5-chloro-2-methoxyphenyl)-5-[(3-methyl-2-oxopyridin-1(2H)-yl)methyl]imidazolidine-2,4-dione (I-27)

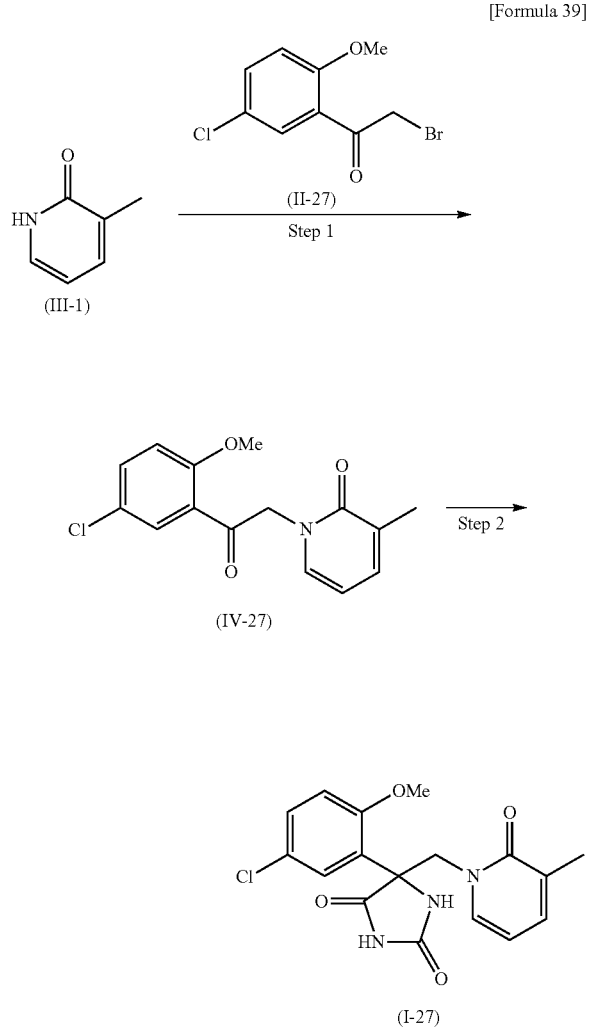

Step 1

Compound (IV-27) (amount 228 mg, yield 72%) was obtained from compound (III-1) and 2-bromo-5'-chloro-2'-methoxyacetophenone (II-27) based on the same production method as for compound (IV-13).

Step 2

Compound (I-27) (amount 61 mg, yield 23%) was obtained as a beige solid from this compound (IV-27) based on the same production method as for compound (I-17). The physical properties are shown below.

$^1$H-NMR (DMSO-$d_6$) δ: 1.99 (3H, s), 3.78 (3H, s), 4.45 (1H, d, J=13.2 Hz), 4.82 (1H, d, J=13.2 Hz), 6.12 (1H, t, J=6.9 Hz), 7.15 (1H, d, J=8.7 Hz), 7.22 (1H, m), 7.29 (1H, m), 7.47 (1H, dd, J=2.3, 8.7 Hz), 7.54 (1H, d, J=2.3 Hz), 7.83 (1H, br s), 10.82 (1H, br s).

MS (ESI-FTMS) m/z 362, 364 [M+H]$^+$.

Working Example 28

Production of 5-(3-fluorophenyl)-5-[(3-methyl-2-oxopyridin-1(2H)-yl)methyl]imidazolidine-2,4-dione (I-28)

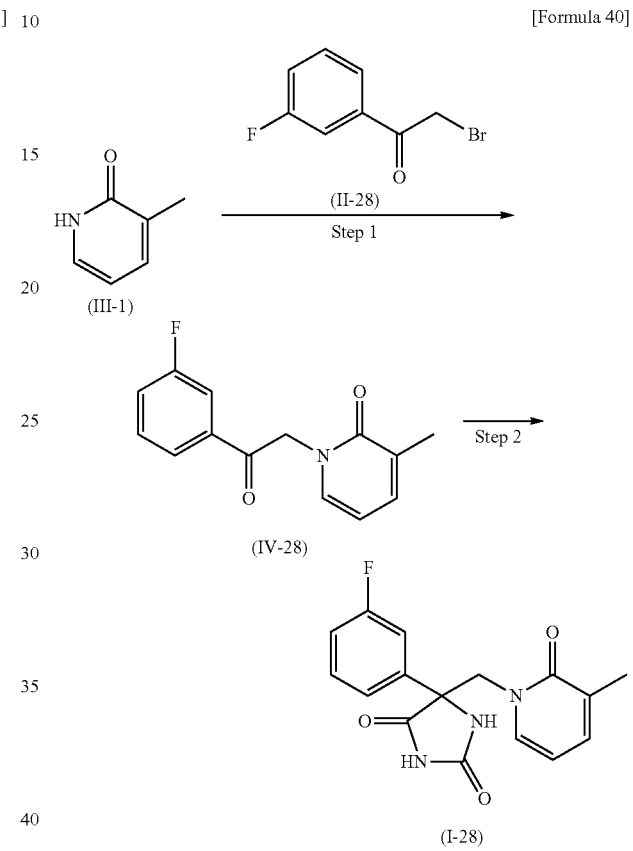

Step 1

Compound (IV-28) (amount 195 mg, yield 46%) was obtained from compound (III-1) and 3'-fluorophenacyl bromide (II-28) based on the same production method as for compound (IV-3).

Step 2

An aqueous ammonia solution (28%, 0.9 mL) was added to a suspension of this compound (IV-28) (195 mg, 0.80 mmol), potassium cyanide (78 mg, 1.19 mmol), and ammonium carbonate (306 mg, 3.18 mmol) in ethanol (0.9 mL). The resultant mixture was sealed, and stirred for 64 hours at 100° C. After leaving to cool, the reaction solution was diluted with water, and the resultant mixture was extracted with ethyl acetate. The solvent was removed under reduced pressure. Then, ethyl acetate-hexane (2:1) was added, and the precipitated solid was collected by filtration to obtain compound (I-28) (amount 140 mg, yield 56%). The physical properties are shown below.

$^1$H-NMR (DMSO-$d_6$) δ: 1.99 (3H, s), 4.47 (1H, d, J=13.7 Hz), 4.62 (1H, d, J=13.7 Hz), 6.12 (1H, d, J=6.9 Hz), 7.20-7.31 (3H, m), 7.44-7.53 (3H, m), 8.63 (1H, s), 10.93 (1H, br s).

MS (ESI-FTMS) m/z 316 [M+H]$^+$.

Working Example 29

Production of 5-[(3-methyl-2-oxopyridin-1(2H)-yl)methyl]-5-(2,4,5-trifluorophenyl)imidazolidine-2,4-dione (I-29)

[Formula 41]

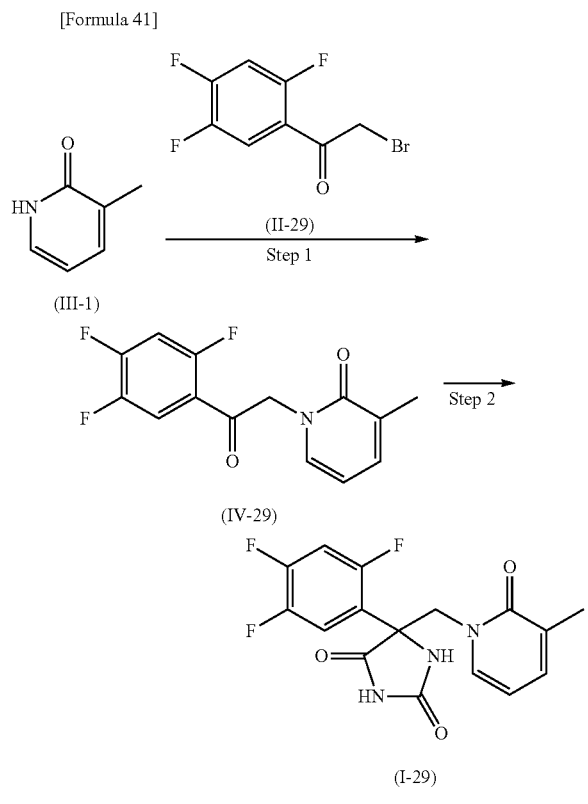

Step 1

Compound (IV-29) (amount 130 mg, yield 25%) was obtained from compound (III-1) and 2',4',5'-trifluorophenacyl bromide (II-29) based on the same production method as for compound (IV-15).

Step 2

An aqueous ammonia solution (28%, 0.8 mL) was added to a suspension of this compound (IV-29) (140 mg, 0.50 mmol), potassium cyanide (49 mg, 0.75 mmol), and ammonium carbonate (192 mg, 2.00 mmol) in ethanol (0.8 mL). The resultant mixture was sealed, and stirred for 64 hours at 100° C. After leaving to cool, the reaction solution was diluted with water, and the resultant mixture was extracted with ethyl acetate. The solvent was removed under reduced pressure, and the resultant product was purified by column chromatography (silica gel) to obtain compound (I-29) (amount 56 mg, yield 32%). The physical properties are shown below.

$^1$H-NMR (CDCl$_3$) δ: 2.11 (3H, s), 4.20 (1H, d, J=13.7 Hz), 5.09 (1H, d, J=13.7 Hz), 6.12 (1H, d, J=6.9 Hz), 7.04 (1H, m), 7.15 (1H, m), 7.23 (1H, m), 7.30 (1H, s), 7.60 (1H, m).

MS (ESI-FTMS) m/z 352 [M+H]$^+$.

Working Example 30

Production of 5-(4-fluoro-3-methylphenyl)-5-[(3-methyl-2-oxopyridin-1(2H)-yl)methyl]imidazolidine-2,4-dione (I-30)

[Formula 42]

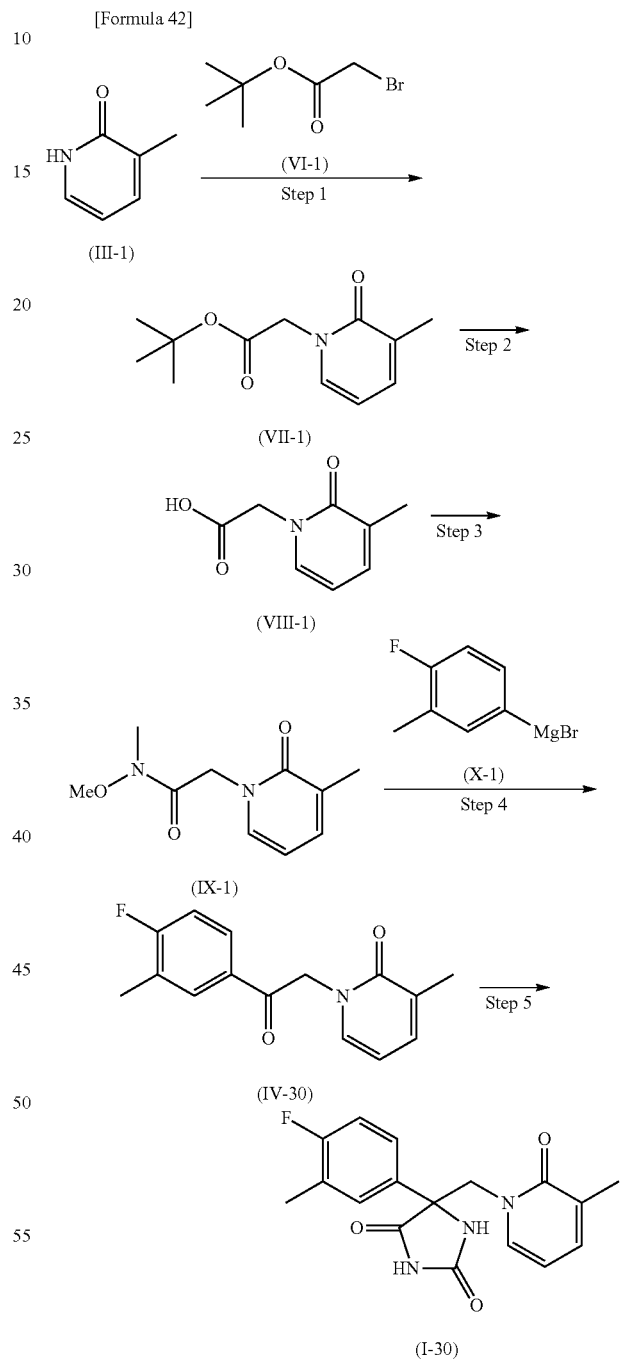

Step 1

Tert-butyl 2-bromoacetate (VI-1) (4.81 mL, 32.99 mmol) was added to a suspension of compound (III-1) (3 g, 27.49 mmol) and potassium carbonate (9.50 g, 68.73 mmol) in dimethyl sulfoxide (27.5 mL), and the resultant mixture was stirred for 3.25 hours at room temperature. Water was added to the reaction solution, and the resultant mixture was extracted with ethyl acetate. The organic layer was washed with saturated brine, and then dried over anhydrous sodium sulfate. The solvent was removed under reduced pressure to obtain compound (VII-1) (amount 5.76 g, yield 94%).

Step 2

Trifluoroacetic acid (26 mL) was added to a solution of this compound (VII-1) (5.76 g, 25.8 mmol) in chloroform (26 mL), and the resultant mixture was stirred for 15 hours at room temperature. The solvent was removed under reduced pressure to obtain compound (VIII-1) (amount 4.52 g, yield 99%).

Step 3

Compound (VIII-1) (4.31 g, 25.8 mmol), N,O-dimethylhydroxylamine hydrochloride (3.02 g, 30.96 mmol), N-methylmorpholine (8.51 mL, 77.40 mmol), and 1-hydroxybenzotriazole monohydrate (4.77 g, 30.96 mmol) were dissolved in N,N-dimethylformamide (25.8 mL). Water-soluble carbodiimide hydrochloride (5.94 g, 30.96 mmol) was then added, and the resultant mixture was stirred for 194.25 hours at room temperature. Water was added to the reaction solution, and the resultant mixture was extracted with chloroform. The organic layer was washed with saturated brine, and then dried over anhydrous sodium sulfate. The solvent was removed under reduced pressure, and the resultant product was purified by column chromatography (silica gel) to obtain compound (IX-1) (amount 4.63 g, yield 85%) as a white solid.

Step 4

4-Fluoro-3-methylphenylmagnesium bromide (X-1) in 1.0 mol/L tetrahydrofuran solution (1.1 mL, 1.1 mmol) was added dropwise to a solution (10 mL) cooled to −78° C. of compound (IX-1) in tetrahydrofuran, and the resultant mixture was stirred for 30 minutes at −78° C. To the reaction solution was added 2 mol/L hydrochloric acid, and the resultant mixture was extracted with ethyl acetate. The organic layer was washed with saturated brine, and then dried over anhydrous sodium sulfate, and the solvent was removed under reduced pressure. The resultant product was purified by column chromatography (silica gel) to obtain compound (IV-30) (amount 90 mg, yield 34%) as a colorless oily substance.

Step 5

Compound (I-30) (amount 30 mg, yield 26%) was obtained as a colorless solid from this compound (IV-30) based on the same production method as for compound (IV-17).

¹H-NMR (CDCl₃) δ: 2.11 (3H, s), 2.29 (3H, d, J=1.4 Hz), 4.22 (1H, d, J=13.7 Hz), 4.82 (1H, d, J=13.7 Hz), 6.10 (1H, t, J=6.9 Hz), 7.02 (1H, t, J=8.7 Hz), 7.14 (1H, m), 7.21 (1H, m), 7.42-7.50 (2H, m), 8.77 (1H, br s).

MS (ESI-FTMS) m/z 330 [M+H]⁺.

Working Example 31

Production of 5-[(3-methyl-2-oxopyridin-1(2H)-yl)methyl]-5-[4-(pyridin-4-yl)phenyl]imidazolidine-2,4-dione (I-31)

[Formula 43]

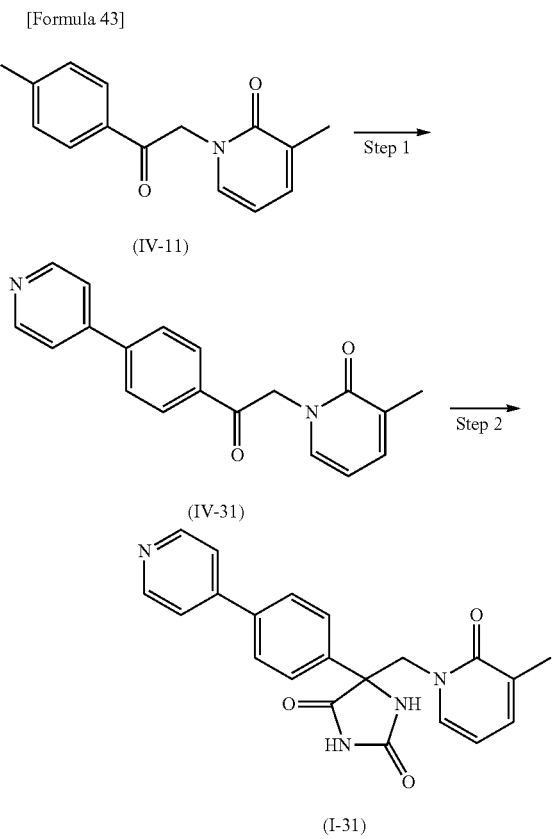

Step 1

A solution of compound (IV-11) (400 mg, 1.32 mmol), (4-pyridine)cyclic triolborate sodium salt (320 mg, 1.44 mmol), and triphenylphosphine (34 mg, 0.13 mmol) in N,N-dimethylformamide (6.5 mL) was degassed. Then, under an argon atmosphere, palladium acetate (15 mg, 0.065 mmol) and copper iodide (50 mg, 0.26 mmol) were added, and the resultant mixture was heated for 15.5 hours at 90° C. A saturated aqueous solution of ammonium chloride was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-31) (amount 109 mg, yield 22%).

Step 2

An autoclave was charged with this compound (IV-31) (90 mg, 0.30 mmol), potassium cyanide (23 mg, 0.36 mmol), ammonium carbonate (114 mg, 1.18 mmol), ethanol (0.3 mL), and saturated ammonia water (0.3 mL). The autoclave was sealed, and the mixture was stirred for 63.75 hours at 100° C. The solvent was removed under reduced pressure and the resultant product was then purified by silica gel column chromatography to obtain compound (I-31) (amount 42 mg, yield 38%). The physical properties are shown below.

¹H-NMR (DMSO-d₆) δ: 2.00 (3H, s), 4.51 (1H, d, J=13.3 Hz), 4.68 (1H, d, J=13.7 Hz), 6.14 (1H, t, J=6.9 Hz), 7.27-7.32 (2H, m), 7.75 (2H, dd, J=1.8, 4.6 Hz), 7.78 (2H, d, J=8.7 Hz), 7.90 (2H, d, J=8.7 Hz), 8.66 (2H, d, J=6.0 Hz), 8.69 (1H, s), 10.91 (1H, s).

MS (ESI-FTMS) m/z: 375 [M+H]⁺.

Working Example 32

Production of 5-[(3-methyl-2-oxopyridin-1(2H)-yl)methyl]-5-[4-(pyridin-3-yl)phenyl]imidazolidine-2,4-dione (I-32)

[Formula 44]

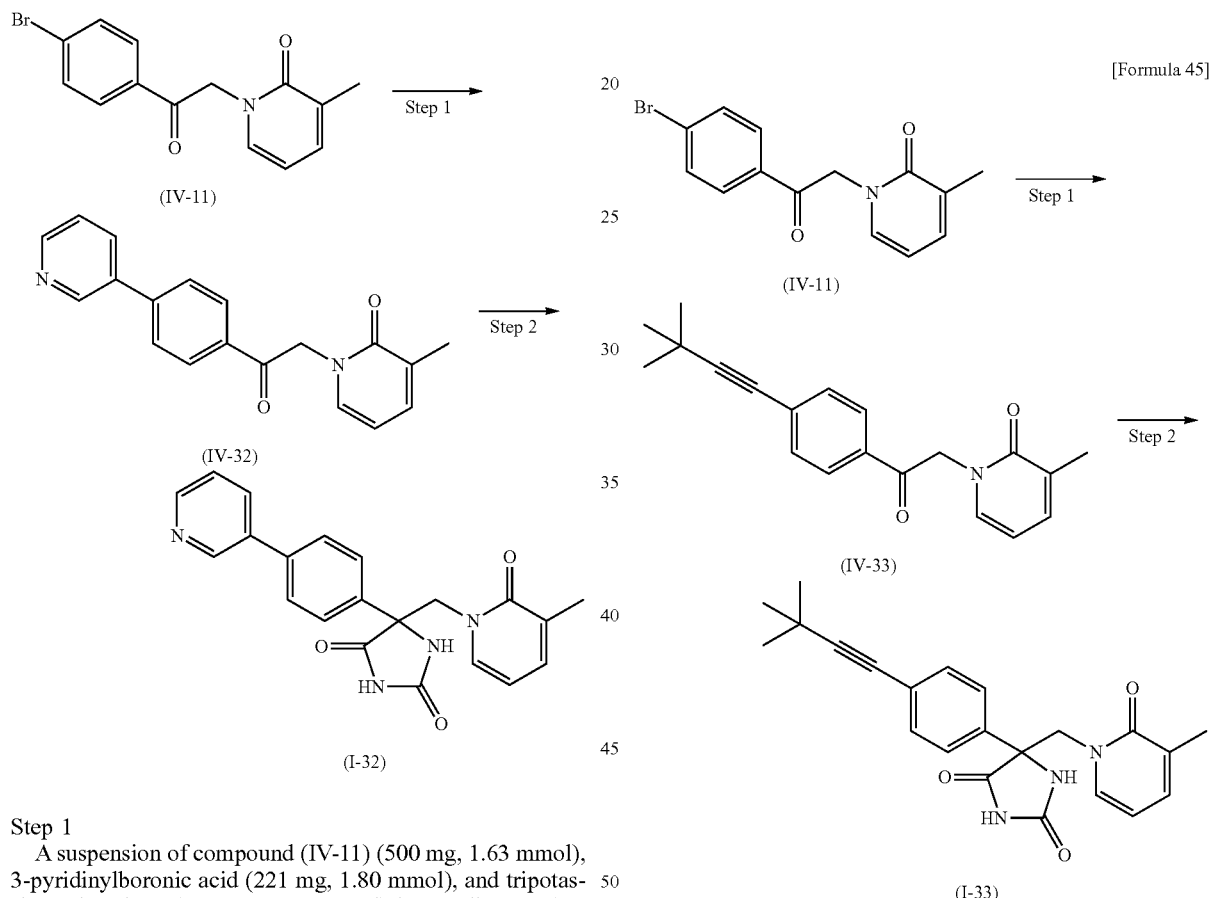

Step 1

A suspension of compound (IV-11) (500 mg, 1.63 mmol), 3-pyridinylboronic acid (221 mg, 1.80 mmol), and tripotassium phosphate (555 mg, 2.61 mmol) in 1,4-dioxane (3.3 mL) was degassed. Then, under an argon atmosphere, tetrakis(triphenylphosphine)palladium (94 mg, 0.082 mmol) was added, and the resultant mixture was heated for 22.5 hours at 90° C. Water was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-32) (amount 232 mg, yield 47%).

An autoclave was charged with this compound (IV-32) (196 mg, 0.64 mmol), potassium cyanide (50 mg, 0.77 mmol), ammonium carbonate (248 mg, 2.58 mmol), ethanol (0.64 mL), and saturated ammonia water (0.64 mL). The autoclave was sealed, and the mixture was stirred for 66 hours at 100° C. Water was added to the reaction solution, and the precipitated solid was collected by filtration to obtain compound (I-32) (amount 184 mg, yield 76%). The physical properties are shown below.

¹H-NMR (DMSO-d₆) δ: 2.01 (3H, s), 4.52 (1H, d, J=13.7 Hz), 4.68 (1H, d, J=13.7 Hz), 6.14 (1H, t, J=6.9 Hz), 7.29 (2H, d, J=6.9 Hz), 7.51 (1H, dd, J=4.8, 8.0 Hz), 7.76 (2H, d, J=8.7 Hz), 7.83 (2H, d, J=8.7 Hz), 8.11 (1H, td, J=2.3, 8.2 Hz), 8.59 (1H, dd, J=1.4, 4.6 Hz), 8.66 (1H, s), 8.93 (1H, d, J=1.8 Hz), 10.89 (1H, s).

MS (ESI-FTMS) m/z: 375 [M+H]⁺.

Working Example 33

Production of 5-[4-(3,3-dimethylbut-1-yn-1-yl)phenyl]-5-[(3-methyl-2-oxopyridin-1(2H)-yl)methyl]imidazolidine-2,4-dione (I-33)

[Formula 45]

Step 1

A solution of compound (IV-11) (500 mg, 1.63 mmol), 3,3-dimethylbut-1-yn (222 µL, 1.80 mmol), and triethylamine (250 µL, 1.80 mmol) in tetrahydrofuran (3.3 mL) was degassed. Then, under an argon atmosphere, tetrakis(triphenylphosphine)palladium (94 mg, 0.082 mmol) and copper iodide (31 mg, 0.16 mmol) were added, and the resultant mixture was heated under reflux for 22.5 hours. Water was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-33) (amount 531 mg, quantitative yield).

Compound (I-33) (amount 270 mg, yield 73%) was obtained from compound (IV-33) based on the same production method as for compound (I-32). The physical properties are shown below.

$^1$H-NMR (DMSO-d$_6$) δ: 1.29 (9H, s), 1.99 (3H, s), 4.44 (1H, d, J=13.3 Hz), 4.62 (1H, d, J=13.7 Hz), 6.11 (1H, t, J=6.9 Hz), 7.22-7.29 (2H, m), 7.41 (2H, d, J=8.7 Hz), 7.59 (2H, d, J=8.2 Hz), 8.58 (1H, s), 10.88 (1H, s).

MS (ESI-FTMS) m/z: 378 [M+H]$^+$.

Working Example 34

Production of 5-[(3-methyl-2-oxopyridin-1(2H)-yl)methyl]-5-[4-(p-tolyloxy)phenyl]imidazolidine-2,4-dione (I-34)

was removed under reduced pressure, and the resultant product was purified by column chromatography (silica gel) to obtain compound (I-34) (amount 56 mg, yield 38%) as a colorless solid. The physical properties are shown below.

$^1$H-NMR (DMSO-d$_6$) δ: 1.99 (3H, s), 2.30 (3H, s), 4.45 (1H, d, J=13.3 Hz), 4.60 (1H, d, J=13.3 Hz), 6.12 (1H, t, J=6.9 Hz), 6.93 (2H, td, J=2.5, 8.2 Hz), 7.01 (2H, td, J=2.5, 8.7 Hz), 7.17-7.32 (4H, m), 7.60 (2H, td, J=2.5, 9.2 Hz), 8.57 (1H, d, J=1.4 Hz), 10.85 (1H, s).

MS (ESI-FTMS) m/z 404 [M+H]$^+$.

Working Example 35

Production of 5-[(3-methyl-2-oxopyridin-1(2H)-yl)methyl]-5-[4-(o-tolyloxy)phenyl]imidazolidine-2,4-dione (I-35)

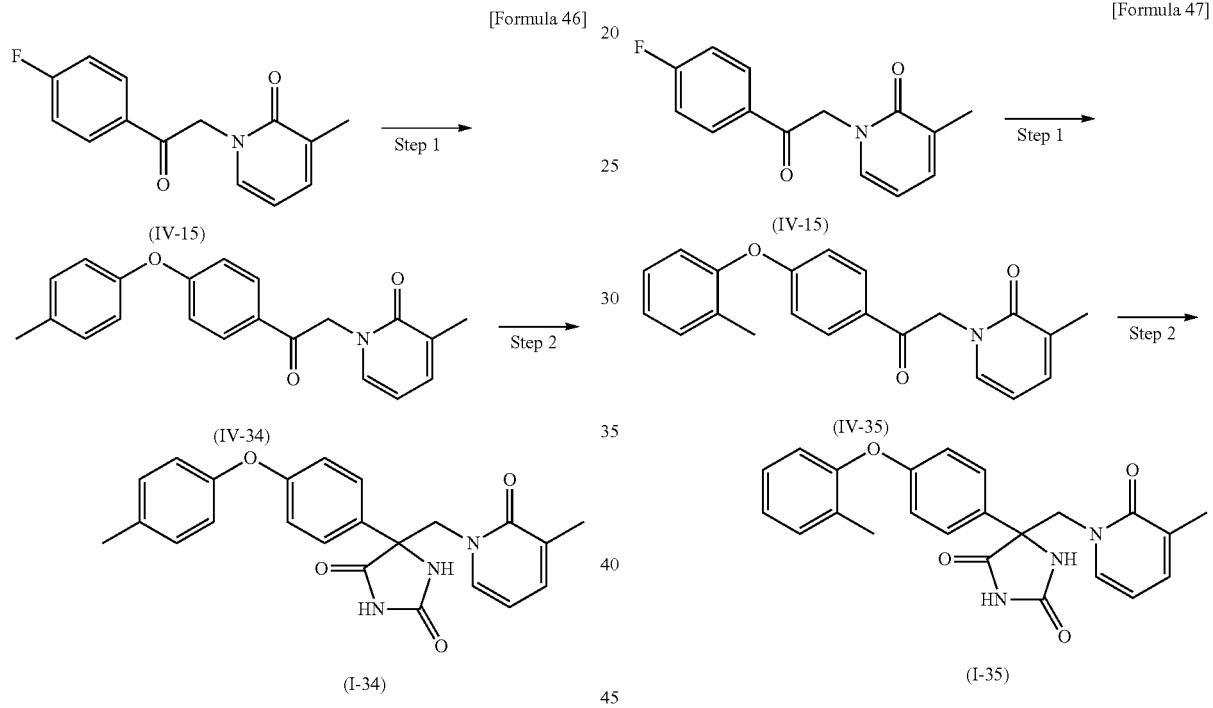

[Formula 46]

[Formula 47]

Step 1

A suspension of compound (IV-15) (150 mg, 0.61 mmol), 4-methylphenol (66 mg, 0.61 mmol), and potassium carbonate (127 mg, 0.92 mmol) in N,N-dimethylacetamide was heated under reflux for 3 hours. After leaving to cool, the reaction solution was diluted with water, and the resultant mixture was extracted with ethyl acetate. The organic layer was washed with saturated brine, and then dried over anhydrous magnesium sulfate. The solvent was removed under reduced pressure, and the resultant product was purified by column chromatography (silica gel) to obtain compound (IV-34) (amount 122 mg, yield 60%).

Step 2

An aqueous ammonia solution (28%, 0.35 mL) was added to a suspension of this compound (IV-34) (122 mg, 0.37 mmol), potassium cyanide (29 mg, 0.44 mmol), and ammonium carbonate (141 mg, 1.46 mmol) in ethanol (0.35 mL). The resultant mixture was sealed, and stirred for 63 hours at 100° C. After leaving to cool, the solvent was removed under reduced pressure, methanol was added, and the precipitated solid was removed by suction filtration. The filtrate solvent Step 1

Compound (IV-35) (amount 188 mg, yield 92%) was obtained as a green oily substance from compound (IV-15) based on the same production method as for compound (IV-34).

An aqueous ammonia solution (28%, 0.6 mL) was added to a suspension of this compound (IV-35) (188 mg, 0.56 mmol), potassium cyanide (44 mg, 0.68 mmol), and ammonium carbonate (217 mg, 2.27 mmol) in ethanol (0.6 mL). The resultant mixture was sealed, and stirred for 63 hours at 100° C. After leaving to cool, the reaction solution was diluted with water, and the precipitated solid was collected by filtration. The resultant product was purified by column chromatography (silica gel) to obtain compound (I-35) (amount 101 mg, yield 45%) as a colorless solid. The physical properties are shown below.

$^1$H-NMR (DMSO-d$_6$) δ: 1.99 (3H, s), 2.16 (3H, s), 4.45 (1H, d, J=13.3 Hz), 4.60 (1H, d, J=13.3 Hz), 6.11 (1H, t, J=6.4 Hz), 6.89-6.95 (3H, m), 7.14 (1H, dt, J=1.4, 7.2 Hz), 7.20-7.36 (4H, m), 7.59 (2H, td, J=2.5, 8.7 Hz), 8.55 (1H, s), 10.84 (1H, s).

MS (ESI-FTMS) m/z 404 [M+H]+.

Working Example 36

Production of 5-[4-(cyclohex-2-en-1-yloxy)phenyl]-5-[(3-methyl-2-oxopyridin-1(2H)-yl)methyl]imidazolidine-2,4-dione (I-36)

[Formula 48]

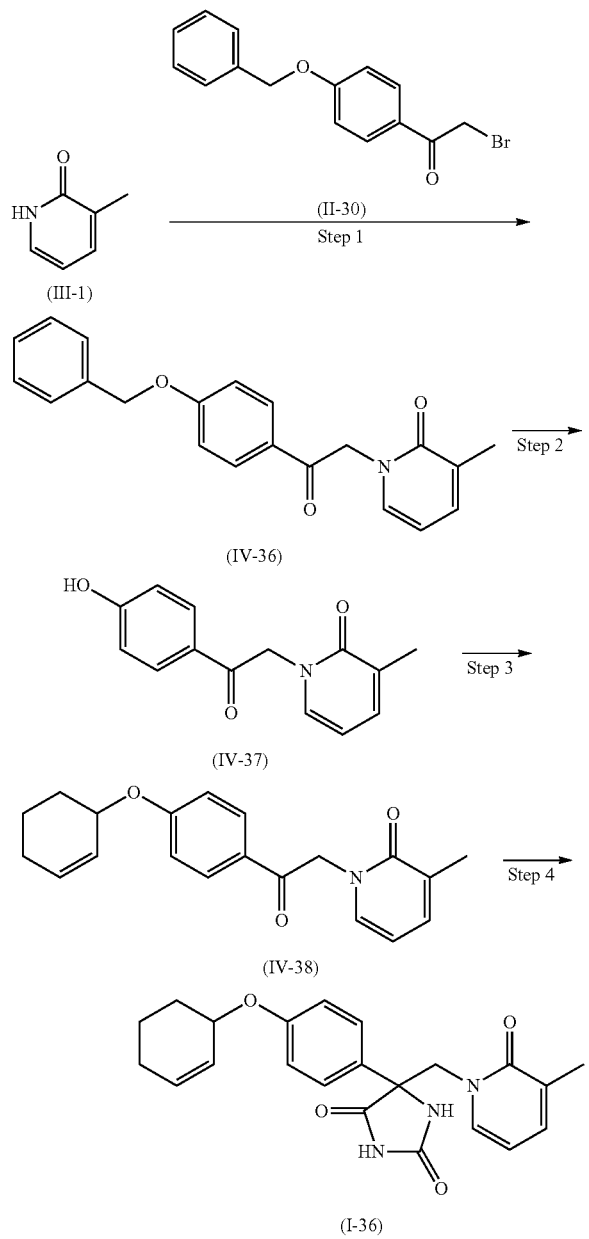

Step 1

Cesium carbonate (2.2 g, 6.9 mmol) and 1-[4-(benzyloxy)phenyl]-2-bromoethanone (II-30) (2.0 g, 6.6 mmol) were added to a solution of compound (III-1) (681 mg, 6.2 mmol) in N,N-dimethylformamide (20 mL), and the resultant mixture was stirred for 2.5 hours at room temperature. Water was added under ice cooling. The precipitated solid was collected by filtration, and the resultant product was washed with water to obtain compound (IV-36) (amount 1.9 g, yield 89%).

Step 2

Trifluoroacetic acid (10 mL) was added to a solution of this compound (IV-36) (1.3 g, 3.9 mmol) in chloroform (10 mL), and the resultant mixture was heated under reflux for 10 hours. After leaving to cool, the solvent was removed under reduced pressure and ethyl acetate was added. The precipitated solid was collected by filtration and washed with hexane to obtain compound (IV-37) (amount 813 mg, yield 86%).

Step 3

3-Bromocyclohexene (50 μL, 0.43 mmol) was added to a suspension of this compound (IV-37) (100 mg, 0.41 mmol) and potassium carbonate (85 mg, 0.62 mmol) in N,N-dimethylformamide (5.0 mL), and the resultant mixture was stirred for 23 hours at room temperature. The reaction solution was diluted with water, and the resultant mixture was extracted with ethyl acetate. The organic layer was washed with saturated brine, and then dried over anhydrous magnesium sulfate. The solvent was removed under reduced pressure, and the resultant product was purified by column chromatography (silica gel) to obtain compound (IV-38) (amount 115 mg, yield 86%) as a yellow amorphous substance.

Step 4

Compound (I-36) (amount 77 mg, yield 52%) was obtained as a colorless solid from compound (IV-38) based on the same production method as for compound (I-34). The physical properties are shown below.

$^1$H-NMR (DMSO-$d_6$) δ: 1.47-1.81 (3H, m), 1.85-2.16 (6H, m), 4.44 (1H, d, J=13.7 Hz), 4.53 (1H, d, J=13.3 Hz), 4.89 (1H, m), 5.79 (1H, m), 5.92 (1H, m), 6.11 (1H, t, J=6.9 Hz), 6.96-7.03 (2H, m), 7.17-7.32 (2H, m), 7.48-7.56 (2H, m), 8.51 (1H, d, J=1.4 Hz), 10.79 (1H, s).

MS (ESI-FTMS) m/z 394 [M+H]$^+$.

Working Example 37

Production of 5-[4-(cyclohexyloxy)phenyl]-5-[(3-methyl-2-oxopyridin-1(2H)-yl)methyl]imidazolidine-2,4-dione (I-37)

[Formula 49]

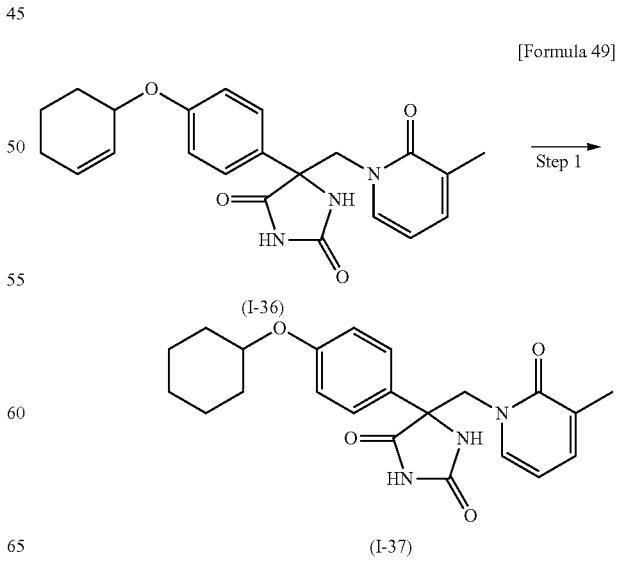

Step 1

To a solution of compound (I-36) (50 mg, 0.13 mmol) in methanol (2.0 mL) was added 10% palladium carbon (20 mg), and the resultant mixture was stirred for 4 hours under a hydrogen atmosphere. The reaction solution was filtered through a pad of Celite, and the pad was washed with methanol. The solvent was removed under reduced pressure, and the resultant product was purified by column chromatography (silica gel) to obtain compound (I-37) (amount 36 mg, yield 72%) as a colorless solid. The physical properties are shown below.

$^1$H-NMR (DMSO-$d_6$) δ: 1.20-1.46 (5H, m), 1.48-1.58 (1H, m), 1.66-1.76 (2H, m), 1.87-1.95 (2H, m), 1.99 (3H, s), 4.32-4.40 (1H, m), 4.43 (1H, d, J=13.7 Hz), 4.56 (1H, d, J=13.7 Hz), 6.11 (1H, t, J=6.9 Hz), 6.97 (2H, d, J=8.7 Hz), 7.20-7.33 (2H, m), 7.50 (2H, d, J=8.7 Hz), 8.50 (1H, s), 10.78 (1H, s).

MS (ESI-FTMS) m/z 396 [M+H]$^+$.

Working Example 38

Production of 5-[4-(cyclohex-2-en-1-yloxy)-1-methylphenyl]-5-[(3-methyl-2-oxopyridin-1(2H)-yl)methyl]imidazolidine-2,4-dione (I-38)

[Formula 50]

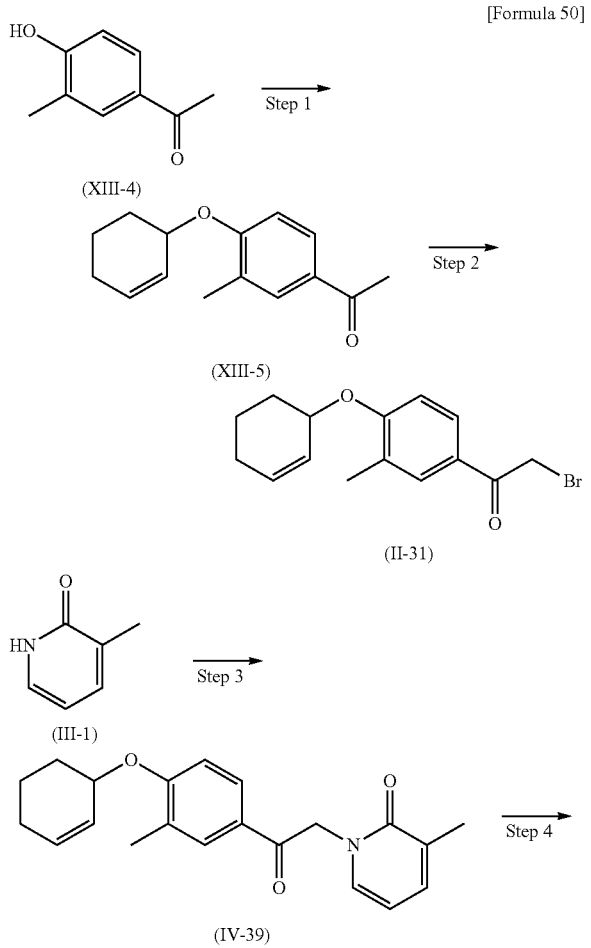

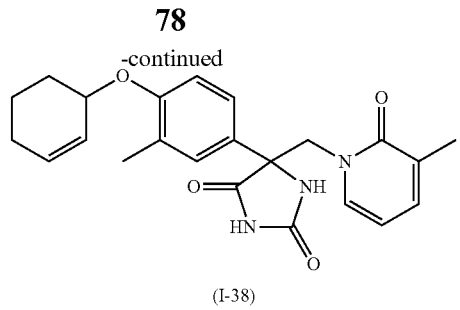

(I-38)

Step 1

To a solution of 1-(4-hydroxy-3-methylphenyl)ethanone (XIII-4) (1.2 g, 8.0 mmol) in N,N-dimethylformamide (10 mL) was added 60% sodium hydride (384 mg, 9.6 mmol), and the resultant mixture was stirred for 30 minutes at room temperature. 3-Bromocyclohexene (1.5 g, 9.6 mmol) was added, and the resultant mixture was stirred overnight at room temperature. Ice water was added to stop the reaction, and the mixture was extracted with ethyl acetate. The organic layer was washed with water, and then dried over anhydrous sodium sulfate. The solvent was removed under reduced pressure, and the resultant product was purified by column chromatography (silica gel) to obtain compound (XIII-5) (amount 1.71 g, yield 88%).

Step 2

Phenyltrimethylammonium tribromide (1.7 g, 4.0 mmol) was added to a solution of compound (XIII-5) (1.0 g, 4.1 mmol) in tetrahydrofuran (40 mL), and the resultant mixture was stirred for 2 hours at room temperature, and then heated under reflux for 4 hours. After leaving to cool, the precipitated solid was collected by filtration, and the filtrate solvent was removed to obtain a crude compound (II-31) (amount 1.2 g).

Step 3

Cesium carbonate (1.5 g, 4.1 mmol) and the crude compound (II-31) (1.2 g) were added to a solution of compound (III-1) (407 mg, 3.7 mmol) in N,N-dimethylformamide (7.5 mL), and the resultant mixture was stirred overnight at room temperature. The reaction solution was diluted with water, and the resultant mixture was extracted with ethyl acetate. The organic layer was washed with saturated brine, and then dried over anhydrous sodium sulfate. The solvent was removed under reduced pressure, and the resultant product was purified by column chromatography (silica gel) to obtain compound (IV-39) (amount 449 mg, two steps, cumulative yield 33%).

Step 4

An aqueous ammonia solution (28%, 1.5 mL) was added to a suspension of this compound (IV-39) (449 mg, 1.3 mmol), potassium cyanide (130 mg, 2.0 mmol), and ammonium carbonate (511 mg, 5.3 mmol) in ethanol (1.5 mL). The resultant mixture was sealed, and stirred at 100° C. After leaving to cool, water was added to the reaction solution, and the mixture was extracted with ethyl acetate. The organic layer was then washed with water, and dried over anhydrous sodium sulfate. The solvent was removed under reduced pressure to obtain compound (I-38) (amount 410 mg, yield 76%). The physical properties are shown below.

$^1$H-NMR (CDCl$_3$) δ: 1.58-1.97 (4H, m), 2.08-2.18 (2H, m), 2.13 (3H, s), 2.23 (3H, s), 4.20 (1H, d, J=13.7 Hz), 4.78 (1H, m), 4.85 (1H, d, J=13.7 Hz), 5.85 (1H, m), 5.96 (1H, m), 6.09 (1H, t, J=6.9 Hz), 6.88 (1H, d, J=8.7 Hz), 6.93 (1H, s), 7.14 (1H, d, J=6.9 Hz), 7.20 (1H, d, J=6.9 Hz), 7.34-7.41 (2H, m).

MS (ESI-FTMS) m/z 408 [M+H]$^+$.

Working Example 39

Production of 5-[4-(cyclopentyloxy)-3-methylphenyl]-5-[(3-methyl-2-oxopyridin-1(2H)-yl)methyl]imidazolidine-2,4-dione (I-39)

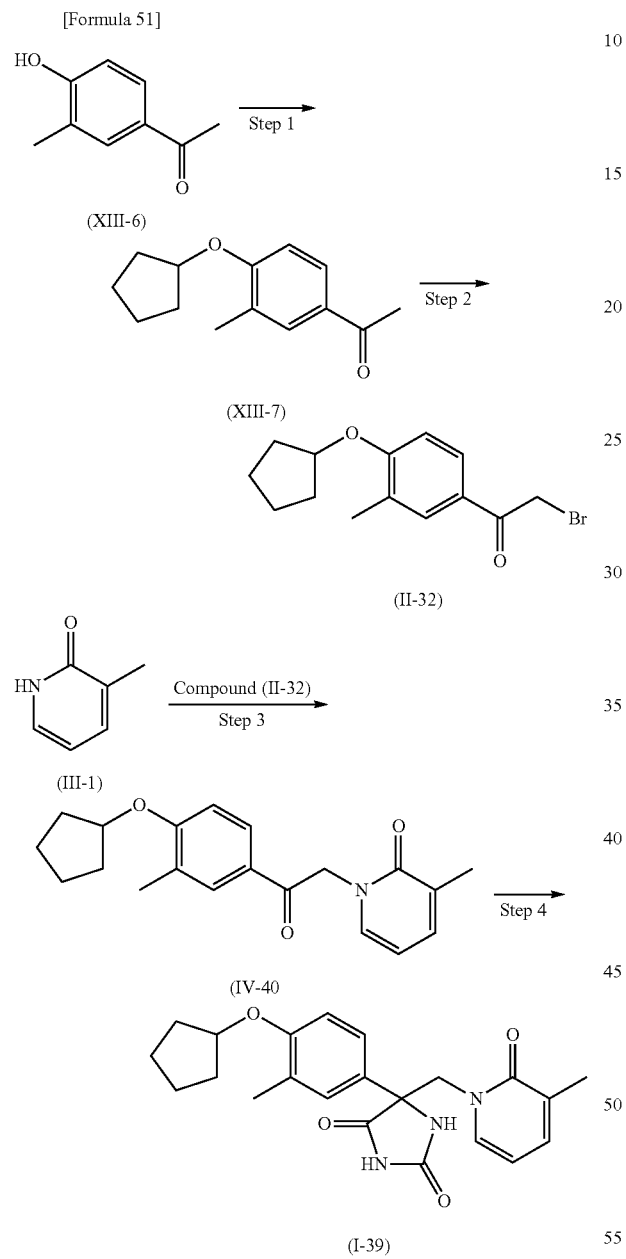

Step 1

To a solution of compound (XIII-6) (800 mg, 5.3 mmol) in N,N-dimethylformamide (8.0 mL) was added 60% sodium hydride (235 mg, 5.9 mmol), and the resultant mixture was stirred at room temperature. Cyclopentyl iodide (1.2 g, 5.9 mmol) was added, the resultant mixture was stirred for 3 hours at 60° C., and then for 4 hours at 80° C. Ice water was added to stop the reaction, and the mixture was then extracted with ethyl acetate. The organic layer was washed with water, and dried over anhydrous sodium sulfate. The solvent was removed under reduced pressure, and the resultant product was purified by column chromatography (silica gel) to obtain compound (XIII-7) (amount 635 mg, yield 52%).

Compound (I-39) (amount 490 mg, three steps, cumulative yield 45%) was obtained from this compound (XIII-7) in three steps based on the same production method (step 2 to step 4 of Working Example 38) as for compound (I-38) of Working Example 38. The physical properties are shown below.

$^1$H-NMR (CDCl$_3$) δ: 1.57-1.94 (8H, m), 2.13 (3H, s), 2.19 (3H, s), 4.20 (1H, d, J=13.7 Hz), 4.77 (1H, m), 4.85 (1H, d, J=13.7 Hz), 6.08 (1H, t, J=6.9 Hz), 6.81 (1H, d J=9.2 Hz), 6.90 (1H, br s), 7.14 (1H, d, J=6.9 Hz), 7.20 (1H, d, J=6.9 Hz), 7.34-7.36 (1H, m), 7.37 (1H, s).

MS (ESI-FTMS) m/z 396 [M+H]$^+$.

Working Example 40

Production of 5-(4-benzylphenyl)-5-[(3-methyl-2-oxopyridin-1(2H)-yl)methyl]imidazolidine-2,4-dione (I-40)

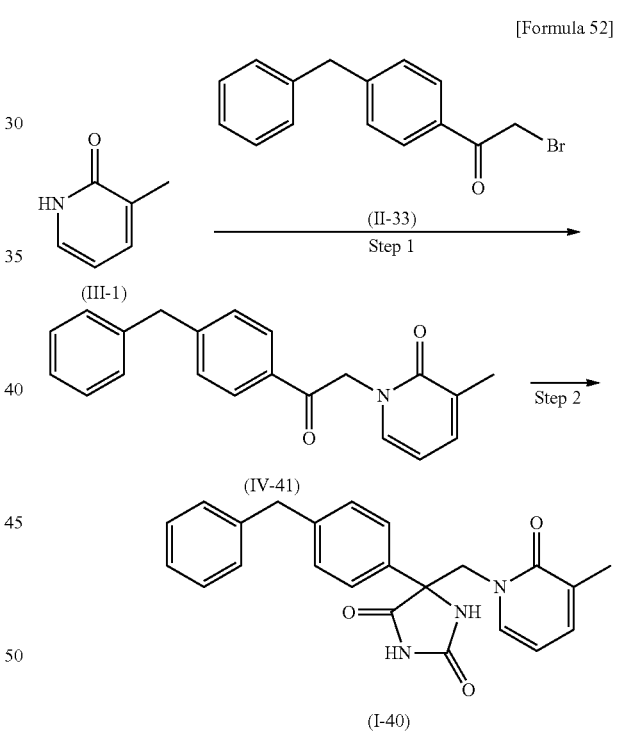

Step 1

Cesium carbonate (590 mg, 1.8 mmol) and 1-(4-benzylphenyl)-2-bromoethanone (II-33) (500 mg, 1.7 mmol) were added to a solution of compound (III-1) (180 mg, 1.6 mmol) in N,N-dimethylformamide (5.0 mL), and the resultant mixture was stirred for 3 hours at room temperature. Water was added to the reaction solution. The precipitated solid was collected by filtration and washed with water to obtain compound (IV-41) (amount 475 mg, yield 91%).

Step 2

An aqueous ammonia solution (28%, 1.5 mL) was added to a suspension of this compound (IV-41) (475 mg, 1.5 mmol), potassium cyanide (117 mg, 1.8 mmol), and ammonium carbonate (575 mg, 6.0 mmol) in ethanol (1.5 mL). The resultant mixture was sealed, and stirred for 64 hours at 100° C. After leaving to cool, water was added to the reaction solution, and the mixture was extracted with ethyl acetate. The organic layer was then washed with water, and dried over anhydrous sodium sulfate. The solvent was then removed under reduced pressure, and the resultant product was purified by column chromatography (silica gel) to obtain compound (I-40) (amount 466 mg, yield 80%) as a colorless solid. The physical properties are shown below.

$^1$H-NMR (DMSO-$d_6$) δ: 1.99 (3H, s), 3.95 (2H, s), 4.43 (1H, d, J=13.7 Hz), 4.59 (1H, d, J=13.7 Hz), 6.10 (1H, t, J=6.6 Hz), 7.15-7.31 (9H, m), 7.53 (2H, d, J=8.7 Hz), 8.52 (1H, s), 10.81 (1H, s).

MS (ESI-FTMS) m/z 388 [M+H]$^+$.

Working Example 41

Production of 5-[4-(4-fluorobenzyl)phenyl]-5-[(3-methyl-2-oxopyridin-1(2H)-yl)methyl] imidazolidine-2,4-dione (I-41)

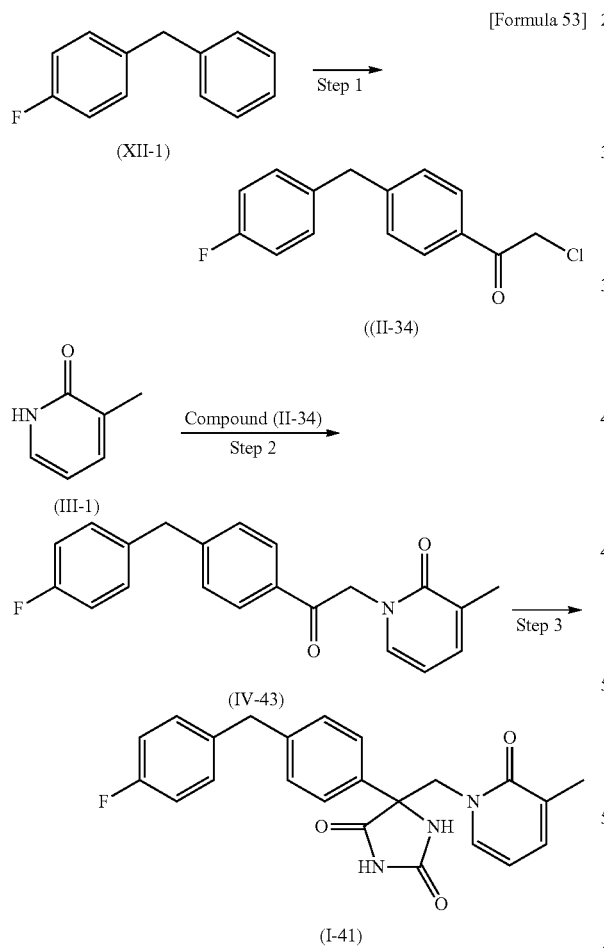

[Formula 53]

Step 1

Under ice cooling, chloroacetyl chloride (427 μL, 5.4 mmol) and aluminium chloride (716 mg, 5.4 mmol) were added to a solution of 1-benzyl-4-fluorobenzene (XII-1) (1.0 g, 5.4 mmol) in dichloromethane (5.4 mL), and the resultant mixture was stirred for 15 minutes. After adding water to the reaction solution and extracting with chloroform, the mixture was successively washed with saturated sodium bicarbonate water and saturated brine, and dried over anhydrous sodium sulfate. The solvent was removed under reduced pressure to obtain a crude compound (II-34).

Step 2

The crude compound (II-34) was dissolved in N,N-dimethylformamide (3.0 mL). After adding potassium carbonate (1.9 g, 13.4 mmol), a solution of compound (III-1) (586 mg, 5.4 mmol) in N,N-dimethylformamide (2.4 mL) was added dropwise, and the resultant mixture was stirred for 2 hours at room temperature. The reaction solution was diluted with water, and the resultant mixture was extracted with ethyl acetate. The organic layer was washed with saturated brine, and dried over sodium sulfate. The solvent was then removed under reduced pressure, and the resultant product was purified by column chromatography (silica gel) to obtain compound (IV-43) (amount 1.5 g, two steps, yield 84%).

Step 3

Water (4.2 mL) was added to a suspension of this compound (IV-43) (1.4 g, 4.2 mmol), potassium cyanide (326 mg, 5.0 mmol), and ammonium carbonate (1.6 g, 16.7 mmol) in ethanol (4.2 mL). The resultant mixture was sealed, and stirred for 16 hours at 100° C. After leaving to cool, water was added to the reaction solution. The precipitated solid was collected by filtration, and washed with chloroform to obtain compound (I-41) (amount 1.6 g, yield 95%). The physical properties are shown below.

$^1$H-NMR (DMSO-$d_6$) δ: 1.99 (3H, s), 3.94 (2H, s), 4.44 (1H, d, J=13.3 Hz), 4.60 (1H, d, J=13.7 Hz), 6.10 (1H, t, J=6.7 Hz), 7.10 (2H, t, J=9.0 Hz), 7.20-7.32 (6H, m), 7.54 (2H, d, J=8.2 Hz), 8.51 (1H, s), 10.81 (1H, s).

MS (ESI-FTMS) m/z 406 [M+H]$^+$.

Working Example 42

Production of 5-[4-(2H-tetrazol-5-yl)phenyl]-5-[(3-methyl-2-oxopyridin-1(2H)-yl)methyl]imidazolidine-2,4-dione (I-42)

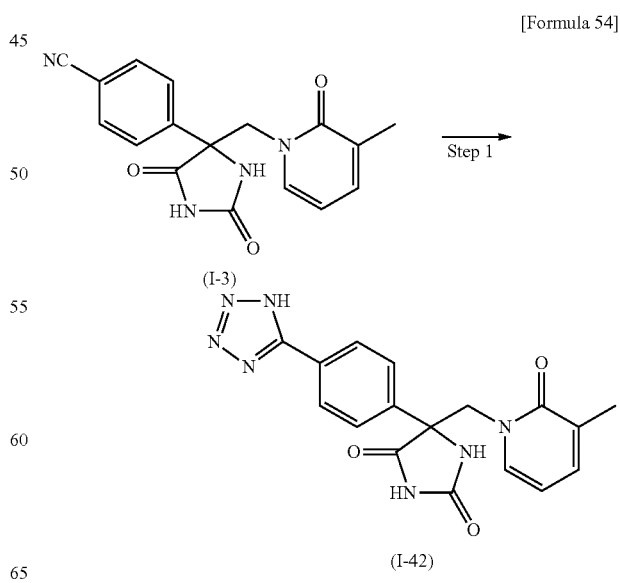

[Formula 54]

Step 1

N,N-dimethylformamide (3.4 mL) was added to compound (I-3) (221 mg, 0.69 mmol), ammonium chloride (110 mg, 2.06 mmol), and sodium azide (124 mg, 2.06 mmol), and the resultant mixture was heated and stirred for 1 hour at 80° C., and for 12.5 hours at 110° C. After leaving the reaction solution to cool, 2 mol/L hydrochloric acid was added, and the precipitated solid was collected by filtration. The resultant solid was dissolved, and then purified by silica gel column chromatography to obtain compound (I-42) (amount 101 mg, yield 40%). The physical properties are shown below.

$^1$H-NMR (DMSO-$d_6$) δ: 2.00 (3H, s), 4.51 (1H, d, J=13.7 Hz), 4.72 (1H, d, J=13.7 Hz), 6.13 (1H, t, J=6.9 Hz), 7.30 (2H, d, J=6.4 Hz), 7.86 (2H, d, J=8.7 Hz), 8.10 (2H, d, J=8.7 Hz), 8.68 (1H, d, J=1.4 Hz), 10.56 (1H, s).

MS (ESI-FTMS) m/z: 366 [M+H]$^+$.

Working Example 43

Production of 5-[(3-methyl-2-oxopyridin-1(2H)-yl) methyl]-5-(4-vinylphenyl)imidazolidine-2,4-dione (I-43)

[Formula 55]

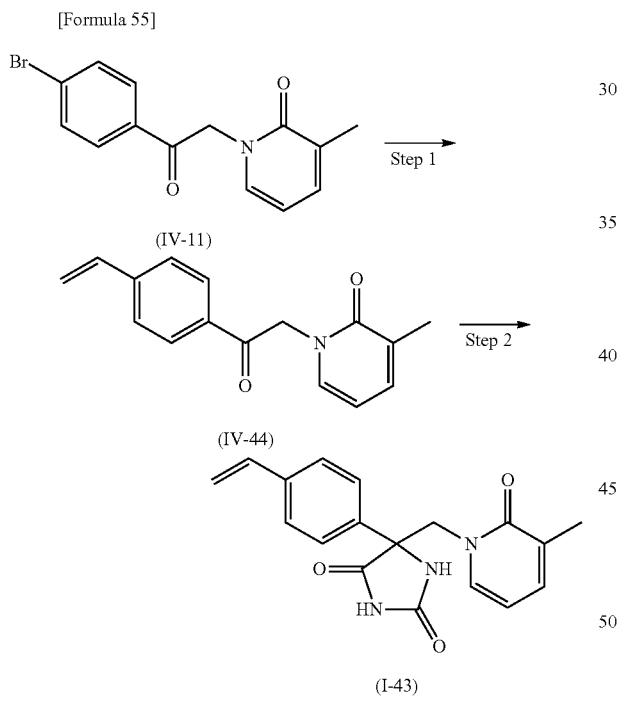

Step 1

A suspension of compound (IV-11) (400 mg, 1.3 mmol), 4,4,5,5-tetramethyl-2-vinyl-1,3,2-dioxaborolane (242 mg, 1.6 mmol), and tripotassium phosphate (695 mg, 3.3 mmol) in 1,4-dioxane (6.5 mL) was degassed. Then, under an argon atmosphere, tetrakis(triphenylphosphine)palladium (76 mg, 0.066 mmol) was added, and the resultant mixture was heated and stirred at 90° C. After confirming the completion of the reaction by TLC, water was added to the reaction solution, and the resultant mixture was extracted with ethyl acetate. The organic layer was washed with saturated brine, and then dried over anhydrous sodium sulfate. The solvent was removed under reduced pressure, and the resultant residue was purified by column chromatography (silica gel) to obtain compound (IV-44) (amount 253 mg, yield 76%).

Step 2

Compound (I-43) (amount 182 mg, yield 59%) was obtained from compound (IV-44) based on the same production method as for compound (I-17). The physical properties are shown below.

$^1$H-NMR (DMSO-$d_6$) δ: 2.00 (3H, s), 4.47 (1H, d, J=13.3 Hz), 4.62 (1H, d, J=13.7 Hz), 5.31 (1H, d, J=11.4 Hz), 5.89 (1H, d, J=17.9 Hz), 6.11 (1H, t, J=6.9 Hz), 6.75 (1H, dd, J=10.8, 17.7 Hz), 7.27 (2H, dd, J=6.7, 11.7 Hz), 7.53 (2H, d, J=8.7 Hz), 7.60 (2H, d, J=8.7 Hz), 8.58 (1H, s), 10.85 (1H, s).

MS (ESI-FTMS) m/z 324 [M+H]$^+$.

Working Example 44

Production of 5-[(3-methyl-2-oxopyridin-1(2H)-yl) methyl]-5-(3,4,5-trifluorophenyl)imidazolidine-2,4-dione (I-44)

[Formula 56]

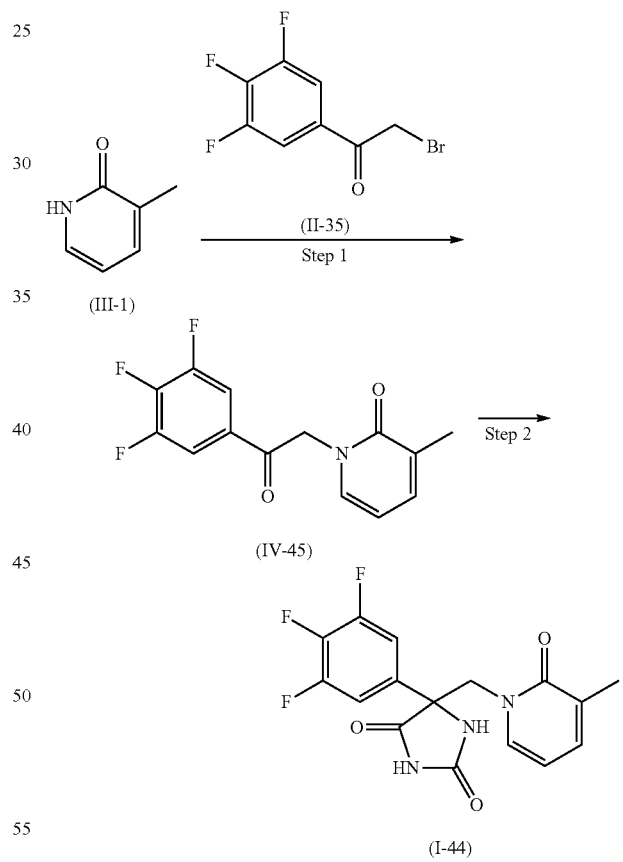

Step 1

Compound (IV-45) (amount 189 mg, yield 19%) was obtained from compound (III-1) and 2-bromo-3',4',5'-trifluoroacetophenone (II-35) based on the same production method as for compound (IV-3).

Step 2

Compound (I-44) (amount 158 mg, yield 70%) was obtained as a pale yellow solid from compound (IV-45) based on the same production method as for compound (I-11).

$^1$H-NMR (DMSO-d$_6$) δ: 1.98 (3H, s), 4.47 (1H, m), 4.61 (1H, d, J=13.7 Hz), 6.14 (1H, t, J=6.9 Hz), 7.22-7.33 (2H, m), 7.48-7.65 (2H, m), 8.64 (1H, br s), 11.07 (1H, br s).
MS (ESI-FTMS) m/z 352 [M+H]$^+$.

Working Example 45

Production of 5-[(3-methyl-2-oxopyridin-1(2H)-yl)methyl]-5-(4-propylphenyl)imidazolidine-2,4-dione (I-45)

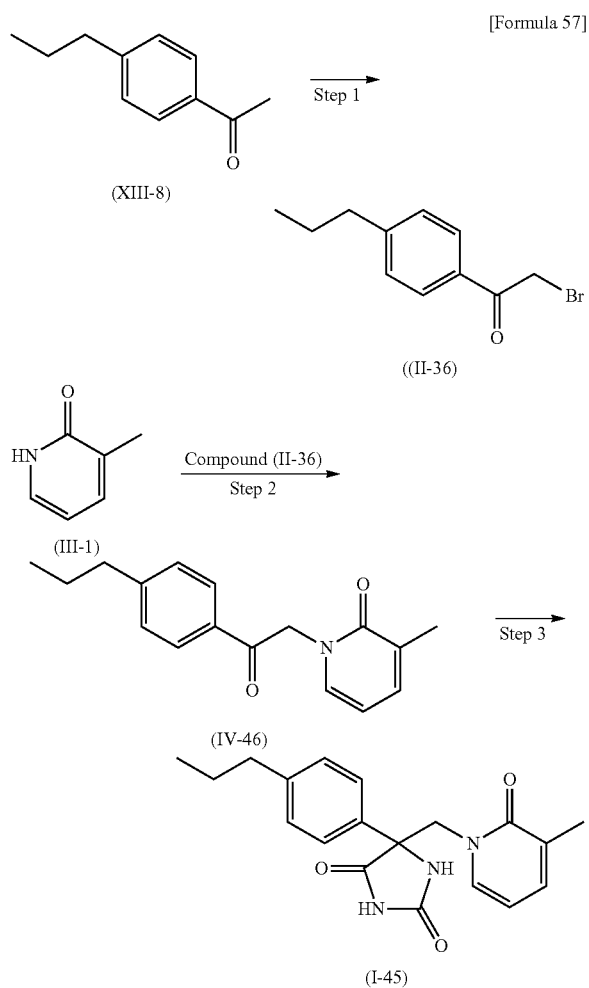

Step 1
Compound (II-36) (amount 743 mg, yield>99%) was obtained as a colorless oily substance from 4'-propylacetophenone (XIII-8) based on the same production method as for compound (II-21).

Step 2
Compound (IV-46) (amount 294 mg, yield 69%) was obtained from compound (III-1) and compound (II-36) based on the same production method as for compound (IV-4).

Step 3
Compound (I-45) (amount 21 mg, yield 5.8%) was obtained as a colorless solid from compound (IV-46) based on the same production method as for compound (IV-24). The physical properties are shown below.

$^1$H-NMR (DMSO-d$_6$) δ: 0.88 (3H, t, J=7.3 Hz), 1.58 (2H, sext, J=7.3 Hz), 2.00 (3H, s), 2.56 (2H, t, J=7.6 Hz), 4.45 (1H, d, J=13.7 Hz), 4.60 (1H, d, J=13.7 Hz), 6.11 (1H, t, J=6.6 Hz), 7.18-7.31 (4H, m), 7.52 (2H, d, J=8.7 Hz), 8.52 (1H, s), 10.80 (1H, s).
MS (ESI-FTMS) m/z 340 [M+H]$^+$.

Working Example 46

Production of 5-[(2-oxopyridin-1(2H)-yl)methyl]-5-phenylimidazolidine-2,4-dione (I-46)

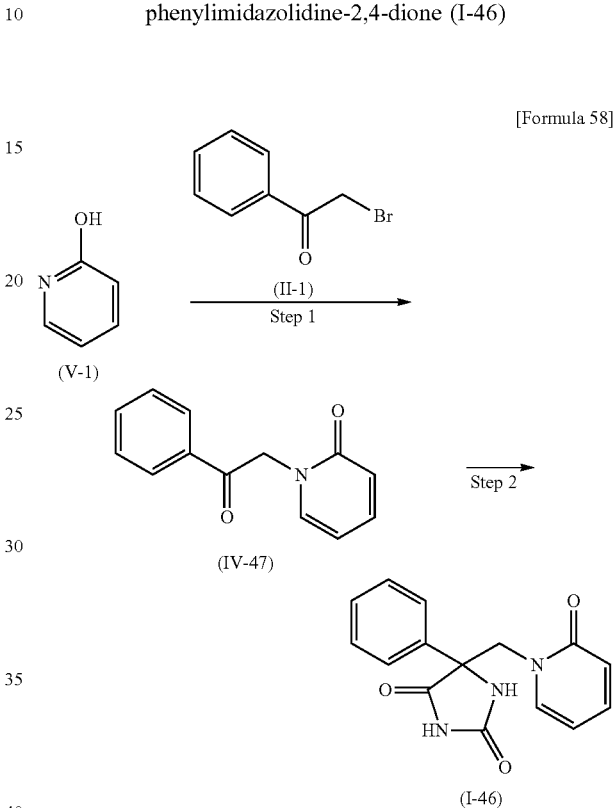

Step 1
N,N-dimethylformamide (6.3 mL) was added to pyridin-2-ol (V-1) (300 mg, 3.15 mmol) and cesium carbonate (1.13 g, 3.47 mmol), and then compound (II-1) (691 mg, 3.47 mmol) was added, and the resultant mixture was stirred for 1 hour at room temperature. Water was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-47) (amount 602 mg, yield 90%).

Step 2
An autoclave was charged with this compound (IV-47) (300 mg, 1.41 mmol), potassium cyanide (110 mg, 1.69 mmol), ammonium carbonate (542 mg, 5.64 mmol), ethanol (1.4 mL), and water (1.4 mL). The autoclave was sealed, and the mixture was stirred for 21.5 hours at 100° C. Water was added to the reaction solution, and the precipitated solid was collected by filtration to obtain compound (I-46) (amount 226 mg, yield 57%). The physical properties are shown below.

$^1$H-NMR (DMSO-d$_6$) δ: 4.25 (1H, d, J=13.7 Hz), 4.65 (1H, d, J=13.7 Hz), 6.19 (1H, dt, J=1.4, 6.9 Hz), 6.39 (1H, dt, J=1.4, 8.7 Hz), 7.35-7.48 (5H, m), 7.60-7.66 (2H, m), 8.58 (1H, s), 10.85 (1H, s).
MS (ESI-FTMS) m/z: 284 [M+H]$^+$.

Working Example 47

Production of 5-(4-methoxyphenyl)-5-[(2-oxopyridin-1(2H)-yl)methyl]imidazolidine-2,4-dione (I-47)

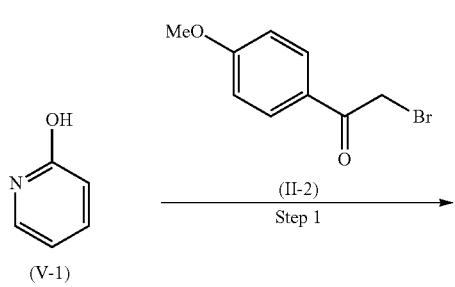

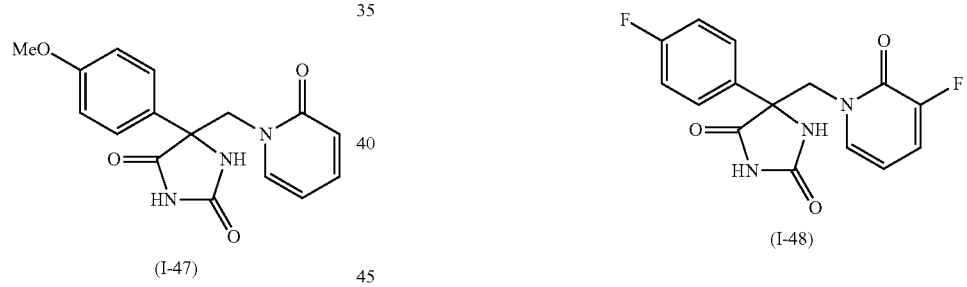

Step 1
Compound (IV-48) (amount 384 mg, yield 90%) was obtained from compound (V-1) and compound (II-2) based on the same production method as for compound (IV-47).

Step 2
An autoclave was charged with this compound (IV-48) (300 mg, 1.23 mmol), potassium cyanide (96 mg, 1.48 mmol), ammonium carbonate (474 mg, 4.93 mmol), ethanol (1.2 mL), and saturated ammonia water (1.2 mL). The autoclave was sealed, and the mixture was stirred for 63.75 hours at 100° C. Water was added to the reaction solution, the precipitated solid was collected by filtration, and the collected solid was washed with chloroform to obtain compound (I-47) (amount 112 mg, yield 29%).

$^1$H-NMR (DMSO-d$_6$) δ: 3.76 (3H, s), 4.42 (1H, d, J=13.7 Hz), 4.58 (1H, d, J=13.7 Hz), 6.19 (1H, dt, J=1.4, 6.9 Hz), 6.39 (1H, d, J=9.2 Hz), 6.99 (2H, d, J=9.2 Hz), 7.35-7.43 (2H, m), 7.53 (2H, d, J=9.2 Hz), 8.53 (1H, s), 10.81 (1H, s).

MS (ESI-FTMS) m/z: 314 [M+H]$^+$.

Working Example 48

Production of 5-[(3-fluoro-2-oxopyridin-1(2H)-yl)methyl]-5-(4-fluorophenyl)-imidazolidine-2,4-dione (I-48)

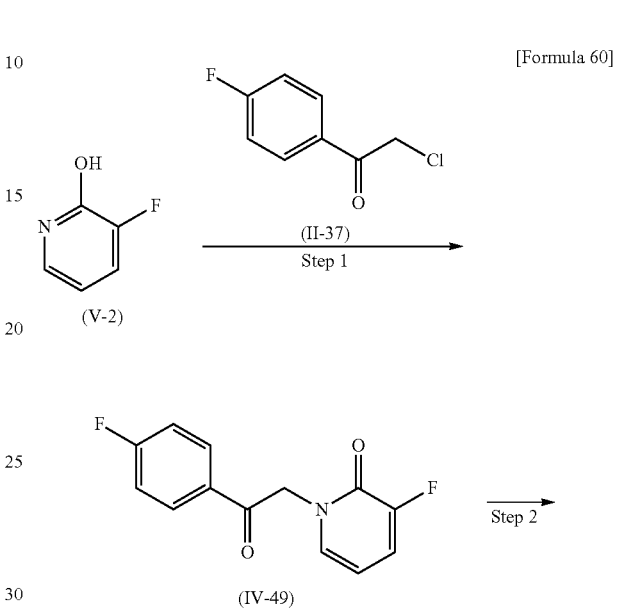

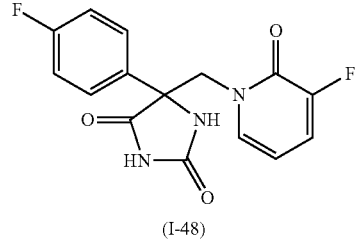

Step 1
Acetone (6.3 mL) was added to 3-fluoropyridin-2-ol (V-2) (300 mg, 3.15 mmol) and potassium carbonate (1.13 g, 3.47 mmol), and then 2-chloro-1-(4-fluorophenyl)ethanone (II-37) (691 mg, 3.47 mmol) was added, and the resultant mixture was heated under reflux for 1 hour. The reaction solution was filtered, and then the solvent was removed under reduced pressure. The resultant product was purified by silica gel column chromatography to obtain compound (IV-49) (amount 395 mg, yield 90%).

Step 2
Compound (I-48) (amount 166 mg, yield 43%) was obtained from compound (IV-49) based on the same production method as for compound (I-46). The physical properties are shown below.

$^1$H-NMR (DMSO-d$_6$) δ: 4.48 (1H, d, J=13.3 Hz), 4.72 (1H, d, J=13.7 Hz), 6.19 (1H, dt, J=4.6, 7.3 Hz), 7.19-7.24 (1H, m), 7.26-7.34 (2H, m), 7.40 (1H, ddd, J=1.6, 7.6, 9.4 Hz), 7.63-7.70 (2H, m), 8.77 (1H, s), 10.96 (1H, s).

MS (ESI-FTMS) m/z: 320 [M+H]$^+$.

Working Example 49

Production of 5-([1,1'-biphenyl]-4-yl)-5-[(3-fluoro-2-oxopyridin-1(2H)-yl)methyl]imidazolidine-2,4-dione (I-49)

[Formula 61]

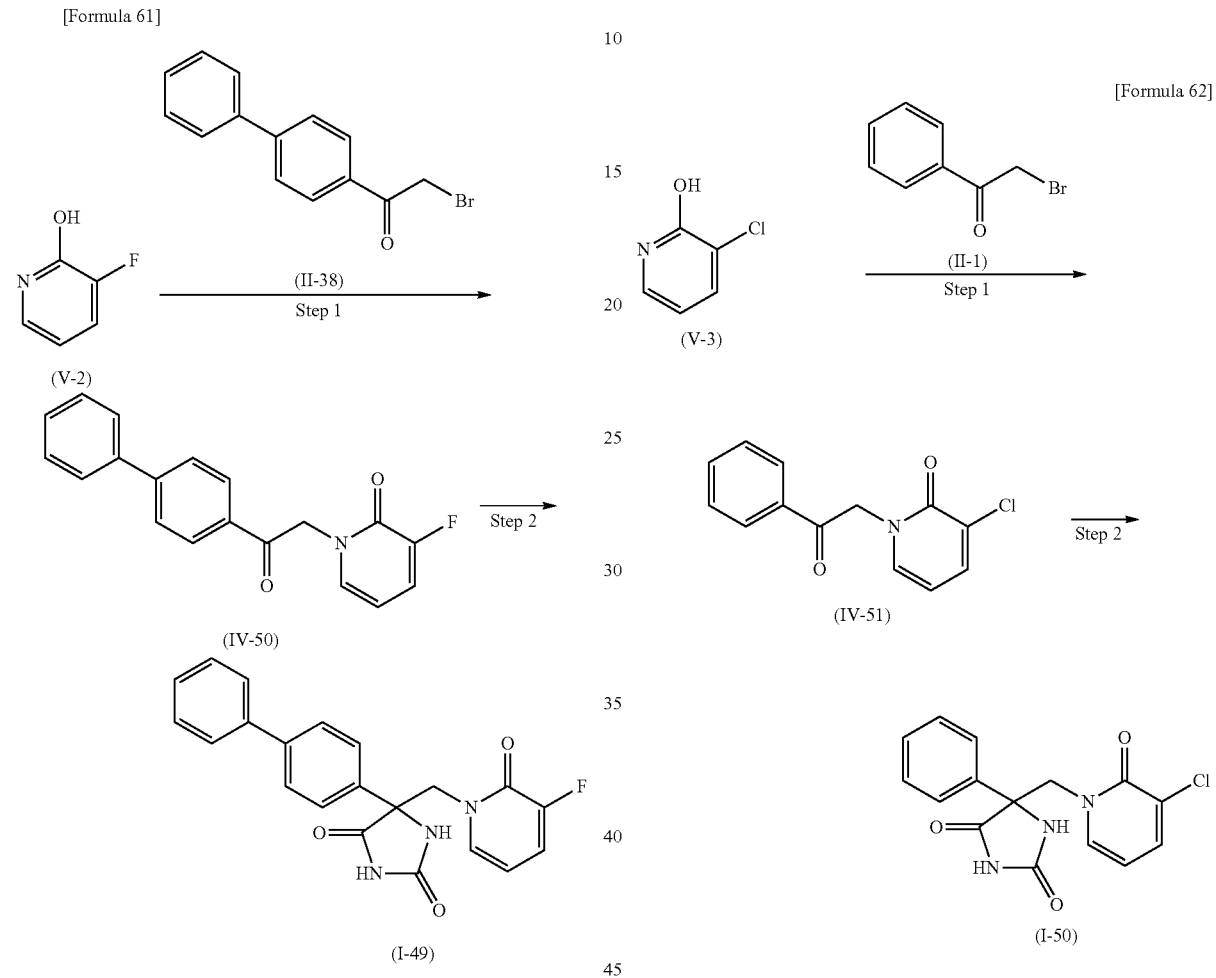

Step 1

Dimethyl sulfoxide (3.6 mL) was added to compound (V-2) (226 mg, 2.00 mmol) and potassium carbonate (628 mg, 4.54 mmol), and then 1-([1,1'-biphenyl]-4-yl)-2-bromoethanone (II-38) (500 mg, 1.87 mmol) was added, and the resultant mixture was stirred for 1.25 hours at room temperature. Water was added to the reaction solution and the precipitated solid was collected by filtration to obtain compound (IV-50) (amount 665 mg, quantitative yield).

Step 2

An autoclave was charged with this compound (IV-50) (300 mg, 0.98 mmol), potassium cyanide (76 mg, 1.17 mmol), ammonium carbonate (375 mg, 3.90 mmol), ethanol (0.98 mL), and water (0.98 mL). The autoclave was sealed, and the mixture was stirred for 43 hours at 100° C. Water was added to the reaction solution, the precipitated solid was collected by filtration, and the collected solid was washed with chloroform to obtain compound (I-49) (amount 176 mg, yield 48%).

$^1$H-NMR (DMSO-$d_6$) δ: 4.54 (1H, d, J=13.7 Hz), 4.79 (1H, d, J=13.7 Hz), 6.21 (1H, dt, J=4.6, 6.9 Hz), 7.26 (1H, d, J=7.3 Hz), 7.36-7.58 (4H, m), 7.67-7.84 (6H, m), 8.80 (1H, s), 10.96 (1H, s). MS (ESI-FTMS) m/z: 378 [M+H]$^+$.

Working Example 50

Production of 5-[(3-chloro-2-oxopyridin-1(2H)-yl)methyl]-5-phenylimidazolidine-2,4-dione (I-50)

[Formula 62]

Step 1

Compound (IV-51) (amount 529 mg, yield 92%) was obtained from 3-chloropyridin-2-ol (V-3) and compound (II-1) based on the same production method as for compound (IV-47).

Step 2

An autoclave was charged with this compound (IV-51) (300 mg, 1.21 mmol), potassium cyanide (95 mg, 1.45 mmol), ammonium carbonate (465 mg, 4.84 mmol), ethanol (1.2 mL), and water (1.2 mL). The autoclave was sealed, and the mixture was stirred for 62.25 hours at 100° C. The solvent was removed under reduced pressure, and the resultant product was purified by silica gel column chromatography to obtain compound (I-50) (amount 323 mg, yield 84%). The physical properties are shown below.

$^1$H-NMR (DMSO-$d_6$) δ: 4.49 (1H, d, J=13.7 Hz), 4.76 (1H, d, J=13.7 Hz), 6.24 (1H, t, J=7.1 Hz), 7.36-7.49 (4H, m), 7.59-7.66 (2H, m), 7.75 (1H, dd, J=1.8, 7.3 Hz), 8.68 (1H, s), 10.91 (1H, s).

MS (ESI-FTMS) m/z: 318, 320 [M+H]$^+$.

Working Example 51

Production of 5-(benzofuran-2-yl)-5-[(3-chloro-2-oxopyridin-1(2H)-yl)methyl]imidazolidine-2,4-dione (I-51)

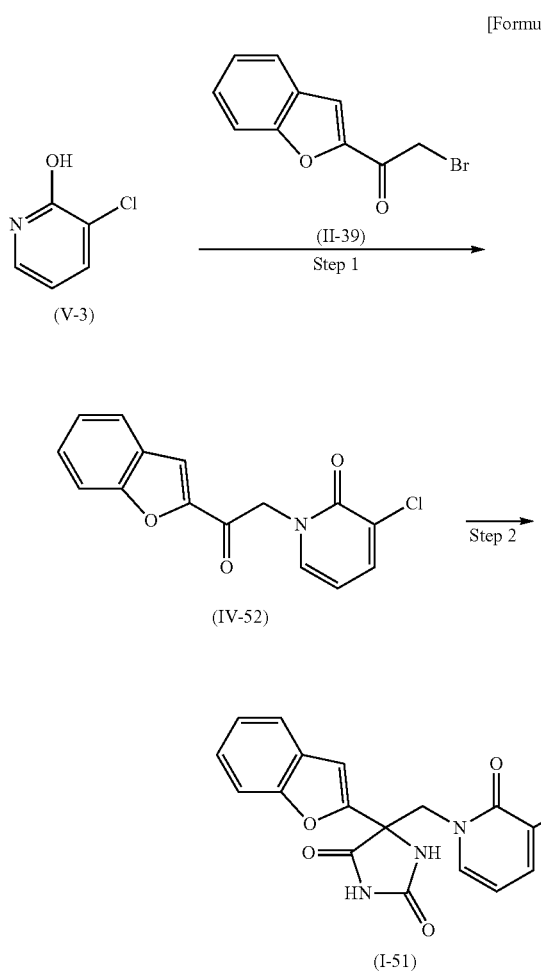

Step 1

Compound (IV-52) (amount 277 mg, yield 50%) was obtained from compound (V-3) and 1-benzofuran-2-yl-2-bromoethanone (II-39) based on the same production method as for compound (IV-50).

An autoclave was charged with this compound (IV-52) (250 mg, 0.87 mmol), potassium cyanide (68 mg, 1.04 mmol), ammonium carbonate (334 mg, 3.48 mmol), ethanol (0.87 mL), and saturated ammonia water (0.87 mL). The autoclave was sealed, and the mixture was stirred for 64.75 hours at 100° C. The solvent was removed under reduced pressure, and the resultant product was purified by silica gel column chromatography to obtain compound (I-51) (amount 163 mg, yield 52%). The physical properties are shown below.

$^1$H-NMR (DMSO-$d_6$) δ: 4.81 (2H, s), 6.26 (1H, t, J=7.1 Hz), 7.14 (1H, s), 7.29 (1H, dt, J=0.9, 7.3 Hz), 7.37 (1H, dt, J=1.3, 7.3 Hz), 7.46 (1H, dd, J=2.1, 7.6 Hz), 7.60-7.72 (2H, m), 7.76 (1H, dd, J=1.8, 7.3 Hz), 8.77 (1H, s), 11.16 (1H, s).

MS (ESI-FTMS) m/z: 358, 360 [M+H]$^+$.

Working Example 52

Production of 5-[(3-bromo-2-oxopyridin-1(2H)-yl)methyl]-5-(4-methoxyphenyl)imidazolidine-2,4-dione (I-52)

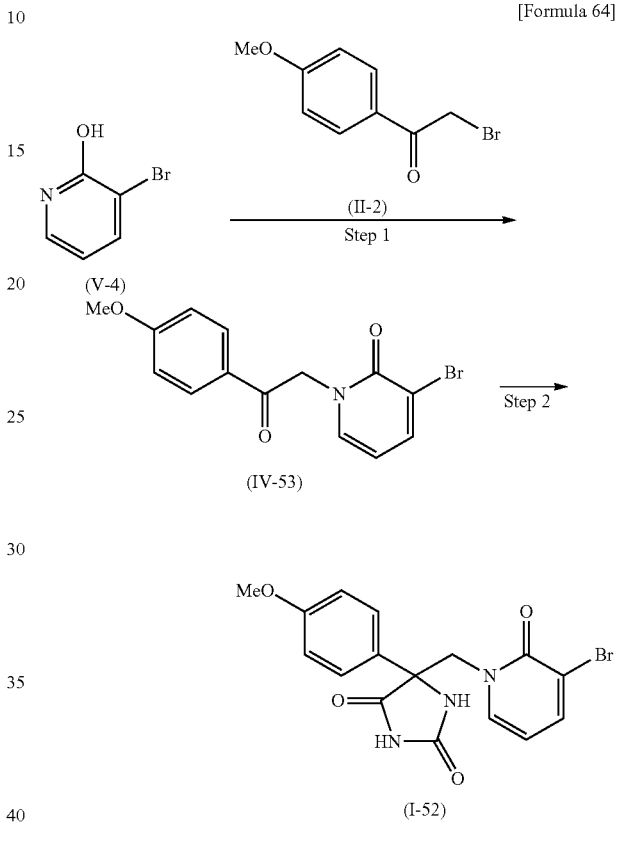

Step 1

N,N-dimethylformamide (23 mL) was added to 3-bromopyridin-2-ol (V-4) (2.0 g, 11.49 mmol) and cesium carbonate (4.49 g, 13.79 mmol), and then compound (II-2) (2.90 g, 12.64 mmol) was added, and the resultant mixture was stirred for 1.75 hours at room temperature. Water was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-53) (amount 2.09 g, yield 56%).

Compound (I-52) (amount 144 mg, yield 39%) was obtained from compound (IV-53) based on the same production method as for compound (IV-47). The physical properties are shown below.

$^1$H-NMR (DMSO-$d_6$) δ: 3.76 (3H, s), 4.46 (1H, d, J=13.7 Hz), 4.69 (1H, d, J=13.7 Hz), 6.17 (1H, t, J=6.9 Hz), 6.99 (2H, d, J=9.2 Hz), 7.41 (1H, dd, J=1.6, 6.6 Hz), 7.53 (2H, d, J=8.7 Hz), 7.91 (1H, dd, J=1.8, 7.3 Hz), 8.68 (1H, s), 10.86 (1H, s).

MS (ESI-FTMS) m/z: 392, 394 [M+H]$^+$.

Working Example 53

Production of 5-[(3-ethyl-2-oxopyridin-1(2H)-yl)methyl]-5-(4-methoxyphenyl)imidazolidine-2,4-dione (I-53)

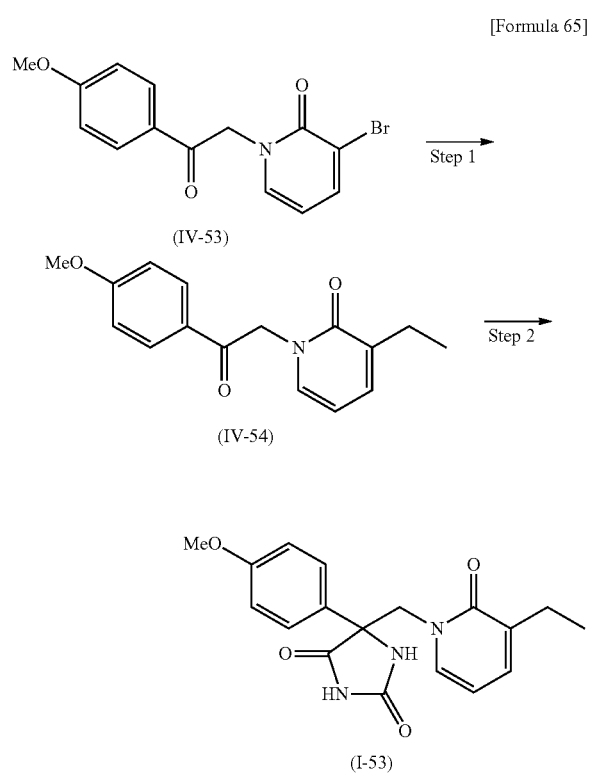

Step 1

A suspension of compound (IV-53) (500 mg, 1.55 mmol), ethyl boronic acid (126 mg, 1.71 mmol), and tripotassium phosphate (822 mg, 3.88 mmol) in 1,4-dioxane (7.8 mL) was degassed. Under an argon atmosphere, tetrakis(triphenylphosphine)palladium (90 mg, 0.078 mmol) was added, and the resultant mixture was heated and stirred for 17 hours at 90° C. Water was added to the reaction solution, and the resultant mixture was extracted with ethyl acetate. The organic layer was washed with saturated brine, and then dried over anhydrous sodium sulfate. The solvent was removed under reduced pressure, and the resultant product was purified by silica gel column chromatography to obtain compound (IV-54) (amount 286 mg, yield 68%).

Step 2

Compound (I-53) (amount 113 mg, yield 31%) was obtained from compound (IV-54) based on the same production method as for compound (I-47). The physical properties are shown below.

$^1$H-NMR (DMSO-d$_6$) δ: 1.07 (3H, t, J=7.3 Hz), 2.40 (2H, q, J=7.3 Hz), 3.77 (3H, s), 4.46 (1H, d, J=13.7 Hz), 4.56 (1H, d, J=13.7 Hz), 6.14 (1H, t, J=6.9 Hz), 6.95-7.02 (2H, m), 7.20-7.28 (2H, m), 7.50-7.58 (2H, m), 8.49 (1H, s), 10.80 (1H, s).

MS (ESI-FTMS) m/z: 342 [M+H]$^+$.

Working Example 54

Production of 5-(3-hydroxyphenyl)-5-[(3-methyl-2-oxopyridin-1(2H)-yl)methyl]imidazolidine-2,4-dione (I-54)

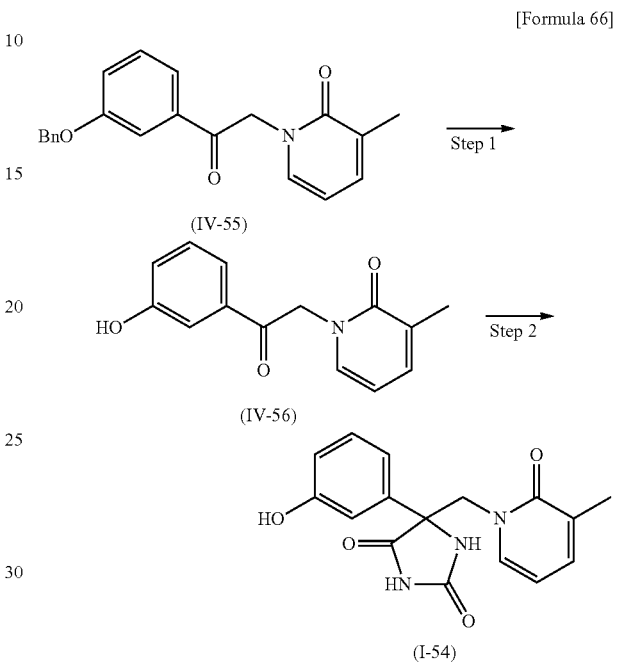

Step 1

Trifluoroacetic acid (1 mL) was added to a solution of 1-(2-(3-(benzyloxy)phenyl)-2-oxoethyl)-3-methylpyridin-2-(1H)-one (IV-55) (361 mg, 1.08 mmol) in chloroform (1 mL), and the resultant mixture was stirred for 14.5 hours at room temperature, and then heated under reflux for 23.5 hours. A saturated aqueous solution of sodium bicarbonate was added to the reaction solution, and the resultant mixture was extracted with ethyl acetate. The organic layer was washed with saturated brine, and then dried over anhydrous sodium sulfate. The solvent was removed under reduced pressure, chloroform was added, and the precipitated solid was collected by filtration to obtain compound (IV-56) (amount 116 mg, yield 44%).

Step 2

This compound (IV-56) (100 mg, 0.41 mmol), potassium cyanide (32 mg, 0.49 mmol), ammonium carbonate (158 mg, 1.64 mmol), ethanol (0.41 mL), and saturated ammonia water (0.41 mL) were added together. The resultant mixture was sealed, and stirred for 65 hours at 100° C. The solvent was removed under reduced pressure, and the resultant product was purified by silica gel column chromatography to obtain compound (I-54) (amount 93 mg, yield 72%). The physical properties are shown below.

$^1$H-NMR (DMSO-d$_6$) δ: 2.00 (3H, s), 4.42 (1H, d, J=13.3 Hz), 4.59 (1H, d, J=13.3 Hz), 6.11 (1H, t, J=6.9 Hz), 6.76 (1H, dd, J=1.2, 8.0 Hz), 7.00-7.07 (2H, m), 7.18-7.32 (3H, m), 8.49 (1H, s), 9.60 (1H, s), 10.79 (1H, s).

MS (ESI-FTMS) m/z: 378 [M+H]$^+$.

Compound I-55 was synthesized based on the same method as for compound I-7. The structure and the physical properties of the compound are shown in Table 1.

Compounds I-145, 1-146, 1-147, 1-148, 1-151, 1-153, 1-154, 1-155, 1-156, and I-157 were synthesized based on the same method as for compound I-10. The structure and the physical properties of each compound are shown in Table 12 or Table 13.

Compounds I-56 and I-57 were synthesized based on the same method as for compound I-11. The structure and the physical properties of each compound are shown in Table 1.

Compounds I-59 and I-77 were synthesized based on the same method as for compound I-15. The structure and the physical properties of each compound are shown in Table 1 or Table 3.

Compound I-60 was synthesized based on the same method as for compound I-16. The structure and the physical properties of the compound are shown in Table 1.

Compound I-61 was synthesized based on the same method as for compound I-18. The structure and the physical properties of the compound are shown in Table 1.

Compounds I-69 and I-70 were synthesized based on the same method as for compound I-19. The structure and the physical properties of each compound are shown in Table 2.

Compound I-105 was synthesized based on the same method as for compound I-20. The structure and the physical properties of the compound are shown in Table 7.

Compounds I-65 and I-67 were synthesized based on the same method as for compound I-21. The structure and the physical properties of each compound are shown in Table 2.

Compounds I-76 and I-120 were synthesized based on the same method as for compound I-22. The structure and the physical properties of each compound are shown in Table 3 or Table 8.

Compounds I-66 and I-119 were synthesized based on the same method as for compound I-24. The structure and the physical properties of each compound are shown in Table 2 or Table 8.

Compounds I-78, 1-79, 1-89, 1-125, 1-126, 1-127, and I-128 were synthesized based on the same method as for compound I-25. The structure and the physical properties of each compound are shown in Table 3, Table 5, or Table 9.

Compounds I-92, 1-93, 1-94, and 1-95 were synthesized based on the same method as for compound I-31. The structure and the physical properties of each compound are shown in Table 5.

Compounds I-62, 1-72, 1-73, 1-74, 1-75, 1-90, 1-91, 1-96, and I-109 were synthesized based on the same method as for compound I-32. The structure and the physical properties of each compound are shown in Table 1, Table 2, Table 3, Table 5, or Table 7.

Compounds I-58, 1-63, 1-71, 1-106, and I-110 were synthesized based on the same method as for compound I-33. The structure and the physical properties of each compound are shown in Table 1, Table 2, or Table 7.

Compounds I-64, I-68, I-80, I-81, I-86, I-97, I-100, and I-113 were synthesized based on the same method as for compound I-34. The structure and the physical properties of each compound are shown in Table 2, Table 3, Table 4, Table 6, or Table 8.

Compounds I-82, I-83, I-84, I-85, I-87, I-98, I-99, I-101, I-102, I-103, I-104, I-111, I-112, I-114, I-122, and I-123 were synthesized based on the same method as for compound I-35. The structure and the physical properties of each compound are shown in Table 4, Table 6, Table 7, Table 8, or Table 9.

Compound I-88 was synthesized based on the same method as for compound I-36. The structure and the physical properties of the compound are shown in Table 4.

Compounds I-107, 1-115, 1-116, 1-117, 1-118, and I-131 were synthesized based on the same method as for compound I-37. The structure and the physical properties of each compound are shown in Table 7, Table 8, or Table 10.

Compounds I-124 and I-129 were synthesized based on the same method as for compound I-39. The structure and the physical properties of each compound are shown in Table 9 or Table 10.

Compounds I-149, 1-150, and 1-152 were synthesized based on the same method as for compound I-40. The structure and the physical properties of each compound are shown in Table 13.

Compound I-130 was synthesized based on the same method as for compound I-41. The structure and the physical properties of the compound are shown in Table 10.

Compound I-108 was synthesized based on the same method as for compound I-43. The structure and the physical properties of the compound are shown in Table 7.

Compound I-121 was synthesized based on the same method as for compound I-45. The structure and the physical properties of the compound are shown in Table 9.

Compounds I-132, 1-133, 1-134, 1-137, 1-138, 1-139, and I-140 were synthesized based on the same method as for compound I-46. The structure and the physical properties of each compound are shown in Table 11 or Table 12.

Compounds I-141 and I-142 were synthesized based on the same method as for compound I-47. The structure and the physical properties of each compound are shown in Table 12.

Compound I-135 was synthesized based on the same method as for compound I-49. The structure and the physical properties of the compound are shown in Table 11.

Compounds I-136 and I-143 were synthesized based on the same method as for compound I-50. The structure and the physical properties of each compound are shown in Table 11 or Table 12.

Compound I-144 was synthesized based on the same method as for compound I-53. The structure and the physical properties of the compound are shown in Table 12.

TABLE 1

| Compound | Structure | $^1$H-NMR | MS (M + H)$^+$ |
|---|---|---|---|
| I-55 | 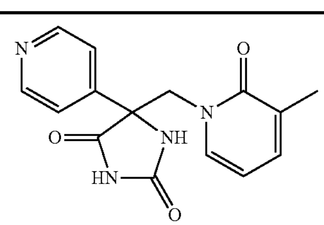 | (DMSO-d$_6$) δ: 1.98 (3H, s), 4.47 (1H, d, J = 13.7 Hz), 4.66 (1H, d, J = 13.7 Hz), 6.13 (1H, t, J = 6.9 Hz), 7.24-7.32 (2H, m), 7.60-7.64 (2H, m), 8.60-8.66 (2H, m), 8.73 (1H, d, J = 1.4 Hz), 11.01 (1H, s). | 299 |

TABLE 1-continued

| Compound | Structure | ¹H-NMR | MS (M + H)⁺ |
|---|---|---|---|
| I-56 | 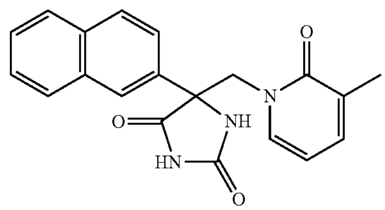 [SMILES: Cc1cccn(CC2(c3ccc4ccccc4c3)NC(=O)NC2=O)c1=O] | (DMSO-d$_6$) δ: 2.00 (3H, s), 4.57 (1H, d, J = 13.3 Hz), 4.78 (1H, d, J = 13.7 Hz), 6.13 (1H, t, J = 6.9 Hz), 7.30 (2H, t, J = 6.4 Hz), 7.52-7.60 (2H, m), 7.79 (1H, dd, J = 1.8, 8.7 Hz), 7.91-8.01 (3H, m), 8.16 (1H, s), 8.69 (1H, s), 10.89 (1H, s). | 348 |
| I-57 | 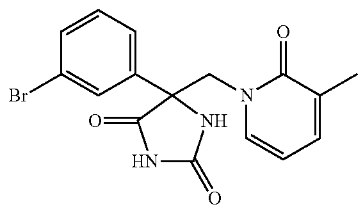 [SMILES: Cc1cccn(CC2(c3cccc(Br)c3)NC(=O)NC2=O)c1=O] | (DMSO-d$_6$) δ: 1.99 (3H, s), 4.46 (1H, d, J = 13.7 Hz), 4.62 (1H, d, J = 13.7 Hz), 6.13 (1H, t, J = 6.9 Hz), 7.27 (1H, d, J = 7.8 Hz), 7.29 (1H, d, J = 7.8 Hz), 7.41 (1H, t, J = 7.8 Hz), 7.58-7.68 (2H, m), 7.83 (1H, t, J = 1.8 Hz), 8.67 (1H, s), 10.96 (1H, s). | 376 378 |
| I-58 | 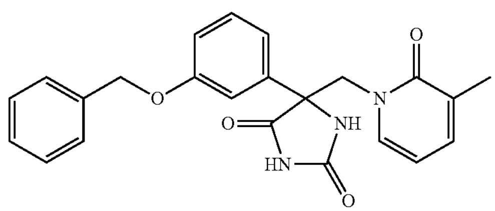 [SMILES: Cc1cccn(CC2(c3cccc(OCc4ccccc4)c3)NC(=O)NC2=O)c1=O] | (DMSO-d$_6$) δ: 2.00 (3H, s), 4.47 (1H, d, J = 13.3 Hz), 4.60 (1H, d, J = 13.7 Hz), 5.12 (2H, s), 6.12 (1H, t, J = 6.7 Hz), 7.03 (1H, dd, J = 2.0, 8.0 Hz), 7.18-7.54 (10H, m), 8.59 (1H, s), 10.87 (1H, s). | 404 |
| I-59 | 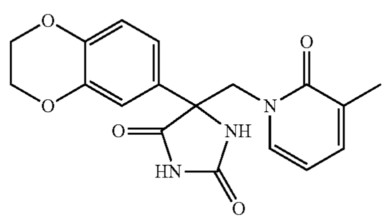 [SMILES: Cc1cccn(CC2(c3ccc4c(c3)OCCO4)NC(=O)NC2=O)c1=O] | (DMSO-d$_6$) δ: 2.00 (3H, s), 4.25 (4H, s), 4.43 (1H, d, J = 13.7 Hz), 4.52 (1H, d, J = 13.7 Hz), 6.11 (1H, t, J = 6.9 Hz), 6.90 (1H, d, J = 8.7 Hz), 7.07 (1H, dd, J = 2.3, 8.7 Hz), 7.13 (1H, d, J = 2.3 Hz), 7.19-7.32 (2H, m), 8.50 (1H, s), 10.73 (1H, s). | 356 |
| I-60 | 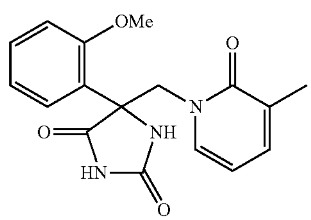 [SMILES: COc1ccccc1C1(Cn2cccc(C)c2=O)NC(=O)NC1=O] | (DMSO-d$_6$) δ: 1.99 (3H, s), 3.78 (3H, s), 4.42 (1H, d, J = 13.3 Hz), 4.89 (1H, d, J = 13.3 Hz), 6.12 (1H, t, J = 6.9 Hz), 7.00 (1H, dt, J = 1.4, 7.3 Hz), 7.11 (1H, m), 7.23 (1H, dd, J = 1.4, 6.9 Hz), 7.29 (1H, m), 7.40 (1H, m), 7.51 (1H, dd, J = 1.4, 7.8 Hz), 7.73 (1H, s), 10.72 (1H, s). | 328 |
| I-61 | 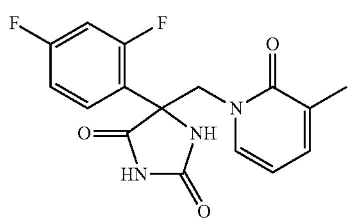 [SMILES: Cc1cccn(CC2(c3ccc(F)cc3F)NC(=O)NC2=O)c1=O] | (DMSO-d$_6$) δ: 1.99 (3H, s), 4.68 (1H, d, J = 13.3 Hz), 4.78 (1H, d, J = 13.3 Hz), 6.14 (1H, t, J = 6.9 Hz), 7.18 (1H, dt, J = 2.7, 8.7 Hz), 7.27 (1H, d, J = 6.9 Hz), 7.31 (1H, d, J = 6.4 Hz), 7.38 (1H, ddd, J = 2.7, 9.2, 11.9 Hz), 7.64-7.72 (1H, m), 8.26 (1H, s), 10.93 (1H, s). | 334 |
| I-62 | 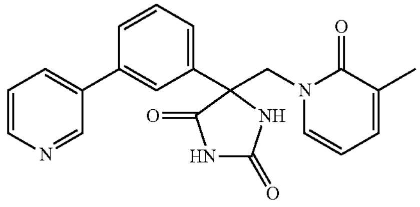 [SMILES: Cc1cccn(CC2(c3cccc(-c4cccnc4)c3)NC(=O)NC2=O)c1=O] | (DMSO-d$_6$) δ: 2.00 (3H, s), 4.59 (1H, d, J = 13.7 Hz), 4.67 (1H, d, J = 13.7 Hz), 6.13 (1H, t, J = 6.9 Hz), 7.30 (2H, d, J = 6.9 Hz), 7.51-7.60 (2H, m), 7.71 (1H, d, J = 7.8 Hz), 7.76 (1H, d, J = 7.8 Hz), 7.99 (1H, t, J = 1.6 Hz), 8.10-8.14 (1H, m), 8.61 (1H, dd, J = 1.6, 4.8 Hz), 8.68 (1H, s), 8.95 (1H, dd, J = 0.9, 2.3 Hz), 10.92 (1H, s). | 375 |

TABLE 1-continued

| Compound | Structure | ¹H-NMR | MS (M + H)⁺ |
|---|---|---|---|
| I-63 | 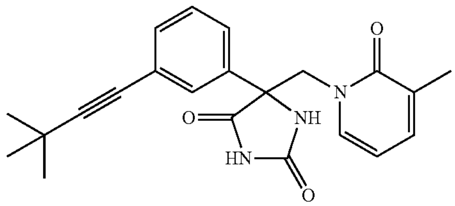 [SMILES: Cc1cccn(CC2(c3cccc(C#CC(C)(C)C)c3)NC(=O)NC2=O)c1=O] | (DMSO-d₆) δ: 1.31 (9H, s), 1.99 (3H, s), 4.42 (1H, d, J = 13.7 Hz), 4.63 (1H, d, J = 13.7 Hz), 6.12 (1H, t, J = 6.7 Hz), 7.23-7.31 (2H, m), 7.32-7.44 (2H, m), 7.56-7.74 (2H, m), 8.60 (1H, s), 10.89 (1H, s). | 378 |

TABLE 2

| Compound | Structure | ¹H-NMR | MS (M + H)⁺ |
|---|---|---|---|
| I-64 | 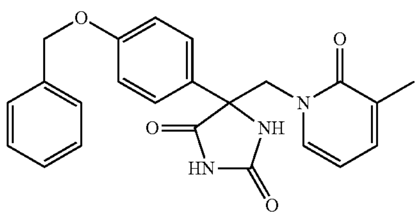 [SMILES: Cc1cccn(CC2(c3ccc(OCc4ccccc4)cc3)NC(=O)NC2=O)c1=O] | (DMSO-d₆) δ: 2.00 (3H, s), 4.36 (1H, d, J = 13.7 Hz), 4.57 (1H, d, J = 13.7 Hz), 5.12 (2H, s), 6.11 (1H, t, J = 6.9 Hz), 7.07 (2H, d, J = 9.2 Hz), 7.24 (1H, d, J = 6.9 Hz), 7.28 (1H, d, J = 6.0 Hz), 7.33 (1H, t, J = 6.9 Hz), 7.39 (2H, t, J = 7.3 Hz), 7.42-7.48 (2H, m), 7.53 (2H, d, J = 8.7 Hz), 8.52 (1H, s), 10.80 (1H, s). | 404 |
| I-65 | 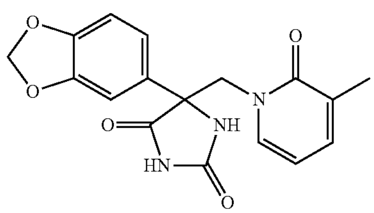 [SMILES: Cc1cccn(CC2(c3ccc4c(c3)OCO4)NC(=O)NC2=O)c1=O] | (DMSO-d₆) δ: 2.00 (3H, s), 4.44 (1H, d, J = 13.7 Hz), 4.58 (1H, d, J = 13.7 Hz), 6.04 (2H, s), 6.11 (1H, t, J = 6.6 Hz), 6.96 (1H, d, J = 8.2 Hz), 7.10 (1H, dd, J = 2.3, 8.2 Hz), 7.18-7.31 (3H, m), 8.51 (1H, s), 10.83 (1H, s). | 342 |
| I-66 | 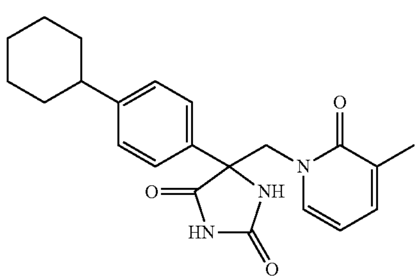 [SMILES: Cc1cccn(CC2(c3ccc(C4CCCCC4)cc3)NC(=O)NC2=O)c1=O] | (DMSO-d₆) δ: 1.17-1.47 (5H, m), 1.66-1.84 (6H, m), 2.00 (3H, s), 4.45 (1H, d, J = 13.7 Hz), 4.60 (1H, d, J = 13.7 Hz), 6.12 (1H, t, J = 6.9 Hz), 7.23-7.31 (4H, m), 7.52 (2H, d, J = 8.7 Hz), 8.51 (1H, s), 10.79 (1H, s). | 380 |
| I-67 | 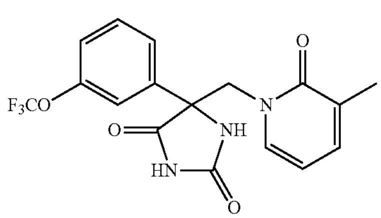 [SMILES: Cc1cccn(CC2(c3cccc(OC(F)(F)F)c3)NC(=O)NC2=O)c1=O] | (DMSO-d₆) δ: 1.98 (3H, s), 4.48 (1H, d, J = 13.7 Hz), 4.64 (1H, d, J = 13.7 Hz), 6.11 (1H, t, J = 6.6 Hz), 7.24-7.33 (2H, m), 7.40 (1H, m), 7.55-7.63 (2H, m), 7.68 (1H, m), 8.70 (1H, s), 10.97 (1H, s). | 382 |

TABLE 2-continued

| Compound | Structure | ¹H-NMR | MS (M + H)⁺ |
|---|---|---|---|
| I-68 | 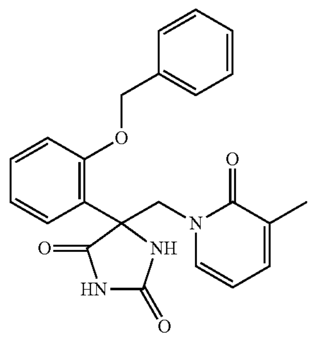 [SMILES: Cc1cccn(CC2(c3ccccc3OCc3ccccc3)NC(=O)NC2=O)c1=O] | (DMSO-d₆) δ: 1.99 (3H, s), 4.52 (1H, d, J = 12.8 Hz), 4.90 (1H, d, J = 13.3 Hz), 5.20 (2H, s), 6.04 (1H, t, J = 13.7 Hz), 7.00 (1H, m), 7.09 (1H, m), 7.16 (1H, dd, J = 1.4, 6.9 Hz), 7.24-7.40 (5H, m), 7.48-7.52 (2H, m), 7.55 (1H, dd, J = 1.4, 7.8 Hz), 7.70 (1H, s), 10.66 (1H, s). | 404 |
| I-69 | 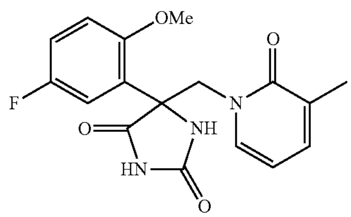 [SMILES: COc1ccc(F)cc1C1(Cn2cccc(C)c2=O)NC(=O)NC1=O] | (DMSO-d₆) δ: 1.99 (3H, s), 3.76 (3H, s), 4.44 (1H, d, J = 13.3 Hz), 4.83 (1H, d, J = 13.3 Hz), 6.12 (1H, t, J = 6.9 Hz), 7.13 (1H, dd, J = 4.6, 9.2 Hz), 7.19-7.32 (3H, m), 7.39 (1H, dd, J = 2.7, 10.1 Hz), 7.83 (1H, s), 10.79 (1H, s). | 346 |
| I-70 | 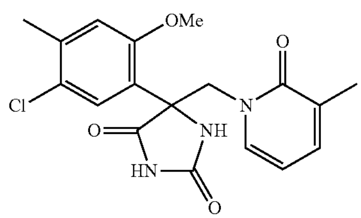 [SMILES: COc1cc(C)c(Cl)cc1C1(Cn2cccc(C)c2=O)NC(=O)NC1=O] | (DMSO-d₆) δ: 1.99 (3H, s), 2.34 (3H, s), 3.78 (3H, s), 4.41 (1H, d, J = 13.3 Hz), 4.81 (1H, d, J = 13.3 Hz), 6.12 (1H, t, J = 6.9 Hz), 7.14 (1H, s), 7.21 (1H, d, J = 6.9 Hz), 7.29 (1H, d, J = 6.0 Hz), 7.49 (1H, s), 7.79 (1H, s), 10.80 (1H, s). | 376 |
| I-71 | 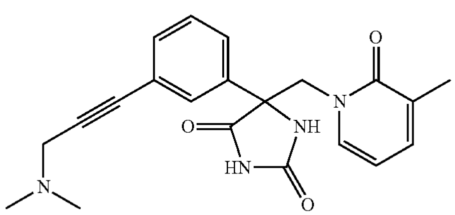 | (DMSO-d₆) δ: 1.99 (3H, s), 2.26 (6H, s), 3.47 (2H, s), 4.46 (1H, d, J = 13.3 Hz), 4.63 (1H, d, J = 13.7 Hz), 6.12 (1H, t, J = 6.9 Hz), 7.24- 7.31 (2H, m), 7.42-7.48 (2H, m), 7.61-7.67 (1H, m), 7.71 (1H, d, J = 0.9 Hz), 8.63 (1H, s), 10.91 (1H, s). | 379 |
| I-72 | 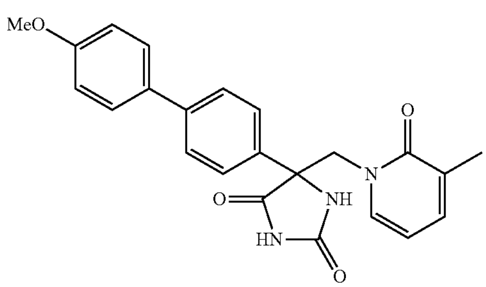 [SMILES: COc1ccc(-c2ccc(C3(Cn4cccc(C)c4=O)NC(=O)NC3=O)cc2)cc1] | (DMSO-d₆) δ: 2.01 (3H, s), 3.80 (3H, s), 4.51 (1H, d, J = 13.7 Hz), 4.66 (1H, d, J = 13.7 Hz), 6.13 (1H, t, J = 6.9 Hz), 7.04 (2H, d, J = 9.2 Hz), 7.26-7.32 (2H, m), 7.64 (2H, d, J = 8.7 Hz), 7.69 (4H, s), 8.62 (1 H, s), 10.82 (1H, s). | 404 |

TABLE 3

| Compound | Structure | ¹H-NMR | MS (M + H)⁺ |
|---|---|---|---|
| I-73 | 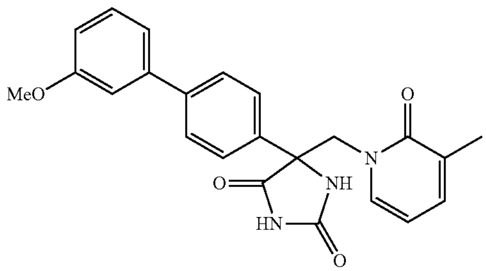 [SMILES: COc1cccc(-c2ccc(C3(Cn4cccc(C)c4=O)NC(=O)NC3=O)cc2)c1] | (DMSO-d$_6$) δ: 2.01 (3H, s), 3.83 (3H, s), 4.51 (1H, d, J = 13.7 Hz), 4.67 (1H, d, J = 13.7 Hz), 6.14 (1H, t, J = 6.7 Hz), 6.96 (1H, dd, J = 2.3, 8.2 Hz), 7.19-7.33 (5H, m), 7.71 (2H, d, J = 8.7 Hz), 7.75 (2H, d, J = 8.7 Hz), 8.64 (1H, s), 10.87 (1H, s). | 404 |
| I-74 | 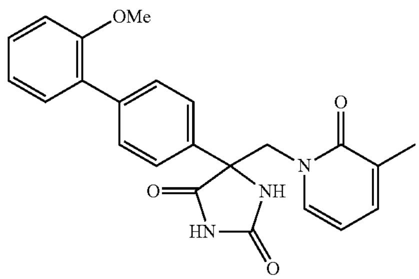 [SMILES: COc1ccccc1-c1ccc(C2(Cn3cccc(C)c3=O)NC(=O)NC2=O)cc1] | (DMSO-d$_6$) δ: 2.01 (3H, s), 3.77 (3H, s), 4.52 (1H, d, J = 13.7 Hz), 4.67 (1H, d, J = 13.3 Hz), 6.14 (1H, t, J = 6.7 Hz), 7.04 (1H, t, J = 7.3 Hz), 7.12 (1H, d, J = 7.8 Hz), 7.27-7.40 (4H, m), 7.54 (2H, d, J = 8.7 Hz), 7.66 (2H, d, J = 8.2 Hz), 8.60 (1H, s), 10.84 (1H, s). | 404 |
| I-75 | 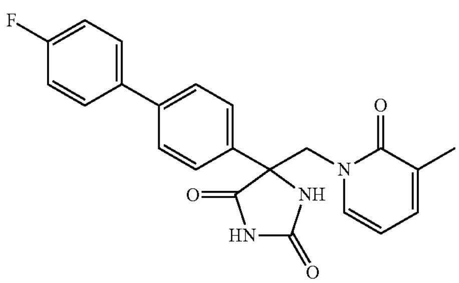 [SMILES: Cc1cccn(CC2(c3ccc(-c4ccc(F)cc4)cc3)NC(=O)NC2=O)c1=O] | (DMSO-d$_6$) δ: 2.01 (3H, s), 4.51 (1H, d, J = 13.3 Hz), 4.66 (1H, d, J = 13.3 Hz), 6.13 (1H, t, J = 6.9 Hz), 7.27-7.35 (4H, m), 7.69-7.78 (6H, m), 8.63 (1H, s), 10.84 (1H, s). | 392 |
| I-76 | 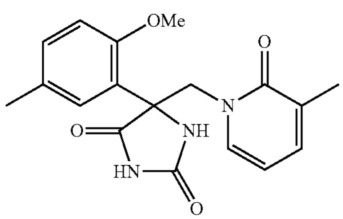 | (DMSO-d$_6$) δ: 1.99 (3H, s), 2.27 (3H, s), 3.74 (3H, s), 4.41 (1H, d, J = 13.3 Hz), 4.87 (1H, d, J = 13.3 Hz), 6.12 (1H, t, J = 6.4 Hz), 7.00 (1H, d, J = 8.7 Hz), 7.16-7.25 (2H, m), 7.29 (1H, m), 7.32 (1H, d, J = 1.8 Hz), 7.69 (1H, s), 10.71 (1H, s). | 342 |
| I-77 | 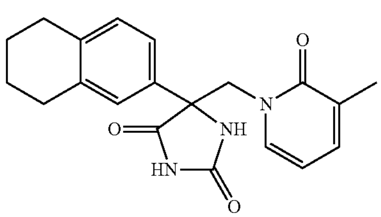 [SMILES: Cc1cccn(CC2(c3ccc4c(c3)CCCC4)NC(=O)NC2=O)c1=O] | (DMSO-d$_6$) δ: 1.68-1.79 (4H, m), 2.00 (3H, s), 2.68-2.76 (4H, m), 4.43 (1H, d, J = 13.7 Hz), 4.57 (1H, d, J = 13.7 Hz), 6.12 (1H, t, J = 6.9 Hz), 7.10 (1H, d, J = 8.7 Hz), 7.23-7.34 (4H, m), 8.46 (1H, s), 10.7 (1H, s). | 352 |
| I-78 | 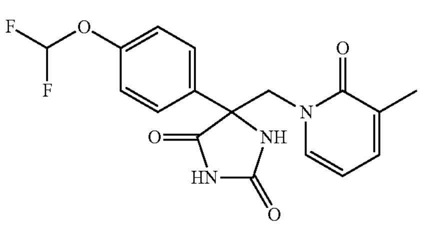 [SMILES: Cc1cccn(CC2(c3ccc(OC(F)F)cc3)NC(=O)NC2=O)c1=O] | (DMSO-d$_6$) δ: 1.99 (3H, s), 4.46 (1H, d, J = 13.7 Hz), 4.62 (1H, d, J = 13.7 Hz), 6.12 (1H, t, J = 6.9 Hz), ,7.22-7.31 (4H, m), 7.27 (1H, t, J = 74.0 Hz), 7.68 (2H, d, J = 8.7 Hz), 8.60 (1H, s), 10.88 (1H, s). | 364 |

TABLE 3-continued

| Compound | Structure | ¹H-NMR | MS (M + H)⁺ |
|---|---|---|---|
| I-79 | 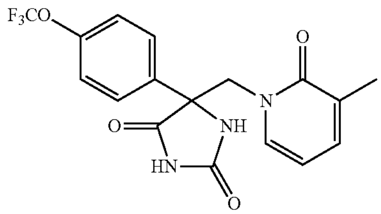 [SMILES: Cc1cccn(CC2(c3ccc(OC(F)(F)F)cc3)NC(=O)NC2=O)c1=O] | (DMSO-d₆) δ: 1.99 (3H, s), 4.46 (1H, d, J = 13.3 Hz), 4.65 (1H, d, J = 13.7 Hz), 6.12 (1H, t, J = 6.7 Hz), 7.24-7.32 (2H, m), 7.46 (2H, d, J = 7.8 Hz), 7.76 (2H, d, J = 9.2 Hz), 8.65 (1H, s), 10.93 (1H, s). | 382 |
| I-80 | 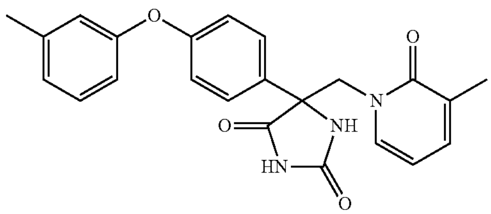 | (DMSO-d₆) δ: 2.00 (3H, s), 2.29 (3H, s), 4.46 (1H, d, J = 13.7 Hz), 4.61 (1H, d, J = 13.7 Hz), 6.12 (1H, t, J = 6.9 Hz), 6.80 (1H, dd, J = 2.5, 8.2 Hz), 6.85 (1H, s), 6.98 (1H, m), 7.04 (2H, td, J = 2.5, 8.7 Hz), 7.23-7.31 (3H, m), 7.62 (2H, td, J = 2.5, 9.2 Hz), 8.57 (1H, d, J = 1.4 Hz), 10.86 (1H, s). | 404 |

TABLE 4

| Compound | Structure | ¹H-NMR | MS (M + H)⁺ |
|---|---|---|---|
| I-81 | 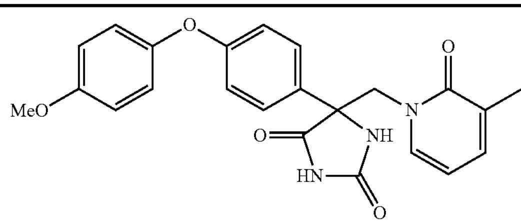 | (DMSO-d₆) δ: 1.99 (3H, s), 3.76 (3H, s), 4.46 (1H, d, J = 13.7 Hz), 4.59 (1H, d, J = 13.7 Hz), 6.12 (1H, t, J = 6.9 Hz), 6.93-7.04 (6H, m), 7.23-7.31 (2H, m), 7.59 (2H, td, J = 2.5, 9.2 Hz), 8.55 (1H, s), 10.83 (1H, s). | 420 |
| I-82 | 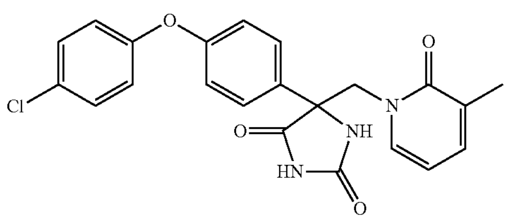 [SMILES: Cc1cccn(CC2(c3ccc(Oc4ccc(Cl)cc4)cc3)NC(=O)NC2=O)c1=O] | (DMSO-d₆) δ: 1.99 (3H, s), 4.46 (1H, d, J = 13.7 Hz), 4.61 (1H, d, J = 13.7 Hz), 6.12 (1H, t, J = 6.4 Hz), 7.04 (2H, d, J = 8.7 Hz), 7.10 (2H, d, J = 8.7 Hz), 7.26 (1H, d, J = 6.9 Hz), 7.29 (1H, d, J = 6.4 Hz), 7.44 (2H, d, J = 9.2 Hz), 7.65 (2H, d, J = 8.7 Hz), 8.60 (1H, s), 10.87 (1H, s). | 424 426 |
| I-83 | 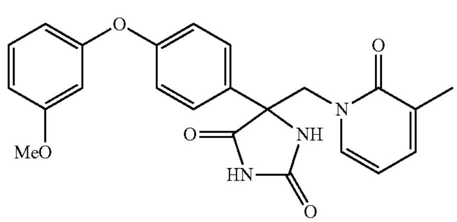 [SMILES: COc1cccc(Oc2ccc(C3(Cn4cccc(C)c4=O)NC(=O)NC3=O)cc2)c1] | (DMSO-d₆) δ: 1.99 (3H, s), 3.74 (3H, s), 4.46 (1H, d, J = 13.7 Hz), 4.61 (1H, d, J = 13.7 Hz), 6.12 (1H, t, J = 6.9 Hz), 6.55 (1H, ddd, J = 0.9, 2.3, 8.2 Hz), 6.61 (1H, t, J = 2.3 Hz), 6.74 (1H, m), 7.07 (2H, td, J = 2.5, 8.7 Hz), 7.23-7.32 (3H, m), 7.63 (2H, td, J = 2.5, 9.2 Hz), 8.58 (1H, d, J = 1.4 Hz), 10.86 (1H, s). | 420 |
| I-84 | 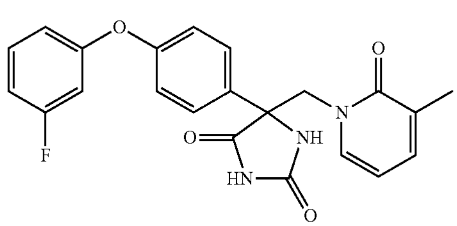 [SMILES: Cc1cccn(CC2(c3ccc(Oc4cccc(F)c4)cc3)NC(=O)NC2=O)c1=O] | (DMSO-d₆) δ: 1.99 (3H, s), 4.48 (1H, d, J = 13.7 Hz), 4.62 (1H, d, J = 13.7 Hz), 6.12 (1H, t, J = 6.9 Hz), 6.83 (1H, dd, J = 2.3, 8.7 Hz), 6.89 (1H, td, J = 2.3, 10.5 Hz), 6.99 (1H, dt, J = 1.8, 7.8 Hz), 7.13 (2H, td, J = 2.5, 8.7 Hz), 7.24-7.31 (2H, m), 7.42 (1H, m), 7.66 (2H, td, J = 2.5, 8.7 Hz), 8.61 (1H, s), 10.88 (1H, s). | 408 |

TABLE 4-continued

| Compound | Structure | ¹H-NMR | MS (M + H)⁺ |
|---|---|---|---|
| I-85 | 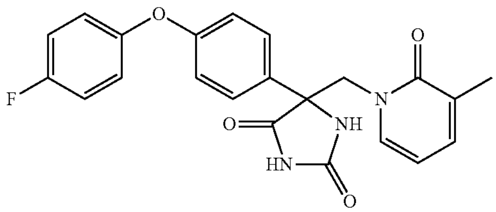 [SMILES: Cc1cccn(CC2(c3ccc(Oc4ccc(F)cc4)cc3)NC(=O)NC2=O)c1=O] | (DMSO-d₆) δ: 1.99 (3H, s), 4.45 (1H, d, J = 13.7 Hz), 4.60 (1H, d, J = 13.7 Hz), 6.12 (1H, t, J = 6.9 Hz), 7.04 (2H, td, J = 2.5, 9.2 Hz), 7.06-7.11 (2H, m), 7.20-7.31 (4H, m), 7.62 (2H, td, J = 2.5, 8.7 Hz), 8.58 (1H, s), 10.86 (1H, s). | 408 |
| I-86 | 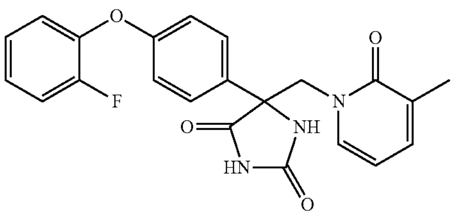 [SMILES: Cc1cccn(CC2(c3ccc(Oc4ccccc4F)cc3)NC(=O)NC2=O)c1=O] | (DMSO-d₆) δ: 1.99 (3H, s), 4.45 (1H, d, J = 13.3 Hz), 4.60 (1H, d, J = 13.3 Hz), 6.12 (1H, t, J = 6.9 Hz), 7.02 (2H, d, J = 9.2 Hz), 7.16-7.31 (5H, m), 7.41 (1H, m), 7.62 (2H, td, J = 2.5, 8.7 Hz), 8.55 (1H, s), 10.86 (1H, s). | 408 |
| I-87 | 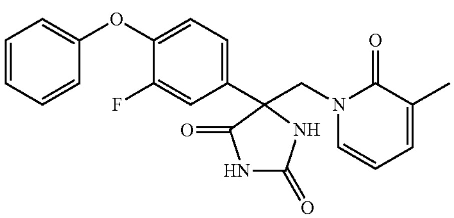 [SMILES: Cc1cccn(CC2(c3ccc(Oc4ccccc4)c(F)c3)NC(=O)NC2=O)c1=O] | (DMSO-d₆) δ: 1.99 (3H, s), 4.50 (1H, d, J = 13.7 Hz), 4.61 (1H, d, J = 13.7 Hz), 6.13 (1H, t, J = 6.9 Hz), 6.95-7.10 (2H, m), 7.14 (1H, m), 7.22 (1H, t, J = 8.7 Hz), 7.25-7.32 (2H, m), 7.35-7.43 (2H, m), 7.47 (1H, m), 7.64 (1H, dd, J = 2.3, 12.3 Hz), 8.66 (1H, s), 10.96 (1H, s). | 408 |
| I-88 | 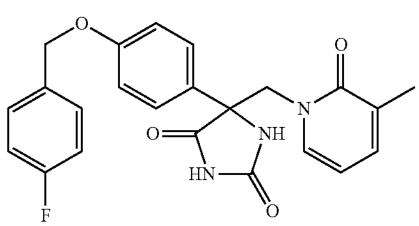 [SMILES: Cc1cccn(CC2(c3ccc(OCc4ccc(F)cc4)cc3)NC(=O)NC2=O)c1=O] | (DMSO-d₆) δ: 1.99 (3H, s), 4.44 (1H, d, J = 13.7 Hz), 4.57 (1H, d, J = 13.7 Hz), 5.10 (2H, s), 6.11 (1H, t, J = 6.6 Hz), 7.03-7.10 (2H, m), 7.13-7.36 (5H, m), 7.37-7.78 (3H, m), 8.52 (1H, s), 10.80 (1H, s). | 422 |

TABLE 5

| Compound | Structure | ¹H-NMR | MS (M + H)⁺ |
|---|---|---|---|
| I-89 | 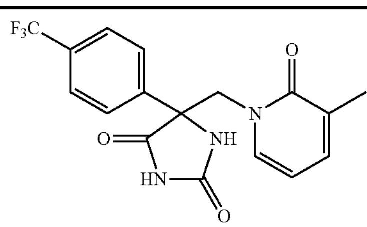 | (DMSO-d₆) δ: 1.97 (3H, s), 4.36 (1H, d, J = 13.3 Hz), 4.53 (1H, d, J = 13.3 Hz), 6.07 (1H, t, J = 6.9 Hz), 7.20 (1H, br s), 7.27 (2H, dd, J = 6.9, 11.4 Hz), 7.72 (2H, d, J = 8.2 Hz), 7.85 (2H, d, J = 8.2 Hz). | 366 |

TABLE 5-continued

| Compound | Structure | ¹H-NMR | MS (M + H)⁺ |
|---|---|---|---|
| I-90 | 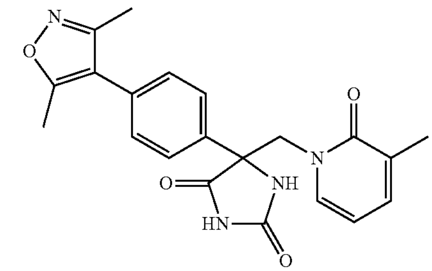 [SMILES: Cc1noc(C)c1-c1ccc(C2(Cn3cccc(C)c3=O)NC(=O)NC2=O)cc1] | (DMSO-d₆) δ: 2.00 (3H, s), 2.24 (3H, s), 2.41 (3H, s), 4.51 (1H, d, J = 13.3 Hz), 4.66 (1H, d, J = 13.7 Hz), 6.13 (1H, t, J = 6.7 Hz), 7.29 (2H, t, J = 6.4 Hz), 7.47 (2H, d, J = 8.7 Hz), 7.73 (2H, d, J = 8.7 Hz), 8.66 (1H, s), 10.89 (1H, s). | 393 |
| I-91 | 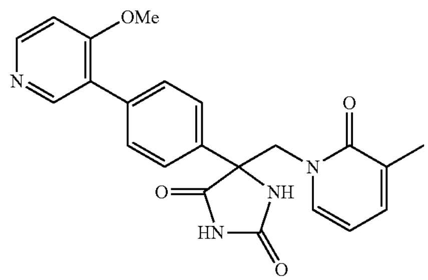 [SMILES: COc1ccncc1-c1ccc(C2(Cn3cccc(C)c3=O)NC(=O)NC2=O)cc1] | (DMSO-d₆) δ: 2.01 (3H, s), 3.90 (3H, s), 4.51 (1H, d, J = 13.3 Hz), 4.66 (1H, d, J = 13.7 Hz), 6.13 (1H, t, J = 6.9 Hz), 6.93 (1H, d, J = 8.7 Hz), 7.29 (2H, t, J = 5.5 Hz), 7.72 (2H, d, J = 8.7 Hz), 7.75 (2H, d, J = 8.7 Hz), 8.05 (1H, dd, J = 2.5, 8.5 Hz), 8.52 (1H, d, J = 2.3 Hz), 8.65 (1H, s), 10.88 (1H, s). | 405 |
| I-92 | 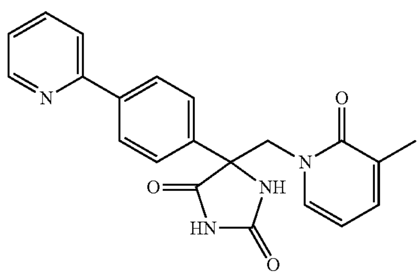 [SMILES: Cc1cccn(CC2(c3ccc(-c4ccccn4)cc3)NC(=O)NC2=O)c1=O] | (DMSO-d₆) δ: 2.00 (3H, s), 4.52 (1H, d, J = 13.3 Hz), 4.69 (1H, d, J = 13.7 Hz), 6.13 (1H, t, J = 6.9 Hz), 7.29 (2H, d, J = 6.9 Hz), 7.38 (1H, ddd, J = 0.9, 4.6, 5.5 Hz), 7.75 (2H, d, J = 8.2 Hz), 7.90 (1H, dt, J = 1.8, 7.3 Hz), 8.01 (1H, d, J = 8.2 Hz), 8.15 (2H, d, J = 8.2 Hz), 8.64 (1H, s), 8.67-8.70 (1H, m), 10.89 (1H, s). | 375 |
| I-93 | 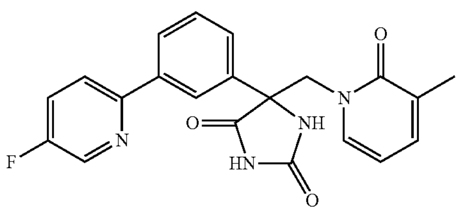 [SMILES: Cc1cccn(CC2(c3cccc(-c4ccc(F)cn4)c3)NC(=O)NC2=O)c1=O] | (DMSO-d₆) δ: 2.00 (3H, s), 4.53 (1H, d, J = 13.3 Hz), 4.71 (1H, d, J = 13.3 Hz), 6.13 (1H, t, J = 6.9 Hz), 7.27-7.32 (2H, m), 7.57 (1H, t, J = 7.8 Hz), 7.71 (1H, d, J = 8.7 Hz), 7.90 (1H, dt, J = 3.2, 8.7 Hz), 8.06 (1H, d, J = 7.8 Hz), 8.11 (1H, dd, J = 4.3, 9.2 Hz), 8.32 (1H, s), 8.69 (1H, s), 8.70 (1H, d, J = 3.2 Hz), 10.91 (1H, s). | 393 |
| I-94 | 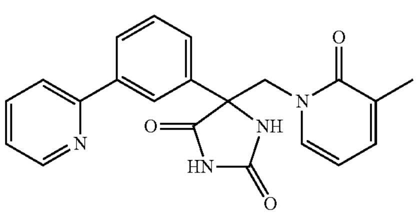 [SMILES: Cc1cccn(CC2(c3cccc(-c4ccccn4)c3)NC(=O)NC2=O)c1=O] | (DMSO-d₆) δ: 2.00 (3H, s), 4.53 (1H, d, J = 13.7 Hz), 4.72 (1H, d, J = 13.3 Hz), 6.13 (1H, t, J = 6.9 Hz), 7.27-7.34 (2H, m), 7.37-7.43 (1H, m), 7.57 (1H, t, J = 7.8 Hz), 7.72 (1H, d, J = 8.2 Hz), 7.94 (1H, t, J = 7.8 Hz), 8.02 (1H, d, J = 7.3 Hz), 8.09 (1H, d, J = 7.8 Hz), 8.36 (1H, s), 8.67-8.73 (2H, m), 10.90 (1H, s). | 375 |
| I-95 | 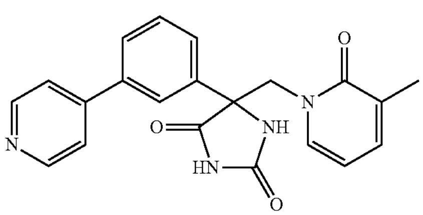 [SMILES: Cc1cccn(CC2(c3cccc(-c4ccncc4)c3)NC(=O)NC2=O)c1=O] | (DMSO-d₆) δ: 2.00 (3H, s), 4.59 (1H, d, J = 13.7 Hz), 4.68 (1H, d, J = 13.7 Hz), 6.13 (1H, t, J = 6.9 Hz), 7.30 (2H, d, J = 6.9 Hz), 7.60 (1H, J = 7.8 Hz), 7.73-7.79 (3H, m), 7.83 (1H, d, J = 7.8 Hz), 8.05 (1H, t, J = 1.8 Hz), 8.68 (2H, dd, J = 1.4, 4.6 Hz), 8.71 (1H, s), 10.93 (1H, s). | 375 |

TABLE 5-continued

| Compound | Structure | ¹H-NMR | MS (M + H)⁺ |
|---|---|---|---|
| I-96 | 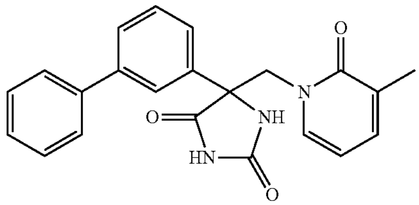 [SMILES: Cc1cccn(CC2(c3cccc(-c4ccccc4)c3)NC(=O)NC2=O)c1=O] | (DMSO-d₆) δ: 2.00 (3H, s), 4.57 (1H, d, J = 13.7 Hz), 4.67 (1H, d, J = 13.7 Hz), 6.13 (1H, t, J = 6.9 Hz), 7.30 (2H, d, J = 6.9 Hz), 7.40 (1H, J = 7.4 Hz), 7.46-7.76 (7H, m), 7.93 (1H, t, J = 1.8 Hz), 8.68 (1H, s), 10.89 (1H, s). | 374 |

TABLE 6

| Compound | Structure | ¹H-NMR | MS (M + H)⁺ |
|---|---|---|---|
| I-97 | 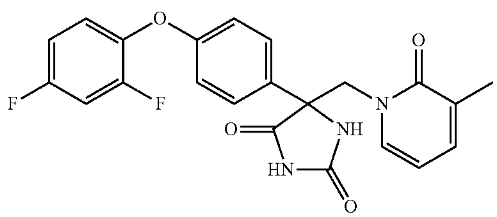 [SMILES: Cc1cccn(CC2(c3ccc(Oc4ccc(F)cc4F)cc3)NC(=O)NC2=O)c1=O] | (DMSO-d₆) δ: 1.99 (3H, s), 4.45 (1H, d, J = 13.3 Hz), 4.60 (1H, d, J = 13.3 Hz), 6.11 (1H, t, J = 6.9 Hz), 7.01 (2H, td, J = 2.5, 8.7 Hz), 7.15 (1H, m), 7.23-7.35 (3H, m), 7.50 (1H, m), 7.61 (2H, td, J = 2.5, 9.2 Hz), 8.57 (1H, d, J = 1.4 Hz), 10.85 (1H, s). | 426 |
| I-98 | 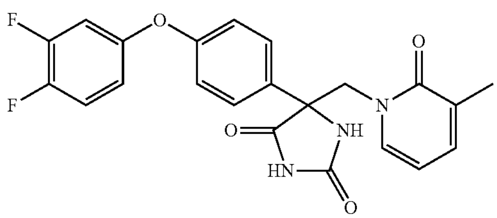 [SMILES: Cc1cccn(CC2(c3ccc(Oc4ccc(F)c(F)c4)cc3)NC(=O)NC2=O)c1=O] | (DMSO-d₆) δ: 1.99 (3H, s), 4.47 (1H, d, J = 13.7 Hz), 4.60 (1H, d, J = 13.7 Hz), 6.12 (1H, t, J = 6.9 Hz), 6.87 (1H, m), 7.10 (2H, td, J = 2.5, 9.2 Hz), 7.20-7.32 (3H, m), 7.47 (1H, m), 7.65 (2H, td, J = 2.5, 8.7 Hz), 8.60 (1H, s), 10.87 (1H, s). | 426 |
| I-99 | 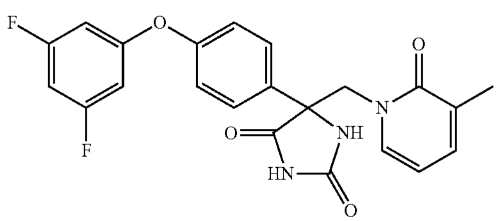 [SMILES: Cc1cccn(CC2(c3ccc(Oc4cc(F)cc(F)c4)cc3)NC(=O)NC2=O)c1=O] | (DMSO-d₆) δ: 1.99 (3H, s), 4.49 (1H, d, J = 13.7 Hz), 4.61 (1H, d, J = 13.7 Hz), 6.11 (1H, t, J = 6.9 Hz), 6.75 (2H, dd, J = 2.3, 8.7 Hz), 7.03 (1H, tt, J = 2.3, 9.2 Hz), 7.19 (2H, td, J = 2.5, 9.2 Hz), 7.23- 7.31 (2H, m), 7.69 (2H, td, J = 2.5, 9.2 Hz), 8.64 (1H, d, J = 1.4 Hz), 10.90 (1H, s). | 426 |
| I-100 | 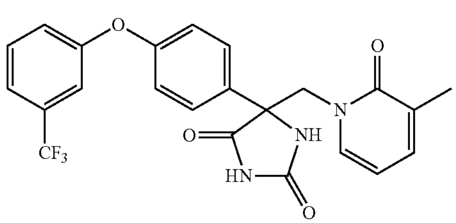 | (DMSO-d₆) δ: 1.99 (3H, s), 4.48 (1H, d, J = 13.7 Hz), 4.63 (1H, d, J = 13.7 Hz), 6.12 (1H, t, J = 6.9 Hz), 7.16 (2H, td, J = 2.5, 8.7 Hz), 7.24-7.32 (3H, m), 7.34 (1H, s), 7.52 (1H, d, J = 7.8 Hz), 7.63 (1H, t, J = 7.9 Hz), 7.68 (2H, td, J = 2.5, 8.7 Hz), 8.62 (1H, d, J = 0.9 Hz) 10.89 (1H, s). | 458 |
| I-101 | 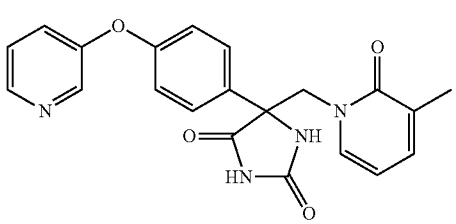 [SMILES: Cc1cccn(CC2(c3ccc(Oc4cccnc4)cc3)NC(=O)NC2=O)c1=O] | (DMSO-d₆) δ: 1.99 (3H, s), 4.47 (1H, d, J = 13.7 Hz), 4.62 (1H, d, J = 13.7 Hz), 6.12 (1H, t, J = 6.9 Hz), 7.13 (2H, td, J = 2.5, 9.2 Hz), 7.24-7.32 (2H, m), 7.43-7.47 (2H, m), 7.67 (2H, td, J = 2.5, 8.7 Hz), 8.38-8.42 (2H, m), 8.61 (1H, d, J = 1.4 Hz), 10.88 (1H, s). | 391 |

TABLE 6-continued

| Compound | Structure | ¹H-NMR | MS (M + H)⁺ |
|---|---|---|---|
| I-102 | 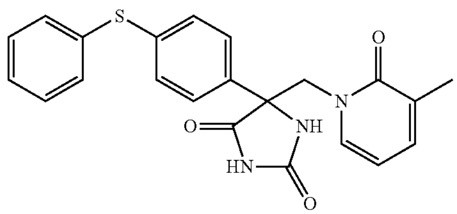 [SMILES: Cc1cccn(CC2(c3ccc(Sc4ccccc4)cc3)NC(=O)NC2=O)c1=O] | (DMSO-d$_6$) δ: 1.99 (3H, s), 4.45 (1H, d, J = 13.7 Hz), 4.61 (1H, d, J = 13.7 Hz), 6.11 (1H, d, J = 6.9 Hz), 7.23-7.31 (2H, m), 7.32-7.43 (7H, m), 7.61 (2H, d, J = 8.7 Hz), 8.59 (1H, s), 10.89 (1H, s). | 406 |
| I-103 | 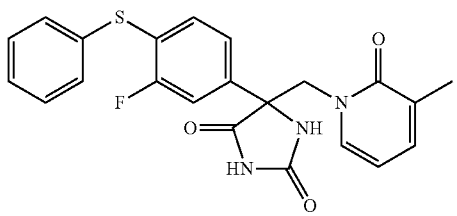 | (DMSO-d$_6$) δ: 1.98 (3H, s), 4.48 (1H, d, J = 13.7 Hz), 4.61 (1H, d, J = 13.7 Hz), 6.12 (1H, t, J = 6.9 Hz), 7.24-7.43 (8H, m), 7.46 (1H, dd, J = 1.8, 8.2 Hz), 7.56 (1H, dd, J = 1.8, 11.0 Hz), 8.64 (1H, s), 10.98 (1H, s). | 424 |
| I-104 | 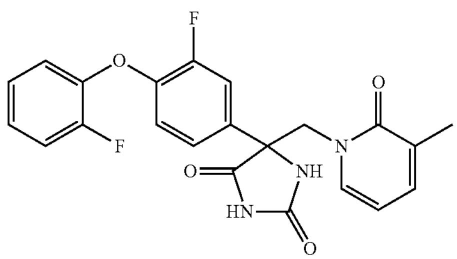 [SMILES: Cc1cccn(CC2(c3ccc(Oc4ccccc4F)c(F)c3)NC(=O)NC2=O)c1=O] | (DMSO-d$_6$) δ: 1.99 (3H, s), 4.48 (1H, d, J = 13.3 Hz), 4.60 (1H, d, J = 13.3 Hz), 6.13 (1H, t, J = 6.9 Hz), 7.08-7.16 (2H, m), 7.18-7.32 (4H, m), 7.37-7.47 (2H, m), 7.65 (1H, dd, J = 2.3, 12.4 Hz), 8.64 (1H, s), 10.96 (1H, s). | 426 |

TABLE 7

| Compound | Structure | ¹H-NMR | MS (M + H)⁺ |
|---|---|---|---|
| I-105 | 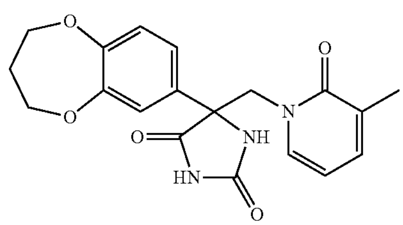 [SMILES: Cc1cccn(CC2(c3ccc4c(c3)OCCCO4)NC(=O)NC2=O)c1=O] | (DMSO-d$_6$) δ: 1.99 (3H, s), 2.11 (2H, tt, J = 5.5, 5.5 Hz), 4.07-4.19 (4H, m), 4.42 (1H, d, J = 13.7 Hz), 4.54 (1H, d, J = 13.7 Hz), 6.11 (1H, t, J = 6.9 Hz), 7.01 (1H, t, J = 8.2 Hz), 7.18 (1H, dd, J = 2.3, 8.2 Hz), 7.21-7.25 (1H, m), 7.23 (1H, d, J = 2.3 Hz), 7.28 (1H, m), 8.51 (1H, s), 10.76 (1H, m). | 370 |
| I-106 | 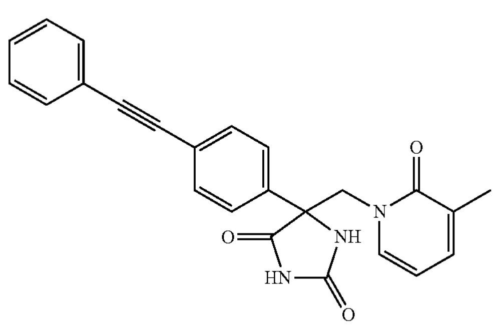 [SMILES: Cc1cccn(CC2(c3ccc(C#Cc4ccccc4)cc3)NC(=O)NC2=O)c1=O] | (DMSO-d$_6$) δ: 2.00 (3H, s), 4.48 (1H, d, J = 13.7 Hz), 4.66 (1H, d, J = 13.7 Hz), 6.12 (1H, t, J = 6.6 Hz), 7.24-7.31 (2H, m), 7.38-7.46 (3H, m), 7.53-7.60 (2H, m), 7.63 (2H, d, J = 1.8 Hz), 7.68 (2H, d, J = 1.8 Hz), 8.64 (1H, s), 10.71 (1H, s). | 398 |

TABLE 7-continued

| Compound | Structure | $^1$H-NMR | MS (M + H)$^+$ |
|---|---|---|---|
| I-107 | 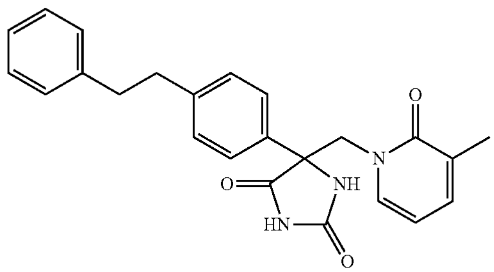 [SMILES: Cc1cccn(CC2(c3ccc(CCc4ccccc4)cc3)NC(=O)NC2=O)c1=O] | (DMSO-d$_6$) δ: 2.00 (3H, s), 2.84-2.92 (4H, m), 4.39 (1H, d, J = 13.7 Hz), 4.60 (1H, d, J = 13.7 Hz), 6.10 (1H, t, J = 6.9 Hz), 7.18 (1H, m), 7.21-7.32 (8H, m), 7.52 (2H, d, J = 8.2 Hz), 8.52 (1H, s), 10.81 (1H, s). | 402 |
| I-108 | 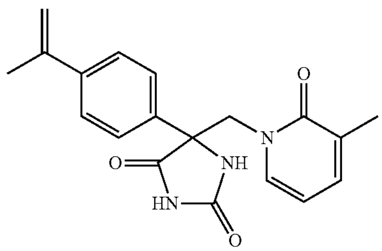 [SMILES: C=C(C)c1ccc(C2(Cn3cccc(C)c3=O)NC(=O)NC2=O)cc1] | (DMSO-d$_6$) δ: 2.00 (3H, s), 2.11 (3H, s), 4.47 (1H, d, J = 13.7 Hz), 4.63 (1H, d, J = 13.7 Hz), 5.14 (1H, m), 5.47 (1H, s), 6.12 (1H, t, J = 6.9 Hz), 7.28 (2H, dd, J = 7.1, 9.9 Hz), 7.52-7.67 (4H, m), 8.59 (1H, s), 10.84 (1H, s). | 338 |
| I-109 | 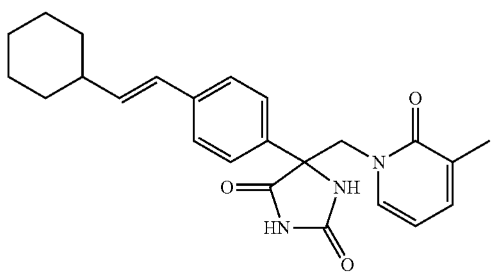 [SMILES: Cc1cccn(CC2(c3ccc(/C=C/C4CCCCC4)cc3)NC(=O)NC2=O)c1=O] | (DMSO-d$_6$) δ: 1.12-1.36 (5H, m), 1.60-1.81 (5H, m), 1.99 (3H, s), 2.06-2.20 (1H, m), 4.45 (1H, d, J = 13.7 Hz), 4.60 (1H, d, J = 13.7 Hz), 6.11 (1H, t, J = 6.9 Hz), 6.26-6.40 (2H, m), 7.25 (1H, d, J = 7.3 Hz), 7.28 (1H, d, J = 6.4 Hz), 7.43 (2H, d, J = 8.7 Hz), 7.54 (2H, d, J = 8.3 Hz), 8.55 (1H, s), 10.83 (1H, s). | 406 |
| I-110 | 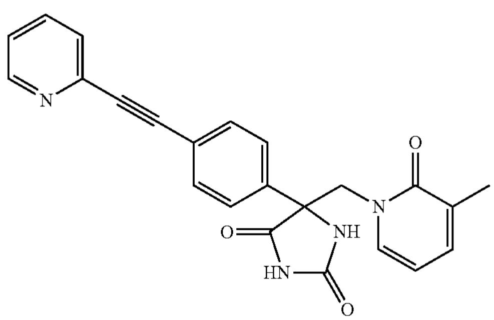 [SMILES: Cc1cccn(CC2(c3ccc(C#Cc4ccccn4)cc3)NC(=O)NC2=O)c1=O] | (DMSO-d$_6$) δ: 2.00 (3H, s), 4.49 (1H, d, J = 13.7 Hz), 4.64 (1H, d, J = 13.7 Hz), 6.12 (1H, t, J = 6.9 Hz), 7.23-7.32 (2H, m), 7.43 (1H, ddd, J = 1.4, 5.0, 7.8 Hz), 7.65-7.74 (5H, m), 7.85 (1H, dt, J = 1.8, 7.8 Hz), 8.54 (1H, s), 8.62 (1H, m), 10.94 (1H, s). | 399 |
| I-111 | 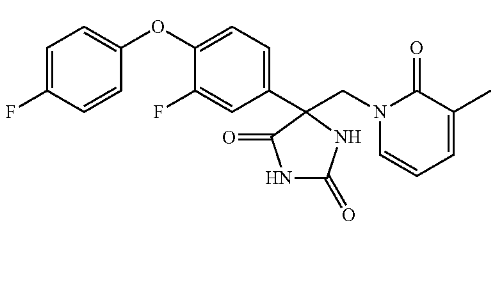 [SMILES: Cc1cccn(CC2(c3ccc(Oc4ccc(F)cc4)c(F)c3)NC(=O)NC2=O)c1=O] | (DMSO-d$_6$) δ: 1.99 (3H, s), 4.48 (1H, d, J = 13.7 Hz), 4.60 (1H, d, J = 13.7 Hz), 6.13 (1H, t, J = 6.9 Hz), 7.02-7.09 (2H, m), 7.16-7.32 (5H, m), 7.46 (1H, m), 7.64 (1H, dd, J = 2.3, 12.3 Hz), 8.65 (1H, s), 10.97 (1H, s). | 426 |

TABLE 7-continued

| Compound | Structure | $^1$H-NMR | MS (M + H)$^+$ |
|---|---|---|---|
| I-112 | 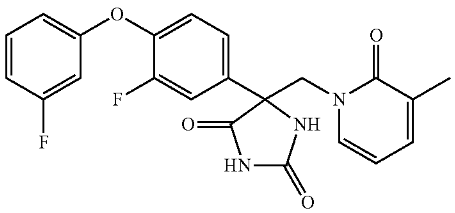 | (DMSO-d$_6$) δ: 1.98 (3H, s), 4.51 (1H, d, J = 13.3 Hz), 4.61 (1H, d, J = 13.3 Hz), 6.13 (1H, t, J = 6.9 Hz), 6.80 (1H, dd, J = 2.3, 8.7 Hz), 6.89 (1H, td, J = 2.3, 10.5 Hz), 7.00 (1H, dt, J = 2.3, 8.3 Hz), 7.25-7.35 (3H, m), 7.41 (1H, m), 7.49 (1H, dd, J = 1.8, 8.2 Hz), 7.66 (1H, dd, J = 2.3, 12.4 Hz), 8.68 (1H, s), 10.99 (1H, s). | 426 |

TABLE 8

| Compound | Structure | $^1$H-NMR | MS (M + H)$^+$ |
|---|---|---|---|
| I-113 | 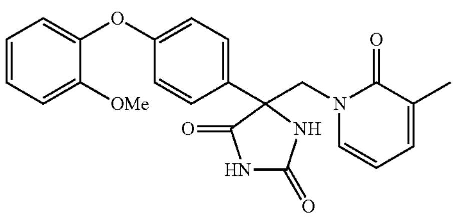 [SMILES: COc1ccccc1Oc1ccc(C2(Cn3cccc(C)c3=O)NC(=O)NC2=O)cc1] | (DMSO-d$_6$) δ: 1.99 (3H, s), 3.74 (3H, s), 4.44 (1H, d, J = 13.7 Hz), 4.57 (1H, d, J = 13.7 Hz), 6.11 (1H, t, J = 6.9 Hz), 6.88 (2H, td, J = 2.5, 8.7 Hz), 6.99 (1H, dt, J = 1.8, 7.8 Hz), 7.06 (1H, dd, J = 1.8, 7.8 Hz), 7.16-7.31 (4H, m), 7.54 (2H, td, J = 2.5, 9.2 Hz), 8.52 (1H, d, J = 1.4 Hz), 10.82 (1H, s). | 420 |
| I-114 | 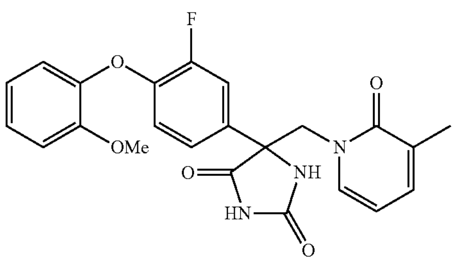 [SMILES: COc1ccccc1Oc1ccc(C2(Cn3cccc(C)c3=O)NC(=O)NC2=O)cc1F] | (DMSO-d$_6$) δ: 1.99 (3H, s), 3.76 (3H, s), 4.46 (1H, d, J = 13.7 Hz), 4.59 (1H, d, J = 13.7 Hz), 6.12 (1H, t, J = 6.9 Hz), 6.80 (1H, t, J = 8.7 Hz), 6.93-7.04 (2H, m), 7.16-7.36 (5H, m), 7.59 (1H, dd, J = 2.3, 17.8 Hz), 8.59 (1H, d, J = 1.4 Hz), 10.93 (1H, s). | 438 |
| I-115 | 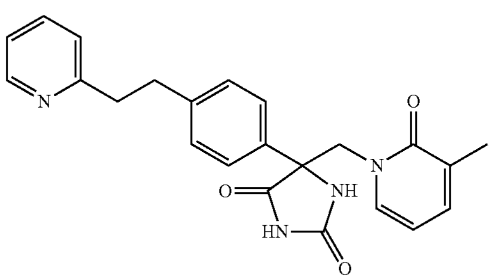 [SMILES: Cc1cccn(CC2(c3ccc(CCc4ccccn4)cc3)NC(=O)NC2=O)c1=O] | (DMSO-d$_6$) δ: 2.00 (3H, s), 2.97-3.07 (4H, m), 4.44 (1H, d, J = 13.7 Hz), 4.60 (1H, d, J = 13.7 Hz), 6.11 (1H, t, J = 6.9 Hz), 7.20-7.32 (6H, m), 7.52 (2H, d, J = 8.2 Hz), 7.70 (1H, dt, J = 1.8, 7.6 Hz), 8.49-8.54 (2H, m), 10.81 (1H, s). | 403 |
| I-116 | 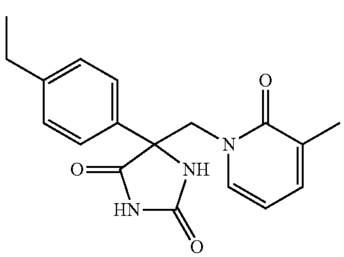 [SMILES: CCc1ccc(C2(Cn3cccc(C)c3=O)NC(=O)NC2=O)cc1] | (DMSO-d$_6$) δ: 1.17 (3H, t, J = 7.8 Hz), 2.00 (3H, s), 2.61 (2H, q, J = 7.5 Hz), 4.45 (1H, d, J = 13.7 Hz), 4.60 (1H, d, J = 13.7 Hz), 6.11 (1H, t, J = 6.9 Hz), 7.23-7.31 (4H, m), 7.53 (2H, d, J = 8.2 Hz), 8.52 (1H, s), 10.80 (1H, s). | 326 |

TABLE 8-continued

| Compound | Structure | ¹H-NMR | MS (M + H)⁺ |
|---|---|---|---|
| I-117 | 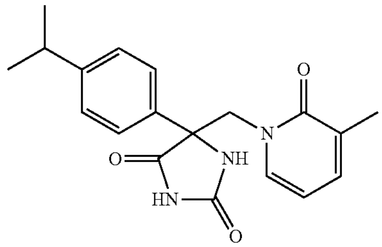 [SMILES: Cc1cccn(CC2(c3ccc(C(C)C)cc3)NC(=O)NC2=O)c1=O] | (DMSO-d₆) δ: 1.20 (6H, d, J = 6.9 Hz), 2.00 (3H, s), 2.90 (1H, sept, J = 6.9 Hz), 4.45 (1H, d, J = 13.7 Hz), 4.61 (1H, d, J = 13.7 Hz), 6.12 (1H, t, J = 6.9 Hz), 7.23-7.28 (2H, m), 7.31 (2H, d, J = 8.3 Hz), 7.54 (2H, d, J = 8.7 Hz), 8.52 (1H, d, J = 1.4 Hz), 10.79 (1H, s). | 340 |
| I-118 | 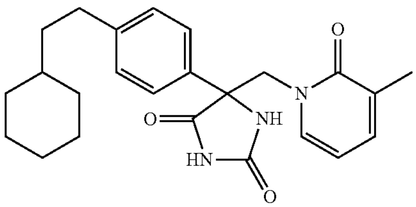 [SMILES: Cc1cccn(CC2(c3ccc(CCC4CCCCC4)cc3)NC(=O)NC2=O)c1=O] | (DMSO-d₆) δ: 0.84-0.96 (2H, m), 1.09-1.28 (4H, m), 1.40-1.49 (2H, m), 1.57-1.80 (5H, m), 200 (3H, s), 2.56-2.61 (2H, m), 4.45 (1H, d, J = 13.7 Hz), 4.60 (1H, d, J = 13.7 Hz), 6.10 (1H, t, J = 6.6 Hz), 7.22-7.30 (4H, m), 7.51 (2H, d, J = 8.2 Hz), 8.51 (1H, d, J = 1.4 Hz), 10.80 (1H, s). | 408 |
| I-119 | 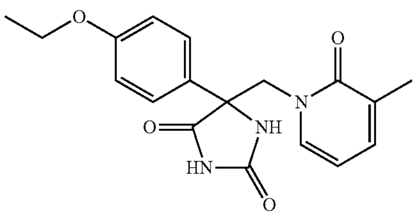 [SMILES: CCOc1ccc(C2(Cn3cccc(C)c3=O)NC(=O)NC2=O)cc1] | (DMSO-d₆) δ: 1.32 (3H, t, J = 7.1 Hz), 2.00 (3H, s), 4.03 (2H, q, J = 6.9 Hz), 4.44 (1H, d, J = 13.7 Hz), 4.57 (1H, d, J = 13.7 Hz), 6.11 (1H, t, J = 6.6 Hz), 6.92-7.02 (2H, m), 7.19-7.32 (2H, m), 7.48-7.56 (2H, m), 8.51 (1H, s), 10.79 (1H, s). | 342 |
| I-120 | 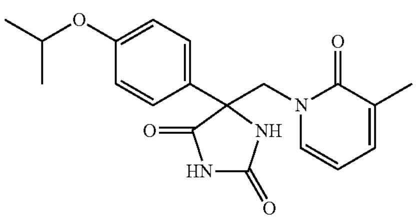 [SMILES: Cc1cccn(CC2(c3ccc(OC(C)C)cc3)NC(=O)NC2=O)c1=O] | (DMSO-d₆) δ: 1.26 (6H, d, J = 6.0 Hz), 2.00 (3H, s), 4.44 (1H, d, J = 13.7 Hz), 4,56 (1H, d, J = 13.7 Hz), 4.63 (1H, sept, J = 6.0 Hz), 6.11 (1H, t, J = 6.6 Hz), 6.92-6.99 (2H, m), 7.21-7.31 (2H, m), 7.51 (2H, td, J = 2.5, 8.7 Hz), 8.51 (1H, d, J = 1.4 Hz), 10.79 (1H, s). | 356 |

TABLE 9

| Compound | Structure | ¹H-NMR | MS (M + H)⁺ |
|---|---|---|---|
| I-121 | 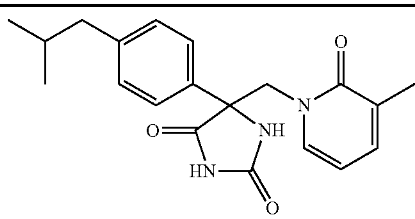 | (DMSO-d₆) δ: 0.85 (6H, d, J = 6.9 Hz), 1.83 (1H, m), 1.99 (3H, s), 2.45 (2H, d, J = 7.3 Hz), 4.45 (1H, d, J = 13.7 Hz), 4.61 (1H, d, J = 13.7 Hz), 6.10 (1H, t, J = 6.9 Hz), 7.19-7.30 (4H, m), 7.52 (2H, d, J = 8.4 Hz), 8.52 (1H, d, J = 1.4 Hz), 10.81 (1H, s). | 354 |
| I-122 | 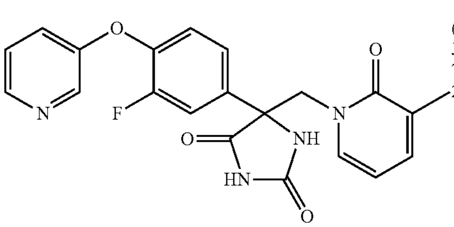 | (CDCl₃) δ: 2.13 (3H, s), 4.30 (1H, d, J = 13.7 Hz), 4.80 (1H, d, J = 13.7 Hz), 6.13 (1H, t, J = 6.9 Hz), 7.11 (1H, t, J = 8.2 Hz), 7.21-7.32 (3H, m), 7.39 (1H, s), 7.45 (1H, m), 7.58 (1H, dd, J = 2.3, 11.4 Hz), 8.34-8.42 (2H, m), 8.67 (1H, s). | 409 |

TABLE 9-continued

| Compound | Structure | ¹H-NMR | MS (M + H)⁺ |
|---|---|---|---|
| I-123 | 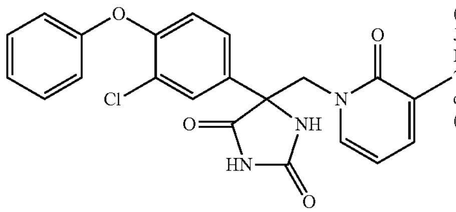 | (DMSO-d₆) δ: 1.99 (3H, s), 4.49 (1H, d, J = 13.7 Hz), 4.61 (1H, d, J = 13.7 Hz), 6.13 (1H, t, J = 6.9 Hz), 6.97 (1H, dd, J = 0.9, 8.7 Hz), 7.11-7.19 (2H, m), 7.22-7.32 (3H, m), 7.35-7.43 (2H, m), 7.60 (1H, dd, J = 2.3, 8.7 Hz), 7.83 (1H, d, J = 2.3 Hz), 8.66 (1H, s), 10.97 (1H, s). | 424 |
| I-124 | 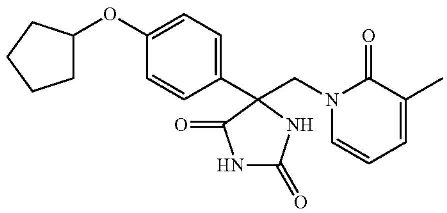 [SMILES: Cc1cccn(CC2(c3ccc(OC4CCCC4)cc3)NC(=O)NC2=O)c1=O] | (CDCl₃) δ: 1.58-1.68 (2H, m), 1.72-1.98 (6H, m), 2.12 (3H, s), 4.22 (1H, d, J = 13.7 Hz), 4.75 (1H, m), 4.83 (1H, d, J = 13.7 Hz), 6.07 (1H, t, J = 13.7 Hz), 6.88 (2H, td, J = 2.5, 6.9 Hz), 7.02 (1H, s), 7.13 (1H, dd, J = 1.4, 6.9 Hz), 7.17-7.22 (1H, m), 7.51 (2H, td, J = 2.5, 9.2 Hz), 8.10 (1H, s). | 382 |
| I-125 | 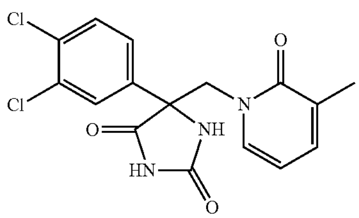 [SMILES: Cc1cccn(CC2(c3ccc(Cl)c(Cl)c3)NC(=O)NC2=O)c1=O] | (DMSO-d₆) δ: 1.98 (3H, s), 4.47 (1H, d, J = 13.7 Hz), 4.61 (1H, d, J = 13.7 Hz), 6.13 (1H, t, J = 6.9 Hz), 7.24-7.31 (2H, m), 7.62 (1H, dd, J = 2.3, 8.7 Hz), 7.73 (1H, d, J = 8.7 Hz), 7.87 (1H, d, J = 2.3 Hz), 8.65 (1H, br s), 10.93 (1H, m). | 366 368 |
| I-126 | 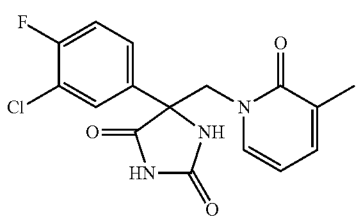 [SMILES: Cc1cccn(CC2(c3ccc(F)c(Cl)c3)NC(=O)NC2=O)c1=O] | (DMSO-d6) δ: 1.98 (3H, s), 4.47 (1H, d, J = 13.7 Hz), 4.60 (1H, d, J = 13.7 Hz), 6.12 (1H, t, J = 6.4 Hz), 7.24-7.31 (2H, m), 7.50 (1H, t, J = 8.7 Hz), 7.64 (1H, ddd, J = 2.7, 4.6, 8.7 Hz), 7.83 (1H, dd, J = 2.7, 7.3 Hz), 8.63 (1H, br s), 10.96 (1H, m). | 350 352 |
| I-127 | 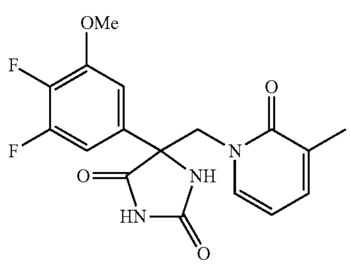 [SMILES: COc1cc(C2(Cn3cccc(C)c3=O)NC(=O)NC2=O)cc(F)c1F] | (DMSO-d₆) δ: 1.99 (3H, s), 3.90 (3H, s), 4.48 (1H, d, J = 13.7 Hz), 4.57 (1H, d, J = 13.7 Hz), 6.13 (1H, t, J = 6.9 Hz), 7.22-7.32 (4H, m), 8.64 (1H, br s), 11.00 (1H, br s). | 364 |
| I-128 | 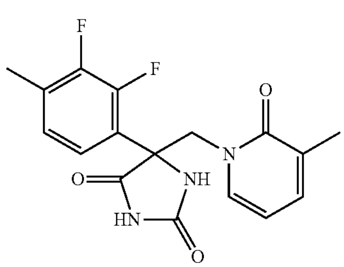 | (DMSO-d₆) δ: 1.99 (3H, s), 2.30 (3H, s), 4.70 (1H, d, J = 13.7 Hz), 4.76 (1H, d, J = 13.7 Hz), 6.14 (1H, t, J = 6.9 Hz), 7.18 (1H, br t, J = 7.3 Hz), 7.24-7.34 (3H, m), 8.31 (1H, br s), 10.94 (1H, br s). | 348 |

TABLE 10

| Compound | Structure | ¹H-NMR | MS (M + H)⁺ |
|---|---|---|---|
| I-129 | 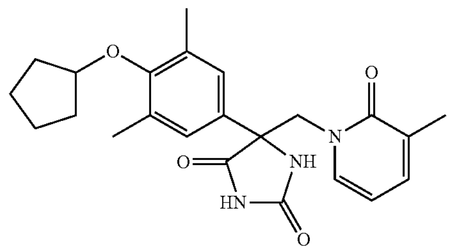 [SMILES: Cc1cc(C2(Cn3cccc(C)c3=O)NC(=O)NC2=O)cc(C)c1OC1CCCC1] | (CDCl₃) δ: 1.53-1.92 (8H, m), 2.13 (3H, s), 2.28 (6H, s), 4.21 (1H, d, J = 13.7 Hz), 4.46 (1H, m), 4.84 (1H, d, J = 13.7 Hz), 6.08 (1H, t, J = 6.9 Hz), 6.93 (2H, s), 7.13 (1H, d, J = 6.4 Hz), 7.20 (1H, d, J = 6.4 Hz), 7.24 (1H, s). | 410 |
| I-130 | 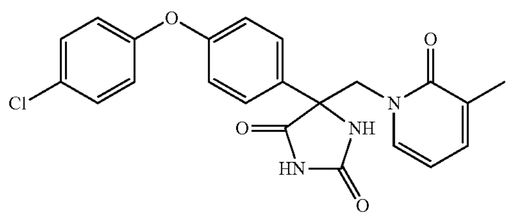 [SMILES: Cc1cccn(CC2(c3ccc(Oc4ccc(Cl)cc4)cc3)NC(=O)NC2=O)c1=O] | (DMSO-d₆) δ: 1.99 (3H, s), 3.94 (2H, s), 4.44 (1H, d, J = 13.7 Hz), 4.58 (1H, d, J = 13.3 Hz), 6.10 (1H, t, J = 6.7 Hz), 7.22-7.38 (8H, m), 7.54 (2H, d, J = 8.2 Hz), 8.44 (1H, s), 10.76 (1H, s). | 422 424 |
| I-131 | 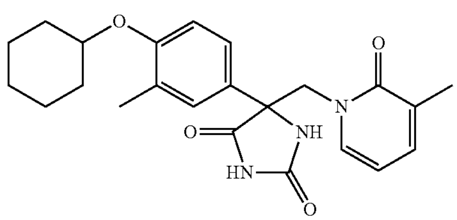 [SMILES: Cc1cc(C2(Cn3cccc(C)c3=O)NC(=O)NC2=O)ccc1OC1CCCCC1] | (CDCl₃) δ: 1.30-1.98 (10H, m), 2.11 (3H, s), 2.22 (3H, s), 4.19 (1H, d, J = 13.7 Hz), 4.28 (1H, m), 4.87 (1H, d, J = 13.7 Hz), 6.07 (1H, t, J = 6.9 Hz), 6.83 (1H, d, J = 8.7 Hz), 7.10-7.22 (3H, m), 7.34-7.42 (2H, m), 8.96 (1H, br s). | 410 |

TABLE 11

| Compound | Structure | ¹H-NMR | MS (M + H)⁺ |
|---|---|---|---|
| I-132 | 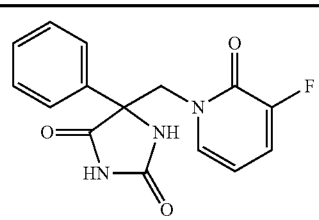 | (DMSO-d₆) δ: 4.49 (1H, d, J = 13.7 Hz), 4.75 (1H, d, J = 13.7 Hz), 6.18 (1H, dt, J = 4.6, 7.3 Hz), 7.22 (1H, dt, J = 1.4, 6.9 Hz), 7.36-7.48 (4H, m), 7.60-7.65 (2H, m), 8.72 (1H, s), 10.83 (1H, s). | 302 |
| I-133 | 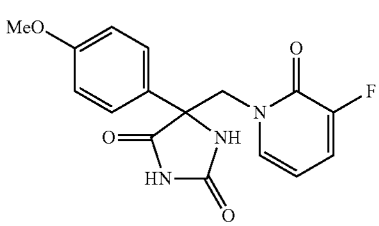 [SMILES: COc1ccc(C2(Cn3cccc(F)c3=O)NC(=O)NC2=O)cc1] | (DMSO-d₆) δ: 3.76 (3H, s), 4.46 (1H, d, J = 13.7 Hz), 4.69 (1H, d, J = 13.7 Hz), 6.18 (1H, dt, J = 4.6, 7.3 Hz), 7.00 (2H, d, J = 8.7 Hz), 7.20 (1H, d, J = 6.9 Hz), 7.36-7.43 (1H, m), 7.53 (2H, d, J = 8.7 Hz), 8.69 (1H, s), 10.87 (1H, s). | 332 |

TABLE 11-continued

| Compound | Structure | ¹H-NMR | MS (M + H)⁺ |
|---|---|---|---|
| I-134 | 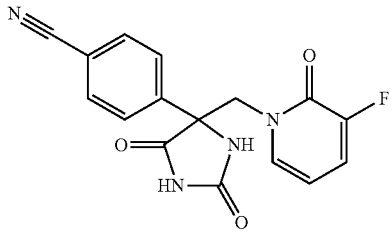 [SMILES: N#Cc1ccc(C2(Cn3cccc(F)c3=O)NC(=O)NC2=O)cc1] | (DMSO-d₆) δ: 4.51 (1H, d, J = 13.7 Hz), 4.78 (1H, d, J = 13.7 Hz), 6.20 (1H, dt, J = 4.6, 7.3 Hz), 7.21-7.26 (1H, m), 7.40 (1H, ddd, J = 1.8, 7.8, 9.6 Hz), 7.82 (2H, d, J = 8.7 Hz), 7.95 (2H, d, J = 8.7 Hz), 8.88 (1H, s), 11.08 (1H, s). | 327 |
| I-135 | 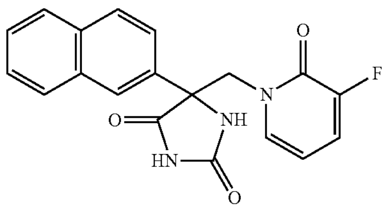 [SMILES: O=C1NC(=O)C(Cn2cccc(F)c2=O)(c2ccc3ccccc3c2)N1] | (DMSO-d₆) δ: 4.60 (1H, d, J = 13.7 Hz), 4.89 (1H, d, J = 13.7 Hz), 6.20 (1H, dt, J = 4.6, 6.9 Hz), 7.28 (1H, d, J = 6.9 Hz), 7.41 (1H, ddd, J = 1.8, 7.3, 9.2 Hz), 7.54-7.61 (2H, m), 7.78 (1H, dd, J = 1.8, 8.7 Hz), 7.92-7.98 (2H, m), 8.01 (1H, d, J = 8.7 Hz), 8.15 (1H, d, J = 1.8 Hz), 8.84 (1H, s), 10.98 (1H, s). | 352 |
| I-136 | 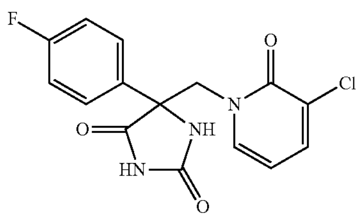 [SMILES: O=C1NC(=O)C(Cn2cccc(Cl)c2=O)(c2ccc(F)cc2)N1] | (DMSO-d₆) δ: 4.48 (1H, d, J = 13.3 Hz), 4.73 (1H, d, J = 13.7 Hz), 6.24 (1H, t, J = 7.1 Hz), 7.26-7.33 (2H, m), 7.39 (1H, dd, J = 1.8, 6.9 Hz), 7.63-7.70 (2H, m), 7.75 (1H, dd, J = 1.8, 7.3 Hz), 8.78 (1H, s), 10.96 (1H, s). | 336 338 |
| I-137 | 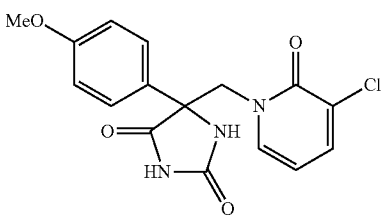 [SMILES: COc1ccc(C2(Cn3cccc(Cl)c3=O)NC(=O)NC2=O)cc1] | (DMSO-d₆) δ: 3.77 (3H, s), 4.46 (1H, d, J = 13.7 Hz), 4.70 (1H, d, J = 13.7 Hz), 6.23 (1H, t, J = 7.1 Hz), 7.00 (2H, d, J = 9.2 Hz), 7.37 (1H, dd, J = 1.8, 6.9 Hz), 7.53 (2H, d, J = 9.2 Hz), 7.74 (1H, dd, J = 1.8, 7.3 Hz), 8.69 (1H, s), 10.87 (1H, s). | 348 |
| I-138 | 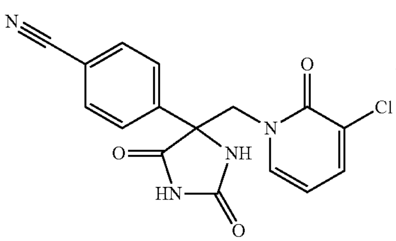 [SMILES: N#Cc1ccc(C2(Cn3cccc(Cl)c3=O)NC(=O)NC2=O)cc1] | (DMSO-d₆) δ: 4.51 (1H, d, J = 13.3 Hz), 4.75 (1H, d, J = 13.7 Hz), 6.26 (1H, t, J = 7.1 Hz), 7.41 (1H, dd, J = 1.8, 6.9 Hz), 7.75 (1H, dd, J = 1.8, 7.3 Hz), 7.82 (2H, d, J = 8.7 Hz), 7.95 (2H, d, J = 8.7 Hz), 8.86 (1H, s), 10.99 (1H, s). | 343 345 |
| I-139 | 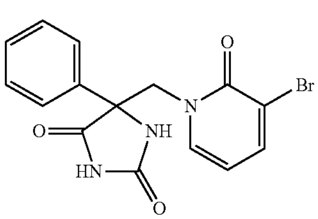 [SMILES: O=C1NC(=O)C(Cn2cccc(Br)c2=O)(c2ccccc2)N1] | (DMSO-d₆) δ: 4.49 (1H, d, J = 13.3 Hz), 4.75 (1H, d, J = 13.7 Hz), 6.18 (1H, t, J = 7.1 Hz), 7.36-7.48 (4H, m), 7.60-7.65 (2H, m), 7.92 (1H, dd, J = 1.8, 7.3 Hz), 8.74 (1H, s), 10.91 (1H, s). | 362 364 |

TABLE 12

| | Structure | $^1$H-NMR | MS (M + H)$^+$ |
|---|---|---|---|
| I-140 | 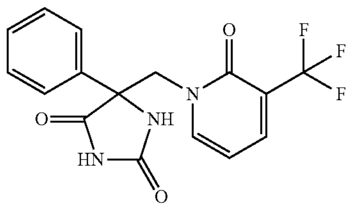 [SMILES: O=C1NC(=O)C(Cn2cccc(C(F)(F)F)c2=O)(c2ccccc2)N1] | (DMSO-d$_6$) δ: 4.49 (1H, d, J = 13.7 Hz), 4.76 (1H, d, J = 13.7 Hz), 6.37 (1H, t, J = 6.9 Hz), 7.36-7.48 (3H, m), 7.59-7.66 (2H, m), 7.71 (1H, dd, J = 1.8, 6.9 Hz), 7.95 (1H, ddt, J = 1.2, 7.1 Hz), 6.77 (1H, s), 10.92 (1H, s). | 350 (M − H)$^−$ |
| I-141 | 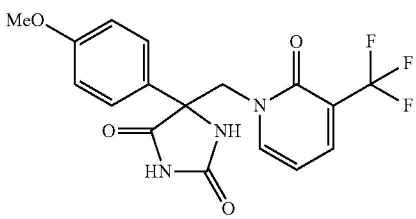 [SMILES: COc1ccc(C2(Cn3cccc(C(F)(F)F)c3=O)NC(=O)NC2=O)cc1] | (DMSO-d$_6$) δ: 3.76 (3H, s), 4.46 (1H, d, J = 13.3 Hz), 4.70 (1H, d, J = 13.3 Hz), 6.36 (1H, t, J = 6.9 Hz), 6.99 (2H, d, J = 9.2 Hz), 7.53 (2H, d, J = 8.7 Hz), 7.69 (1H, m), 7.94 (1H, m), 8.72 (1H, s), 10.87 (1H, s). | 382 |
| I-142 | 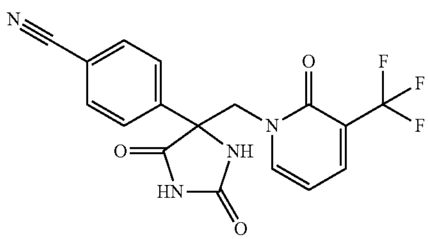 [SMILES: N#Cc1ccc(C2(Cn3cccc(C(F)(F)F)c3=O)NC(=O)NC2=O)cc1] | (DMSO-d$_6$) δ: 4.52 (1H, d, J = 13.7 Hz), 4.78 (1H, d, J = 13.7 Hz), 6.39 (1H, t, J = 7.1 Hz), 7.72-7.77 (1H, m), 7.81 (2H, d, J = 8.7 Hz), 7.91-7.98 (3H, m), 8.92 (1H, s), 11.08 (1H, s). | 377 |
| I-143 | 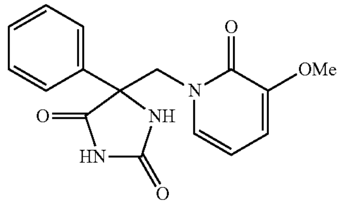 [SMILES: COc1cccn(CC2(c3ccccc3)NC(=O)NC2=O)c1=O] | (DMSO-d$_6$) δ: 3.69 (3H, s), 4.47 (1H, d, J = 13.3 Hz), 4.64 (1H, d, J = 13.3 Hz), 6.12 (1H, t, J = 7.1 Hz), 6.78 (1H, dd, J = 1.6, 7.6 Hz), 6.96 (1H, dd, J = 1.8, 6.9 Hz), 7.35-7.48 (3H, m), 7.60-7.66 (2H, m), 8.59 (1H, s), 10.84 (1H, s). | 314 |
| I-144 | 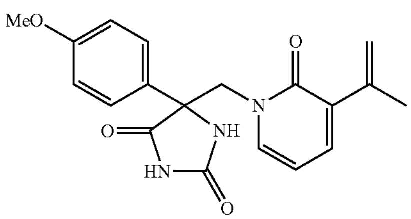 [SMILES: C=C(C)c1cccn(CC2(c3ccc(OC)cc3)NC(=O)NC2=O)c1=O] | (DMSO-d$_6$) δ: 2.01 (3H, s), 3.76 (3H, s), 4.47 (1H, d, J = 13.7 Hz), 4.62 (1H, d, J = 13.7 Hz), 5.15 (1H, s), 5.83 (1H, d, J = 2.3 Hz), 6.22 (1H, t, J = 6.9 Hz), 6.99 (2H, d, J = 8.7 Hz), 7.38 (2H, ddd, J = 1.8, 6.9, 8.7 Hz), 7.55 (2H, d, J = 8.7 Hz), 8.53 (1H, s), 10.77 (1H, s). | 354 |
| I-145 | 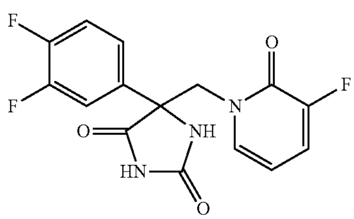 [SMILES: O=C1NC(=O)C(Cn2cccc(F)c2=O)(c2ccc(F)c(F)c2)N1] | (DMSO-d$_6$) δ: 4.49 (1H, d, J = 13.7 Hz), 4.71 (1H, d, J = 13.7 Hz), 6.20 (1H, dt, J = 4.6, 7.3 Hz), 7.22 (1H, d, J = 6.9 Hz), 7.36-7.60 (3H, m), 7.69 (1H, ddd, J = 2.3, 7.8, 12.4 Hz), 8.78 (1H, s), 11.05 (1H, s). | 338 |
| I-146 | 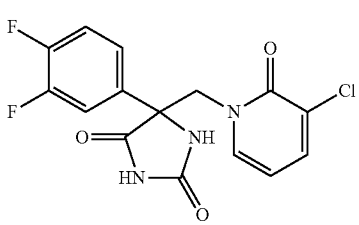 [SMILES: O=C1NC(=O)C(Cn2cccc(Cl)c2=O)(c2ccc(F)c(F)c2)N1] | (DMSO-d$_6$) δ: 4.44 (1H, d, J = 13.7 Hz), 4.55 (1H, d, J = 13.7 Hz), 6.25 (1H, t, J = 6.9 Hz), 7.39 (1H, dd, J = 1.8, 6.9 Hz), 7.43-7.58 (2H, m), 7.69 (1H, ddd, J = 2.3, 7.3, 11.9 Hz), 7.75 (1H, dd, J = 1.8, 7.3 Hz), 8.71 (1H, s), 11.04 (1H, s). | 354 |

TABLE 12-continued

| | Structure | ¹H-NMR | MS (M + H)⁺ |
|---|---|---|---|
| I-147 | 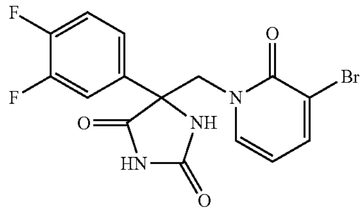 [SMILES: O=C1NC(=O)C(Cn2cccc(Br)c2=O)(c2ccc(F)c(F)c2)N1] | (DMSO-d$_6$) δ: 4.49 (1H, d, J = 13.7 Hz), 4.70 (1H, d, J = 13.7 Hz), 6.19 (1H, t, J = 6.9 Hz), 7.39-7.59 (3H, m), 7.68 (1H, ddd, J = 2.3, 7.3, 11.9 Hz), 7.92 (1H, dd, J = 1.8, 7.3 Hz), 8.74 (1H, s), 11.04 (1H, s). | 398 400 |
| I-148 | 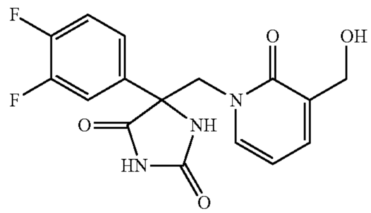 [SMILES: O=C1NC(=O)C(Cn2cccc(CO)c2=O)(c2ccc(F)c(F)c2)N1] | (DMSO-d$_6$) δ: 4.29 (2H, d, J = 5.0 Hz), 4.47 (1H, d, J = 13.7 Hz), 4.61 (1H, d, J = 13.7 Hz), 5.11 (1H, t, J = 5.0 Hz), 6.25 (1H, t, J = 6.9 Hz), 7.30 (1H, dd, J = 1.8, 6.9 Hz), 7.40(1H, dd, J = 1.8, 6.9 Hz), 7.45-7.56 (2H, m), 7.66-7.71 (1H, m), 8.64 (1H, s), 10.95 (1H, s). | 350 |

TABLE 13

| Compound | Structure | ¹H-NMR | MS (M + H)⁺ |
|---|---|---|---|
| I-149 | 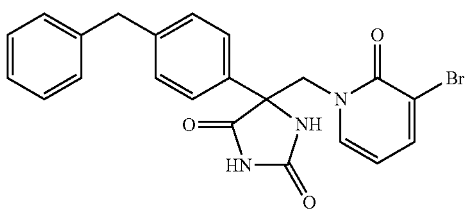 [SMILES: O=C1NC(=O)C(Cn2cccc(Br)c2=O)(c2ccc(Cc3ccccc3)cc2)N1] | (DMSO-d$_6$) δ: 3.95 (2H, s), 4.45 (1H, d, J = 13.7 Hz), 4.72 (1H, d, J = 13.7 Hz), 6.17 (1H, t, J = 7.1 Hz), 7.18-7.31 (7H, m), 7.42 (1H, dd, J = 1.8, 6.9 Hz), 7.53 (2H, d, J = 8.2 Hz), 7.91 (1H, dd, J = 1.8, 7.3 Hz), 8.69 (1H, s), 10.88 (1H, s). | 452 454 |
| I-150 | 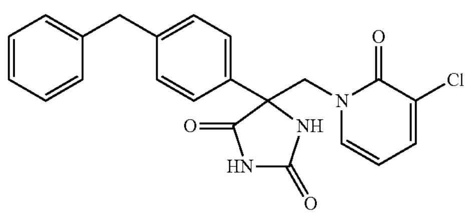 [SMILES: O=C1NC(=O)C(Cn2cccc(Cl)c2=O)(c2ccc(Cc3ccccc3)cc2)N1] | (DMSO-d$_6$) δ: 3.95 (2H, s), 4.46 (1H, d, J = 13.7 Hz), 4.73 (1H, d, J = 13.7 Hz), 6.23 (1H, t, J = 7.1 Hz), 7.18-7.31 (7H, m), 7.38 (1H, dd, J = 1.8, 6.9 Hz), 7.53 (2H, d, J = 8.2 Hz), 7.74 (1H, dd, J = 1.8, 7.3 Hz), 8.68 (1H, s), 10.87 (1H, s). | 408 |
| I-151 | 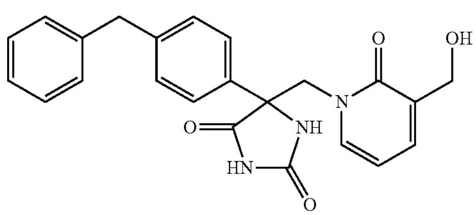 [SMILES: O=C1NC(=O)C(Cn2cccc(CO)c2=O)(c2ccc(Cc3ccccc3)cc2)N1] | (DMSO-d$_6$) δ: 4.30 (2H, d, J = 5.5 Hz), 4.44 (1H, d, J = 13.7 Hz), 4.61 (1H, d, J = 13.7 Hz), 5.12 (1H, t, J = 5.5 Hz), 6.23 (1H, t, J = 6.9 Hz), 7.18-7.30 (10H, m), 7.40 (1H, dd, J = 1.8, 6.4 Hz), 7.53 (2H, d, J = 8.2 Hz), 8.54 (1H, s), 10.82 (1H, s). | 404 |
| I-152 | 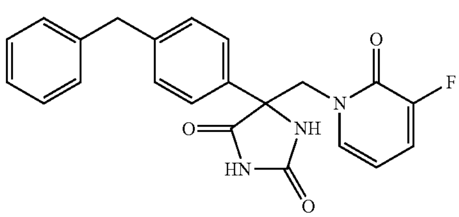 [SMILES: O=C1NC(=O)C(Cn2cccc(F)c2=O)(c2ccc(Cc3ccccc3)cc2)N1] | (DMSO-d$_6$) δ: 3.95 (2H, s), 4.46 (1H, d, J = 13.7 Hz), 4.71 (1H, d, J = 13.7 Hz), 6.17 (1H, dt, J = 4.6, 7.3 Hz), 7.17-7.23 (4H, m), 7.27-7.31 (4H, m), 7.38 (1H, ddd, J = 1.4, 7.3, 10.1 Hz), 7.52 (2H, d, J = 8.2 Hz), 8.67 (1H, s), 10.85 (1H, s). | 392 |

TABLE 13-continued

| Compound | Structure | ¹H-NMR | MS (M + H)⁺ |
|---|---|---|---|
| I-153 | 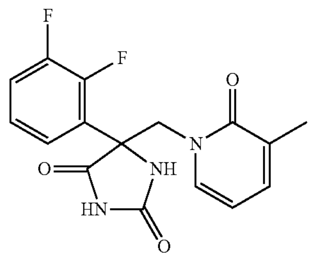 [SMILES: Cc1cccn(CC2(c3cccc(F)c3F)NC(=O)NC2=O)c1=O] | (DMSO-d₆) δ: 1.99 (3H, s), 4.75 (2H, s), 6.14(1H, t, J = 6.6 Hz), 7.28-7.33 (3H, m), 7.42-7.45 (1H, m), 7.51-7.57 (1H, m), 8.37 (1H, s), 10.99 (1H, s). | 334 |
| I-154 | 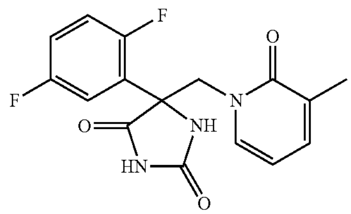 [SMILES: Cc1cccn(CC2(c3cc(F)ccc3F)NC(=O)NC2=O)c1=O] | (DMSO-d₆) δ: 1.99 (3H, s), 4.69 (1H, d, J = 13.7 Hz), 4.77 (1H, d, J = 13.7 Hz), 6.14 (1H, t, J = 6.6 Hz), 7.26-7.40 (4H, m), 7.48-7.52 (1H, m), 8.27 (1H, s), 10.08 (1H, s). | 334 |
| I-155 | 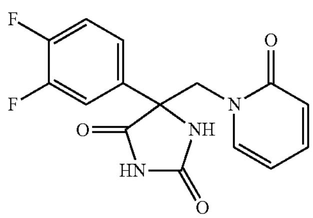 [SMILES: O=C1NC(=O)C(Cn2ccccc2=O)(c2ccc(F)c(F)c2)N1] | (DMSO-d₆) δ: 4.45 (1H, d, J = 13.7 Hz), 4.61 (1H, d, J = 13.7 Hz), 6.21 (1H, dt, J = 1.4, 6.4 Hz), 6.40 (1H, m), 7.38-7.43 (2H, m), 7.45-7.58 (2H, m), 7.69 (1H, ddd, J = 2.3, 7.8, 12.4 Hz), 8.64 (1H, s), 10.98 (1H, br s). | 320 |
| I-156 | 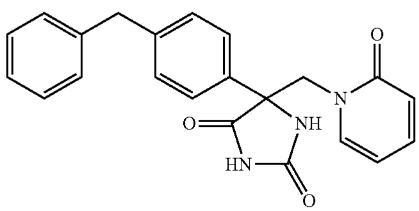 [SMILES: O=C1NC(=O)C(Cn2ccccc2=O)(c2ccc(Cc3ccccc3)cc2)N1] | (DMSO-d₆) δ: 3.94 (2H, s), 4.40 (1H, d, J = 13.3 Hz), 4.61 (1H, d, J = 13.3 Hz), 6.18 (1H, t, J = 6.4 Hz), 6.39 (1H, d, J = 9.2 Hz), 7.15-7.32 (7H, m), 7.53 (2H, d, J = 8.2 Hz), 8.51 (1H, s), 10.81 (1H, br s). | 374 |
| I-157 | 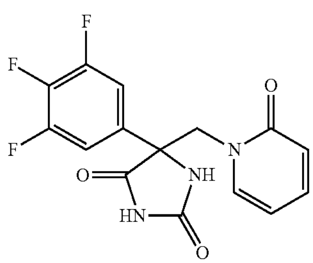 [SMILES: O=C1NC(=O)C(Cn2ccccc2=O)(c2cc(F)c(F)c(F)c2)N1] | (DMSO-d₆) δ: 4.45 (1H, d, J = 13.3 Hz), 4.60 (1H, d, J = 13.7 Hz), 6.21 (1H, m), 6.39 (1H, m), 7.37-7.44 (2H, m), 7.53-7.62 (2H, m), 8.63 (1H, s), 11.08 (1H, br s). | 338 |

Test Example 1

TACE Inhibition Test (In Vitro)

The nucleotide sequence of TACE has been reported by Moss et al. (Moss, M. L. et al., Nature 1997, 385, 733-736). Accordingly, the cDNA of TACE was obtained according to the prescribed method from THP-1 cells or the like, and then incorporated the cDNA into an expression vector. Next, this vector was transformed into mammalian cells or insect cells, and TACE expression was obtained.

The TACE inhibition test was carried out by measuring TACE activity in the presence and the absence of the test substance using the thus-obtained TACE as an enzyme, and a fluorescent synthetic substrate Nma(N-methylanthranilic acid)-Leu-Ala-Gln-Ala-Val-Arg-Ser-Ser-Lys(Dnp(dinitrophenyl))-D-Arg-NH₂ (SEQ ID NO: 1) including the TACE-cleaved sequence of a membrane-bound TNF as a substrate. The TACE inhibition test method is shown below.

Namely, 90 μL of an enzyme solution prepared with an assay buffer A (50 mM tris-hydrochloric acid buffer (pH 7.5) including 200 mM sodium chloride, 5 mM calcium chloride, 10 μM zinc sulfate, and 2 mg/mL bovine serum albumin) and 90 μL of a fluorescent synthetic substrate prepared with an assay buffer B (50 mM tris-hydrochloric acid buffer (pH 7.5) including 200 mM sodium chloride, 5 mM calcium chloride, 10 μM zinc sulfate, and 0.05% PLURONIC F-68) were mixed together, and reacted at 37° C. for 1.5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration ($IC_{50}$) of the test substance was calculated.

Tables 14(1), (2) and, Tables 15(1), (2) show the results of evaluation of TACE inhibition. In these Tables, the symbol "A" means that $IC_{50}$ value of test compound is less than 100 nM, and the symbol "B" means that $IC_{50}$ value of test compound is 100 nM or more and less than 1,000 nM.

[Table 14]

TABLE 14(1)

| Compound | TACE $IC_{50}$ |
| --- | --- |
| I-1 | A |
| I-2 | A |
| I-3 | A |
| I-4 | A |
| I-5 | A |
| I-6 | A |
| I-7 | A |
| I-8 | A |
| I-9 | A |
| I-10 | A |
| I-11 | A |
| I-12 | A |
| I-13 | A |
| I-14 | A |
| I-15 | A |
| I-16 | A |
| I-17 | A |
| I-18 | A |
| I-19 | A |
| I-20 | A |
| I-21 | A |
| I-22 | A |
| I-23 | A |
| I-24 | B |
| I-25 | A |
| I-26 | A |
| I-27 | A |
| I-28 | A |
| I-29 | A |
| I-30 | A |
| I-31 | A |
| I-32 | A |
| I-33 | A |
| I-34 | A |
| I-35 | A |
| I-36 | A |
| I-37 | A |
| I-38 | A |
| I-39 | A |
| I-40 | A |

TABLE 14(2)

| Compound | TACE $IC_{50}$ |
| --- | --- |
| I-41 | A |
| I-42 | A |
| I-43 | A |
| I-44 | A |
| I-45 | A |
| I-46 | A |
| I-47 | A |
| I-48 | A |
| I-49 | A |
| I-50 | A |
| I-51 | A |
| I-52 | A |
| I-53 | B |
| I-54 | B |
| I-55 | A |
| I-56 | A |
| I-57 | A |
| I-58 | A |
| I-59 | A |
| I-60 | B |
| I-61 | B |
| I-62 | A |
| I-63 | B |
| I-64 | A |
| I-65 | A |
| I-66 | A |
| I-67 | A |
| I-68 | B |
| I-69 | A |
| I-70 | B |
| I-71 | A |
| I-72 | A |
| I-73 | A |
| I-74 | A |
| I-75 | A |
| I-76 | B |
| I-77 | A |
| I-78 | A |
| I-79 | A |
| I-80 | A |

[Table 15]

TABLE 15(1)

| Compound | TACE $IC_{50}$ |
| --- | --- |
| I-81 | A |
| I-82 | A |
| I-83 | A |
| I-84 | A |
| I-85 | A |
| I-86 | A |
| I-87 | A |
| I-88 | A |
| I-89 | A |
| I-90 | A |
| I-91 | A |
| I-92 | A |
| I-93 | A |
| I-94 | A |
| I-95 | A |
| I-96 | A |
| I-97 | A |
| I-98 | A |
| I-99 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | B |
| I-110 | A |
| I-111 | A |
| I-112 | A |
| I-113 | A |
| I-114 | A |
| I-115 | A |
| I-116 | A |
| I-117 | A |
| I-118 | B |
| I-119 | A |
| I-120 | A |

TABLE 15(2)

| Compound | TACE IC$_{50}$ |
|---|---|
| I-121 | A |
| I-122 | A |
| I-123 | A |
| I-124 | A |
| I-125 | A |
| I-126 | A |
| I-127 | A |
| I-128 | A |
| I-129 | A |
| I-130 | A |
| I-131 | A |
| I-132 | A |
| I-133 | A |
| I-134 | A |
| I-135 | A |
| I-136 | A |
| I-137 | A |
| I-138 | A |
| I-139 | A |
| I-140 | A |
| I-141 | A |
| I-142 | A |
| I-143 | B |
| I-144 | B |
| I-145 | A |
| I-146 | A |
| I-147 | A |
| I-148 | B |
| I-149 | A |
| I-150 | A |
| I-151 | B |
| I-152 | A |
| I-153 | A |
| I-154 | A |
| I-155 | A |
| I-156 | B |
| I-157 | A |

Test Example 2

MMP Inhibition Tests

MMP inhibition tests can be carried out, for example, using a fluorescent synthetic substrate based on the methods described in Bickett et al. (D. Mark Bickett et al., Anal. Biochem., 1993, 212, 58-64) and Nagase et al. (H. Nagase et al., J. Biol. Chem., 1994, 269, 20952-20957). The method for each MMP inhibition test is shown below.

MMP-1 Inhibition Test

180 µL (100 ng) of human MMP-1 (Calbiochem #444208) was mixed with 20 µL of 10 mM p-amino phenyl mercuric acetate (APMA), and activated by reacting at 37° C. for 1 hour. 20 µL of the resultant enzyme solution was diluted to 90 µL with an assay buffer A. The mixture was added to 90 µL of a 20 µM fluorescent substrate (Dnp-Pro-Cha(β-cyclohexylalanyl)-Gly-Cys(Me)-His-Ala-Lys(Nma)-NH$_2$) (SEQ ID NO: 2) prepared with an assay buffer B, and reacted at 37° C. for 5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration (IC$_{50}$) of the test substance was calculated.

MMP-2 Inhibition Test

90 µL (5 ng) of human MMP-2 (Calbiochem #444213) was mixed with 10 µL of 10 mM APMA, and activated by reacting at 37° C. for 1 hour. 10 µL of the resultant enzyme solution was diluted to 90 µL with an assay buffer A. The mixture was added to 90 µL of a 20 µM fluorescent substrate (MOCAc((7-methoxycoumarin-4-yl)acetyl)-Pro-Leu-Gly-Leu-A$_2$pr(Dnp)-Ala-Arg-NH$_2$, Peptide Institute Inc., #3163-v) (SEQ ID NO: 3) prepared with an assay buffer B, and reacted at 37° C. for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration (IC$_{50}$) of the test substance was calculated.

MMP-3 Inhibition Test

90 µL (1.5 ng) of human MMP-3 (Calbiochem #444217) prepared with an assay buffer A was added to 90 µL of a 20 µM fluorescent substrate NFF-3 (MOCAc((7-methoxycoumarin-4-yl)acetyl)-Arg-Pro-Lys-Pro-Val-Glu-Nva-Trp-Arg-Lys(Dnp)-NH$_2$, Peptide Institute Inc., #3168-v) (SEQ ID NO: 4) prepared with an assay buffer B, and reacted at 37° C. for 4 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration (IC$_{50}$) of the test substance was calculated.

MMP-8 Inhibition Test

90 µL (29 ng) of human MMP-8 (Calbiochem #444229) was mixed with 10 µL of 10 mM APMA, and activated by reacting at 37° C. for 1 hour. 10 µL of the resultant enzyme solution was diluted to 90 µL with an assay buffer A. The mixture was added to 90 µL of a 20 µM fluorescent substrate (MOCAc-Pro-Leu-Gly-Leu-A$_2$pr(Dnp)-Ala-Arg-NH$_2$, Peptide Institute Inc., #3163-v) (SEQ ID NO: 3) prepared with an assay buffer B, and reacted at 37° C. for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration (IC$_{50}$) of the test substance was calculated.

MMP-9 Inhibition Test

90 µL (11 ng) of human MMP-9 (Calbiochem #444231) was mixed with 10 µL of 10 mM APMA, and activated by reacting at 37° C. for 2 hours. 10 µL of the resultant enzyme solution was diluted to 90 µL with an assay buffer A. The mixture was added to 90 µL of a 20 µM fluorescent substrate (Dnp-Pro-Cha-Gly-Cys(Me)-His-Ala-Lys(Nma)-NH$_2$) (SEQ ID NO: 2) prepared with an assay buffer B, and reacted at 37° C. for 4 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration (IC$_{50}$) of the test substance was calculated.

MMP-13 Inhibition Test

90 µL (18 ng) of human MMP-13 (Calbiochem # CC068) or 90 µL (130 ng) of human MMP-13 (Calbiochem #444287) was mixed with 10 µL of 10 mM APMA, and activated by reacting at 37° C. for 1 hour. 10 µL of the resultant enzyme solution was diluted to 90 µL with an assay buffer A. The mixture was added to 90 µL of a 20 µM fluorescent substrate (Dnp-Pro-Cha-Gly-Cys(Me)-His-Ala-Lys(Nma)-NH$_2$) (SEQ ID NO: 2) prepared with an assay buffer B, and reacted at 37° C. for 4 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration (IC$_{50}$) of the test substance was calculated.

MMP-14 Inhibition Test

90 μL (1.9 ng) of human MMP-14 (Calbiochem #475935) prepared with an assay buffer A was added to 90 μL of a 20 μM fluorescent substrate (Dnp-Pro-Cha-Gly-Cys(Me)-His-Ala-Lys(Nma)-NH$_2$) (SEQ ID NO: 2) prepared with an assay buffer B, and reacted at 37° C. for 5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration (IC$_{50}$) of the test substance was calculated.

MMP-17 Inhibition Test

90 μL (5.8 ng) of human MMP-17 (Calbiochem #475940) prepared with an assay buffer A was added to 90 μL of a 20 μM fluorescent substrate (MOCAc-Pro-Leu-Gly-Leu-A$_2$pr (Dnp)-Ala-Arg-NH$_2$, Peptide Institute Inc., #3163-v) (SEQ ID NO: 3) prepared with an assay buffer B, and reacted at room temperature for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration (IC$_{50}$) of the test substance was calculated.

The results in these tests are shown in Table 16.

TABLE 16

| Compound | MMPs IC$_{50}$ (nM) | | | | | | | |
|---|---|---|---|---|---|---|---|---|
| | MMP-1 | MMP-2 | MMP-3 | MMP-8 | MMP-9 | MMP-13 | MMP-14 | MMP-17 |
| I-1 | >100,000 | >100,000 | >100,000 | 21,000 | >100,000 | 45,000 | 31,000 | >100,000 |
| I-9 | >100,000 | 29,000 | 74,000 | 14,000 | >100,000 | >100,000 | 12,000 | 21,000 |
| I-10 | >100,000 | >100,000 | >100,000 | 19,000 | >100,000 | >100,000 | 30,000 | >100,000 |
| I-27 | >100,000 | 62,000 | 49,000 | 16,000 | >100,000 | >100,000 | 11,000 | 57,000 |
| I-40 | >100,000 | >100,000 | >100,000 | 16,000 | >100,000 | >100,000 | 22,000 | 30,000 |
| I-41 | 93,000 | 69,000 | >100,000 | >10,000 | >100,000 | >100,000 | 21,000 | 16,000 |
| I-62 | >100,000 | 31,000 | 39,000 | 5,000 | 67,000 | >100,000 | 22,000 | 45,000 |
| I-64 | >100,000 | >10,000 | >100,000 | 6,200 | >100,000 | >100,000 | 6,000 | >100,000 |
| I-86 | >100,000 | 51,000 | >100,000 | 18,000 | >100,000 | >100,000 | 23,000 | 27,000 |

Test Example 3

Inhibition Test of Auricular Oedema Induced by Single Application of TPA (12-O-tetradecanoylphorbol-13-acetate) in Mouse (In Vivo Efficacy Test Based on TNF-α-Related Cutaneous Inflammation)

Auricular oedema was induced by applying 54 μmol/L TPA-acetone solution on both the inner and outer sides of the left ear of BALB/c mice (application volume of 54 μmol/L TPA-acetone solution is 10 μL for each side of the left ear (i.e. 1.08 nmol TPA/auricle)). For a non-induced group, acetone was similarly applied instead of the 54 μmol/L TPA-acetone solution. The test substance was dissolved and prepared in a 1 w/v % solution of acetone containing 10 vol % DMSO (topical administration vehicle), then the test solution was applied onto both the inner and outer sides of the left ear of the mice (application volume of this test solution is 10 μL for each side of the left ear) 1 hour before the TPA application. For a control group, the topical administration vehicle was similarly applied instead of the test substance solution. For an etanercept group, 0.2 mL of a 5 mg/mL etanercept solution was intravenously administered (1 mg/mouse) the day before TPA application and 1.5 hours before TPA application. For a human IgG (hIgG) group (etanercept control group), 0.2 mL of a 5 mg/mL hIgG solution was intravenously administered (1 mg/mouse). Auricle thickness was measured under ether anesthesia the day before TPA application and 6 hours after TPA application for evaluation of the auricular oedema inhibition effect of the test substance based on the increase in auricle thickness as an index.

The auricular oedema inhibition rate (%) of the test substance was calculated based on the following formula using (A) the average value of the increase in auricular thickness of the group administered with the test substance, (B) the average value of the increase in auricular thickness of the non-induced group, and (C) the average value of the increase in auricular thickness of the control group.

Auricular oedema inhibition rate (%) of the test substance=$(C-A)/(C-B) \times 100$ (A): Average value of the increase in auricular thickness of the group administered with the test substance
(B): Average value of the increase in auricular thickness of the non-induced group
(C): Average value of the increase in auricular thickness of the control group The auricular oedema inhibition rate (%) of etanercept was calculated based on the following formula using (B) the average value of the increase in auricular thickness of the non-induced group, (D) the average value of the increase in auricular thickness of the etanercept group, and (E) the average value of the increase in auricular thickness of the hIgG group.

Auricular oedema inhibition rate (%) of etanercept= $(E-D)/(E-B) \times 100$ (D): Average value of the increase in auricular thickness of the etanercept group
(E): Average value of the increase in auricular thickness of the hIgG group Further, each etanercept ratio was calculated based on the following formula by comparing the auricular oedema inhibition rate (%) of each test substance with the auricular oedema inhibition rate (%) of etanercept (used as positive control) at the same time.

"Etanercept ratio"=Auricular oedema inhibition rate (%) of each test substance/auricular oedema inhibition rate (%) of etanercept The auricular oedema inhibition rate (%) of the pyridone derivatives according to the present invention and the respective etanercept ratios are shown in Table 17.

TABLE 17

| Compound | Auricular oedema inhibition rate (%) | Etanercept ratio |
|---|---|---|
| I-9 | 66 | 3.9 |
| I-10 | 46 | 2.7 |
| I-40 | 63 | 3.5 |
| I-62 | 47 | 2.6 |
| I-64 | 50 | 2.8 |
| I-85 | 78 | 3.9 |
| I-86 | 68 | 3.4 |
| I-37 | 78 | 3.9 |
| I-84 | 53 | 2.7 |
| I-36 | 58 | 2.9 |
| I-102 | 50 | 2.5 |
| I-129 | 71 | 5.1 |
| I-38 | 41 | 2.9 |
| I-41 | 51 | 3.6 |
| I-130 | 44 | 3.1 |

The compound according to the present invention exhibited a superior effect by topical administration than the intravenous administration of etanercept, which is a commercially available drug for TNF-α related diseases.

Test Example 4

Pharmacokinetic Study after Percutaneous Administration in Hairless Mice
Intravenous Administration Test substances (0.1 to 0.5 mg/5 mL/kg) were administered by bolus injection into the tail vein of hairless mice under anesthesia.
Percutaneous Administration A 4 cm² administration site (2 cm×2 cm) was marked on the back skin of hairless mice under anesthesia (ingested) using an oil-based marker. Test substances were applied to the administration site at 50 μL/animal (1 w/v % Macrogol 400 solution). Gauze (BEMCOT®) about 2 cm×2 cm in size was fixed using double-sided tape to an approximately 4 cm×4 cm polyethylene sheet, and the gauze face was placed over the face on which the test substance had been applied. An adhesive elastic bandage (Elastopore, about 10 cm) was stuck over the gauze to fix and protect the face on which the test substance had been applied. The mice were then returned to its cage. Twenty-four hours after administration, occlusive application was confirmed to have been properly carried out.
Blood Collection The tail vein of an anesthesitized mice was cut with a razor, and blood was collected from the tail vein using a micropipette. The blood samples were collected 5, 15, 30 minutes, 1, 3, and 6 hours after intravenous administration, and 30 minutes, 1, 3, 6, and 24 hours after percutaneous administration, respectively. The amount of blood collected at each point was about 30 to 50 pt. The blood was transferred to a tube containing heparin sodium (1,000 units/mL), and the plasma was obtained by centrifugation (4° C., 19,200×g, 10 min). The plasma was cryopreserved in a freezer with a set temperature of −30° C.
Method for Measuring Plasma Concentration of Test Substance The cryopreserved plasma obtained by the above method was thawed at room temperature. After removing the protein using methanol, the concentration of the test substance in the plasma was measured. The instruments used for the measurement of the plasma concentration were consisted of HTC PAL autosampler manufactured by CTC Analytics, and an Accela HPLC and a TSQ Quantum Ultra manufactured by Thermo Fisher Scientific.
Calculation of Transdermal Absorption Rate Transdermal absorption rate was calculated using the following formula by calculating the AUC (area under the curve of the concentration in plasma) from the plasma concentration of the test substance measured by the method described above.

Transdermal absorption rate (%)=(($Div$×AUC$pc$)/($Dpc$×AUC$iv$))×100

$Div$: Dose of test substance during intravenous administration
$Dpc$: Dose of test substance during percutaneous administration
AUC$iv$: Area under the curve of the plasma concentration of the test substance after intravenous administration
AUC$pc$: Area under the curve of the plasma concentration of the test substance after percutaneous administration It was confirmed that the compound according to the present invention has good transdermal absorbability after percutaneous administration. Therefore, it is inferred that the compound according to the present invention also has good skin permeability.

The pyridone derivative, or a salt thereof, represented by formula (I) according to the present invention exhibits an excellent selective TACE inhibitory effect, and is useful as the active ingredient in a pharmaceutical for the treatment and prevention of a TNF-α-related disease.

The invention claimed is:

1. A method for treating a TNF-α-related disease, comprising administering to a subject in need thereof a therapeutically effective amount of a pyridone derivative, or a salt thereof, represented by formula (I),

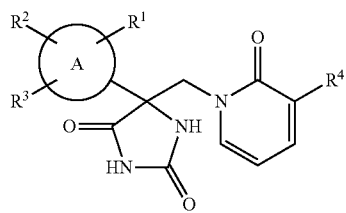

[wherein ring A represents an aryl or a group represented by the following formula (a),

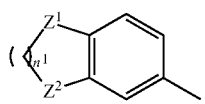

(wherein $Z^1$ and $Z^2$ each independently represent —$CH_2$— or —O—, and $n^1$ denotes an integer of 1 to 3), wherein $R^1$ represents a hydrogen atom, a halogen atom, a hydroxyl group, a cyano group, a nitro group, a C1-C6 haloalkyl group, a carboxyl group, a C1-C6 alkyl group, a C1-C6 alkoxy group optionally substituted with one or more halogen atoms, a C3-C7 cycloalkyl group, an aryl group optionally substituted with one or more substituents independently selected from the group consisting of a halogen atom and a C1-C6 alkoxy group, an aralkyl group optionally substituted with one or more halogen atoms, a pyridyl group optionally substituted with one or more substituents independently selected from the group consisting of a halogen atom and a C1-C6 alkoxy group, a C2-C6 alkenyl group, a C2-C6 alkynyl group, or -$J^1$-$X^1$-$R^5$ {wherein $J^1$ represents a single bond, alkylene, alkenylene, or alkynylene, $X^1$ represents a single bond, an oxygen atom, a sulfur atom, SO, $SO_2$, —CO—, —$NR^6$—, —$NR^6SO_2$—, —$SO_2NR^6$—, —$NR^6CO$—, —$CONR^6$—, —$NR^6COO$—, —$OCONR^6$—, —$NR^6CONR^{7-}$, or —$NR^6SO_2NR^7$— (wherein $R^6$ and $R^7$ each independently represent a hydrogen atom or a C1-C6 alkyl group), and $R^5$ represents (a), (b) and/or (c):

(a) a substituted- or unsubstituted-cycloalkyl or cycloalkylalkyl group, the substituent being selected from the group consisting of:

a hydroxyl group; a halogen atom; a cyano group; a nitro group; a trifluoromethyl group; an unsubstituted C1-C6 alkoxy group; a C1-C6 alkoxy group substituted with a hydroxyl group, a halogen atom, a cyano group, a nitro group, or a C1-C6 alkoxy group; a cycloalkyl group; a carboxyl group; a C1-C6 alkoxycarbonyl group; —$NR^8R^9$; or —$OCOR^{13}$, (b) a substituted- or unsubstituted-aryl, aralkyl, or pyridyl group-, the substituent being selected from the group consisting of:

a hydroxyl group; a halogen atom; a cyano group; a nitro group; a trifluoromethyl group; an unsubstituted C1-C6 alkoxy group; an unsubstituted C1-C6 alkyl group; a C1-C6 alkyl group substituted with a halogen atom, a cyano group, a nitro group, a trifluoromethyl group, or a C1-C6 alkoxy group; a C1-C6 alkoxy group substituted with a hydroxyl group, a halogen atom, a cyano group, a nitro group, a trifluoromethyl group, or a C1-C6 alkoxy group; a cycloalkyl group; a carboxyl group; a C1-C6 alkoxycarboxyl group; —$NR^{14}R^{15}$; —$OCOR^{13}$; an unsubstituted alkyl group; a substituted alkyl group, wherein the alkyl group is substituted with a substituent selected from the group consisting of:

a hydroxyl group; a halogen atom; a cyano group; a nitro group; a trifluoromethyl group; an unsubstituted C1-C6 alkoxy group; a C1-C6 alkoxy group substituted with a halogen atom, a cyano group, a nitro group, or a C1-C6 alkoxy group; a cycloalkyl group; a carboxyl group; a C1-C6 alkoxycarbonyl group; —$NR^8R^9$ (wherein $R^8$ and $R^9$ each independently represent a hydrogen atom; a C1-C6 alkyl group; a formyl group; an alkylcarbonyl group, wherein the alkyl moiety is an unsubstituted C1-C6 alkyl group, or a C1-C6 alkyl group substituted with a halogen atom, a cyano group, a nitro group, or a C1-C6 alkoxy group; —$CONR^{10}R^{11}$ (wherein $R^{10}$ and $R^{11}$ each independently represent a hydrogen atom; a C1-C6 alkyl group; an unsubstituted aryl group; an aryl group substituted with a C1-C6 alkyl group, a C1-C6 alkoxy group, or a halogen atom; or form a nitrogen-containing heterocyclic ring together with the nitrogen atom to which $R^{10}$ and $R^{11}$ are attached); a cycloalkyl group; or form a nitrogen-containing heterocyclic ring together with the nitrogen atom to which $R^8$ and $R^9$ are attached); or —$OCOR^{13}$ (wherein $R^{13}$ represents a C1-C6 alkyl group; an unsubstituted aryl group; an aryl group substituted with a C1-C6 alkyl group, a C1-C6 alkoxy group, or a halogen atom; or —$NR^{14}R^{15}$ (wherein $R^{14}$ and $R^{15}$ each independently represent a hydrogen atom; a C1-C6 alkyl group; an unsubstituted aryl group; an aryl group substituted with a C1-C6 alkyl group, a C1-C6 alkoxy group, or a halogen atom; or form a nitrogen-containing heterocyclic ring together with the nitrogen atom to which $R^{14}$ and $R^{15}$ are attached)), (c) a group represented by the following formula (b):

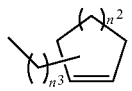

(wherein $n^2$ denotes an integer of 1 to 3 and $n^3$ denotes an integer of 0 to 3), an aryl group optionally substituted with one or more substituents independently selected from the group consisting of a C1-C6 alkyl group; a halogen atom; a C1-C6 alkoxy group; and a trifluoromethyl group, an aralkyl group optionally substituted with one or more halogen atoms, or a pyridyl group optionally substituted with one or more substituents independently selected from the group consisting of a halogen atom and a C1-C6 alkoxy group}, wherein $R^2$ represents a hydrogen atom, a halogen atom, a cyano group, a nitro group, a C1-C6 haloalkyl group, a carboxyl group, a C1-C6 alkyl group, a C1-C6 alkoxy group, wherein $R^3$ represents a hydrogen atom, a halogen atom, or a C1-C6 alkyl group, and wherein $R^4$ represents a hydrogen atom, a halogen atom, a cyano group, a C1-C6 haloalkyl group, a C1-C6 alkoxy group, a hydroxymethyl group, a C1-C6 alkyl group, or a C2-C6 alkenyl group].

2. The method according to claim 1, wherein the TNF-α-related disease is one or more selected from the group consisting of rheumatoid arthritis, psoriatic arthritis, systemic lupus erythematosus (SLE), lupus nephritis, systemic scleroderma, localized scleroderma, Sjogren's syndrome, polymyositis, dermatomyositis, ulcerative colitis, Crohn's disease, Behcet's disease, multiple sclerosis, arteriosclerosis, myasthenia gravis, ankylosing spondylitis, diabetes, arteriosclerosis, sepsis, acute infectious diseases, asthma, chronic obstructive pulmonary disease (COPD), atopic dermatitis, contact dermatitis, psoriasis, acne, osteoporosis, burns, the onset of rejection associated with organs or tissue transplantation, fever, anemia, cancer, periodontal disease, glaucoma, diabetic complications, and uveitis.

3. The method according to claim 1, wherein the TNF-α-related disease is a skin disease.

4. The method according to claim 3, wherein the skin disease is one or more selected from the group consisting of a localized scleroderma, atopic dermatitis, contact dermatitis, psoriasis, and acne.

5. The method according to claim 1, wherein the compound represented by the formula (I) is one selected from the following:

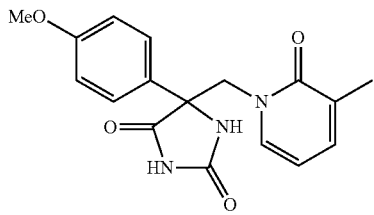

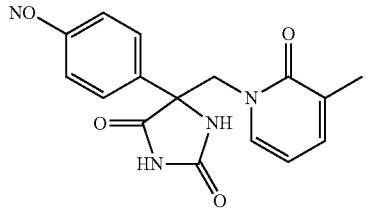

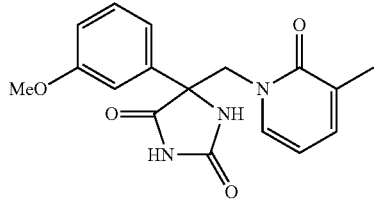

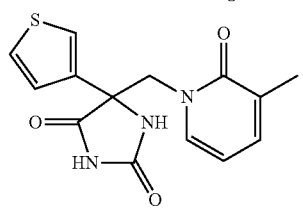

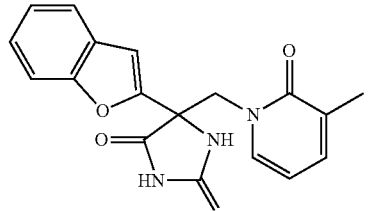

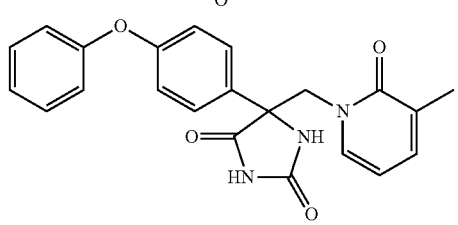

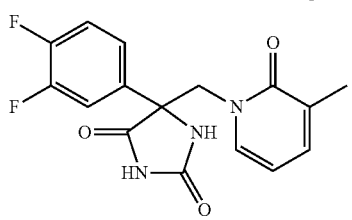

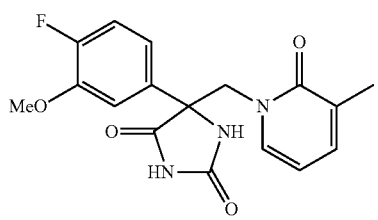

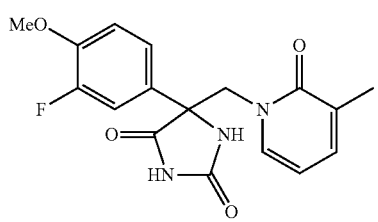

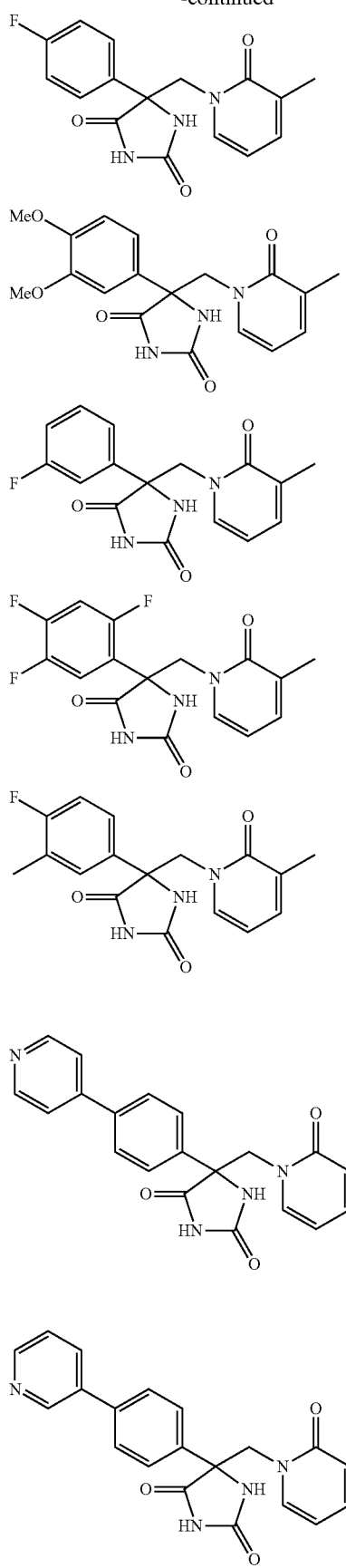
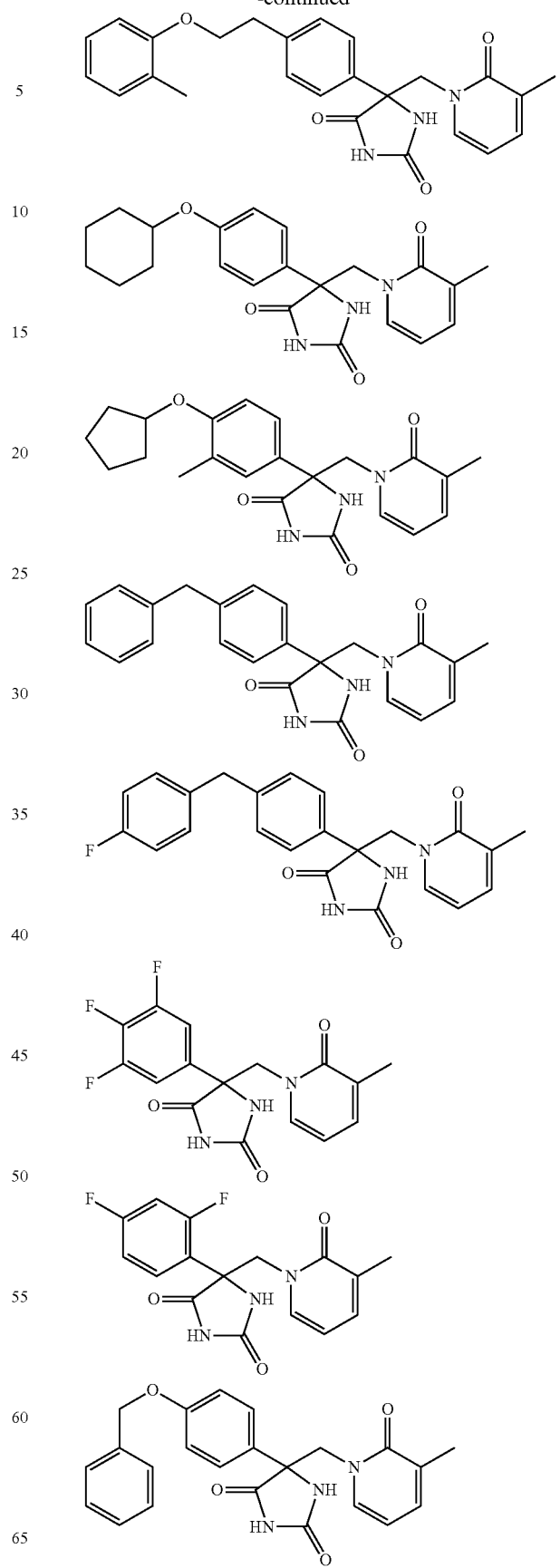

149
-continued
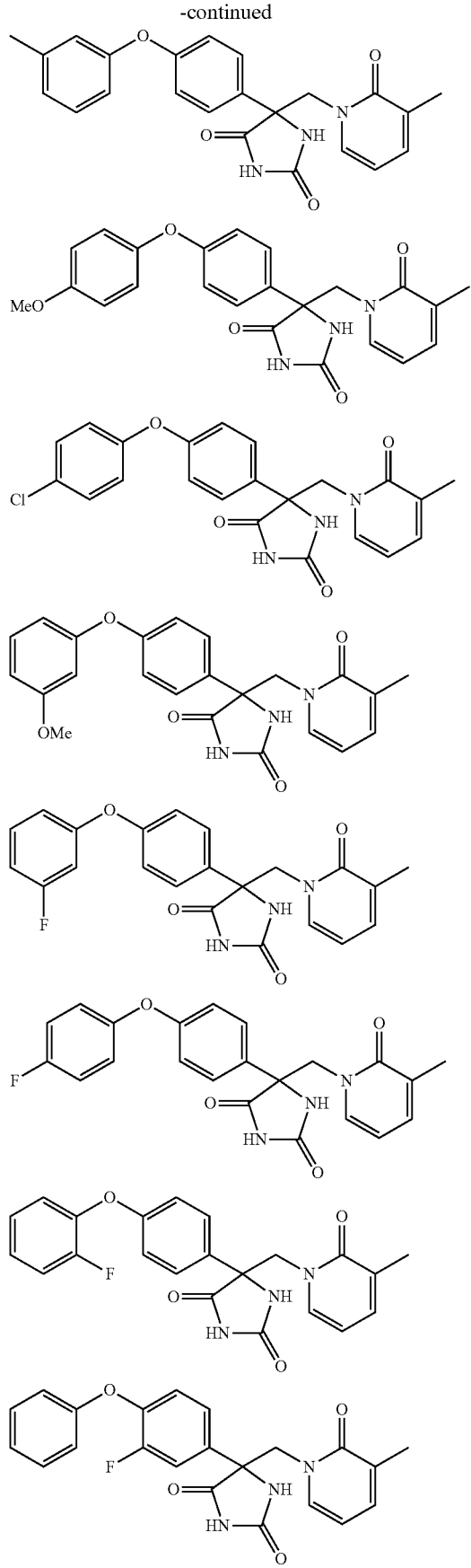
150
-continued
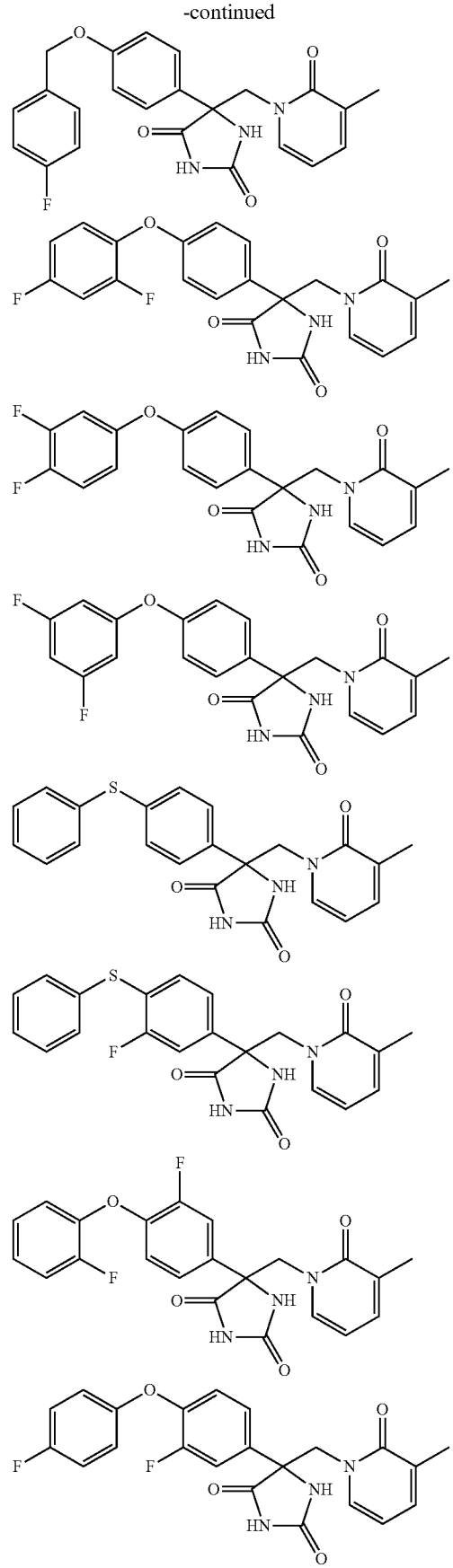

151
-continued
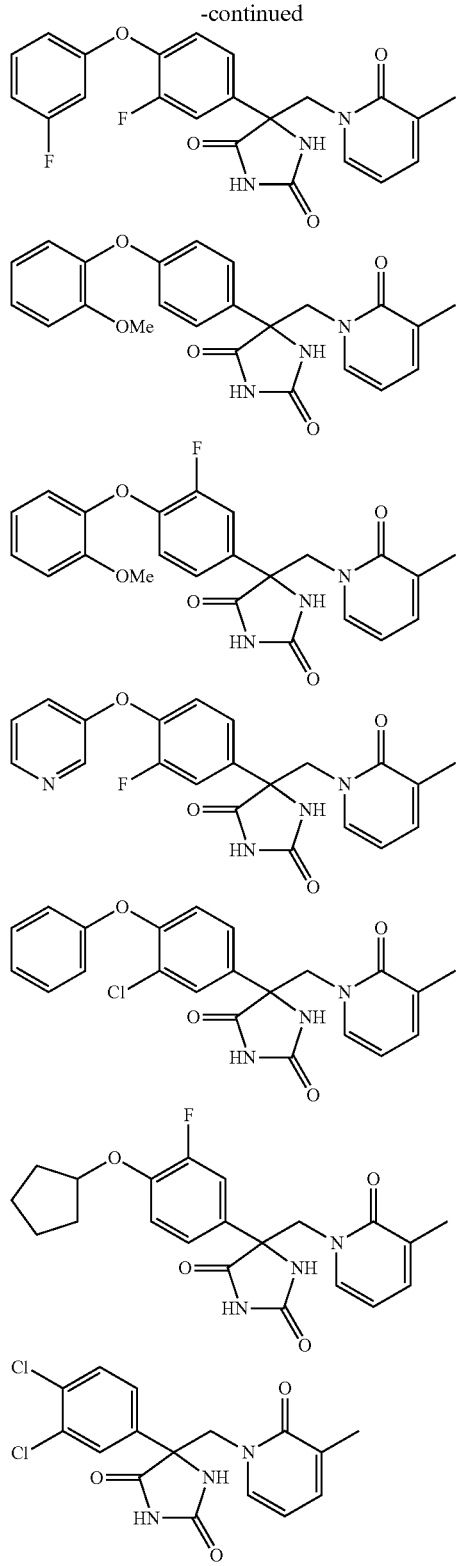
152
-continued
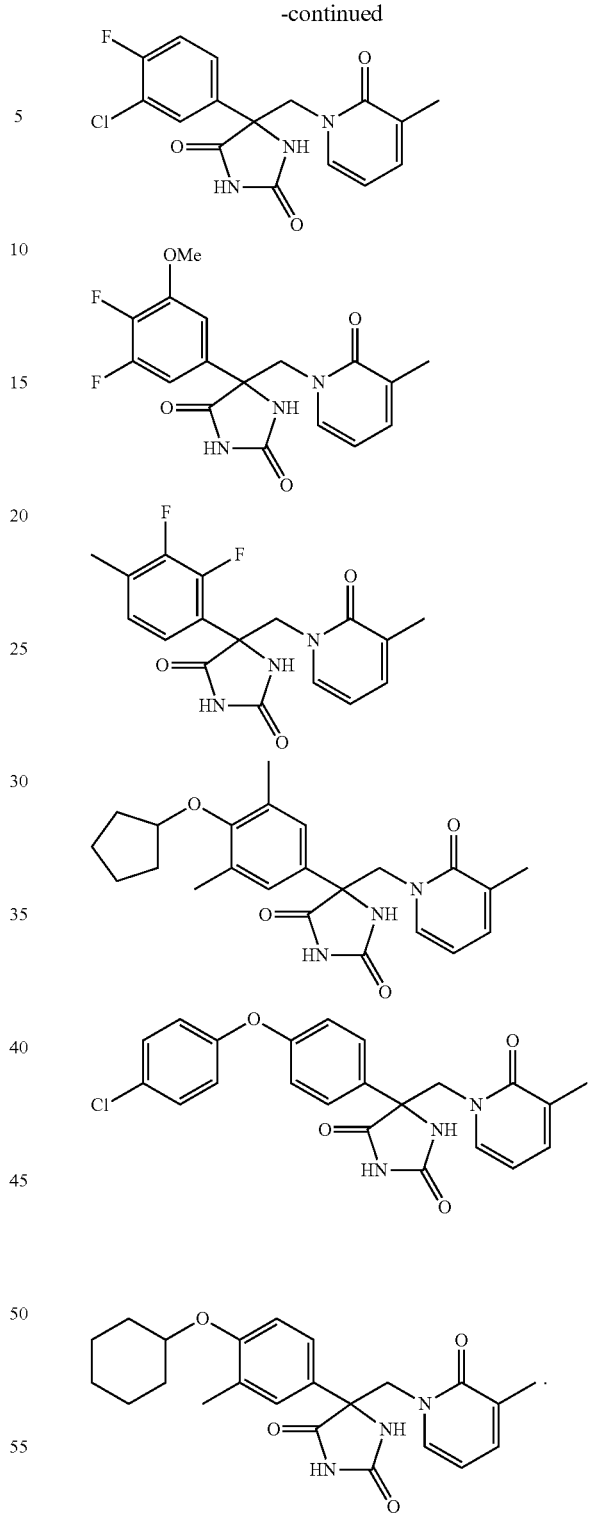
* * * * *

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-methylanthranilic acid

```
-continued

<220> FEATURE:
<221> NAME/KEY: MISC_FEATURE
<222> LOCATION: (11)..(11)
<223> OTHER INFORMATION: dinitrophenyl

<400> SEQUENCE: 1

Xaa Leu Ala Gln Ala Val Arg Ser Ser Lys Xaa Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: dinitrophenyl
<220> FEATURE:
<221> NAME/KEY: MISC_FEATURE
<222> LOCATION: (3)..(3)
<223> OTHER INFORMATION: beta-cyclohexylalanyl
<220> FEATURE:
<221> NAME/KEY: MISC_FEATURE
<222> LOCATION: (5)..(5)
<223> OTHER INFORMATION: cysteine(Me)
<220> FEATURE:
<221> NAME/KEY: MISC_FEATURE
<222> LOCATION: (9)..(9)
<223> OTHER INFORMATION: N-methylanthranilic acid

<400> SEQUENCE: 2

Xaa Pro Xaa Gly Xaa His Ala Lys Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 7-methoxycoumarin-4-yl)acetyl
<220> FEATURE:
<221> NAME/KEY: MISC_FEATURE
<222> LOCATION: (6)..(6)
<223> OTHER INFORMATION: N-beta-(2,4-dinitrophenyl)-L-
      2,3-Diaminopropionyl

<400> SEQUENCE: 3

Xaa Pro Leu Gly Leu Xaa Ala Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 7-methoxycoumarin-4-yl)acetyl
<220> FEATURE:
<221> NAME/KEY: MOD_RES
<222> LOCATION: (8)..(8)
<223> OTHER INFORMATION: Nva
<220> FEATURE:
<221> NAME/KEY: MISC_FEATURE
<222> LOCATION: (12)..(12)
```

```
<223> OTHER INFORMATION: dinitrophenyl

<400> SEQUENCE: 4

Xaa Arg Pro Lys Pro Val Glu Xaa Trp Arg Lys Xaa
1               5                   10
```